(12) United States Patent
Senger et al.

(10) Patent No.: US 9,428,757 B2
(45) Date of Patent: Aug. 30, 2016

(54) REGULATORY NUCLEIC ACID MOLECULES FOR ENHANCING SEED-SPECIFIC GENE EXPRESSION IN PLANTS PROMOTING ENHANCED POLYUNSATURATED FATTY ACID SYNTHESIS

(75) Inventors: Toralf Senger, Heidelberg (DE); Jörg Bauer, Teltow (DE); Josef Martin Kuhn, Ludwigshafen (DE)

(73) Assignee: BASF Plant Science Company GmbH, Ludwigshafen (DE)

(*) Notice: Subject to any disclaimer, the term of this patent is extended or adjusted under 35 U.S.C. 154(b) by 919 days.

(21) Appl. No.: 13/393,063

(22) PCT Filed: Aug. 27, 2010

(86) PCT No.: PCT/EP2010/062561
§ 371 (c)(1),
(2), (4) Date: Feb. 28, 2012

(87) PCT Pub. No.: WO2011/023800
PCT Pub. Date: Mar. 3, 2011

(65) Prior Publication Data
US 2012/0185965 A1    Jul. 19, 2012

Related U.S. Application Data

(60) Provisional application No. 61/238,254, filed on Aug. 31, 2009.

(30) Foreign Application Priority Data

Aug. 31, 2009 (EP) ..................................... 09169079

(51) Int. Cl.
C12N 15/82    (2006.01)

(52) U.S. Cl.
CPC ....... *C12N 15/8216* (2013.01); *C12N 15/8234* (2013.01); *C12N 15/8247* (2013.01)

(58) Field of Classification Search
None
See application file for complete search history.

(56) References Cited

U.S. PATENT DOCUMENTS

| | | | |
|---|---|---|---|
| 5,750,866 A | 5/1998 | Dietrich et al. | |
| 7,456,336 B2 * | 11/2008 | Broglie et al. ................ | 800/281 |
| 8,071,383 B2 | 12/2011 | Arias et al. | |
| 2005/0216967 A1 | 9/2005 | Heim et al. | |
| 2005/0246785 A1 | 11/2005 | Cook et al. | |
| 2006/0195934 A1 | 8/2006 | Apuya et al. | |
| 2006/0195943 A1 * | 8/2006 | Feldmann ............ | C07K 14/415 800/287 |
| 2007/0006335 A1 | 1/2007 | Cook et al. | |
| 2007/0006345 A1 | 1/2007 | Alexandrov et al. | |
| 2007/0006347 A1 | 1/2007 | Plesch et al. | |
| 2009/0172837 A1 | 7/2009 | Geiger et al. | |
| 2010/0192237 A1 | 7/2010 | Ren et al. | |
| 2010/0199365 A1 | 8/2010 | Senger et al. | |
| 2011/0014706 A2 | 1/2011 | Cao et al. | |
| 2012/0084885 A1 | 4/2012 | Alexandrov et al. | |
| 2012/0159670 A1 | 6/2012 | Kuhn et al. | |
| 2012/0167248 A1 | 6/2012 | Kuhn et al. | |

FOREIGN PATENT DOCUMENTS

| | | |
|---|---|---|
| CL | 2007000696 A1 | 6/2008 |
| EP | 1645633 A2 | 4/2006 |
| JP | 2009/529863 A | 8/2009 |
| RU | 2197527 C2 | 1/2003 |
| WO | WO-93/20216 A1 | 10/1993 |
| WO | WO-99/67389 A2 | 12/1999 |
| WO | WO-00/55325 A2 | 9/2000 |
| WO | WO-01/98480 A2 | 12/2001 |
| WO | WO-02/16655 A2 | 2/2002 |
| WO | WO-03/006660 A1 | 1/2003 |
| WO | WO-03/008596 A2 | 1/2003 |
| WO | WO-03/102198 A1 | 12/2003 |
| WO | WO-2006/003186 A1 | 1/2006 |
| WO | WO-2006/032426 A2 | 3/2006 |
| WO | WO-2006/089950 A2 | 8/2006 |
| WO | WO-2007/039454 A1 | 4/2007 |
| WO | WO-2007/098042 A2 | 8/2007 |
| WO | WO-2007/107516 A2 | 9/2007 |
| WO | WO-2007/112326 A1 | 10/2007 |
| WO | WO-2008/009600 A1 | 1/2008 |
| WO | WO-2008/064128 A2 | 5/2008 |
| WO | WO-2008/104559 A1 | 9/2008 |
| WO | WO-2009/016202 A2 | 2/2009 |
| WO | WO-2009/037329 A2 | 3/2009 |
| WO | WO-2011/023537 A1 | 3/2011 |

(Continued)

OTHER PUBLICATIONS

"Transgenic plant; promoter; ds; gene silencing; RNA interference; gene expression; PT0723", Genbank Database, Accession No. AJV39144, Nov. 29, 2007.
"Petroselinum crispum ubiquitin promoter DNA", NCBI database, Accession No. ADH50767, Mar. 25, 2004.
"A. thaliana At5g17920 gene constitutive promoter pSUH303GB", NCBI database, Accession No. AEH04981, Jun. 15, 2006.
"Petroselinum crispum UBI4-2 promoter sequence, SEQ ID 7", NCBI database, Accession No. AJV61209, Nov. 29, 2007.
"Sequence 230 from Patent WO0198480", EMBL Database, Accession No. AX461301, Jul. 8, 2002.

(Continued)

*Primary Examiner* — Elizabeth McElwain
(74) *Attorney, Agent, or Firm* — Drinker Biddle & Reath LLP

(57) ABSTRACT

The invention in principle pertains to the field of recombinant manufacture of fatty acids. It provides novel nucleic acid molecules comprising nucleic acid sequences encoding fatty acid desaturases, elongases, acyltransferases, terminator sequences and high expressing seed-specific promoters operatively linked to the said nucleic acid sequences wherein nucleic acid expression enhancing nucleic acids (NEENAs) are functionally linked to said promoters.

16 Claims, 6 Drawing Sheets

(56) References Cited

FOREIGN PATENT DOCUMENTS

| WO | WO-2011/023539 A1 | 3/2011 |
| WO | WO-2011/023800 A1 | 3/2011 |

OTHER PUBLICATIONS

Baeumlein, H., et al., "A Novel Seed Protein Gene from *Vicia faba* is Developmentally Regulated in Transgenic Tobacco and *Arabidopsis* Plants", Mol. Gen. Genet., vol. 225, (1991), pp. 459-467.

Bruce, W. B., et al., "*cis*-Acting Elements Involved in Photoregulation of an Oat Phytochrome Promoter in Rice", The Plant Cell, vol. 2, (1990), pp. 1081-1089.

Callis, J., et al., "Introns Increase Gene Expression in Cultured Maize Cells", Genes & Development, vol. 1, (1987), pp. 1183-1200.

Chung, B., et al., "Effect of 5_UTR Introns on Gene Expression in *Arabidopsis thaliana*", BMC Genomics, vol. 7, No. 120, (2006), pp. 1-13.

Fu, H., et al., "High-Level Tuber Expression and Sucrose Inducibility of a Potato *Sus4* Sucrose Synthase Gene Require 5' and 3' Flanking Sequences and the Leader Intron", The Plant Cell, vol. 7, (1995), pp. 1387-1394.

Fu, H., et al., "A Potato *Sus3* Sucrose Synthase Gene Contains a Context-Dependent 3' Element and a Leader Intron with Both Positive and Negative Tissue-Specific Effects", The Plant Cell, vol. 7, (1995), pp. 1395-1403.

Lu, J., et al., "Gene Expression Enhancement Mediated by the 5' UTR Intron of the Rice *rubi3* Gene Varied Remarkably Among Tissues in Transgenic Rice Plants", Mol. Genet. Genomics, vol. 279, (2008), pp. 563-572.

Rose, A. B., "The Effect of Intron Location on Intron-Mediated Enhancement of Gene Expression in *Arabidopsis*", The Plant Journal, vol. 40, (2004), pp. 744-751.

Rose, A., B., et al., "Promoter-Proximal Introns in *Arabidopsis thaliana* are Enriched in Dispersed Signals that Elevate Gene Expression", The Plant Cell, vol. 20, (2008), pp. 543-551.

Schünmann, P.H.D., et al., "Characterization of Promoter Expression Patterns Derived from the Pht1 Phosphate Transporter Genes of Barley (*Hordeum vulgare* L.)", Journal of Experimental Botany, vol. 55, No. 398, (2004), pp. 855-865.

Sieburth, L. E., "Molecular Dissection of the *AGAMOUS* Control Region Shows that *cis* Elements for Spatial Regulation are Located Intragenically", The Plant Cell, vol. 9, (1997), pp. 355-365.

Vasil, V., et al., "Increased Gene Expression by the First Intron of Maize *Shrunken*-1 Locus in Grass Species", Plant Physiol., vol. 91, (1989), pp. 1575-1579.

Wang, S., et al., "Control of Plant Trichome Development by a Cotton Fiber MYB Gene", The Plant Cell, vol. 16, (2004), pp. 2323-2334.

Xie, M., et al., "Bidirectionalization of Polar Promoters in Plants", Nature Biotechnology, vol. 19, (2001), pp. 677-678.

Wilmink, A., et al., "Activity of Constitutive Promoters in Various Species from the Liliaceae", Plant Molecular Biology, 1995, vol. 28, pp. 949-955.

"*Arabidopsis thaliana* Chromosome 1 BAC T23K8 Sequence, Complete Sequence", GenBank Accession No. AC007230, May 13, 1999.

International Preliminary Report on Patentability for PCT/EP2010/062561, issued Mar. 6, 2012.

"*Arabidopsis thaliana* DNA chromosome 6, BAC clone F13G24 (ESSA project)", EMBL database, Accession No. AL133421, Dec. 10, 1999.

Chen, Z.L., et al., "A DNA Sequence Element That Confers Seed-Specific Enhancement to a Constitutive Promoter", The EMBO Journal, vol. 7, No. 2, (1988), pp. 297-302.

Huang, M.T.F., et al., "Intervening Sequences Increase Efficiency of RNA 3' Processing and Accumulation of Cytoplasmic RNA", Nucleic Acid Research, vol. 18, No. 4, (1990), pp. 937-947.

Kim, M. J., et al., "Seed-Specific Expression of Sesame Microsomal Oleic Acid Desaturase is Controlled by Combinatorial Properties Between Negative *cis*-Regulatory Elements in the *SeFAD2* Promoter and Enhancers in the 5'-UTR Intron", Mol. Gen., Genomics, vol. 276, (2006), pp. 351-368.

Le Hir, H., et al., "How Introns Influence and Enhance Eukaryotic Gene Expression", Trends in Biochemical Sciences, vol. 28, No. 4, (2003), pp. 215-220.

Nott, A., et al., "Splicing Enhances Translation in Mammalian Cells: an Additional Function of the Exon Junction Complex", Genes & Development, vol. 18, (2004), pp. 210-222.

Thomas, M. S., et al, "Identification of an Enhancer Element for the Endosperm-Specific Expression of High Molecular Weight Glutenin", The Plant Cell, vol. 2, (1990), pp. 1171-1180.

Vitale, A., et al., "Multiple Conserved 5' Elements are Required for High-Level Pollen Expression of the *Arabidopsis* Reproductive Actin Acts", Plant Molecular Biology, vol. 52, (2003), pp. 1135-1151.

Chilean Office Action Issued in Chilean Patent Application No. 2012-000550 Dated Feb. 11, 2015.

Decision of Grant Issued in Russian Patent Application No. 2012 112 347 Dated Apr. 1, 2015.

Decision of Grant Issued in Russian Patent Application No. 2012 112 346 Dated Apr. 1, 2015.

\* cited by examiner

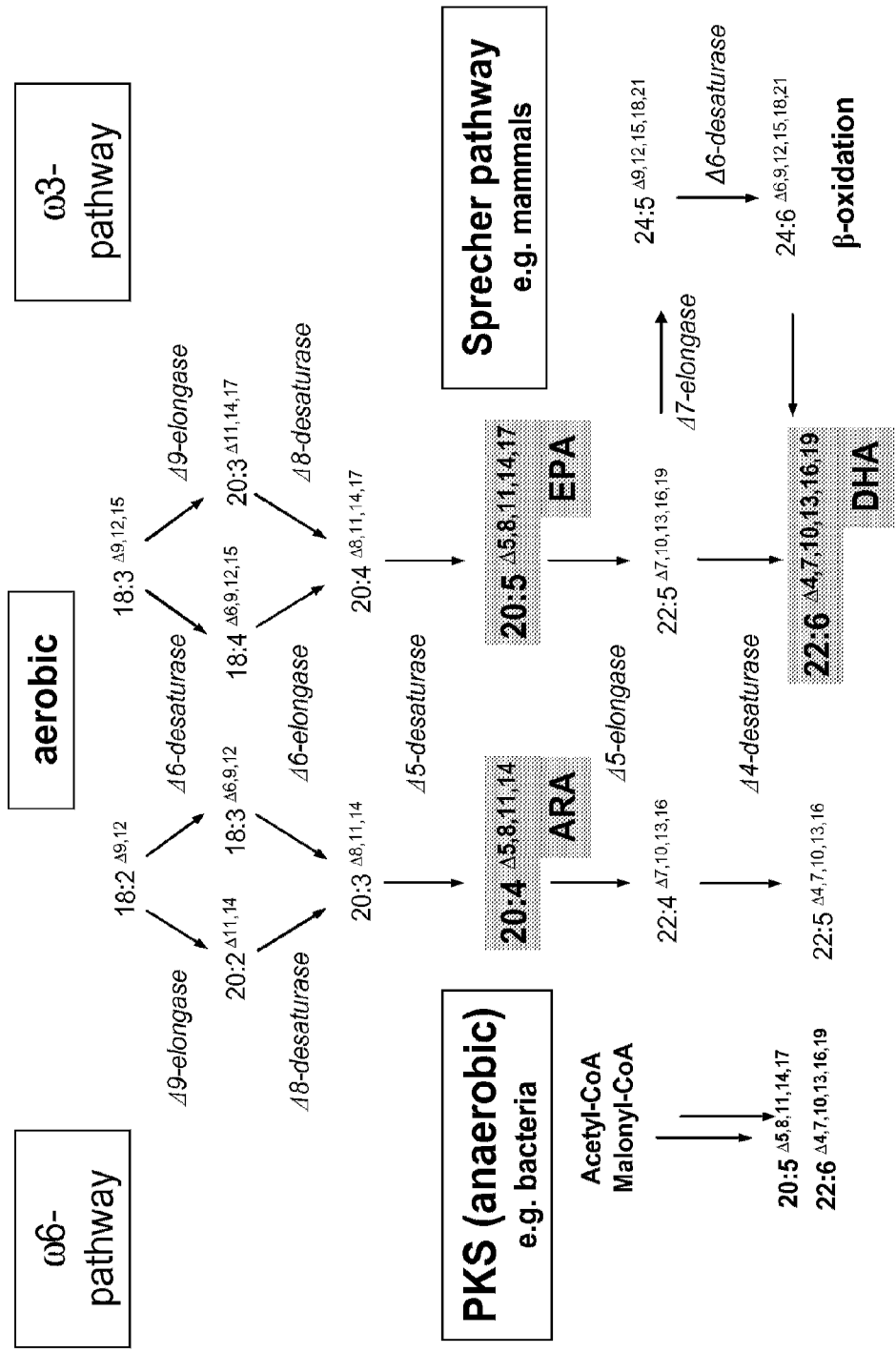
Figure 1 Schematical figure of the different enzymatic activities leading to the production of ARA, EPA and DHA.

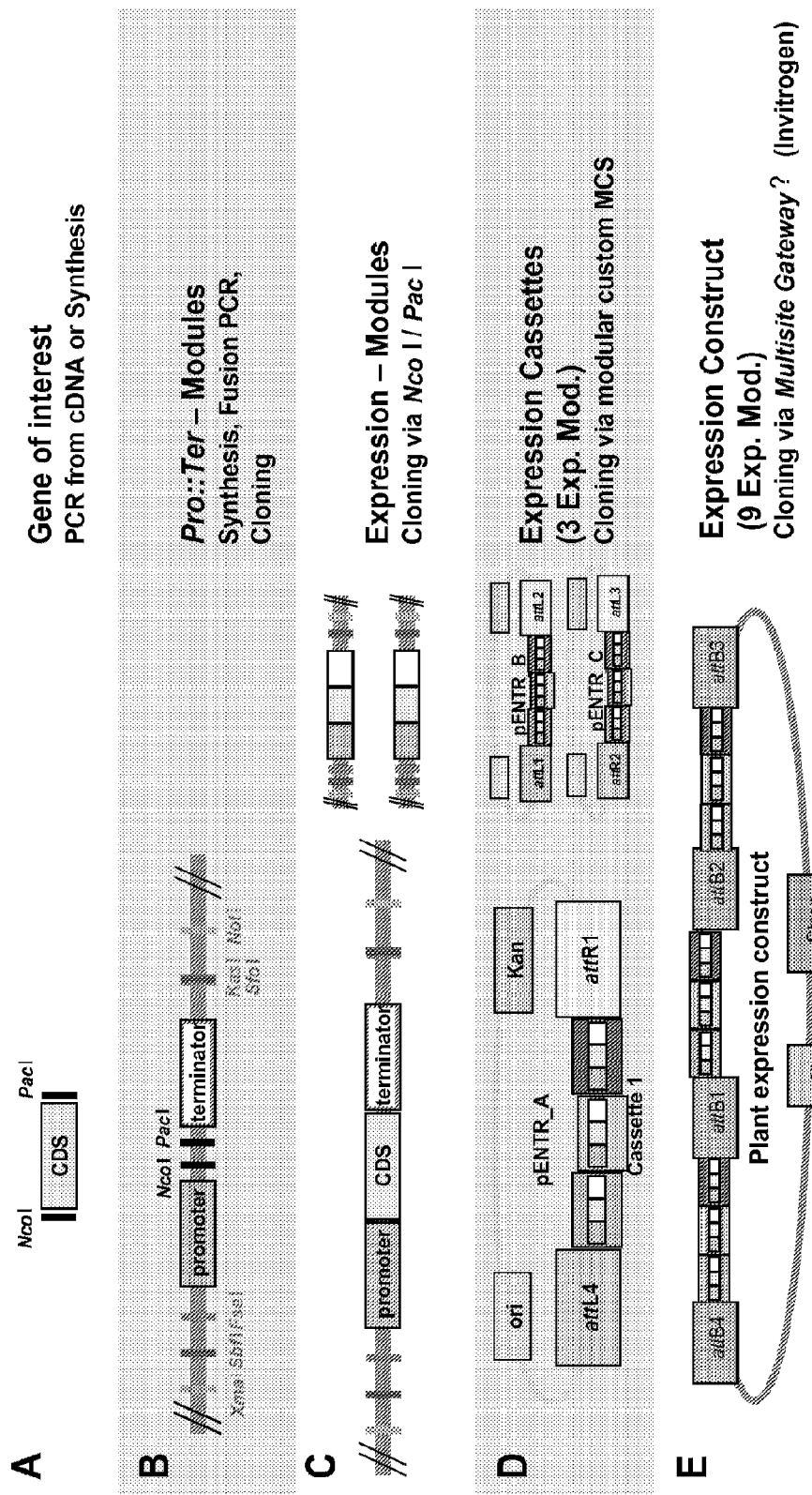
Figure 2 Strategy employed for stepwise buildup of plant expression plasmids of the invention Figure 3 A – D: Orientation and combination of the functional elements (promotor, NEENA, gene, terminator) of the plant expression VC-LJB913-1qcz (SEQ-ID 33), VC-LJB1327-1qcz (SEQ-ID 34), VC-LJB2003-1qcz (SEQ-ID 35) and VC-LJB2197(SEQ_ID 146).
Figure A
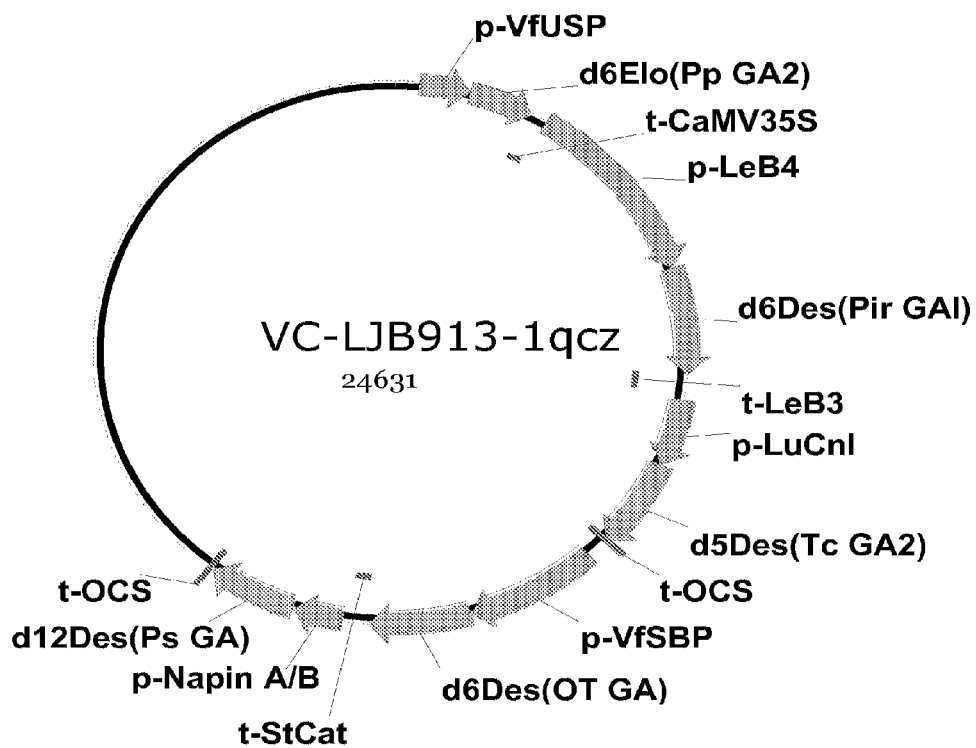

Figure B
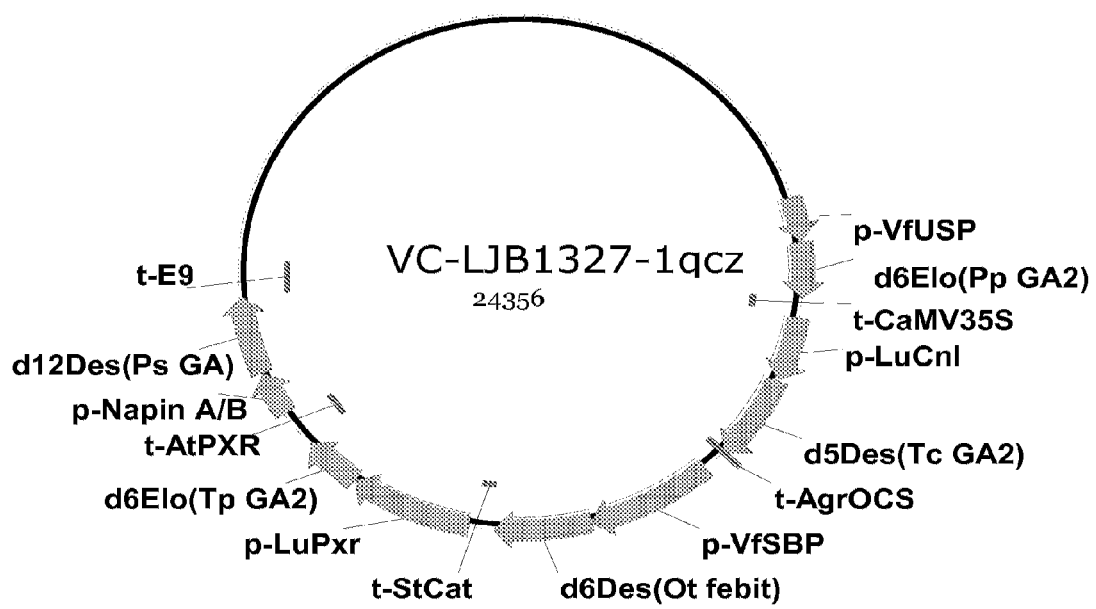

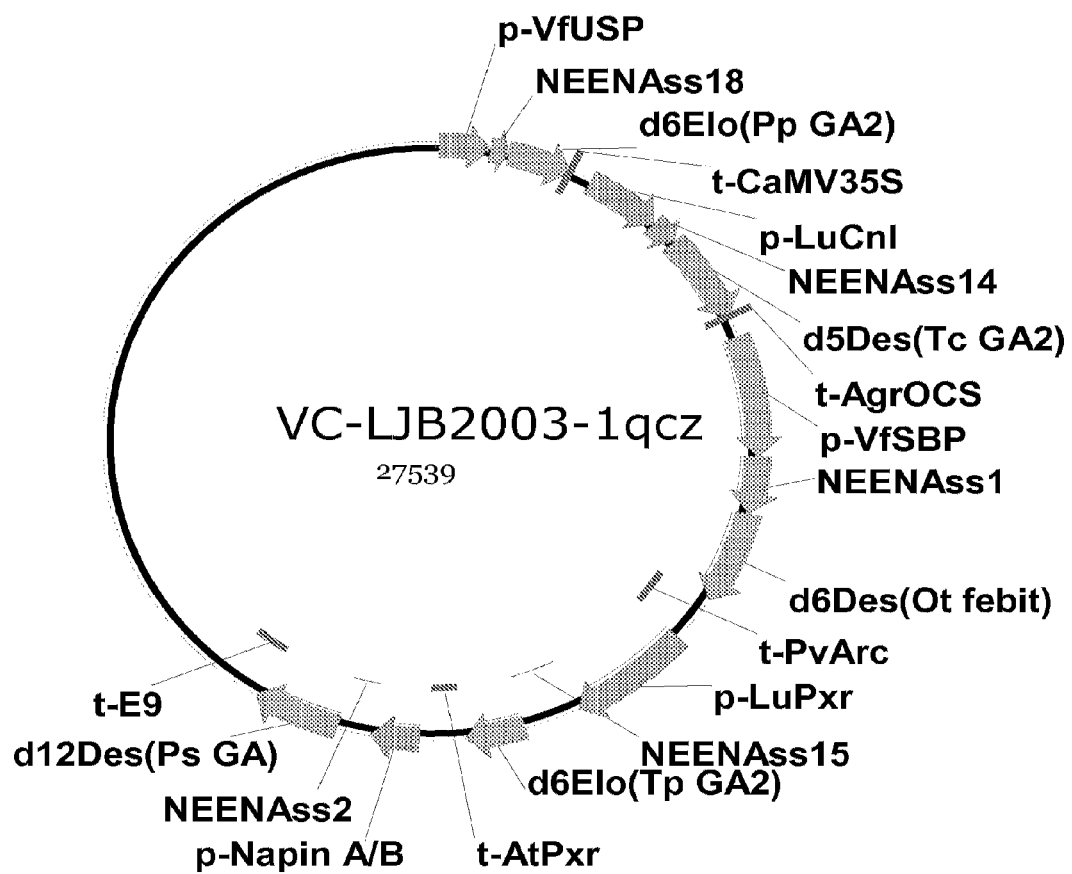
Figure C

Figure D
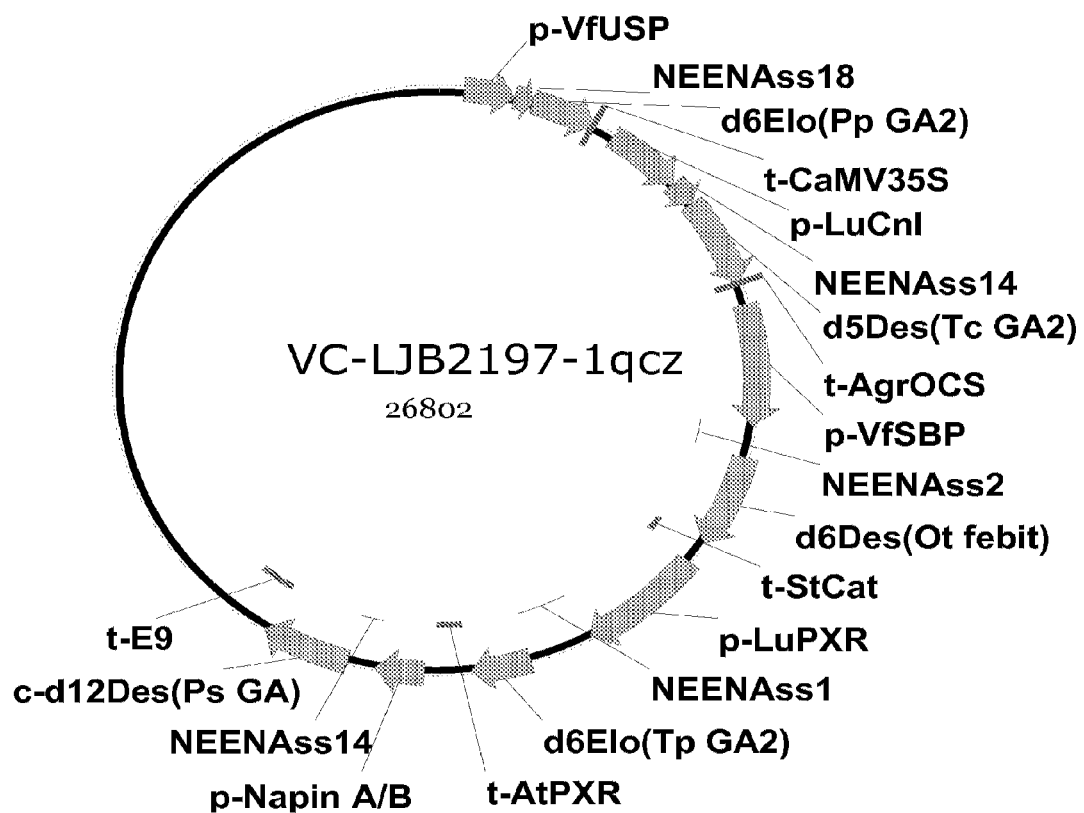

SEQUENCE LISTING

```
<160> NUMBER OF SEQ ID NOS: 155

<210> SEQ ID NO 1
<211> LENGTH: 2646
<212> TYPE: DNA
<213> ORGANISM: Artificial Sequence
<220> FEATURE:
<223> OTHER INFORMATION: p-VfSBP-NEENAss1 expression element

<400> SEQUENCE: 1
tcgacggccc ggactgtatc caacttctga tctttgaatc tctctgttcc aacatgttct     60
gaaggagttc taagactttt cagaaagctt gtaacatgct ttgtagactt tctttgaatt    120
actcttgcaa actctgattg aacctacgtg aaaactgctc cagaagttct aaccaaattc    180
cgtcttggga aggcccaaaa tttattgagt acttcagttt catggacgtg tcttcaaaga    240
tttataactt gaaatcccat cattttttaag agaagttctg ttccgcaatg tcttagatct    300
cattgaaatc tacaactctt gtgtcagaag ttcttccaga atcaacttgc atcatggtga    360
aaatctggcc agaagttctg aacttgtcat atttcttaac agttagaaaa atttctaagt    420
gtttagaatt ttgacttttc caaagcaaac ttgacttttg actttcttaa taaacaaac    480 ttcatattct aacatgtctt gatgaaatgt gattcttgaa atttgatgtt gatgcaaaag    540
tcaaagtttg actttttcagt gtgcaattga ccatttttgct cttgtgccaa ttccaaacct    600
aaattgatgt atcagtgctg caaacttgat gtcatggaag atcttatgag aaaattcttg    660
aagactgaga ggaaaaattt tgtagtacaa cacaaagaat cctgtttttc atagtcggac    720
tagacacatt aacataaaac accacttcat tcgaagagtg attgaagaag gaaatgtgca    780 gttaccttttc tgcagttcat aagagcaact tacagacact tttactaaaa tactacaaag    840
aggaagattt taacaactta gagaagtaat gggagttaaa gagcaacaca ttaagggga    900 gtgttaaaat taatgtgttg taaccaccac tacctttagt aagtattata agaaaattgt    960
```

```
aatcatcaca ttataattat tgtccttatt taaaattatg ataaagttgt atcattaaga    1020
ttgagaaaac caaatagtcc tcgtcttgat ttttgaatta ttgttttcta tgttactttt    1080
cttcaagcct atataaaaac tttgtaatgc taaattgtat gctggaaaaa aatgtgtaat    1140
gaattgaata gaaattatgg tatttcaaag tccaaaatcc atcaatagaa atttagtaca    1200
aaacgtaact caaaaatatt ctcttatttt aaattttaca acaatataaa aatattctct    1260
tattttaaat tttacaataa tataattat cacctgtcac ctttagaata ccaccaacaa    1320
tattaatact tagatatttt attcttaata attttgagat ctctcaatat atctgatatt    1380
tattttatat ttgtgtcata ttttcttatg ttttagagtt aacccttata tcttggtcaa    1440
actagtaatt caatatatga gtttgtgaag gacacattga catcttgaaa cattggtttt    1500
aaccttgttg gaatgttaaa ggtaataaaa cattcagaat tatgaccatc tattaatata    1560
cttcctttgt cttttaaaaa agtgtgcatg aaaatgctct atggtaagct agagtgtctt    1620
gctggcctgt gtatatcaat tccatttcca gatggtagaa actgccacta cgaataatta    1680
gtcataagac acgtatgtta acacacgtcc ccttgcatgt ttttgccat atattccgtc    1740 tctttctttt tcttcacgta taaaacaatg aactaattaa tagagcgatc aagctgaact    1800
ggtgcttaaa cactctggtg agttctagta cttctgctat gatcgatctc attaccattt    1860
cttaaatttc tctccctaaa tattccgagt tcttgatttt tgataacttc aggttttctc    1920
tttttgataa atctggtctt tccattttt tttttttgtg gttaatttag tttcctatgt    1980
tcttcgattg tattatgcat gatctgtgtt tggattctgt tagattatgt attggtgaat    2040
atgtatgtgt ttttgcatgt ctggttttgg tcttaaaaat gttcaaatct gatgatttga    2100
ttgaagcttt tttagtgttg gtttgattct tctcaaaact actgttaatt tactatcatg    2160
ttttccaact ttgattcatg atgacacttt tgttctgctt tgttataaaa ttttggttgg    2220
tttgattttg taattatagt gtaattttgt taggaatgaa catgttttaa tactctgttt    2280
tcgatttgtc acacattcga attattaatc gataatttaa ctgaaaattc atggttctag    2340
atcttgttgt catcagatta tttgtttcga taattcatca aatatgtagt ccttttgctg    2400
atttgcgact gtttcatttt ttctcaaaat tgttttttgt taagtttatc taacagttat    2460
cgttgtcaaa agtctctttc attttgcaaa atcttctttt ttttttttgtt tgtaactttg    2520 ttttttaagc tacacattta gtctgtaaaa tagcatcgag gaacagttgt cttagtagac    2580
ttgcatgttc ttgtaacttc tatttgtttc agtttgttga tgactgcttt gattttgtag    2640
gtcaaa                                                               2646
```

<210> SEQ ID NO 2
<211> LENGTH: 1119
<212> TYPE: DNA
<213> ORGANISM: Artificial Sequence
<220> FEATURE:
<223> OTHER INFORMATION: p-BnNapin-NEENAss2 expression element

<400> SEQUENCE: 2

```
taaggatgac ctacccattc ttgagacaaa tgttacattt tagtatcaga gtaaaatgtg     60
tacctataac tcaaattcga ttgacatgta tccattcaac ataaaattaa accagcctgc    120
acctgcatcc acatttcaag tatttcaaa ccgttcggct cctatccacc gggtgtaaca    180
agacggattc cgaatttgga agattttgac tcaaattccc aatttatatt gaccgtgact    240
aaatcaactt taacttctat aattctgatt aagctcccaa tttatattcc caacggcact    300
```

| | |
|---|---:|
| acctccaaaa tttatagact ctcatcccct tttaaaccaa cttagtaaac gttttttttt | 360 |
| taattttatg aagttaagtt tttaccttgt ttttaaaaag aatcgttcat aagatgccat | 420 |
| gccagaacat tagctacacg ttacacatag catgcagccg cggagaattg ttttttcttcg | 480 |
| ccacttgtca ctcccttcaa acacctaaga gcttctctct cacagcacac acatacaatc | 540 |
| acatgcgtgc atgcattatt acacgtgatc gccatgcaaa tctcctttat agcctataaa | 600 |
| ttaactcatc ggcttcactc tttactcaaa ccaaaactca tcaatacaaa caagattaaa | 660 |
| aacaagttct ttgctttcga agttgccgca acctaaacag gttttttcctt cttctttctt | 720 |
| cttattaact acgaccttgt cctttgccta tgtaaaatta ctaggttttc atcagttaca | 780 |
| ctgattaagt tcgttatagt ggaagataaa atgccctcaa agcattttgc aggatatctt | 840 |
| tgattttca aagatatgga actgtagagt ttgatagtgt tcttgaatgt ggttgcatga | 900 |
| agttttttg gtctgcatgt tatttttttcc tcgaaatatg ttttgagtcc aacaagtgat | 960 |
| tcacttggga ttcagaaagt tgttttctca atatgtaaca gttttttttct atggagaaaa | 1020 |
| atcataggga ccgttggttt tggcttcttt aattttgagc tcagattaaa cccatttttac | 1080 |
| ccggtgttct tggcagaatt gaaaacagta cgtagtacc | 1119 |

<210> SEQ ID NO 3
<211> LENGTH: 1441
<212> TYPE: DNA
<213> ORGANISM: Artificial Sequence
<220> FEATURE:
<223> OTHER INFORMATION: p-LuCnl-NEENAss14 expression element

<400> SEQUENCE: 3

| | |
|---|---:|
| ttagcagata tttggtgtct aaatgtttat tttgtgatat gttcatgttt gaaatggtgg | 60 |
| tttcgaaacc agggacaacg ttgggatctg atagggtgtc aaagagtatt atggattggg | 120 |
| acaatttcgg tcatgagttg caaattcaag tatatcgttc gattatgaaa attttcgaag | 180 |
| aatatcccat ttgagagagt ctttacctca ttaatgtttt tagattatga aattttatca | 240 |
| tagttcatcg tagtcttttt ggtgtaaagg ctgtaaaaag aaattgttca cttttgtttt | 300 |
| cgtttatgtg aaggctgtaa aagattgtaa aagactattt tggtgttttg gataaaatga | 360 |
| tagtttttat agattctttt gcttttagaa gaaatacatt tgaaattttt tccatgttga | 420 |
| gtataaaata ccgaaatcga ttgaagatca tagaaatatt ttaactgaaa acaaatttat | 480 |
| aactgattca attctctcca tttttatacc tatttaaccg taatcgattc taatagatga | 540 |
| tcgattttt atataatcct aattaaccaa cggcatgtat tggataatta accgatcaac | 600 |
| tctcacccct aatagaatca gtattttcct tcgacgttaa ttgatcctac actatgtagg | 660 |
| tcatatccat cgttttaatt tttggccacc attcaattct gtcttgcctt tagggatgtg | 720 |
| aatatgaacg gccaaggtaa gagaataaaa ataatccaaa ttaaagcaag agaggccaag | 780 |
| taagataatc caaatgtaca cttgtcattg ccaaaattag taaaatactc ggcatattgt | 840 |
| attcccacac attattaaaa taccgtatat gtattggctg catttgcatg aataatacta | 900 |
| cgtgtaagcc caaagaaacc cacgtgtagc ccatgcaaag ttaacactca cgaccccatt | 960 |
| cctcagtctc cactatataa acccaccatc cccaatctca ccaaaccac cacacaactc | 1020 |
| acaactcact ctcacacctt aaagaaccaa tcaccaccaa aaaatttcac gatttggaat | 1080 |
| ttgattcctg cgatcacagg tatgacaggt tagattttgt tttgtatagt tgtatacata | 1140 |
| cttctttgtg atgttttgtt tacttaatcg aattttggga gtgttttaag gtctctcgtt | 1200 |
| tagaaatcgt ggaaaatatc actgtgtgtg tgttcttatg attcacagtg tttatgggtt | 1260 |

```
tcatgttctt tgttttatca ttgaatggga agaaatttcg ttgggataca aatttctcat    1320
gttcttactg atcgttatta ggagtttggg gaaaaaggaa gagttttttt ggttggttcg    1380
agtgattatg aggttatttc tgtatttgat ttatgagtta atggtcgttt taatgttgta    1440
g                                                                    1441

<210> SEQ ID NO 4
<211> LENGTH: 2485
<212> TYPE: DNA
<213> ORGANISM: Artificial Sequence
<220> FEATURE:
<223> OTHER INFORMATION: p-LuPxr-NEENAss15 expression element

<400> SEQUENCE: 4
cacgggcagg acatagggac tactacaagc atagtatgct tcagacaaag agctaggaaa      60
gaactcttga tggaggttaa gagaaaaaag tgctagaggg gcatagtaat caaacttgtc     120
aaaaccgtca tcatgatgag ggatgacata atataaaaag ttgactaagg tcttggtagt     180
actctttgat tagtattata tattggtgag aacatgagtc aagaggagac aagaaaccga     240
ggaaccatag tttagcaaca agatggaagt tgcaaagttg agctagccgc tcgattagtt     300
acatctccta agcagtacta caaggaatgg tctctatact ttcatgttta gcacatggta     360
gtgcggattg acaagttaga aacagtgctt aggagacaaa gagtcagtaa aggtattgaa     420
agagtgaagt tgatgctcga caggtcagga gaagtccctc cgccagatgg tgactaccaa     480
ggggttggta tcagctgaga cccaaataag attcttcggt tgaaccagtg gttcgaccga     540
gactcttagg gtgggatttc actgtaagat tgtgcatttt tgttgaatat aaattgacaa     600
ttttttttat ttaattatag attatttaga atgaattaca tatttagttt ctaacaagga     660
tagcaatgga tgggtatggg tacaggttaa acatatctat tacccaccca tctagtcgtc     720 gggtttttaca cgtacccacc cgttacata aaccagaccg gaattttaaa ccgtacccgt     780
ccgttagcgg gtttcagatt tacccgttta atcgggtaaa acctgattac taaatatata     840 tttttttattt gataaacaaa acaaaaatgt taatattttc atattggatg caattttaag     900
aaacacatat tcataaattt ccatatttgt aggaaaataa aaagaaaaat atattcaaga     960
acacaaattt caccgacatg acttttatta cagagttgga attagatcta acaattgaaa    1020
aattaaaatt aagatagaat atgttgagga acatgacata gtataatgct gggttacccg    1080
tcgggtaggt atcgaggcgg atactactaa atccatccca ctcgctatcc gataatcact    1140
ggtttcgggt atacccattc ccgtcaacag gcctttttaa ccggataatt tcaacttata    1200
gtgaatgaat tttgaataaa tagttagaat accaaaatcc tggattgcat ttgcaatcaa    1260
attttgtgaa ccgttaaatt ttgcatgtac ttgggataga tataatagaa ccgaattttc    1320
attagtttaa tttataactt actttgttca agaaaaaaa atatctatcc aatttactta    1380
taataaaaaa taatctatcc aagttactta ttataatcaa cttgtaaaaa ggtaagaata    1440
caaatgtggt agcgtacgtg tgattatatg tgacgaaatg ttatatctaa caaaagtcca    1500
aattcccatg gtaaaaaaaa tcaaaatgca tggcaggctg tttgtaacct tggaataaga    1560
tgttggccaa ttctggagcc gccacgtacg caagactcag ggccacgttc tcttcatgca    1620
aggatagtag aacaccactc cacccacctc ctatattaga cctttgccca accctcccca    1680
actttcccat cccatccaca aagaaaccga cattttatc ataaatcagg gtttcgtttt    1740
tgtttcatcg ataaactcaa aggtgatgat tttagggtct tgtgagtgtg cttttttgtt    1800
```

| | |
|---|---:|
| tgattctact gtagggttta tgttctttag ctcataggtt ttgtgtattt cttagaaatg | 1860 |
| tggcttcttt aatctctggg tttgtgactt tttgtgtggt ttctgtgttt ttcatatcaa | 1920 |
| aaacctattt ttttccgagtt ttttttttaca aattcttact ctcaagcttg aatacttcac | 1980 |
| atgcagtgtt cttttgtaga ttttagagtt aatgtgttaa aaagtttgga ttttttcttgc | 2040 |
| ttatagagct tcttcacttt gattttgtgg gttttttttgt tttaaaggtg agattttga | 2100 |
| tgaggttttt gcttcaaaga tgtcaccttt ctgggtttgt cttttgaata aagctatgaa | 2160 |
| ctgtcacatg gctgacgcaa ttttgttact atgtcatgaa agctgacgtt tttccgtgtt | 2220 |
| atacatgttt gcttacactt gcatgcgtca aaaaaattgg ggcttttag ttttagtcaa | 2280 |
| agattttact tctcttttgg gatttatgaa ggaaagttgc aaactttctc aaatttttacc | 2340 |
| atttttgctt tgatgtttgt ttagattgcg acagaacaaa ctcatatatg ttgaaatttt | 2400 |
| tgcttggttt tgtataggat tgtgtctttt gcttataaat gttgaaatct gaactttttt | 2460 |
| tttgtttggt ttctttgagc aggag | 2485 |

<210> SEQ ID NO 5
<211> LENGTH: 936
<212> TYPE: DNA
<213> ORGANISM: Artificial Sequence
<220> FEATURE:
<223> OTHER INFORMATION: p-VfUSP-NEENAss18 expression element

<400> SEQUENCE: 5

| | |
|---|---:|
| ctgcagcaaa tttacacatt gccactaaac gtctaaaccc ttgtaatttg tttttgtttt | 60 |
| actatgtgtg ttatgtattt gatttgcgat aaatttttat atttggtact aaatttataa | 120 |
| caccttttat gctaacgttt gccaacactt agcaatttgc aagttgatta attgattcta | 180 |
| aattatttt gtcttctaaa tacatatact aatcaactgg aaatgtaaat atttgctaat | 240 |
| atttctacta taggagaatt aaagtgagtg aatatggtac cacaaggttt ggagatttaa | 300 |
| ttgttgcaat gctgcatgga tggcatatac accaaacatt caataattct tgaggataat | 360 |
| aatggtacca cacaagattt gaggtgcatg aacgtcacgt ggacaaaagg tttagtaatt | 420 |
| tttcaagaca acaatgttac cacacacaag ttttgaggtg catgcatgga tgccctgtgg | 480 |
| aaagtttaaa aatatttgg aaatgatttg catggaagcc atgtgtaaaa ccatgacatc | 540 |
| cacttggagg atgcaataat gaagaaaact acaaatttac atgcaactag ttatgcatgt | 600 |
| agtctatata atgaggattt tgcaatactt tcattcatac acactcacta agttttacac | 660 |
| gattataatt tcttcatagc cagtactgtt taagcttcac tgtctctgaa tcggcaaagg | 720 |
| taaacgtatc aattattcta caaacccttt tatttttctt ttgaattacc gtcttcattg | 780 |
| gttatatgat aacttgataa gtaaagcttc aataattgaa tttgatctgt gttttttttgg | 840 |
| ccttaatact aaatccttac ataagctttg ttgcttctcc tcttgtgagt tgagtgttaa | 900 |
| gttgtaataa tggttcactt tcagctttag aagaaa | 936 |

<210> SEQ ID NO 6
<211> LENGTH: 847
<212> TYPE: DNA
<213> ORGANISM: Arabidopsis thaliana

<400> SEQUENCE: 6

| | |
|---|---:|
| tggtgcttaa acactctggt gagttctagt acttctgcta tgatcgatct cattaccatt | 60 |
| tcttaaattt ctctccctaa atattccgag ttccttgatt ttgataactt caggttttct | 120 |
| cttttgata aatctggtct ttccattttt ttttttttgt ggttaattta gtttcctatg | 180 |

```
ttcttcgatt gtattatgca tgatctgtgt ttggattctg ttagattatg tattggtgaa      240
tatgtatgtg tttttgcatg tctggttttg gtcttaaaaa tgttcaaatc tgatgatttg      300
attgaagctt ttttagtgtt ggtttgattc ttctcaaaac tactgttaat ttactatcat      360
gttttccaac tttgattcat gatgacactt tgttctgct  ttgttataaa attttggttg      420
gtttgatttt gtaattatag tgtaattttg ttaggaatga acatgtttta atactctgtt      480
ttcgatttgt cacacattcg aattattaat cgataattta actgaaaatt catggttcta      540
gatcttgttg tcatcagatt atttgtttcg ataattcatc aaatatgtag tccttttgct      600
gatttgcgac tgtttcattt tttctcaaaa tgttttttg  ttaagtttat ctaacagtta      660
tcgttgtcaa aagtctcttt cattttgcaa aatcttcttt ttttttttgt ttgtaacttt      720
gttttttaag ctacacattt agtctgtaaa atagcatcga ggaacagttg tcttagtaga      780
cttgcatgtt cttgtaactt ctatttgttt cagtttgttg atgactgctt tgattttgta      840
ggtcaaa                                                                847

<210> SEQ ID NO 7
<211> LENGTH: 455
<212> TYPE: DNA
<213> ORGANISM: Arabidopsis thaliana

<400> SEQUENCE: 7
agttctttgc tttcgaagtt gccgcaacct aaacaggttt ttccttcttc tttcttctta       60
ttaactacga ccttgtcctt tgcctatgta aaattactag gttttcatca gttacactga      120
ttaagttcgt tatagtggaa gataaaatgc cctcaaagca ttttgcagga tatctttgat      180
ttttcaaaga tatggaactg tagagtttga tagtgttctt gaatgtggtt gcatgaagtt      240
tttttggtct gcatgttatt ttttcctcga aatatgtttt gagtccaaca agtgattcac      300
ttgggattca gaaagttgtt ttctcaatat gtaacagttt ttttctatgg agaaaaatca      360
tagggaccgt tggttttggc ttctttaatt ttgagctcag attaaaccca ttttacccgg      420
tgttcttggc agaattgaaa acagtacgta gtacc                                 455

<210> SEQ ID NO 8
<211> LENGTH: 377
<212> TYPE: DNA
<213> ORGANISM: Arabidopsis thaliana

<400> SEQUENCE: 8
tttcacgatt tggaatttga ttcctgcgat cacaggtatg acaggttaga ttttgttttg       60
tatagttgta tacatacttc tttgtgatgt tttgtttact taatcgaatt tttggagtgt      120
tttaaggtct ctcgtttaga aatcgtggaa aatatcactg tgtgtgtgtt cttatgattc      180
acagtgttta tgggtttcat gttctttgtt ttatcattga atgggaagaa atttcgttgg      240
gatacaaatt tctcatgttc ttactgatcg ttattaggag tttggggaaa aaggaagagt      300 tttttttggtt ggttcgagtg attatgaggt tatttctgta tttgatttat gagttaatgg      360
tcgttttaat gttgtag                                                     377

<210> SEQ ID NO 9
<211> LENGTH: 758
<212> TYPE: DNA
<213> ORGANISM: Arabidopsis thaliana

<400> SEQUENCE: 9
```

```
agggtttcgt ttttgtttca tcgataaact caaaggtgat gattttaggg tcttgtgagt      60 gtgcttttt gtttgattct actgtagggt ttatgttctt tagctcatag gttttgtgta     120
tttcttagaa atgtggcttc tttaatctct gggtttgtga cttttgtgt ggtttctgtg     180 tttttcatat caaaaaccta ttttttccga gtttttttt acaaattctt actctcaagc     240
ttgaatactt cacatgcagt gttcttttgt agattttaga gttaatgtgt taaaaagttt     300 ggattttttct tgcttataga gcttcttcac tttgattttg tgggtttttt tgttttaaag    360
gtgagatttt tgatgaggtt tttgcttcaa agatgtcacc tttctgggtt tgtcttttga     420
ataaagctat gaactgtcac atggctgacg caattttgtt actatgtcat gaaagctgac     480 gttttttccgt gttatacatg tttgcttaca cttgcatgcg tcaaaaaaat tggggctttt    540
tagttttagt caaagatttt acttctcttt tgggatttat gaaggaaagt tgcaaacttt     600
ctcaaatttt accattttg ctttgatgtt tgtttagatt gcgacagaac aaactcatat      660
atgttgaaat ttttgcttgg ttttgtatag gattgtgtct tttgcttata aatgttgaaa     720
tctgaacttt tttttgttt ggtttctttg agcaggag                              758
```

```
<210> SEQ ID NO 10
<211> LENGTH: 252
<212> TYPE: DNA
<213> ORGANISM: Arabidopsis thaliana

<400> SEQUENCE: 10
actgtttaag cttcactgtc tctgaatcgg caaaggtaaa cgtatcaatt attctacaaa      60 ccctttatt tttcttttga attaccgtct tcattggtta tatgataact tgataagtaa     120
agcttcaata attgaatttg atctgtgttt ttttggcctt aatactaaat ccttacataa     180
gctttgttgc ttctcctctt gtgagttgag tgttaagttg taataatggt tcactttcag     240
ctttagaaga aa                                                         252
```

```
<210> SEQ ID NO 11
<211> LENGTH: 718
<212> TYPE: DNA
<213> ORGANISM: Arabidopsis thaliana

<400> SEQUENCE: 11
gtccagaatt ttctccattg aagctggatt ctaaggtcag ttcttacttc tttatctcaa      60
tctgatgatt ccatatcgaa agtcttactt tttcacttca atttcaatct gatgattcta    120
agatctttga ttcgaggtcg atctctgata gttactacat gtttctgggt ttatttattt     180
ttaatccata tagtaattaa aaactcttat gaggtttaat tatggttact tgagaatttg     240
caatcgtcat ctttctttga ctcctatcca tttttttggtt ttttcctttgt ttaatttctg   300 tttcataatt gtaattgtaa attaaccaaa acaaattgat cagaaacctt ttccctatgg     360
aatatttatc acacgcaagc ctgtgagttg tgactctgta atcacttcct tgttctggta     420
atttcagtgg ttaaggctct ccttttttct gatgttgtca gcaaaagtta gttttttcttc   480 ttctttaatg ggttaattac acctaaatct ctggttatta acaatccag aaagaaaaaa      540 agtttattcc ttcctctatg tatatagttt cacatgcaag catcacttgt ttgttctgac     600
aaattgcaga gttttgagtt ctgttttttt tttttttctaa tgttttgtct ttaagaaagt    660
tctgtttttt tttctgcagg aaagttatca aaagttttga gagctttgga tagtgaag      718
```

```
<210> SEQ ID NO 12
<211> LENGTH: 495
```

<212> TYPE: DNA
<213> ORGANISM: Arabidopsis thaliana

<400> SEQUENCE: 12

```
ctagcttaat ctcagattcg aatcgttcca tagtggtgag cttcgtgttc ttctttcgtc      60
tcttactcct gattctcgat tttagggttt tcagtaattg cgtcggcggc gaaagtcttt     120
atcgccgatc gatcttcctt atctagaaat tattgatcag aaactgttgg gttttgtttg     180
attcttgtca agttttgatt tttcatgcga aattgctcaa tcccaattca aagttacgat     240
ttttattgaa aaccctagat tggtttcttc aagtttgtca ctttgattca atctaatagc     300
ttagcttaat cgttaagtct cttttttggt tttaggtttc atttgcgatt taaaggttct     360
tgttttggta tttgttttgc tttggtcctt aagtttgag aggcttatgt agattataag      420
agagaagagt attgctttgc atgtttaaag gaagaacttt taactgaaca tttgtatgat     480
tggtatgtag atact                                                      495
```

<210> SEQ ID NO 13
<211> LENGTH: 139
<212> TYPE: DNA
<213> ORGANISM: Arabidopsis thaliana

<400> SEQUENCE: 13

```
atttccacac gctttctatc atttccaccc aaaaggtaac gcgcttttta tttcctttcc      60
tgcattcata aatttgtctc ctgcatgttg aaaaaaaaaa atttacatcg agattcgttt     120
ttattttta gagagagat                                                    139
```

<210> SEQ ID NO 14
<211> LENGTH: 889
<212> TYPE: DNA
<213> ORGANISM: Arabidopsis thaliana

<400> SEQUENCE: 14

```
gtctactttc attacagtga ctctgcatgc ttcaggtctc gtctaattct tgaattctct      60
tcttttctgt tccgtaattt actttctagg gtctctagat ttgtgtctcc tctaacaaaa     120
gatcctatct ttcgacaaat ttaatttcat cattgacctt tgtcgattcc attctctctc     180
tatctctctg tttcttcgaa aacctagagg ttttgaattt aatgattcct ttttatgtca     240
ataaatttgc aatcaatggg agcttttaa aatcatcgtt atatctataa acaaaaaaac      300
agtaattact cttcttagat ctaaaacaat taataaatct ttcccttttt tctcatcata     360
atttttcgt atttaactct tgtaaaaatt tgcttagccg tttcgctttc tcaggcccca      420
ggtgattcgt gtcttctagg tcagcttgtg aaacctgaga gaagccatct tttgtttgcg     480
gttacaaact ttgccgcttc aatatttcat tgctgttttc tgggaaaacc tttttctagt     540
tttttcggct tattatgcct tttaactttt tgtgcattta acatttattg ttagtgcttt     600
gcttagtgta aagtagtagt tctctttgta atattaccat aaggttcaga gtaaattt       660
tctaaaattg tttcttgtg ggaaattcag actgatttca gcaacatgca tgggcttaaa      720
atcagcttct aagactgaga tttagtgacc agtgtggtgg tgtcttgttc tctgttcttg     780
ggagaacaca aaggcagtgt gggtctggt gagttttctg attcttgaaa agatttataa      840
attttcttgc aaaattagtc tttatgttga attgtgttgc aggtaaaat                 889
```

<210> SEQ ID NO 15
<211> LENGTH: 433
<212> TYPE: DNA

<213> ORGANISM: Arabidopsis thaliana

<400> SEQUENCE: 15

| gcacaatctt | agcttacctt | gaatcacaac | ttcaggtata | tgtaactgat | tctaaattga | 60 |
| agattgtgtg | caaatcttat | atccattttt | tattattaaa | tttattgaaa | aagctagcgg | 120 |
| tgtaaattaa | tgtcacaaaa | tcagtatatt | gttagttttt | gttttttttg | aagttttatg | 180 |
| caaatcttca | aaaagtatat | tcagtgttgt | aattgacaaa | tagagactct | agttcttttt | 240 |
| tttttttct | tttttttaac | atctgactct | tatagagact | ctagttcatg | tacacttttt | 300 |
| ttaatggaaa | aacaaatttg | aaactgaata | tcttatttcc | acgtagattg | tatattagtt | 360 |
| taatttgatt | gttatatttg | taaatgtcta | ctaaacagga | attggatggt | gaggaggcaa | 420 |
| ggcttgtgga | tta | | | | | 433 |

<210> SEQ ID NO 16
<211> LENGTH: 354
<212> TYPE: DNA
<213> ORGANISM: Arabidopsis thaliana

<400> SEQUENCE: 16

| atcttagggt | ttcgcgagat | ctcactctca | ctggtatgtc | tgtgtttctt | cttccattt | 60 |
| ctgtttctat | tggaaacttc | tctctccaat | ttcgttttct | tcacttcttt | gatcctttag | 120 |
| ctttgacaaa | accgtagtaa | aggatcaaaa | gttatcatct | ttggtccatg | ttgtgaatcg | 180 |
| tgctctgctt | gggtcgtgac | tcccaaatcc | ggatttgaaa | ccagcatatc | tgagcttaat | 240 |
| tcgagcatgc | atgcgcttct | ttttttctga | ttttttttag | actttggttc | taaatccctt | 300 |
| aactttggat | taactgtcaa | tctacaattt | tatattaaca | gagatagctt | agca | 354 |

<210> SEQ ID NO 17
<211> LENGTH: 143
<212> TYPE: DNA
<213> ORGANISM: Arabidopsis thaliana

<400> SEQUENCE: 17

| cagaagctca | tttcttcgat | acgatcaacc | attaggtgat | ttttttctct | gatcttcgag | 60 |
| ttctgataat | tgctcttttt | tctctggctt | tgttatcgat | aatttctctg | gattttcttt | 120 |
| ctggggtgaa | ttttgcgca | gag | | | | 143 |

<210> SEQ ID NO 18
<211> LENGTH: 182
<212> TYPE: DNA
<213> ORGANISM: Arabidopsis thaliana

<400> SEQUENCE: 18

| attttgttg | gtgaaaggta | gaattcgtaa | atttcttctg | ctcactttat | tgtttcgact | 60 |
| catacccgat | aatctcttct | atgtttggta | gagatatctt | ctcaaagtct | tatctttcct | 120 |
| taccgtgttc | tgtgtttttt | gatgatttag | gtgaagaaga | agaagcagag | acaaaaacga | 180 |
| tt | | | | | | 182 |

<210> SEQ ID NO 19
<211> LENGTH: 665
<212> TYPE: DNA
<213> ORGANISM: Arabidopsis thaliana

<400> SEQUENCE: 19

| ttaagctttt | aagaatctct | actcacattt | tctctgtgag | tgttcttta | tacttctttg | 60 |

```
ttatttccaa ttttcttttc ttccctctaa aaattttagg aactattgaa tcatttaatt       120
tctgtttgtt gataaaattt cgatcaactg ttctcggctt accgatgcat ttttgtaaa         180 accgtctttt tttggtgaat aaattttaa attcatacaa aaaaaaaaca tatttgatac         240
tattttagct ccattgtatc tgaatcttca tttgttaatt tttttgtttc ctctgttctc        300
acttgaattt tggaatattt tctctaggtt ttaccttata ttcttcactt taagaactat        360
atgaagattt gattggaagt aataatattc ggtgatagaa tctgagtttg tttgattctg        420
gtgtggggct tatatctaac tttttcttt gtaccaatac attttcaatt ttacatttt         480 gattagctta aaatgtgaag ataccttgt aaataactat tacactattg cttgtcttag        540
tctaatagtc ttcactaata ttttgtgcag tagaagtaaa tattataaag agttgttgtt       600
tgattataga gagttgttgt ctattcttta acttgatgtg atgttgtttt tgatgacagg       660
taaaa                                                                   665
```

```
<210> SEQ ID NO 20
<211> LENGTH: 252
<212> TYPE: DNA
<213> ORGANISM: Arabidopsis thaliana

<400> SEQUENCE: 20
tctgggaaat atcgattttg atctattaag agctggtgag agccaaagtt tccttttgt        60 ttgtttgttt gtttgtttgt tgtttgtatt tttgtatctc tgtgatcgct tctacgtgtt       120
gggtcatgca gagaaactca ttttgttttg atttgcaatg tgtcaattcc actttgaaat      180
ataagattca tcgcctctct ctcctttgtt ttttttcttc ttctgcagct acgagctttg      240
ggatgtggtg ag                                                           252
```

```
<210> SEQ ID NO 21
<211> LENGTH: 186
<212> TYPE: DNA
<213> ORGANISM: Arabidopsis thaliana

<400> SEQUENCE: 21
tattcacaat ctcctgccac ctctcatttc tctagttgag ttgttatctg cgttttaag       60 cactcgaata ctgcatgcaa attccctgat tgtttgttag taccttagag attctcgatt      120
ttttagttgt ttagattgaa ccaggattac taaattgtta ttgttttctg tgtaaaggct      180
acatat                                                                  186
```

```
<210> SEQ ID NO 22
<211> LENGTH: 345
<212> TYPE: DNA
<213> ORGANISM: Arabidopsis thaliana

<400> SEQUENCE: 22
ctttgcagct tctgcagcac ctctccctac tccaggtact tatgtttttg ataatttat        60 tgatagactc tttacaatta tacttaagct tgttacttt tattgttacc aacaaaagct       120
aatgtatagt tcataactca caggtcctgc gtctttcggt ccgaccactt ctcctacaga      180
ttcgcaaact tctgatcctg aaggtactcg cgaacttttt actgcaactt ctagttctaa      240
ctccaaaaca ttttgttcag aatttgtttc taaagatttt cgggtttgt tgacgtcaca      300 taactcgcag ggtctgcttc tttccgtccg cccacttctc cgaca                      345
```

```
<210> SEQ ID NO 23
```

```
<211> LENGTH: 285
<212> TYPE: DNA
<213> ORGANISM: Arabidopsis thaliana

<400> SEQUENCE: 23
aacaactatg gcctgagggt aacaagagta tcaggtatat gtgaaaactc tacttttgaa      60
gtttaccaaa aaaatactc tacttttgga aagacattgc tcctaaaatc ttattagttg     120
tatataattt actaaaacac atagttcttg aattcttgtt aatgagcatg ttaccttgga     180
caagtgaccc tttttctaca ttttgttttt ctatcacacg tcatgcgttt tgattgtttc     240
cttacgagtt ttaattttat tttttggtta aaaacagtaa gataa                    285

<210> SEQ ID NO 24
<211> LENGTH: 137
<212> TYPE: DNA
<213> ORGANISM: Arabidopsis thaliana

<400> SEQUENCE: 24
tctaaaaata cagggcaccg aaccaaataa aggtgagaat gatgagaagc cgtttcttac      60
tcttcattgt tttcttctct ctatccctct tcatttcctc tctgatcgcc agtgatttag     120
gcttctgcaa cgaagag                                                    137

<210> SEQ ID NO 25
<211> LENGTH: 664
<212> TYPE: DNA
<213> ORGANISM: Brassica napus thaliana

<400> SEQUENCE: 25
taaggatgac ctacccattc ttgagacaaa tgttacattt tagtatcaga gtaaaatgtg      60
tacctataac tcaaattcga ttgacatgta tccattcaac ataaaattaa accagcctgc     120
acctgcatcc acatttcaag tattttcaaa ccgttcggct cctatccacc gggtgtaaca     180
agacggattc cgaatttgga agattttgac tcaaattccc aatttatatt gaccgtgact     240
aaatcaactt taacttctat aattctgatt aagctcccaa tttatattcc aacggcact      300
acctccaaaa tttatagact ctcatcccct tttaaaccaa cttagtaaac gttttttttt     360
taatttatg aagttaagtt tttaccttgt ttttaaaaag aatcgttcat aagatgccat     420
gccagaacat tagctacacg ttacacatag catgcagccg cggagaattg tttttcttcg     480
ccacttgtca ctcccttcaa acacctaaga gcttctctct cacagcacac atacacatc     540
acatgcgtgc atgcattatt acacgtgatc gccatgcaaa tctcctttat agcctataaa     600
ttaactcatc ggcttcactc tttactcaaa ccaaaactca tcaatacaaa caagattaaa     660
aaca                                                                  664

<210> SEQ ID NO 26
<211> LENGTH: 1064
<212> TYPE: DNA
<213> ORGANISM: Linum usitatissimum thaliana

<400> SEQUENCE: 26
ttagcagata tttggtgtct aaatgtttat tttgtgatat gttcatgttt gaaatggtgg      60
tttcgaaacc agggacaacg ttgggatctg ataggtgtc aaagagtatt atggattggg     120
acaatttcgg tcatgagttg caaattcaag tatatcgttc gattatgaaa attttcgaag     180
aatatcccat ttgagagagt ctttacctca ttaatgtttt tagattatga aattttatca     240
tagttcatcg tagtcttttt ggtgtaaagg ctgtaaaaag aaattgttca cttttgtttt     300
```

```
cgtttatgtg aaggctgtaa aagattgtaa aagactattt tggtgttttg gataaaatga    360
tagtttttat agattctttt gcttttagaa gaaatacatt tgaaatttt tccatgttga    420 gtataaaata ccgaaatcga ttgaagatca tagaaatatt ttaactgaaa acaaatttat    480
aactgattca attctctcca tttttatacc tatttaaccg taatcgattc taatagatga    540
tcgatttttt atataatcct aattaaccaa cggcatgtat tggataatta accgatcaac    600
tctcacccct aatagaatca gtattttcct tcgacgttaa ttgatcctac actatgtagg    660
tcatatccat cgttttaatt tttggccacc attcaattct gtcttgcctt tagggatgtg    720
aatatgaacg gccaaggtaa gagaataaaa ataatccaaa ttaaagcaag agaggccaag    780
taagataatc caaatgtaca cttgtcattg ccaaaattag taaaatactc ggcatattgt    840
attcccacac attattaaaa taccgtatat gtattggctg catttgcatg aataatacta    900
cgtgtaagcc caaagaaacc cacgtgtagc ccatgcaaag ttaacactca cgaccccatt    960
cctcagtctc cactatataa acccaccatc cccaatctca ccaaacccac cacacaactc   1020
acaactcact ctcacacctt aaagaaccaa tcaccaccaa aaaa                   1064
```

<210> SEQ ID NO 27
<211> LENGTH: 1727
<212> TYPE: DNA
<213> ORGANISM: Linum usitatissimum thaliana

<400> SEQUENCE: 27

```
cacgggcagg acatagggac tactacaagc atagtatgct tcagacaaag agctaggaaa     60
gaactcttga tggaggttaa gagaaaaaag tgctagaggg gcatagtaat caaacttgtc    120
aaaaccgtca tcatgatgag ggatgacata atataaaaag ttgactaagg tcttggtagt    180
actctttgat tagtattata tattggtgag aacatgagtc aagaggagac aagaaaccga    240
ggaaccatag tttagcaaca agatggaagt tgcaaagttg agctagccgc tcgattagtt    300
acatctccta agcagtacta caaggaatgg tctctatact ttcatgttta gcacatggta    360
gtgcggattg acaagttaga aacagtgctt aggagacaaa gagtcagtaa aggtattgaa    420
agagtgaagt tgatgctcga caggtcagga gaagtccctc cgccagatgg tgactaccaa    480
ggggttggta tcagctgaga cccaaataag attcttcggt tgaaccagtg gttcgaccga    540
gactcttagg gtgggatttc actgtaagat ttgtgcattt tgttaatat aaattgacaa    600 ttttttttat ttaattatag attatttaga atgaattaca tatttagttt ctaacaagga    660
tagcaatgga tgggtatggg tacaggttaa acatatctat tacccaccca tctagtcgtc    720
gggttttaca cgtacccacc cgtttacata aaccagaccg gaattttaaa ccgtacccgt    780
ccgttagcgg gtttcagatt tacccgttta atcgggtaaa acctgattac taaatatata    840
ttttttattt gataaacaaa acaaaaatgt taatattttc atattggatg caattttaag    900
aaacacatat tcataaattt ccatatttgt aggaaaataa aagaaaaat atattcaaga    960 acacaaattt caccgacatg actttttatta cagagttgga attagatcta acaattgaaa   1020
aattaaaatt aagatagaat atgttgagga acatgacata gtataatgct gggttacccg   1080
tcgggtaggt atcgaggcgg atactactaa atccatccca ctcgctatcc gataatcact   1140
ggtttcgggt atacccattc ccgtcaacag gcctttttaa ccggataatt tcaacttata   1200
gtgaatgaat tttgaataaa tagttagaat accaaaatcc tggattgcat ttgcaatcaa   1260
attttgtgaa ccgttaaatt ttgcatgtac ttgggataga tataatagaa ccgaatttc   1320
```

| | |
|---|---|
| attagtttaa tttataactt actttgttca aagaaaaaaa atatctatcc aatttactta | 1380 |
| taataaaaaa taatctatcc aagttactta ttataatcaa cttgtaaaaa ggtaagaata | 1440 |
| caaatgtggt agcgtacgtg tgattatatg tgacgaaatg ttatatctaa caaaagtcca | 1500 |
| aattcccatg gtaaaaaaaa tcaaaatgca tggcaggctg tttgtaacct tggaataaga | 1560 |
| tgttggccaa ttctggagcc gccacgtacg caagactcag ggccacgttc tcttcatgca | 1620 |
| aggatagtag aacaccactc cacccacctc ctatattaga cctttgccca accctcccca | 1680 |
| actttcccat cccatccaca aagaaaccga catttttatc ataaatc | 1727 |

```
<210> SEQ ID NO 28
<211> LENGTH: 1799
<212> TYPE: DNA
<213> ORGANISM: Vicia faba

<400> SEQUENCE: 28
```

| | |
|---|---|
| tcgacggccc ggactgtatc caacttctga tctttgaatc tctctgttcc aacatgttct | 60 |
| gaaggagttc taagactttt cagaaagctt gtaacatgct ttgtagactt tctttgaatt | 120 |
| actcttgcaa actctgattg aacctacgtg aaaactgctc cagaagttct aaccaaattc | 180 |
| cgtcttggga aggcccaaaa tttattgagt acttcagttt catggacgtg tcttcaaaga | 240 |
| tttataactt gaaatcccat catttttaag agaagttctg ttccgcaatg tcttagatct | 300 |
| cattgaaatc tacaactctt gtgtcagaag ttcttccaga atcaacttgc atcatggtga | 360 |
| aaatctggcc agaagttctg aacttgtcat atttcttaac agttagaaaa atttctaagt | 420 |
| gtttagaatt ttgactttc caaagcaaac ttgacttttg actttcttaa taaaacaaac | 480 |
| ttcatattct aacatgtctt gatgaaatgt gattcttgaa atttgatgtt gatgcaaaag | 540 |
| tcaaagtttg acttttcagt gtgcaattga ccatttttgct cttgtgccaa ttccaaacct | 600 |
| aaattgatgt atcagtgctg caaacttgat gtcatggaag atcttatgag aaaattcttg | 660 |
| aagactgaga ggaaaaattt tgtagtacaa cacaaagaat cctgttttc atagtcggac | 720 |
| tagacacatt aacataaaac accacttcat tcgaagagtg attgaagaag gaaatgtgca | 780 |
| gttaccttc tgcagttcat aagagcaact tacagacact tttactaaaa tactacaaag | 840 |
| aggaagattt taacaactta gagaagtaat gggagttaaa gagcaacaca ttaagggga | 900 |
| gtgttaaaat taatgtgttg taaccaccac taccttagt aagtattata agaaaattgt | 960 |
| aatcatcaca ttataattat tgtccttatt taaaattatg ataaagttgt atcattaaga | 1020 |
| ttgagaaaac caaatagtcc tcgtcttgat ttttgaatta ttgttttcta tgttactttt | 1080 |
| cttcaagcct atataaaaac tttgtaatgc taaattgtat gctggaaaaa aatgtgtaat | 1140 |
| gaattgaata gaaattatgg tatttcaaag tccaaaatcc atcaatagaa atttagtaca | 1200 |
| aaacgtaact caaaaatatt ctcttatttt aaatttaca acaatataaa atattctct | 1260 |
| tattttaaat tttacaataa tataattat cacctgtcac ctttagaata ccaccaacaa | 1320 |
| tattaatact tagatatttt attcttaata attttgagat ctctcaatat atctgatatt | 1380 |
| tattttatat ttgtgtcata ttttcttatg ttttagagtt aacccttata tcttggtcaa | 1440 |
| actagtaatt caatatatga gtttgtgaag gacacattga catctgaaa cattggtttt | 1500 |
| aaccttgttg gaatgttaaa ggtaataaaa cattcagaat tatgaccatc tattaatata | 1560 |
| cttcctttgt cttttaaaaa agtgtgcatg aaaatgctct atggtaagct agagtgtctt | 1620 |
| gctggcctgt gtatatcaat tccatttcca gatggtagaa actgccacta cgaataatta | 1680 |
| gtcataagac acgtatgtta acacacgtcc ccttgcatgt tttttgccat atattccgtc | 1740 | tctttctttt tcttcacgta taaaacaatg aactaattaa tagagcgatc aagctgaac      1799

<210> SEQ ID NO 29
<211> LENGTH: 684
<212> TYPE: DNA
<213> ORGANISM: Vicia faba

<400> SEQUENCE: 29
ctgcagcaaa tttacacatt gccactaaac gtctaaaccc ttgtaatttg ttttttgtttt     60
actatgtgtg ttatgtattt gatttgcgat aaatttttat atttggtact aaatttataa    120
caccttttat gctaacgttt gccaacactt agcaatttgc aagttgatta attgattcta    180
aattattttt gtcttctaaa tacatatact aatcaactgg aaatgtaaat atttgctaat    240
atttctacta taggagaatt aaagtgagtg aatatggtac acaaggttt  ggagatttaa    300
ttgttgcaat gctgcatgga tggcatatac accaaacatt caataattct tgaggataat    360
aatggtacca cacaagattt gaggtgcatg aacgtcacgt ggacaaaagg tttagtaatt    420
tttcaagaca acaatgttac cacacacaag ttttgaggtg catgcatgga tgccctgtgg    480
aaagtttaaa aatattttgg aaatgatttg catggaagcc atgtgtaaaa ccatgacatc    540
cacttggagg atgcaataat gaagaaaact acaaatttac atgcaactag ttatgcatgt    600
agtctatata tgaggatttt tgcaatactt tcattcatac acactcacta agttttacac    660
gattataatt tcttcatagc cagt                                            684

<210> SEQ ID NO 30
<211> LENGTH: 2742
<212> TYPE: DNA
<213> ORGANISM: Vicia faba

<400> SEQUENCE: 30
gtcgtctcaa actcattcat cagaaccttc ttgaacttag ttatctcttg ttcagagctt     60
cctgttagca atatgtcatc aacatataaa catgtcccag aagccagaag atagaagttg    120
gatgatagaa gtaaagtaat gttactggtg gagtaccaca atacaagttc atacaaactt    180
tattgtccag aaactaacaa agttgagttc agcatagatg aaagacaaaa agaatatatt    240
aaatgacggc tgcaaaataa ggagtaatga atacattgac ctacctacta ctaggctatt    300
tatacacaat attagggtat aataaaatat taaaataccc tctatcagac ttagtcaata    360
agacattcct aaaatataaa ttatttccaa caataatttg tctcaaataa aatatagagg    420
tgcaaaagtt aaactaagag tgcaaagtaa aattttgaga gggctcaaaa ttgaatataa    480
taacaatatt agtgtagttt aagaaaactc aggggatgca gttgaactcc ctcaactgta    540
cgtagctcct cccctggatg cagtgtaaag atttgaagat atattttagt actttggata    600
ttgtaggcca gagggtgttg aagataaagg ttcaggaact aacacattca tccacaactt    660
ctatgtgtcc atcgtcagtg aaatacatgc caaataggg  agttaagaag agtagaaagg    720
gtcaagatag tgatgtgcat cgtgatcctt cataatggga gtgtggtgag ggctcgcatg    780
ggagtcatac tacaaagaga tcatgcataa aaccaactag aagtcaactg tcaagtatga    840
cggctgacaa ttaaccgtcc accaaatctt ccagacatgt ttacttgtcc cagttttctg    900
atttcttata tccatacatt gatgacatta ttgatgttgg tggcgatgga gattggggtt    960
ttcatgctat tacagctttta cttggatggg gtgaagagtc atagcctttg attcagacgc   1020
agttagatac tcaagttcat caacaccctc aattgttttt taagttgttt tgtgacacga   1080

-continued

```
tctctacagt tagaaatgcg ttacgagtag aacacttggc tgtgcagggt atagataaat    1140
gaatgacgat ttatgatatg ggttaccota ttgcttctag atacaatgtc gtatttgtct    1200
cccttccaaa agacttaaca tcacgttttt tcctcttgcc ttatctccac ctatgtatac    1260
aagcaggcat aaaatcattg ttgttggttt tgtcaacaac aatcattgag tttaggtaaa    1320
gttgaaactt gattgtccat tacctcttgt cactgactgt tgaagacaga attgtactga    1380
ctgtatatat caacatatgc gagacgcgtt aggcagtgga aagacgtagt taggatgtca    1440
tcataatttg tttcgtattt ttatatgtag cacagttttt atatgtatat attttatcgg    1500 gtagttttt atcgattcag ttatttgaga aaaagtaatg cagacaaaaa gtggaaaaga    1560
caatctgact gtacataaga aatttccaat ttttgaaatt tttttataat tatcagaaat    1620
tttaaaattt ccgataaaaa catacatgta tagatcgaaa atttcaaatt tctagtactt    1680
tcaaatttct tgcagtaaaa gttgtaattt tttaaaaatt tacgataatt tacagtattt    1740 aaaaaaaat ccaatcttaa ataaagggta taagaataaa agcactcatg tggagtggca    1800
ggtttcgtca caccctaaga acatccctaa atacaccaca tatgtataag tattaagtga    1860
ttgatgttaa gtgaaacgaa aatatttata tgtgaaattt aatattcagc ttacttgatt    1920
aaactccata gtgacccaat aagtgctaac ttttactgtc tttacctta aatgttatat    1980 tgatttattt atgcatttct ttttcctgca tctcaatagt atatagggta tcaaatagtg    2040
attatccaaa cttaaataag ttagaggaaa caccaagata tgccatatac tctcaaattt    2100
gacactatga ttcaaagttg cacttgcata aaacttatta attcaatagt aaaaccaaac    2160
ttgtgcgtga tacagttaaa atgactaaac tactaattaa ggtccctccc attagtaaat    2220
aagttatttt tttagaaaaa gaaaataata aaaagaatga cgagtctatc taaatcatat    2280
taacaagtaa tacatattga ttcattcgat ggaggaggcc aataattgta gtaaacaagc    2340
agtgccgagg ttaatatatg ctcaagacag taaataatct aaatgaatta agacagtgat    2400
ttgcaaagag tagatgcaga gaagagaact aaagatttgc tgctacacgt atataagaat    2460
agcaacagat attcattctg tctctttgtg gaatatggat atctactaat catcatctat    2520
ctgtgaagaa taaagaagc ggccacaagc gcagcgtcgc acatatgatg tgtatcaaat    2580
taggactcca tagccatgca tgctgaagaa tgtcacacac gttctgtcac acgtgttact    2640
ctctcactgt tctcctcttc ctataaatca ccgcgccaca gcttctccac ttcaccactt    2700
caccacttca ctcacaatcc ttcattagtt gtttactatc ac                        2742
```

<210> SEQ ID NO 31
<211> LENGTH: 445
<212> TYPE: DNA
<213> ORGANISM: Arabidopsis thaliana

<400> SEQUENCE: 31

```
ggccgcagat atcagatctg gtcgacctag aggatccccg gccgcaaaga taataacaaa     60
agcctactat ataacgtaca tgcaagtatt gtatgatatt aatgttttta cgtacgtgta    120
aacaaaaata attacgtttg taacgtatgg tgatgatgtg gtgcactagg tgtaggcctt    180
gtattaataa aaagaagttt gttctatata gagtggttta gtacgacgat ttatttacta    240
gtcggattgg aatagagaac cgaattcttc aatccttgct tttgatcaag aattgaaacc    300
gaatcaaatg taaagttga tatatttgaa aaacgtattg agcttatgaa aatgctaata    360
ctctcatctg tatggaaaag tgactttaaa accgaactta aaagtgacaa aaggggaata    420
tcgcatcaaa ccgaatgaaa ccgat                                            445
```

<210> SEQ ID NO 32
<211> LENGTH: 216
<212> TYPE: DNA
<213> ORGANISM: Cauliflower mosaic virus

<400> SEQUENCE: 32

| | | | | | |
|---|---|---|---|---|---|
| tcgacaagct | cgagtttctc | cataataatg | tgtgagtagt | tcccagataa | gggaattagg | 60 |
| gttcctatag | ggtttcgctc | atgtgttgag | catataagaa | acccttagta | tgtatttgta | 120 |
| tttgtaaaat | acttctatca | ataaaatttc | taattcctaa | aaccaaaatc | cagtactaaa | 180 |
| atccagatcc | cccgaattaa | ttcggcgtta | attcag | | | 216 |

<210> SEQ ID NO 33
<211> LENGTH: 568
<212> TYPE: DNA
<213> ORGANISM: Pisum sativum

<400> SEQUENCE: 33

| | | | | | |
|---|---|---|---|---|---|
| taattgattg | gttcgagtat | tatggcattg | ggaaaactgt | ttttcttgta | ccatttgttg | 60 |
| tgcttgtaat | ttactgtgtt | ttttattcgg | ttttcgctat | cgaactgtga | aatggaaatg | 120 |
| gatggagaag | agttaatgaa | tgatatggtc | cttttgttca | ttctcaaatt | aatattattt | 180 |
| gttttttctc | ttatttgttg | tgtgttgaat | ttgaaattat | aagagatatg | caaacatttt | 240 |
| gttttgagta | aaaatgtgtc | aaatcgtggc | ctctaatgac | cgaagttaat | atgaggagta | 300 |
| aaacacttgt | agttgtacca | ttatgcttat | tcactaggca | acaaatatat | tttcagacct | 360 |
| agaaaagctg | caaatgttac | tgaatacaag | tatgtcctct | tgtgttttag | acatttatga | 420 |
| actttccttt | atgtaatttt | ccagaatcct | tgtcagattc | taatcattgc | tttataatta | 480 |
| tagttatact | catggatttg | tagttgagta | tgaaaatatt | ttttaatgca | ttttatgact | 540 |
| tgccaattga | ttgacaacat | gcatcaat | | | | 568 |

<210> SEQ ID NO 34
<211> LENGTH: 235
<212> TYPE: DNA
<213> ORGANISM: Agrobacterium tumefaciens

<400> SEQUENCE: 34

| | | | | | |
|---|---|---|---|---|---|
| ggccgcctcg | agcatgcatc | tagagggccc | gctagcgtta | accctgcttt | aatgagatat | 60 |
| gcgagacgcc | tatgatcgca | tgatatttgc | tttcaattct | gttgtgcacg | ttgtaaaaaa | 120 |
| cctgagcatg | tgtagctcag | atccttaccg | ccggtttcgg | ttcattctaa | tgaatatatc | 180 |
| acccgttact | atcgtatttt | tatgaataat | attctccgtt | caatttactg | attgt | 235 |

<210> SEQ ID NO 35
<211> LENGTH: 605
<212> TYPE: DNA
<213> ORGANISM: Phaseolus vulgaris

<400> SEQUENCE: 35

| | | | | | |
|---|---|---|---|---|---|
| ctaagactcc | caaaaccacc | ttccctgtga | cagttaaacc | ctgcttatac | ctttcctcct | 60 |
| aataatgttc | atctgtcaca | caaactaaaa | taaataaaat | gggagcaata | aataaaatgg | 120 |
| gagctcatat | atttacacca | tttacactgt | ctattattca | ccatgccaat | tattacttca | 180 |
| taattttaaa | attatgtcat | ttttaaaaat | tgcttaatga | tggaaaggat | tattataagt | 240 |
| taaaagtata | acatagataa | actaaccaca | aaacaaatca | atataaacta | acttactctc | 300 |

```
ccatctaatt tttatttaaa tttctttaca cttctcttcc atttctattt ctacaacatt      360
atttaacatt tttattgtat ttttcttact ttctaactct attcatttca aaaatcaata      420
tatgtttatc accacctctc taaaaaaaac tttacaatca ttggtccaga aaagttaaat      480
cacgagatgg tcattttagc attaaaacaa cgattcttgt atcactattt ttcagcatgt      540
agtccattct cttcaaacaa agacagcggc tatataatcg ttgtgttata ttcagtctaa      600
aacaa                                                                 605

<210> SEQ ID NO 36
<211> LENGTH: 254
<212> TYPE: DNA
<213> ORGANISM: Solanum tuberosum

<400> SEQUENCE: 36
ggccgcctcg accgtacccc ctgcagatag actatactat gttttagcct gcctgctggc       60
tagctactat gttatgttat gttgtaaaat aaacacctgc taaggtatat ctatctatat      120
tttagcatgg ctttctcaat aaattgtctt tccttatcgt ttactatctt atacctaata      180
atgaaataat aatatcacat atgaggaacg gggcaggttt aggcatatat atacgagtgt      240
agggcggagt gggg                                                        254

<210> SEQ ID NO 37
<211> LENGTH: 297
<212> TYPE: DNA
<213> ORGANISM: Vicia faba

<400> SEQUENCE: 37
atcctgcaat agaatgttga ggtgaccact ttctgtaata aaataattat aaaataaatt       60
tagaattgct gtagtcaaga acatcagttc taaaatatta ataagttat ggccttttga      120 catatgtgtt tcgataaaaa aatcaaaata aattgagatt tattcgaaat acaatgaaag      180
tttgcagata tgagatatgt ttctacaaaa taataactta aaactcaact atatgctaat      240
gtttttcttg gtgtgtttca tagaaaattg tatccgtttc ttagaaaatg ctcgtaa        297

<210> SEQ ID NO 38
<211> LENGTH: 24631
<212> TYPE: DNA
<213> ORGANISM: Artificial Sequence
<220> FEATURE:
<223> OTHER INFORMATION: Plant Expression Plasmid

<400> SEQUENCE: 38
acatacaaat ggacgaacgg ataaaccttt tcacgccctt ttaaatatcc gattattcta       60
ataaacgctc ttttctctta ggtttacccg ccaatatatc ctgtcaaaca ctgatagttt      120
aaactgaagg cgggaaacga caatcagatc tagtaggaaa cagctatgac catgattacg      180
ccaagcttat ttaaatcgta ccgtactagt aacggccgcc agtgtgctgg aattcgccct      240 taaaaagat atcgattacg ccaagctatc aactttgtat agaaaagttg ccatgattac      300
gccaagcttg gcgcgccctg cagcaaattt acacattgcc actaaacgtc taaacccttg      360
taatttgttt ttgtttttact atgtgtgtta tgtatttgat ttgcgataaa ttttatatt      420 tggtactaaa tttataacac cttttatgct aacgtttgcc aacacttagc aatttgcaag      480
ttgattaatt gattctaaat tatttttgtc ttctaaatac atatactaat caactggaaa      540
tgtaaatatt tgctaatatt tctactatag gagaattaaa gtgagtgaat atggtaccac      600
aaggtttgga gatttaattg ttgcaatgct gcatggatgg catatacacc aaacattcaa      660
```

```
taattcttga ggataataat ggtaccacac aagatttgag gtgcatgaac gtcacgtgga    720
caaaaggttt agtaattttt caagacaaca atgttaccac acacaagttt tgaggtgcat    780
gcatggatgc cctgtggaaa gttttaaaaat attttggaaa tgatttgcat ggaagccatg   840
tgtaaaacca tgcatccac ttggaggatg caataatgaa gaaaactaca aatttacatg     900
caactagtta tgcatgtagt ctatataatg aggattttgc aatactttca ttcatacaca   960
ctcactaagt tttacacgat tataatttct tcatagccag taccatggaa gttgttgaga   1020
ggttctacgg agagttggat ggaaaggttt cccaaggagt gaacgctttg ttgggatctt   1080
tcggagttga gttgactgat accccaacta ctaaggatt gccactcgtt gattctccaa    1140
ctccaattgt gttgggagtg tctgtttact tgaccatcgt gatcggagga ttgctttgga   1200
tcaaggctag agatctcaag ccaagagctt ctgagccatt cttgttgcaa gctttggtgt   1260
tggtgcacaa cttgttctgc ttcgctttgt ctctttacat gtgcgtgggt atcgcttacc   1320
aagctatcac ctggagatat tccttgtggg gaaacgctta tacccaaag cacaaggaga    1380 tggctatcct cgtttacctc ttctacatgt ccaagtacgt ggagttcatg gataccgtga   1440
tcatgatcct caagagatcc accagacaga tttctttcct ccacgtgtac caccactctt   1500
ctatctccct tatctggtgg gctattgctc accacgctcc aggaggagag gcttattgga   1560
gtgctgctct caactctgga gtgcacgtgt tgatgtacgc ttactacttc ttggctgctt   1620
gcttgagatc ttccccaaag ctcaagaaca agtacctctt ctggggaaga taccctcaccc  1680 aattccagat gttccagttc atgctcaact tggtgcaagc ttactacgat atgaaaacca   1740
acgctccata tccacaatgg ctcatcaaga tcctcttcta ctacatgatc tccctcttgt   1800
tcctcttcgg aaacttctac gtgcaaaagt acatcaagcc atccgatgga aagcaaaagg   1860
gagctaagac cgagtgatcg acaagctcga gtttctccat aataatgtgt gagtagttcc   1920
cagataaggg aattagggtt cctatagggt ttcgctcatg tgttgagcat ataagaaacc   1980
cttagtatgt atttgtattt gtaaaatact tctatcaata aaatttctaa ttcctaaaac   2040
caaaatccag tactaaaatc cagatccccc gaattaattc ggcgttaatt cagggccggc   2100
cgatctgtcg tctcaaactc attcatcaga accttcttga acttagttat ctcttgttca   2160
gagcttcctg ttagcaatat gtcatcaaca tataaacatg tcccagaagc cagaagatag   2220 aagttggatat atagaagtaa agtaatgtta ctggtggagt accacaatac aagttcatac   2280
aaactttatt gtccagaaac taacaaagtt gagttcagca tagatgaaag acaaaaagaa   2340
tatattaaat gacggctgca aaataaggag taatgaatac attgacctac ctactactag   2400
gctatttata cacaatatta gggtataata aaatattaaa ataccctcta tcagacttag   2460
tcaataagac attcctaaaa tataaattat ttccaacaat aatttgtctc aaataaaata   2520
tagaggtgca aaagttaaac taagagtgca agtaaaatt ttgagagggc tcaaaattga   2580
atataataac aatattagtg tagttttaaga aaactcaggg gatgcagttg aactccctca   2640
actgtacgta gctcctcccc tggatgcagt gtaaagattt gaagatatat tttagtactt   2700
tggatattgt aggccagagg gtgttgaaga taaaggttca ggaactaaca cattcatcca   2760
caacttctat gtgtccatcg tcagtgaaat acatgccaaa tagggggagtt aagaagagta   2820 gaaagggtca agatagtgat gtgcatcgtg atccttcata atgggagtgt ggtgagggct   2880
cgcatgggag tcatactaca aagagatcat gcataaaacc aactagaagt caactgtcaa   2940
gtatgacggc tgacaattaa ccgtccacca aatcttccag acatgtttac ttgtcccagt   3000
```

```
tttctgattt cttatatcca tacattgatg acattattga tgttggtggc gatggagatt    3060
ggggttttca tgctattaca gctttacttg gatggggtga agagtcatag cctttgattc    3120
agacgcagtt agatactcaa gttcatcaac accctcaatt gttttttaag ttgttttgtg    3180
acacgatctc tacagttaga aatgcgttac gagtagaaca cttggctgtg cagggtatag    3240
ataaatgaat gacgatttat gatatgggtt accctattgc ttctagatac aatgtcgtat    3300
ttgtctccct tccaaaagac ttaacatcac gttttttcct cttgccttat ctccacctat    3360
gtatacaagc aggcataaaa tcattgttgt tggttttgtc aacaacaatc attgagttta    3420
ggtaaagttg aaacttgatt gtccattacc tcttgtcact gactgttgaa gacagaattg    3480
tactgactgt atatatcaac atatgcgaga cgcgttaggc agtggaaaga cgtagttagg    3540
atgtcatcat aatttgtttc gtattttat atgtagcaca gtttttatat gtatatattt    3600
tatcgggtag tttttatcg attcagttat ttgagaaaaa gtaatgcaga caaaaagtgg    3660
aaaagacaat ctgactgtac ataagaaatt tccaattttt gaatttttt tataattatc    3720
agaaattta aaatttccga taaaaacata catgtataga tcgaaaattt caaatttcta    3780
gtactttcaa atttcttgca gtaaaagttg taatttttta aaaatttacg ataatttaca    3840
gtatttaaaa aaaatccaa tcttaaataa agggtataag aataaaagca ctcatgtgga    3900
gtggcaggtt tcgtcacacc ctaagaacat ccctaaatac accacatatg tataagtatt    3960
aagtgattga tgttaagtga acgaaaata tttatatgtg aaatttaata ttcagcttac    4020
ttgattaaac tccatagtga cccaataagt gctaactttt actgtcttta cctttaaatg    4080
ttatattgat ttatttatgc atttcttttt cctgcatctc aatagtatat agggtatcaa    4140
atagtgatta tccaaactta ataagttag aggaaacacc aagatatgcc atatactctc    4200
aaatttgaca ctatgattca aagttgcact tgcataaaac ttattaattc aatagtaaaa    4260
ccaaacttgt gcgtgataca gttaaaatga ctaaactact aattaaggtc cctcccatta    4320
gtaaataagt tatttttta gaaaagaaa ataataaaaa gaatgacgag tctatctaaa    4380
tcatattaac aagtaataca tattgattca ttcgatggag gaggccaata attgtagtaa    4440
acaagcagtg ccgaggttaa tatatgctca agacagtaaa taatctaaat gaattaagac    4500
agtgatttgc aaagagtaga tgcagagaag agaactaaag atttgctgct acacgtatat    4560
aagaatagca acagatattc attctgtctc tttgtggaat atggatatct actaatcatc    4620
atctatctgt gaagaataaa agaagcggcc acaagcgcag cgtcgcacat atgatgtgta    4680
tcaaattagg actccatagc catgcatgct gaagaatgtc acacacgttc tgtcacacgt    4740
gttactctct cactgttctc ctcttcctat aaatcaccgc gccacagctt ctccacttca    4800
ccacttcacc acttcactca caatccttca ttagttgttt actatcacag tcacaaccat    4860
ggttgatttg aagccaggag tgaagagatt ggtttcctgg aaggagatta gagagcacgc    4920
tactccagct actgcttgga ttgtgatcca ccacaaggtg tacgatatct ccaagtggga    4980
ttctcatcca ggtggaagtg tgatgttgac tcaggctgga gaggatgcta ctgatgcttt    5040
cgctgtgttc catccatctt ccgctttgaa gctcttggag cagttctacg taagtttctg    5100
cttctacctt tgatatatat ataataatta tcattaatta gtagtaatat aatatttcaa    5160
atattttttt caaaataaaa gaatgtagta tatagcaatt gcttttctgt agtttataag    5220
tgtgtatatt ttaatttata actttttctaa tatatgacca aaatttgttg atgtgcaggt    5280
aggagatgtg gatgagactt ccaaggctga gattgaggga gaaccagctt ctgatgagga    5340
gagagctaga agagagagga tcaacgagtt catcgcttct acagaaggc tcagggttaa    5400
```

```
ggttaaggga atgggactct acgatgcttc tgctctttac tacgcttgga agctcgtttc    5460
taccttcgga attgctgtgc tctctatggc tatctgcttc ttcttcaact ccttcgctat    5520
gtacatggtg gctggagtta ttatgggact cttctaccaa caatctggat ggcttgctca    5580
cgatttcttg cacaaccagg tgtgcgagaa cagaactttg ggaaacttga tcggatgcct    5640
tgttggaaat gcttggcagg gattctctat gcaatggtgg aagaacaagc acaacttgca    5700
ccacgctgtg ccaaacttgc actccgctaa ggatgaggga ttcatcggag atccagatat    5760
cgataccatg ccattgcttg cttggtctaa ggagatggct agaaaggctt cgagtctgc     5820 tcacggacca ttcttcatca ggaaccaggc tttcttgtac ttcccattgc tcttgttggc    5880
tagattgtct ggctcgctc agtctttctt ctacgtgttc accgagttct cattcggaat      5940
cttcgataag gtggagttcg atggaccaga aaaggctgga ttgatcgtgc actacatctg    6000
gcaactcgct attccatact tctgcaacat gtccttgttc gagggagttg cttacttctt    6060
gatgggacaa gcttcttgcg gattgctttt ggctctcgtg ttctctattg gacacaacgg    6120
aatgtctgtg tacgagagag agaccaagcc agatttctgg caattgcaag tgactaccac    6180
cagaaacatt agggcttccg tgttcatgga ttggttcacc ggaggactca actaccaaat    6240
cgatcaccac ttgttcccat ggtgccaag acacaacttg ccaaaggtga acgtgttgat     6300
caagtctctc tgcaaggagt tcgatatccc attccacgag actggattct gggagggaat    6360
ctacgaggtt gtggatcacc tcgctgatat ctctaaggag ttcatcactg agttcccagc    6420
tatgtgagat cctgcaatag aatgttgagg tgaccacttt ctgtaataaa ataattataa    6480
aataaattta gaattgctgt agtcaagaac atcagttcta aaatattaat aaagttatgg    6540
ccttttgaca tatgtgtttc gataaaaaaa tcaaaataaa ttgagattta ttcgaaatac    6600
aatgaaagtt tgcagatatg agatatgttt ctacaaaata ataacttaaa actcaactat    6660
atgctaatgt ttttcttggt gtgtttcata gaaaattgta tccgtttctt agaaaatgct    6720
cgtaagttta aacttagcag atatttggtg tctaaatgtt tattttgtga tatgttcatg    6780
tttgaaatgg tggtttcgaa accagggaca acgttgggat ctgataggt gtcaaagagt      6840 attatggatt gggacaattt cggtcatgag ttgcaaattc aagtatatcg ttcgattatg    6900
aaaattttcg aagaatatcc catttgagag agtctttacc tcattaatgt ttttagatta    6960
tgaaatttta tcatagttca tcgtagtctt tttggtgtaa aggctgtaaa agaaattgt      7020 tcacttttgt tttcgtttat gtgaaggctg taaagattg taaagacta ttttggtgtt       7080 ttggataaaa tgatagtttt tatagattct tttgcttta gaagaaatac atttgaaatt      7140
ttttccatgt tgagtataaa ataccgaaat cgattgaaga tcatagaaat attttaactg    7200
aaaacaaatt tataactgat tcaattctct ccatttttat acctatttaa ccgtaatcga    7260
ttctaataga tgatcgattt tttatataat cctaattaac caacggcatg tattggataa    7320
ttaaccgatc aactctcacc cctaatagaa tcagtatttt ccttcgacgt taattgatcc    7380
tacactatgt aggtcatatc catcgtttta atttttggcc accattcaat tctgtcttgc    7440
ctttagggat gtgaatatga acggccaagg taagagaata aaaataatcc aaattaaagc    7500
aagagaggcc aagtaagata atccaaatgt acacttgtca ttgccaaaat tagtaaaata    7560
ctcggcatat tgtattccca cacattatta aaataccgta tatgtattgg ctgcatttgc    7620
atgaataata ctacgtgtaa gcccaaaaga acccacgtgt agcccatgca aagttaacac    7680
tcacgacccc attcctcagt ctccactata taaacccacc atccccaatc tcaccaaacc    7740
```

```
caccacacaa ctcacaactc actctcacac cttaaagaac caatcaccac caaaaaacca    7800
tgggaaaagg atctgaggga agatctgctg ctagagagat gactgctgag gctaacggag    7860
ataagagaaa gaccatcctc attgagggag tgttgtacga tgctaccaac ttcaaacacc    7920
caggaggttc cattattaac ttcctcaccg agggagaagc tggagttgat gctacccaag    7980
cttacagaga gttccatcag agatccggaa aggctgataa gtacctcaag tccctcccaa    8040
agttggatgc ttctaaggtg gagtctaggt tctctgctaa ggagcaggct agaagggacg    8100
ctatgaccag ggattacgct gctttcagag aggagttggt tgctgaggga tacttcgatc    8160
catctatccc acacatgatc tacagagtgg tggagattgt ggctttgttc gctttgtctt    8220
tctggttgat gtctaaggct tctccaacct ctttggtttt gggagtggtg atgaacggaa    8280
tcgctcaagg aagatgcgga tgggttatgc acgagatggg acacggatct ttcactggag    8340
ttatctggct cgatgatagg atgtgcgagt tcttctacgg agttggatgt ggaatgtctg    8400
gacactactg gaagaaccag cactctaagc accacgctgc tccaaacaga ttggagcacg    8460
atgtggattt gaacaccttg ccactcgttg ctttcaacga gagagttgtg aggaaggtta    8520
agccaggatc tttgttggct tgtggctca gagttcaggc ttatttgttc gctccagtgt    8580
cttgcttgtt gatcggattg ggatggacct tgtacttgca cccaagatat atgctcagga    8640
ccaagagaca catggagttt gtgtggatct tcgctagata tatcggatgg ttctccttga    8700
tgggagcttt gggatattct cctggaactt ctgtgggaat gtacctctgc tctttcggac    8760
ttggatgcat ctacatcttc ctccaattcg ctgtgtctca cccacttg ccagttacca    8820
acccagagga tcaattgcac tggcttgagt acgctgctga tcacaccgtg aacatctcta    8880
ccaagtcttg gttggttacc tggtggatgt ctaacctcaa cttccaaatc gagcaccact    8940
tgttcccaac cgctccacaa ttcaggttca aggagatctc tccaagagtt gaggctctct    9000
tcaagagaca caacctccct tactacgatt tgccatacac ctctgctgtt tctactacct    9060
tcgctaacct ctactctgtt ggacactctg ttggagctga taccaagaag caggattgac    9120
tgctttaatg agatatgcga gacgcctatg atcgcatgat atttgctttc aattctgttg    9180
tgcacgttgt aaaaaacctg agcatgtgta gctcagatcc ttaccgccgg tttcggttca    9240
ttctaatgaa tatatcaccc gttactatcg tattttatg aataatattc tccgttcaat    9300
ttactgattg tgtcgacgcg atcgcgtgcg cacgggcccc ctgcaggatt taaatcccgg    9360
gggtacccaa gtttgtacaa aaaagcaggc tccatgatta cgccaagctt cccaattcga    9420
ggtaccctcg acggcccgga ctgtatccaa cttctgatct ttgaatctct ctgttccaac    9480
atgttctgaa ggagttctaa gacttttcag aaagcttgta acatgctttg tagactttct    9540
ttgaattact cttgcaaact ctgattgaac ctacgtgaaa actgctccag aagttctaac    9600
caaattccgt cttgggaagg cccaaaattt attgagtact tcagtttcat ggacgtgtct    9660
tcaaagattt ataacttgaa atcccatcat ttttaagaga agttctgttc cgcaatgtct    9720
tagatctcat tgaaatctac aactcttgtg tcagaagttc ttccagaatc aacttgcatc    9780
atggtgaaaa tctggccaga agttctgaac ttgtcatatt tcttaacagt tagaaaaatt    9840
tctaagtgtt tagaatttg acttttccaa agcaaacttg acttttgact tcttaataa    9900
aacaaacttc atattctaac atgtcttgat gaaatgtgat tcttgaaatt tgatgttgat    9960
gcaaaagtca agtttgact tttcagtgtg caattgacca ttttgctctt gtgccaattc    10020
caaacctaaa ttgatgtatc agtgctgcaa acttgatgtc atggaagatc ttatgagaaa    10080
attcttgaag actgagagga aaaatttgt agtacaacac aaagaatcct gttttcata    10140
```

```
gtcggactag acacattaac ataaaacacc acttcattcg aagagtgatt gaagaaggaa   10200
atgtgcagtt acctttctgc agttcataag agcaacttac agacactttt actaaaatac   10260
tacaaagagg aagattttaa caacttagag aagtaatggg agttaaagag caacacatta   10320 aggggagtg  ttaaaattaa tgtgttgtaa ccaccactac ctttagtaag tattataaga   10380
aaattgtaat catcacatta taattattgt ccttatttaa aattatgata aagttgtatc   10440
attaagattg agaaaaccaa atagtcctcg tcttgatttt tgaattattg ttttctatgt   10500
tacttttctt caagcctata taaaaacttt gtaatgctaa attgtatgct ggaaaaaaat   10560
gtgtaatgaa ttgaatagaa attatggtat ttcaaagtcc aaaatccatc aatagaaatt   10620
tagtacaaaa cgtaactcaa aaatattctc ttatttttaaa ttttacaaca atataaaaat   10680
attctcttat tttaaatttt acaataatat aatttatcac ctgtcacctt tagaatacca   10740
ccaacaatat taatacttag atatttattt cttaataatt ttgagatctc tcaatatatc   10800
tgatatttat tttatatttg tgtcatattt tcttatgttt tagagttaac ccttatatct   10860
tggtcaaact agtaattcaa tatatgagtt tgtgaaggac acattgacat cttgaaacat   10920
tggttttaac cttgttggaa tgttaaaggt aataaaacat tcagaattat gaccatctat   10980
taatatactt cctttgtctt ttaaaaaagt gtgcatgaaa atgctctatg gtaagctaga   11040
gtgtcttgct ggcctgtgta tatcaattcc atttccagat ggtagaaact gccactacga   11100
ataattagtc ataagacacg tatgttaaca cacgtcccct tgcatgtttt ttgccatata   11160
ttccgtctct ttcttttct tcacgtataa aacaatgaac taattaatag agcgatcaag    11220
ctgaaccatg cgcgccacca tgtgtgttga daccgagaac aacgatggaa tccctactgt   11280
ggagatcgct ttcgatggag agagagaaag agctgaggct aacgtgaagt tgtctgctga   11340
gaagatggaa cctgctgctt tggctaagac cttcgctaga agatacgtgg ttatcgaggg   11400
agttgagtac gatgtgaccg atttcaaaca tcctggagga accgtgattt tctacgctct   11460
ctctaacact ggagctgatg ctactgaggc tttcaaggag ttccaccaca gatctagaaa   11520
ggctaggaag gctttggctg ctttgccttc tagacctgct aagaccgcta aagtggatga   11580
tgctgagatg ctccaggatt tcgctaagtg gagaaaggag ttggagaggg acggattctt   11640
caagccttct cctgctcatg ttgcttacag attcgctgag ttggctgcta tgtacgcttt   11700
gggaacctac ttgatgtacg ctagatacgt tgtgtcctct gtgttggttt acgcttgctt   11760
cttcggagct agatgtggat gggttcaaca tgagggagga cattcttctt tgaccggaaa   11820
catctggtgg gataagagaa tccaagcttt cactgctgga ttcggattgg ctggatctgg   11880
agatatgtgg aactccatgc acaacaagca ccatgctact cctcaaaaag tgaggcacga   11940
tatggatttg gataccactc ctgctgttgc tttcttcaac accgctgtgg aggataatag   12000
acctagggga ttctctaagt actggctcag attgcaagct tggaccttca ttcctgtgac   12060
ttctggattg tgttgctct   tctgatgtt  cttcctccat ccttctaagg ctttgaaggg   12120
aggaaagtac gaggagcttg tgtggatgtt ggctgctcat gtgattagaa cctggaccat   12180
taaggctgtt actggattca ccgctatgca atcctacgga ctcttcttgg ctacttcttg   12240
ggtttccgga tgctacttgt tcgctcactt ctctacttct cacacccatt tggatgttgt   12300
tcctgctgat gagcatttgt cttgggttag gtacgctgtg gatcacacca ttgatatcga   12360
tccttctcag ggatgggtta actggttgat gggatacttg aactgccaag tgattcatca   12420
cctcttccct tctatgcctc aattcagaca acctgaggtg tccagaagat tcgttgcttt   12480
```

-continued

| | |
|---|---|
| cgctaagaag tggaacctca actacaaggt gatgacttat gctggagctt ggaaggctac | 12540 |
| tttgggaaac ctcgataatg tgggaaagca ctactacgtg cacggacaac attctggaaa | 12600 |
| gaccgcttga taattaatta aggccgcctc gaccgtaccc cctgcagata gactatacta | 12660 |
| tgttttagcc tgcctgctgg ctagctacta tgttatgtta tgttgtaaaa taaacacctg | 12720 |
| ctaaggtata tctatctata ttttagcatg gctttctcaa taaattgtct ttccttatcg | 12780 |
| tttactatct tatacctaat aatgaaataa taatatcaca tatgaggaac ggggcaggtt | 12840 |
| taggcatata tatacgagtg tagggcggag tggggggat cggggtacc acccagcttt | 12900 |
| cttgtacaaa gtggccatga ttacgccaag ctctccaccg cggtggcggc cgctctagcc | 12960 |
| caagctttaa ggatgaccta cccattcttg agacaaatgt tacattttag tatcagagta | 13020 |
| aaatgtgtac ctataactca aattcgattg acatgtatcc attcaacata aaattaaacc | 13080 |
| agcctgcacc tgcatccaca tttcaagtat tttcaaaccg ttcggctcct atccaccggg | 13140 |
| tgtaacaaga cggattccga atttggaaga ttttgactca aattcccaat ttatattgac | 13200 |
| cgtgactaaa tcaactttaa cttctataat tctgattaag ctcccaattt atattcccaa | 13260 |
| cggcactacc tccaaaattt atagactctc atccccttt aaaccaactt agtaaacgtt | 13320 |
| tttttttaa ttttatgaag ttaagttttt accttgtttt taaaaagaat cgttcataag | 13380 |
| atgccatgcc agaacattag ctacacgtta cacatagcat gcagccgcgg agaattgttt | 13440 |
| ttcttcgcca cttgtcactc ccttcaaaca cctaagagct tctctctcac agcacacaca | 13500 |
| tacaatcaca tgcgtgcatg cattattaca cgtgatcgcc atgcaaatct cctttatagc | 13560 |
| ctataaatta actcatcggc ttcactcttt actcaaacca aaactcatca atacaaacaa | 13620 |
| gattaaaaac ataaggcgcg ccggatccgc catggctatt ttgaaccctg aggctgattc | 13680 |
| tgctgctaac ctcgctactg attctgaggc taagcaaaga caattggctg aggctggata | 13740 |
| cactcatgtt gagggtgctc ctgctccttt gcctttggag ttgcctcatt tctctctcag | 13800 |
| agatctcaga gctgctattc ctaagcactg cttcgagaga tctttcgtga cctccaccta | 13860 |
| ctacatgatc aagaacgtgt tgacttgcgc tgctttgttc tacgctgcta ccttcattga | 13920 |
| tagagctgga gctgctgctt atgttttgtg gcctgtgtac tggttcttcc agggatctta | 13980 |
| cttgactgga gtgtgggtta tcgctcatga gtgtggacat caggcttatt gctcttctga | 14040 |
| ggtggtgaac aacttgattg gactcgtgtt gcattctgct ttgttggtgc cttaccactc | 14100 |
| ttggagaatc tctcacagaa agcaccattc caacactgga tcttgcgaga acgatgaggt | 14160 |
| tttcgttcct gtgaccagat ctgtgttggc ttcttcttgg aacgagacct tggaggattc | 14220 |
| tcctctctac caactctacc gtatcgtgta catgttggtt gttggatgga tgcctggata | 14280 |
| cctcttcttc aacgctactg gacctactaa gtactgggga aagtctaggt ctcacttcaa | 14340 |
| cccttactcc gctatctatg ctgataggga gagatggatg atcgtgctct ccgatatttt | 14400 |
| cttggtggct atgttggctg ttttggctgc tttggtgcac actttctcct tcaacaccat | 14460 |
| ggtgaagttc tacgtggtgc cttacttcat tgtgaacgct tacttggtgt tgattaccta | 14520 |
| cctccaacac accgatacct acatccctca tttcagagag ggagagtgga attggttgag | 14580 |
| aggagctttg tgcactgtgg atagatcatt tggtccattc ctcgattctg tggtgcatag | 14640 |
| aatcgtggat acccatgttt gccaccacat cttctccaag atgccttct atcattgcga | 14700 |
| ggaggctacc aacgctatta agcctctcct cggaaagttc tacttgaagg ataccactcc | 14760 |
| tgttcctgtt gctctctgga gatcttacac ccattgcaag ttcgtgaggg atgatggaaa | 14820 |
| ggtggtgttc tacaagaaca agctctagtt aattaaggcc gcctcgagca tgcatctaga | 14880 |

```
gggcccgcta gcgttaaccc tgctttaatg agatatgcga gacgcctatg atcgcatgat   14940
atttgctttc aattctgttg tgcacgttgt aaaaaacctg agcatgtgta gctcagatcc   15000
ttaccgccgg tttcggttca ttctaatgaa tatatcaccc gttactatcg tattttatg    15060 aataatattc tccgttcaat ttactgattg tccgtcgagc atatgctaga ggatccccgg   15120
gtacccaact ttattataca tagttgataa ttcactggcc ggatatcttt tttaagggcg   15180
aattctgcag atatccatca cactggcggc cgctcgaggt accatcgttc aaacatttgg   15240
caataaagtt tcttaagatt gaatcctgtt gccggtcttg cgatgattat catataattt   15300
ctgttgaatt acgttaagca tgtaataatt aacatgtaat gcatgacgtt atttatgaga   15360
tgggttttta tgattagagt cccgcaatta tacatttaat acgcgataga aaacaaaata   15420
tagcgcgcaa actaggataa attatcgcgc gcggtgtcat ctatgttact agatcgggca   15480
ttaccctgtt atccctagag gggaaaattc gaatccaaaa attacggata tgaatatagg   15540
catatccgta tccgaattat ccgtttgaca gctagcaacg attgtacaat tgcttcttta   15600 aaaaggaag  aagaaagaa  agaaaagaat caacatcagc gttaacaaac ggcccgtta    15660 cggcccaaac ggtcatatag agtaacggcg ttaagcgttg aaagactcct atcgaaatac   15720
gtaaccgcaa acgtgtcata gtcagatccc ctcttccttc accgcctcaa acacaaaaat   15780
aatcttctac agcctatata tacaaccccc ccttctatct ctcctttctc acaattcatc   15840
atctttcttt ctctaccccc aattttaaga aatcctctct tctcctcttc attttcaagg   15900
taaatctctc tctctctctc tctctctgtt attccttgtt ttaattaggt atgtattatt    15960
gctagtttgt taatctgctt atcttatgta tgccttatgt gaatatcttt atcttgttca   16020
tctcatccgt ttagaagcta taaatttgtt gatttgactg tgtatctaca cgtggttatg   16080
tttatatcta atcagatatg aatttcttca tattgttgcg tttgtgtgta ccaatccgaa   16140
atcgttgatt tttttcattt aatcgtgtag ctaattgtac gtatacatat ggatctacgt   16200
atcaattgtt catctgtttg tgtttgtatg tatacagatc tgaaaacatc acttctctca   16260
tctgattgtg ttgttacata catagatata gatctgttat atcatttttt ttattaattg   16320
tgtatatata tatgtgcata gatctggatt acatgattgt gattatttac atgatttgt    16380 tatttacgta tgtatatatg tagatctgga cttttggag ttgttgactt gattgtattt     16440
gtgtgtgtat atgtgtgttc tgatcttgat atgttatgta tgtgcagctg aaccatggcg   16500
gcggcaacaa caacaacaac aacatcttct tcgatctcct tctccaccaa accatctcct   16560
tcctcctcca aatcaccatt accaatctcc agattctccc tcccattctc cctaaacccc   16620
aacaaatcat cctcctcctc ccgccgccgc ggtatcaaat ccagctctcc ctcctccatc   16680
tccgccgtgc tcaacacaac caccaatgtc acaaccactc cctctccaac caaacctacc   16740
aaacccgaaa cattcatctc ccgattcgct ccagatcaac cccgcaaagg cgctgatatc   16800
ctcgtcgaag cttagaaacg tcaaggcgta gaaaccgtat tcgcttaccc tggaggtaca   16860
tcaatggaga ttcaccaagc cttaacccgc tcttcctcaa tccgtaacgt ccttcctcgt   16920
cacgaacaag gaggtgtatt cgcagcagaa ggatacgctc gatcctcagg taaaccaggt   16980
atctgtatag ccacttcagg tcccggagct acaaatctcg ttagcggatt agccgatgcg   17040
ttgttagata gtgttcctct tgtagcaatc acaggacaag tccctcgtcg tatgattggt   17100
acagatgcgt ttcaagagac tccgattgtt gaggtaacgc gttcgattac gaagcataac   17160
tatcttgtga tggatgttga agatatccct aggattattg aggaagcttt cttttagct    17220
```

```
acttctggta gacctggacc tgttttggtt gatgttccta aagatattca acaacagctt    17280
gcgattccta attgggaaca ggctatgaga ttacctggtt atatgtctag gatgcctaaa    17340
cctccggaag attctcattt ggagcagatt gttaggttga tttctgagtc taagaagcct    17400
gtgttgtatg ttggtggtgg ttgtttgaat tctagcgatg aattgggtag gtttgttgag    17460
cttacgggga tccctgttgc gagtacgttg atggggctgg gatcttatcc ttgtgatgat    17520
gagttgtcgt tacatatgct tggaatgcat gggactgtgt atgcaaatta cgctgtggag    17580
catagtgatt tgttgttggc gtttggggta aggtttgatg atcgtgtcac gggtaagctt    17640
gaggcttttg ctagtagggc taagattgtt catattgata ttgactcggc tgagattggg    17700
aagaataaga ctcctcatgt gtctgtgtgt ggtgatgtta agctggcttt gcaagggatg    17760
aataaggttc ttgagaaccg agcggaggag cttaagcttg attttggagt ttggaggaat    17820
gagttgaacg tacagaaaca gaagtttccg ttgagctttt agacgtttgg ggaagctatt    17880
cctccacagt atgcgattaa ggtccttgat gagttgactg atggaaaagc cataataagt    17940
actggtgtcg ggcaacatca aatgtgggcg gcgcagttct acaattacaa gaaaccaagg    18000
cagtggctat catcaggagg ccttggagct atgggatttg gacttcctgc tgcgattgga    18060
gcgtctgttg ctaaccctga tgcgatagtt gtggatattg acggagatgg aagctttata    18120
atgaatgtgc aagagctagc cactattcgt gtagagaatc ttccagtgaa ggtactttta    18180
ttaaacaacc agcatcttgg catggttatg caatgggaag atcggttcta caaagctaac    18240
cgagctcaca catttctcgg ggatccggct caggaggacg agatattccc gaacatgttg    18300
ctgtttgcag cagcttgcgg gattccagcg gcgagggtga caaagaaagc agatctccga    18360
gaagctattc agacaatgct ggatacacca ggaccttacc tgttggatgt gatttgtccg    18420
caccaagaac atgtgttgcc gatgatcccg aatggtggca cttcaacga tgtcataacg    18480 gaaggagatg gccggattaa atactgatag ggataacagg gtaatttccc gacccaagct    18540
ctagatcttg ctgcgttcgg atattttcgt ggagttcccg ccacagaccc ggatgatccc    18600
cgatcgttca acatttggc aataaagttt cttaagattg aatcctgttg ccggtcttgc    18660
gatgattatc atataatttc tgttgaatta cgttaagcat gtaataatta acatgtaatg    18720
catgacgtta tttatgagat gggttttat gattagagtc ccgcaattat acatttaata    18780
cgcgatagaa acaaaatat agcgcgcaaa ctaggataaa ttatcgcgcg cggtgtcatc    18840
tatgttacta gatcgggcct cctgtcaagc tctgcttggt aataattgtc attagattgt    18900
ttttatgcat agatgcactc gaaatcagcc aattttagac aagtatcaaa cggatgttaa    18960
ttcagtacat taaagacgtc cgcaatgtgt tattaagttg tctaagcgtc aatttgttta    19020
caccacaata tatcctgcca ccagccagcc aacagctccc cgaccggcag ctcggcacaa    19080
aatcaccacg cgttaccacc acgccggccg gccgcatggt gttgaccgtg ttcgccggca    19140
ttgccgagtt cgagcgttcc ctaatcatcg accgcacccg gagcgggcgc gaggccgcca    19200
aggcccgagg cgtgaagttt ggcccccgcc ctaccctcac cccggcacag atcgcgcacg    19260
cccgcgagct gatcgaccag gaaggccgca ccgtgaaaga ggcggctgca ctgcttggcg    19320
tgcatcgctc gaccctgtac cgcgcacttg agcagcgga ggaagtgacg cccaccgagg    19380
ccaggcggcg cggtgccttc cgtgaggacg cattgaccga ggccgacgcc ctggcggccg    19440
ccgagaatga acgccaagag gaacaagcat gaaaccgcac caggacggcc aggacgaacc    19500
gtttttcatt accgaagaga tcgaggcgga gatgatcgcg gccgggtacg tgttcgagcc    19560
gcccgcgcac gtctcaaccg tgcggctgca tgaaatcctg gccggtttgt ctgatgccaa    19620
```

```
gctggcggcc tggccggcca gcttggccgc tgaagaaacc gagcgccgcc gtctaaaaag   19680
gtgatgtgta tttgagtaaa acagcttgcg tcatgcggtc gctgcgtata tgatgcgatg   19740
agtaaataaa caaatacgca aggggaacgc atgaaggtta tcgctgtact taaccagaaa   19800
ggcgggtcag gcaagacgac catcgcaacc catctagccc gcgccctgca actcgccggg   19860
gccgatgttc tgttagtcga ttccgatccc cagggcagtg cccgcgattg ggcggccgtg   19920
cgggaagatc aaccgctaac cgttgtcggc atcgaccgcc cgacgattga ccgcgacgtg   19980
aaggccatcg gccggcgcga cttcgtagtg atcgacggag cgcccaggc ggcggacttg    20040 gctgtgtccg cgatcaaggc agccgacttc gtgctgattc cggtgcagcc aagcccttac   20100
gacatatggg ccaccgccga cctggtggag ctggttaagc agcgcattga ggtcacggat   20160
ggaaggctac aagcggcctt tgtcgtgtcg cgggcgatca aaggcacgcg catcggcggt   20220
gaggttgccg aggcgctggc cgggtacgag ctgcccattc ttgagtcccg tatcacgcag   20280
cgcgtgagct acccaggcac tgccgccgcc ggcacaaccg ttcttgaatc agaacccgag   20340
ggcgacgctg cccgcgaggt ccaggcgctg gccgctgaaa ttaaatcaaa actcatttga   20400
gttaatgagg taaagagaaa atgagcaaaa gcacaaacac gctaagtgcc ggccgtccga   20460
gcgcacgcag cagcaaggct gcaacgttgg ccagcctggc agacacgcca gccatgaagc   20520
gggtcaactt tcagttgccg gcggaggatc acaccaagct gaagatgtac gcggtacgcc   20580
aaggcaagac cattaccgag ctgctatctg aatacatcgc gcagctacca gagtaaatga   20640
gcaaatgaat aaatgagtag atgaatttta gcggctaaag gaggcggcat ggaaaatcaa   20700
gaacaaccag gcaccgacgc cgtggaatgc cccatgtgtg gaggaacggg cggttggcca   20760
ggcgtaagcg gctgggttgt ctgccggccc tgcaatggca ctggaacccc caagcccgag   20820
gaatcggcgt gagcggtcgc aaaccatccg gcccggtaca atcggcgcg cgctgggtg     20880 atgacctggt ggagaagttg aaggccgcgc aggccgccca gcggcaacgc atcgaggcag   20940
aagcacgccc cggtgaatcg tggcaagcgg ccgctgatcg aatccgcaaa gaatcccggc   21000
aaccgccggc agccggtgcg ccgtcgatta ggaagccgcc caaggcgac gagcaaccag    21060 attttttcgt tccgatgctc tatgacgtgg gcacccgcga tagtcgcagc atcatggacg   21120
tggccgtttt ccgtctgtcg aagcgtgacc gacgagctgg cgaggtgatc cgctacgagc   21180
ttccagacgg gcacgtagag gtttccgcag ggccggccgg catggccagt gtgtgggatt   21240
acgacctggt actgatggcg gtttcccatc taaccgaatc catgaaccga taccgggaag   21300
ggaagggaga caagcccggc cgcgtgttcc gtccacacgt tgcggacgta ctcaagttct   21360
gccggcgagc cgatggcgga aagcagaaag acgacctggt agaaacctgc attcggttaa   21420
acaccacgca cgttgccatg cagcgtacga agaaggccaa gaacgccgc ctggtgacgg    21480 tatccgaggg tgaagccttg attagccgct acaagatcgt aaagagcgaa accggcggc    21540 cggagtacat cgagatcgag ctagctgatt ggatgtaccg cgagatcaca gaaggcaaga   21600
acccggacgt gctgacggtt caccccgatt actttttgat cgatcccggc atcggccgtt   21660
ttctctaccg cctggcacgc cgcgccgcag gcaaggcaga agccagatgg ttgttcaaga   21720
cgatctacga acgcagtggc agcgccggag agttcaagaa gttctgtttc accgtgcgca   21780
agctgatcgg gtcaaatgac ctgccggagt acgatttgaa ggaggaggcg gggcaggctg   21840
gcccgatcct agtcatgcgc taccgcaacc tgatcgaggg cgaagcatcc gccggttcct   21900
aatgtacgga gcagatgcta gggcaaattg ccctagcagg ggaaaaaggt cgaaaaggtc   21960
```

```
tctttcctgt ggatagcacg tacattggga acccaaagcc gtacattggg aaccggaacc   22020
cgtacattgg gaacccaaag ccgtacattg ggaaccggtc acacatgtaa gtgactgata   22080
taaaagagaa aaaaggcgat ttttccgcct aaaactcttt aaaacttatt aaaactctta   22140
aaacccgcct ggcctgtgca taactgtctg gccagcgcac agccgaagag ctgcaaaaag   22200
cgcctaccct tcggtcgctg cgctccctac gccccgccgc ttcgcgtcgg cctatcgcgg   22260
ccgctggccg ctcaaaaatg ctggcctac ggccaggcaa tctaccaggg cgcggacaag   22320
ccgcgccgtc gccactcgac cgccggcgcc cacatcaagg caccctgcct cgcgcgtttc   22380
ggtgatgacg gtgaaaacct ctgacacatg cagctcccgg agacggtcac agcttgtctg   22440
taagcggatg ccgggagcag acaagcccgt cagggcgcgt cagcgggtgt ggcgggtgt   22500 cggggcgcag ccatgaccca gtcacgtagc gatagcggag tgtatactgg cttaactatg   22560
cggcatcaga gcagattgta ctgagagtgc accatatgcg gtgtgaaata ccgcacagat   22620
gcgtaaggag aaaataccgc atcaggcgct cttccgcttc ctcgctcact gactcgctgc   22680
gctcggtcgt tcggctgcgg cgagcggtat cagctcactc aaaggcggta atacggttat   22740
ccacagaatc aggggataac gcaggaaaga acatgtgagc aaaaggccag caaaaggcca   22800
ggaaccgtaa aaaggccgcg ttgctggcgt ttttccatag gctccgcccc cctgacgagc   22860
atcacaaaaa tcgacgctca agtcagaggt ggcgaaaccc gacaggacta taaagatacc   22920
aggcgtttcc ccctggaagc tccctcgtgc gctctcctgt tccgaccctg ccgcttaccg   22980
gatacctgtc cgcctttctc ccttcgggaa gcgtggcgct ttctcatagc tcacgctgta   23040
ggtatctcag ttcggtgtag tcgttcgct ccaagctggg ctgtgtgcac gaaccccccg   23100
ttcagcccga ccgctgcgcc ttatccggta actatcgtct tgagtccaac ccggtaagac   23160
acgacttatc gccactggca gcagccactg gtaacaggat tagcagagcg aggtatgtag   23220
gcggtgctac agagttcttg aagtggtggc ctaactacgg ctacactaga aggacagtat   23280
ttggtatctg cgctctgctg aagccagtta ccttcggaaa aagagttggt agctcttgat   23340
ccggcaaaca aaccaccgct ggtagcggtg ttttttttgt ttgcaagcag cagattacgc   23400
gcagaaaaaa aggatctcaa gaagatcctt tgatcttttc tacggggtct gacgctcagt   23460
ggaacgaaaa ctcacgttaa gggattttgg tcatgcatga tatatctccc aatttgtgta   23520
gggcttatta tgcacgctta aaaataataa aagcagactt gacctgatag tttggctgtg   23580
agcaattatg tgcttagtgc atctaacgct tgagttaagc cgcgccgcga agcggcgtcg   23640
gcttgaacga atttctagct agacattatt gccgactac cttggtgatc tcgcctttca   23700
cgtagtggac aaattcttcc aactgatctg cgcgcgaggc caagcgatct tcttcttgtc   23760
caagataagc ctgtctagct tcaagtatga cgggctgata ctgggccggc aggcgctcca   23820
ttgcccagtc ggcagcgaca tccttcggcg cgattttgcc ggttactgcg ctgtaccaaa   23880
tgcgggacaa cgtaagcact acatttcgct catcgccagc ccagtcgggc ggcgagttcc   23940
atagcgttaa ggtttcattt agcgcctcaa atagatcctg ttcaggaacc ggatcaaaga   24000
gttcctccgc cgctggacct accaaggcaa cgctatgttc tcttgctttt gtcagcaaga   24060
tagccagatc aatgtcgatc gtggctggct cgaagatacc tgcaagaatg tcattgcgct   24120
gccattctcc aaattgcagt tcgcgcttag ctggataacg ccacggaatg atgtcgtcgt   24180
gcacaacaat ggtgacttct acagcgcgga gaatctcgct ctctccaggg gaagccgaag   24240
tttccaaaag gtcgttgatc aaagctcgcc gcgttgtttc atcaagcctt acggtcaccg   24300
taaccagcaa atcaatatca ctgtgtggct tcaggccgcc atccactgcg gagccgtaca   24360
```

```
aatgtacggc cagcaacgtc ggttcgagat ggcgctcgat gacgccaact acctctgata    24420
gttgagtcga tacttcggcg atcaccgctt cccccatgat gtttaacttt gttttagggc    24480
gactgccctg ctgcgtaaca tcgttgctgc tccataacat caaacatcga cccacggcgt    24540
aacgcgcttg ctgcttggat gcccgaggca tagactgtac cccaaaaaaa cagtcataac    24600
aagccatgaa aaccgccact gcgttccatg g                                   24631
```

<210> SEQ ID NO 39
<211> LENGTH: 24356
<212> TYPE: DNA
<213> ORGANISM: Artificial Sequence
<220> FEATURE:
<223> OTHER INFORMATION: Plant Expression Plasmid

<400> SEQUENCE: 39

```
tgatcatcta aaaggtgat gtgtatttga gtaaaacagc ttgcgtcatg cggtcgctgc       60
gtatatgatg cgatgagtaa ataaacaaat acgcaagggg aacgcatgaa ggttatcgct     120
gtacttaacc agaaaggcgg gtcaggcaag acgaccatcg caacccatct agcccgcgcc     180
ctgcaactcg ccggggccga tgttctgtta gtcgattccg atccccaggg cagtgcccgc     240
gattgggcgg ccgtgcggga agatcaaccg ctaaccgttg tcggcatcga ccgcccgacg     300
attgaccgcg acgtgaaggc catcggccgg cgcgacttcg tagtgatcga cggagcgccc     360
caggcggcgg acttggctgt gtccgcgatc aaggcagccg acttcgtgct gattccggtg     420
cagccaagcc cttacgacat ttgggccacc gccgacctgg tggagctggt taagcagcgc     480
attgaggtca cggatggaag gctacaagcg gcctttgtcg tgtcgcgggc gatcaaaggc     540
acgcgcatcg gcggtgaggt tgccgaggcg ctggccgggt acgagctgcc cattcttgag     600
tcccgtatca cgcagcgcgt gagctaccca ggcactgccg ccgccggcac aaccgttctt     660
gaatcagaac ccgagggcga cgctgcccgc gaggtccagg cgctggccgc tgaaattaaa     720
tcaaaactca tttgagttaa tgaggtaaag agaaaatgag caaaagcaca aacacgctaa     780
gtgccggccg tccgagcgca cgcagcagca aggctgcaac gttggccagc ctggcagaca     840
cgccagccat gaagcgggtc aactttcagt tgccggcgga ggatcacacc aagctgaaga     900
tgtacgcggt acgccaaggc aagaccatta ccgagctgct atctgaatac atcgcgcagc     960
taccagagta aatgagcaaa tgaataaatg agtagatgaa ttttagcggc taaaggaggc    1020
ggcatggaaa atcaagaaca accaggcacc gacgccgtgg aatgccccat gtgtggagga    1080
acgggcggtt ggccaggcgt aagcggctgg gttgtctgcc ggccctgcaa tggcactgga    1140
acccccaagc ccgaggaatc ggcgtgagcg gtcgcaaacc atccggcccg gtacaaatcg    1200
gcgcggcgct gggtgatgac ctggtggaga agttgaaggc cgcgcaggcc gcccagcggc    1260
aacgcatcga ggcagaagca cgccccggtg aatcgtggca aggggccgct gatcgaatcc    1320
gcaaagaatc ccggcaaccg ccggcagccg gtgcgccgtc gattaggaag ccgcccaagg    1380
gcgacgagca accagatttt tcgttccga tgctctatga cgtgggcacc cgcgatagtc     1440
gcagcatcat ggacgtggcc gttttccgtc tgtcgaagcg tgaccgacga gctggcgagg    1500
tgatccgcta cgagcttcca gacgggcacg tagaggtttc cgcaggcccc gccggcatgg    1560
ccagtgtgtg ggattacgac ctggtactga tggcggtttc ccatctaacc gaatccatga    1620
accgataccg ggaagggaag ggagacaagc ccggccgcgt gttccgtcca cacgttgcgg    1680
acgtactcaa gttctgccgg cgagccgatg gcggaaagca gaaagacgac ctggtagaaa    1740
```

```
cctgcattcg gttaaacacc acgcacgttg ccatgcagcg taccaagaag gccaagaacg      1800
gccgcctggt gacggtatcc gagggtgaag ccttgattag ccgctacaag atcgtaaaga      1860
gcgaaaccgg gcggccggag tacatcgaga tcgagcttgc tgattggatg taccgcgaga      1920
tcacagaagg caagaacccg gacgtgctga cggttcaccc cgattacttt ttgatcgacc      1980
ccggcatcgg ccgttttctc taccgcctgg cacgccgcgc cgcaggcaag gcagaagcca      2040
gatggttgtt caagacgatc tacgaacgca gtggcagcgc cggagagttc aagaagttct      2100
gtttcaccgt gcgcaagctg atcgggtcaa atgacctgcc ggagtacgat ttgaaggagg      2160
aggcggggca ggctggcccg atcctagtca tgcgctaccg caacctgatc gagggcgaag      2220
catccgccgg ttcctaatgt acggagcaga tgctagggca aattgcccta gcagggaaa       2280
aaggtcgaaa aggtctcttt cctgtggata gcacgtacat tgggaaccca agccgtaca       2340
ttgggaaccg gaacccgtac attgggaacc caaagccgta cattgggaac cggtcacaca      2400
tgtaagtgac tgatataaaa gagaaaaaag gcgattttc cgcctaaaac tctttaaaac       2460
ttattaaaac tcttaaaacc cgcctggcct gtgcataact gtctggccag cgcacagccg      2520
aagagctgca aaaagcgcct acccttcggt cgctgcgctc cctacgcccc gccgcttcgc      2580
gtcggcctat cgcggcctat gcggtgtgaa ataccgcaca gatgcgtaag gagaaaatac      2640
cgcatcaggc gctcttccgc ttcctcgctc actgactcgc tgcgctcggt cgttcggctg      2700
cggcgagcgg tatcagctca ctcaaaggcg gtaatacggt tatccacaga atcaggggat      2760
aacgcaggaa agaacatgtg agcaaaaggc cagcaaaagg ccaggaaccg taaaaaggcc      2820
gcgttgctgg cgttttttcca taggctccgc cccccctgacg agcatcacaa aaatcgacgc      2880
tcaagtcaga ggtggcgaaa cccgacagga ctataaagat accaggcgtt ccccctggaa     2940
agctccctcg tgcgctctcc tgttccgacc ctgccgctta ccggatacct gtccgccttt      3000
ctcccttcgg gaagcgtggc gctttctcat agctcacgct gtaggtatct cagttcggtg      3060
taggtcgttc gctccaagct gggctgtgtg cacgaacccc ccgttcagcc cgaccgctgc      3120
gccttatccg gtaactatcg tcttgagtcc aacccggtaa gacacgactt atcgccactg      3180
gcagcagcca ctggtaacag gattagcaga gcgaggtatg taggcggtgc tacagagttc      3240
ttgaagtggt ggcctaacta cggctacact agaaggacag tatttggtat ctgcgctctg      3300
ctgaagccaa ttaccttcgg aaaaagagtt ggtagctctt gatccggcaa acaaaccacc      3360
gctggtagcg gtggtttttt tgtttgcaag cagcagatta cgcgcagaaa aaaaggatct      3420
caagaagatc ctttgatctt ttctacgggg tccttcaact catcgatagt ttggctgtga      3480
gcaattatgt gcttagtgca tctaacgctt gagttaagcc gcgccgcgaa gcggcgtcgg      3540
cttgaacgaa tttctagcta gacattattt gccaacgacc ttcgtgatct cgcccttgac      3600
atagtggaca aattcttcga gctggtcggc ccgggacgcg agacggtctt cttcttggcc      3660
cagataggct tggcgcgctt cgaggatcac gggctggtat tgcgccggaa ggcgctccat      3720
cgcccagtcg gcgcgacat ccttcggcgc gatcttgccg gtaaccgccg agtaccaaat      3780
ccggctcagc gtaaggacca cattgcgctc atcgcccgcc caatccggcg gggagttcca     3840
cagggtcagc gtctcgttca gtgcttcgaa cagatcctgt tccggcaccg ggtcgaaaag      3900
ttcctcggcc gcggggccga cgagggccac gctatgctcc cgggccttgg tgagcaggat      3960
cgccagatca atgtcgatgg tggccggttc aaagatacccc gccagaatat cattacgctg      4020
ccattcgccg aactggagtt cgcgtttggc cggatagcgc caggggatga tgtcatcgtg      4080
caccacaatc gtcacctcaa ccgcgcgcag gatttcgctc tcgccggggg aggcggacgt      4140
```

```
ttccagaagg tcgttgataa gcgcgcggcg cgtggtctcg tcgagacgga cggtaacggt    4200
gacaagcagg tcgatgtccg aatggggctt aaggccgccg tcaacggcgc taccatacag    4260
atgcacggcg aggagggtcg gttcgaggtg gcgctcgatg acacccacga cttccgacag    4320
ctgggtggac acctcggcga tgaccgcttc acccatgatg tttaactttg ttttagggcg    4380
actgccctgc tgcgtaacat cgttgctgct ccataacatc aaacatcgac ccacggcgta    4440
acgcgcttgc tgcttggatg cccgaggcat agactgtacc ccaaaaaaac agtcataaca    4500
agccatgaaa accgccactg cgttccatga atattcaaac aaacacatac agcgcgactt    4560
atcatggata ttgacataca aatggacgaa cggataaacc ttttcacgcc cttttaaata    4620
tccgattatt ctaataaacg ctcttttctc ttaggtttac ccgccaatat atcctgtcaa    4680
acactgatag tttaaactga aggcgggaaa cgacaatctg atcactgatt agtaactaag    4740
gcctttaatt aatctagagg cgcgccgggc cccctgcagg gagctcggcc ggccaattta    4800
aattgatatc ggtacatcga ttacgccaag ctatcaactt tgtatagaaa agttgccatg    4860
attacgccaa gcttggcgcg ccctgcagca aatttacaca ttgccactaa acgtctaaac    4920
ccttgtaatt tgttttttgtt ttactatgtg tgttatgtat ttgatttgcg ataaattttt    4980
atatttggta ctaaatttat aacacctttt atgctaacgt ttgccaacac ttagcaattt    5040
gcaagttgat taattgattc taaattattt ttgtcttcta aatacatata ctaatcaact    5100
ggaaatgtaa atatttgcta atatttctac tataggagaa ttaaagtgag tgaatatggt    5160
accacaaggt ttggagattt aattgttgca atgctgcatg gatggcatat acaccaaaca    5220
ttcaataatt cttgaggata taatggtac cacacaagat ttgaggtgca tgaacgtcac    5280
gtggacaaaa ggtttagtaa ttttttcaaga caacaatgtt accacacaca agttttgagg    5340
tgcatgcatg gatgccctgt ggaaagttta aaaatatttt ggaaatgatt tgcatggaag    5400
ccatgtgtaa aaccatgaca tccacttgga ggatgcaata atgaagaaaa ctacaaattt    5460
acatgcaact agttatgcat gtagtctata taatgaggat tttgcaatac tttcattcat    5520
acacactcac taagttttac acgattataa tttcttcata gccagtacca tggaagttgt    5580
tgagaggttc tacggagagt tggatggaaa ggtttcccaa ggagtgaacg cttgtttggg    5640
atctttcgga gttgagttga ctgataccc aactactaag ggattgccac tcgttgattc    5700
tccaactcca attgtgttgg gagtgtctgt ttacttgacc atcgtgatcg gaggattgct    5760
ttggatcaag gctagagatc tcaagccaag agcttctgag ccattcttgt tgcaagcttt    5820
ggtgttggtg cacaacttgt tctgcttcgc tttgtctctt tacatgtgcg tgggtatcgc    5880
ttaccaagct atcacctgga gatattcctt gtggggaaac gcttataacc caaagcacaa    5940
ggagatggct atcctcgttt acctcttcta catgtccaag tacgtggagt tcatggatac    6000
cgtgatcatg atcctcaaga gatccaccag acagatttct ttcctccacg tgtaccacca    6060
ctcttctatc tcccttatct ggtgggctat tgctcaccac gctccaggag agaggcttta    6120
ttggagtgct gctctcaact ctggagtgca cgtgttgatg tacgcttact acttcttggc    6180
tgcttgcttg agatcttccc caaagctcaa gaacaagtac ctcttctggg aagataacct    6240
cacccaattc cagatgttcc agttcatgct caacttggtg caagcttact acgatatgaa    6300
aaccaacgct ccatatccac aatggctcat caagatcctc ttctactaca tgatctccct    6360
cttgttcctc ttcggaaact tctacgtgca aagtacatc aagccatccg atggaaagca    6420
aaagggagct aagaccgagt gatcgacaag ctcgagtttc tccataataa tgtgtgagta    6480
```

```
gttcccagat aagggaatta gggttcctat agggtttcgc tcatgtgttg agcatataag    6540
aaacccttag tatgtatttg tatttgtaaa atacttctat caataaaatt tctaattcct    6600
aaaaccaaaa tccagtacta aaatccagat cccccgaatt aattcggcgt taattcaggg    6660
aaacttagca gatatttggt gtctaaatgt ttattttgtg atatgttcat gtttgaaatg    6720
gtggtttcga aaccagggac aacgttggga tctgataggg tgtcaaagag tattatggat    6780
tgggacaatt tcggtcatga gttgcaaatt caagtatatc gttcgattat gaaaattttc    6840
gaagaatatc ccatttgaga gagtctttac ctcattaatg ttttagatt atgaaatttt    6900 atcatagttc atcgtagtct ttttggtgta aaggctgtaa aaagaaattg ttcacttttg    6960
ttttcgttta tgtgaaggct gtaaaagatt gtaaaagact attttggtgt tttggataaa    7020
atgatagttt ttatagattc ttttgctttt agaagaaata catttgaaat tttttccatg    7080
ttgagtataa ataccgaaa tcgattgaag atcatagaaa tattttaact gaaaacaaat    7140
ttataactga ttcaattctc tccattttta tacctattta accgtaatcg attctaatag    7200
atgatcgatt ttttatataa tcctaattaa ccaacggcat gtattggata attaaccgat    7260
caactctcac ccctaataga atcagtattt tccttcgacg ttaattgatc ctacactatg    7320
taggtcatat ccatcgtttt aattttggc caccattcaa ttctgtcttg cctttaggga    7380
tgtgaatatg aacggccaag gtaagagaat aaaaataatc caaattaaag caagagaggc    7440
caagtaagat aatccaaatg tacacttgtc attgccaaaa ttagtaaaat actcggcata    7500
ttgtattccc acacattatt aaaataccgt atatgtattg gctgcatttg catgaataat    7560
actacgtgta agcccaaaag aacccacgtg tagcccatgc aaagttaaca ctcacgaccc    7620
cattcctcag tctccactat ataaacccac catcccaat ctcaccaaac ccaccacaca    7680
actcacaact cactctcaca ccttaaagaa ccaatcacca ccaaaaaacc atgggaaaag    7740
gatctgaggg aagatctgct gctagagaga tgactgctga ggctaacgga gataagagaa    7800
agaccatcct cattgaggga gtgttgtacg atgctaccaa cttcaaacac ccaggaggtt    7860
ccattattaa cttcctcacc gagggagaag ctggagttga tgctacccaa gcttacagag    7920
agttccatca gagatccgga aaggctgata agtacctcaa gtccctccca aagttggatg    7980
cttctaaggt ggagtctagg ttctctgcta aggagcaggc tagaagggac gctatgacca    8040
gggattacgc tgctttcaga gaggagttgg ttgctgaggg atacttcgat ccatctatcc    8100
cacacatgat ctacagagtg gtggagattg tggctttgtt cgctttgtct ttctggttga    8160
tgtctaaggc ttctccaacc tctttggttt tgggagtggt gatgaacgga atcgctcaag    8220
gaagatgcgg atgggttatg cacgagatgg gacacggatc tttcactgga gttatctggc    8280
tcgatgatag gatgtgcgag ttcttctacg gagttggatg tggaatgtct ggacactact    8340
ggaagaacca gcactctaag caccacgctg ctccaaacag attggagcac gatgtggatt    8400
tgaacacctt gccactcgtt gctttcaacg agagagttgt gaggaaggtt aagccaggat    8460
ctttgttggc tttgtggctc agagttcagg cttatttgtt cgctccagtg tcttgcttgt    8520
tgatcggatt gggatggacc ttgtacttgc acccaagata tatgctcagg accaagagac    8580
acatggagtt tgtgtggatc ttcgctagat atatcggatg gttctccttg atgggagctt    8640
tgggatattc tcctggaact tctgtgggaa tgtacctctg ctctttcgga cttggatgca    8700
tctacatctt cctccaattc gctgtgtctc acccacactt gccagttacc aacccagagg    8760
atcaattgca ctggcttgag tacgctgctg atcacaccgt gaacatctct accaagtctt    8820
ggttggttac ctggtggatg tctaacctca acttccaaat cgagcaccac ttgttcccaa    8880
```

```
ccgctccaca attcaggttc aaggagatct ctccaagagt tgaggctctc ttcaagagac    8940
acaacctccc ttactacgat ttgccataca cctctgctgt ttctactacc ttcgctaacc    9000
tctactctgt tggacactct gttggagctg ataccaagaa gcaggattga ctgctttaat    9060
gagatatgcg agacgcctat gatcgcatga tatttgcttt caattctgtt gtgcacgttg    9120
taaaaaacct gagcatgtgt agctcagatc cttaccgccg gtttcggttc attctaatga    9180
atatatcacc cgttactatc gtatttttat gaataatatt ctccgttcaa tttactgatt    9240
gtgtcgacgc gatcgcgtgc gcacgggccc cctgcaggat ttaaatcccg ggggtaccca    9300
agtttgtaca aaaaagcagg ctccatgatt acgccaagct tggccactaa ggccaattta    9360
aatctactag gccggccatc gacggcccgg actgtatcca acttctgatc tttgaatctc    9420
tctgttccaa catgttctga aggagttcta agacttttca gaaagcttgt aacatgcttt    9480
gtagactttc tttgaattac tcttgcaaac tctgattgaa cctacgtgaa aactgctcca    9540
gaagttctaa ccaaattccg tcttgggaag gcccaaaatt tattgagtac ttcagtttca    9600
tggacgtgtc ttcaaagatt tataacttga atcccatca ttttttaagag aagttctgtt    9660 ccgcaatgtc ttagatctca ttgaaatcta caactcttgt gtcagaagtt cttccagaat    9720
caacttgcat catggtgaaa atctggccag aagttctgaa cttgtcatat ttcttaacag    9780
ttagaaaaat ttctaagtgt ttagaatttt gacttttcca aagcaaactt gacttttgac    9840
tttcttaata aaacaaactt catattctaa catgtcttga tgaaatgtga ttcttgaaat    9900
ttgatgttga tgcaaaagtc aaagtttgac ttttcagtgt gcaattgacc attttgctct    9960
tgtgccaatt ccaaacctaa attgatgtat cagtgctgca aacttgatgt catggaagat   10020
cttatgagaa aattcttgaa gactgagagg aaaaatttg tagtacaaca caaagaatcc   10080 tgttttcat agtcggacta gacacattaa cataaaacac cacttcattc gaagagtgat   10140
tgaagaagga aatgtgcagt tacctttctg cagttcataa gagcaactta cagacacttt   10200
tactaaaata ctacaaagag gaagattta acaacttaga gaagtaatgg gagttaaaga   10260
gcaacacatt aagggggagt gttaaaatta atgtgttgta accaccacta cctttagtaa   10320
gtattataag aaaattgtaa tcatcacatt ataattattg tccttattta aaattatgat   10380
aaagttgtat cattaagatt gagaaaacca aatagtcctc gtcttgattt ttgaattatt   10440
gttttctatg ttactttct tcaagccttat ataaaaactt tgtaatgcta aattgtatgc   10500
tggaaaaaaa tgtgtaatga attgaataga aattatggta tttcaaagtc caaaatccat   10560
caatagaaat ttagtacaaa acgtaactca aaaatattct cttattttaa attttacaac   10620
aatataaaaa tattctctta ttttaaattt tacaataata taatttatca cctgtcacct   10680
ttagaatacc accaacaata ttaatactta gatattttat tcttaataat tttgagatct   10740
ctcaatatat ctgatattta ttttatattt gtgtcatatt ttcttatgtt ttagagttaa   10800
cccttatatc ttggtcaaac tagtaattca atatatgagt ttgtgaagga cacattgaca   10860
tcttgaaaca ttggttttaa ccttgttgga atgttaaagg taataaaaca ttcagaatta   10920
tgaccatcta ttaatatact tcctttgtct tttaaaaaag tgtgcatgaa aatgctctat   10980
ggtaagctag agtgtcttgc tggcctgtgt atatcaattc catttccaga tggtagaaac   11040
tgccactacg aataattagt cataagacac gtatgttaac acacgtcccc ttgcatgttt   11100
tttgccatat attccgtctc tttcttttc ttcacgtata aaacaatgaa ctaattaata   11160
gagcgatcaa gctgaaccct accatgtgtg ttgagaccga gaacaacgat ggaatccta   11220
```

```
ctgtggagat cgctttcgat ggagagagag aaagagctga ggctaacgtg aagttgtctg   11280
ctgagaagat ggaacctgct gctttggcta agaccttcgc tagaagatac gtggttatcg   11340
agggagttga gtacgatgtg accgatttca acatcctgg aggaaccgtg attttctacg    11400
ctctctctaa cactggagct gatgctactg aggctttcaa ggagttccac cacagatcta   11460
gaaaggctag gaaggctttg gctgctttgc cttctagacc tgctaagacc gctaaagtgg   11520
atgatgctga gatgctccag gatttcgcta agtggagaaa ggagttggag agggacggat   11580
tcttcaagcc ttctcctgct catgttgctt acagattcgc tgagttggct gctatgtacg   11640
ctttgggaac ctacttgatg tacgctagat acgttgtgtc ctctgtgttg gtttacgctt   11700
gcttcttcgg agctagatgt ggatgggttc aacacgaggg aggacactct tctttgaccg   11760
gaaacatctg gtgggataag agaatccaag cttcactgc tggattcgga ttggctggat     11820
ctggagatat gtggaactcc atgcacaaca agcaccacgc tactcctcaa aaagtgaggc   11880
acgatatgga tttggatacc actcctgctg ttgctttctt caacaccgct gtggaggata   11940
atagacctag gggattctct aagtactggc tcagattgca agcttggacc ttcattcctg   12000
tgacttctgg attggtgttg ctcttctgga tgttcttcct ccacccttct aaggctttga   12060
agggaggaaa gtacgaggag cttgtgtgga tgttggctgc tcacgtgatt agaacctgga   12120
ccattaaggc tgttactgga ttcaccgcta tgcaatccta cggactcttc ttggctactt   12180
cttgggtttc cggatgctac ttgttcgctc acttctctac ttctcacacc cacttggatg   12240
ttgttcctgc tgatgagcac ttgtcttggg ttaggtacgc tgtggatcac accattgata   12300
tcgatccttc tcagggatgg gttaactggt tgatgggata cttgaactgc caagtgattc   12360
accacctctt cccttctatg cctcaattca gacaacctga ggtgtccaga agattcgttg   12420 cttcgctaa gaagtggaac ctcaactaca aggtgatgac ttatgctgga gcttggaagg    12480
ctactttggg aaacctcgat aatgtgggaa agcactacta cgtgcacgga caacactctg   12540
gaaagaccgc ttgattaatt aaggccgcct cgaccgtacc ccctgcagat agactatact   12600
atgttttagc ctgcctgctg gctagctact atgttatgtt atgttgtaaa ataaacacct   12660
gctaaggtat atctatctat atttagcat ggctttctca ataaattgtc tttccttatc     12720
gtttactatc ttatacctaa taatgaaata ataatatcac atatgaggaa cggggcaggt   12780
ttaggcatat atatacgagt gtagggcgga gtgggggggcg cctactaccg gtaattcccg   12840
ggattagcgg ccgctagtct gtgcgcactt gtatcctgca ggttaggccg gccacacggg   12900
caggacatag ggactactac aagcatagta tgcttcagac aaagagctag gaaagaactc   12960
ttgatggagg ttaagagaaa aaagtgctag aggggcatag taatcaaact tgtcaaaacc   13020
gtcatcatga tgagggatga cataatataa aaagttgact aaggtcttgg tagtactctt   13080
tgattagtat tatatattgg tgagaacatg agtcaagagg agacaagaaa ccgaggaacc   13140
atagtttagc aacaagatgg aagttgcaaa gttgagctag ccgctcgatt agttacatct   13200
cctaagcagt actacaagga atggtctcta tactttcatg tttagcacat ggtagtgcgg   13260
attgacaagt tagaaacagt gcttaggaga caaagagtca gtaaaggtat tgaaagagtg   13320
aagttgatgc tcgacaggtc aggagaagtc cctccgccag atggtgacta ccaaggggtt   13380
ggtatcagct gagacccaaa taagattctt cggttgaacc agtggttcga ccgagactct   13440
tagggtggga tttcactgta agatttgtgc attttgttga atataaattg acaattttttt  13500 ttatttaatt atagattatt tagaatgaat tacatattta gtttctaaca aggatagcaa   13560
tggatgggta tgggtacagg ttaaacatat ctattaccca cccatctagt cgtcgggttt   13620
```

```
tacacgtacc cacccgttta cataaaccag accggaattt taaaccgtac ccgtccgtta   13680
gcgggtttca gatttacccg tttaatcggg taaaacctga ttactaaata tatatttttt   13740
atttgataaa caaaacaaaa atgttaatat tttcatattg gatgcaattt taagaaacac   13800
atattcataa atttccatat ttgtaggaaa ataaaaagaa aaatatattc aagaacacaa   13860
atttcaccga catgactttt attacagagt tggaattaga tctaacaatt gaaaaattaa   13920
aattaagata gaatatgttg aggaacatga catagtataa tgctgggtta cccgtcgggt   13980
aggtatcgag gcggatacta ctaaatccat cccactcgct atccgataat cactggtttc   14040
gggtataccc attcccgtca acaggccttt ttaaccggat aatttcaact tatagtgaat   14100
gaattttgaa taaatagtta gaataccaaa atcctggatt gcatttgcaa tcaaattttg   14160
tgaaccgtta aattttgcat gtacttggga tagatataat agaaccgaat tttcattagt   14220
ttaatttata acttactttg ttcaaagaaa aaaaatatct atccaattta cttataataa   14280
aaaataatct atccaagtta cttattataa tcaacttgta aaaaggtaag aatacaaatg   14340
tggtagcgta cgtgtgatta tatgtgacga aatgttatat ctaacaaaag tccaaattcc   14400
catggtaaaa aaaatcaaaa tgcatggcag gctgtttgta accttggaat aagatgttgg   14460
ccaattctgg agccgccacg tacgcaagac tcagggccac gttctcttca tgcaaggata   14520
gtagaacacc actccaccca cctcctatat tagacctttg cccaaccctc cccaactttc   14580
ccatcccatc cacaaagaaa ccgacatttt tatcataaat cggcgcgccc taccatggat   14640
gcttataacg ctgctatgga taagattgga gctgctatca tcgattggag tgatccagat   14700
ggaaagttca gagctgatag ggaggattgg tggttgtgcg atttcagatc cgctatcacc   14760
attgctctca tctacatcgc tttcgtgatc ttgggatctg ctgtgatgca atctctccca   14820
gctatggacc catcccctat caagttcctc tacaacgtgt ctcaaatctt cctctgcgct   14880
tacatgactg ttgaggctgg attcctcgct tataggaacg gatacaccgt tatgccatgc   14940
aaccacttca acgtgaacga tccaccagtt gctaacttgc tctggctctt ctacatctcc   15000
aaagtgtggg atttctggga taccatcttc attgtgctcg gaaagaagtg gagacaactc   15060
tctttcttgc acgtgtacca ccacaccacc atcttcctct tctactggtt gaacgctaac   15120
gtgctctacg atggagatat cttcttgacc atcctcctca acggattcat tcacaccgtg   15180
atgtacacct actacttcat ctgcatgcac accaaggatt ctaagaccgg aaagtctttg   15240
ccaatctggt ggaagtcatc tttgaccgct ttccaactct tgcaattcac catcatgatg   15300
tcccaagcta cctacttggt tttccacgga tgcgataagg tttccctcag aatcaccatc   15360
gtgtacttcg tgtacattct ctcccttttc ttcctcttcg ctcagttctt cgtgcaatcc   15420
tacatggctc caaagaagaa gaagtccgct tgatgttaat taaggccgca gatatcagat   15480
ctggtcgacc tagaggatcc ccggccgcaa agataataac aaaagcctac tatataacgt   15540
acatgcaagt attgtatgat attaatgttt ttacgtacgt gtaaacaaaa ataattacgt   15600
ttgtaacgta tggtgatgat gtggtgcact aggtgtaggc cttgtattaa taaaaagaag   15660
tttgttctat atagagtggt ttagtacgac gatttattta ctagtcggat tggaatagag   15720
aaccgaattc ttcaatcctt gcttttgatc aagaattgaa accgaatcaa atgtaaaagt   15780
tgatatattt gaaaaacgta ttgagcttat gaaaatgcta atactctcat ctgtatggaa   15840
aagtgacttt aaaaccgaac ttaaaagtga caaaagggga atatcgcatc aaaccgaatg   15900
aaaccgatgg caaacactgt acggaccgtg gcctaatagg ccggtaccac ccagctttct   15960
```

```
tgtacaaagt ggccatgatt acgccaagct tggccactaa ggccaattta aatctactag    16020
gccggccata aggatgacct acccattctt gagacaaatg ttacatttta gtatcagagt    16080
aaaatgtgta cctataactc aaattcgatt gacatgtatc cattcaacat aaaattaaac    16140
cagcctgcac ctgcatccac atttcaagta ttttcaaacc gttcggctcc tatccaccgg    16200
gtgtaacaag acggattccg aatttggaag attttgactc aaattcccaa tttatattga    16260
ccgtgactaa atcaacttta acttctataa ttctgattaa gctcccaatt tatattccca    16320
acggcactac ctccaaaatt tatagactct catccccttt taaaccaact tagtaaacgt    16380 tttttttta atttatgaa gttaagtttt taccttgttt ttaaaaagaa tcgttcataa    16440
gatgccatgc cagaacatta gctacacgtt acacatagca tgcagccgcg gagaattgtt    16500
tttcttcgcc acttgtcact cccttcaaac acctaagagc ttctctctca cagcacacac    16560
atacaatcac atgcgtgcat gcattattac acgtgatcgc catgcaaatc tcctttatag    16620
cctataaatt aactcatcgg cttcactctt tactcaaacc aaaactcatc aatacaaaca    16680
agattaaaaa caccatgcgc gccggatccg ccatggctat tttgaaccct gaggctgatt    16740
ctgctgctaa cctcgctact gattctgagg ctaagcaaag acaattggct gaggctggat    16800
acactcatgt tgagggtgct cctgctcctt gccttttgga gttgcctcat ttctctctca    16860
gagatctcag agctgctatt cctaagcact gcttcgagag atctttcgtg acctccacct    16920
actacatgat caagaacgtg ttgacttgcg ctgctttgtt ctacgctgct accttcattg    16980
atagagctgg agctgctgct tatgttttgt ggcctgtgta ctggttcttc cagggatctt    17040
acttgactgg agtgtgggtt atcgctcatg agtgtggaca tcaggcttat tgctcttctg    17100
aggtggtgaa caacttgatt ggactcgtgt tgcattctgc tttgttggtg ccttaccact    17160
cttggagaat ctctcacaga aagcaccatt ccaacactgg atcttgcgag aacgatgagg    17220
ttttcgttcc tgtgaccaga tctgtgttgg cttcttcttg gaacgagacc ttggaggatt    17280
ctcctctcta ccaactctac cgtatcgtgt acatgttggt tgttggatgg atgcctggat    17340
acctcttctt caacgctact ggacctacta agtactgggg aaagtctagg tctcacttca    17400
acccttactc cgctatctat gctgatagg agagatggat gatcgtgctc tccgatattt    17460
tcttggtggc tatgttggct gttttggctg ctttggtgca cactttctcc ttcaacacca    17520
tggtgaagtt ctacgtggtg ccttacttca ttgtgaacgc ttacttggtg ttgattacct    17580
acctccaaca caccgatacc tacatccctc atttcagaga gggagagtgg aattggttga    17640
gaggagcttt gtgcactgtg gatagatcat ttggtccatt cctcgattct gtggtgcata    17700
gaatcgtgga tacccatgtt tgccaccaca tcttctccaa gatgcctttc tatcattgcg    17760
aggaggctac caacgctatt aagcctctcc tcggaaagtt ctacttgaag gataccactc    17820
ctgttcctgt tgctctctgg agatcttaca cccattgcaa gttcgttgag gatgatggaa    17880
aggtggtgtt ctacaagaac aagctctagt taattaataa ttgattggtt cgagtattat    17940
ggcattggga aaactgtttt tcttgtacca tttgttgtgc ttgtaattta ctgtgttttt    18000
tattcggttt tcgctatcga actgtgaaat ggaaatggat ggagaagagt taatgaatga    18060
tatggtcctt ttgttcattc tcaaattaat attatttgtt ttttctctta tttgttgtgt    18120
gttgaatttg aaattataag agatatgcaa acattttgtt ttgagtaaaa atgtgtcaaa    18180
tcgtggcctc taatgaccga agttaatatg aggagtaaaa cacttgtagt tgtaccatta    18240
tgcttattca ctaggcaaca aatatatttt cagacctaga aaagctgcaa atgttactga    18300
atacaagtat gtcctcttgt gttttagaca tttatgaact ttcctttatg taattttcca    18360
```

```
gaatccttgt cagattctaa tcattgcttt ataattatag ttatactcat ggatttgtag    18420
ttgagtatga aaatattttt taatgcattt tatgacttgc caattgattg acaacatgca    18480
tcaatggcgc ctactaccgg taattcccgg gattagcggc cgctagtctg tgcgcacttg    18540
tatcctgcag gtcaatcgtt taaacactgt acggaccgtg gcctaatagg ccggtaccca    18600
actttattat acatagttga taattcactg gccggatgta ccgaattcgc ggccgcaagc    18660
ttgtacacta gtacgcgtca attggcgatc gcggatctga gatgaaaccg gtgattatca    18720 gaaccttta tggtctttgt atgcatatgg taaaaaaact tagtttgcaa tttcctgttt    18780
gttttggtaa tttgagtttc ttttagttgt tgatctgcct gcttttggt ttacgtcaga    18840 ctactactgc tgttgttgtt tggtttcctt tctttcattt tataaataaa taatccggtt    18900
cggtttactc cttgtgactg gctcagtttg gttattgcga aatgcgaatg gtaaattgag    18960
taattgaaat tcgttattag ggttctaagc tgttttaaca gtcactgggt taatatctct    19020
cgaatcttgc atggaaaatg ctcttaccat tggttttaa ttgaaatgtg ctcatatggg    19080
ccgtggtttc caaattaaat aaaactacga tgtcatcgag aagtaaaatc aactgtgtcc    19140
acattatcag ttttgtgtat acgatgaaat agggtaattc aaaatctagc ttgatatgcc    19200
ttttggttca ttttaacctt ctgtaaacat tttttcagat tttgaacaag taaatccaaa    19260
aaaaaaaaaa aaaatctca actcaacact aaattatttt aatgtataaa agatgcttaa    19320
aacatttggc ttaaaagaaa gaagctaaaa acatagagaa ctcttgtaaa ttgaagtatg    19380
aaaatatact gaattgggta ttatatgaat ttttctgatt taggattcac atgatccaaa    19440
aaggaaatcc agaagcacta atcagacatt ggaagtagga atatttcaaa aagtttttt    19500 tttttaagta agtgacaaaa gcttttaaaa aatagaaaag aaactagtat taaagttgta    19560
aatttaataa acaaaagaaa tttttatat tttttcattt cttttttccag catgaggtta    19620 tgatggcagg atgtggattt catttttttc cttttgatag cctttaatt gatctattat    19680 aattgacgaa aaaatattag ttaattatag atatatttta ggtagtatta gcaatttaca    19740
cttccaaaag actatgtaag ttgtaaatat gatgcgttga tctcttcatc attcaatggt    19800
tagtcaaaaa aataaaagct taactagtaa actaaagtag tcaaaaattg tactttagtt    19860
taaaatatta catgaataat ccaaaacgac atttatgtga aacaaaaaca atatagatcc    19920 attccctgt tatccctaga ggggaaaatt cgaatccaaa aattacggat atgaaatatag    19980 gcatatccgt atccgaatta tccgtttgac agctagcaac gattgtacaa ttgcttcttt    20040
aaaaaaggaa gaaagaaaga aagaaagaa tcaacatcag cgttaacaaa cggccccgtt    20100
acggcccaaa cggtcatata gagtaacggc gttaagcgtt gaaagactcc tatcgaaata    20160
cgtaaccgca aacgtgtcat agtcagatcc cctcttcctt caccgcctca aacacaaaaa    20220
taatcttcta cagcctatat atacaacccc cccttctatc tctcctttct cacaattcat    20280
catctttctt tctctacccc caattttaag aaatcctctc ttctcctctt catttttcaag    20340 gtaaatctct ctctctctct ctctctctgt tattccttgt tttaattagg tatgtattat    20400
tgctagtttg ttaatctgct tatcttatgt atgccttatg tgaatatctt tatcttgttc    20460
atctcatccg tttagaagct ataaatttgt tgatttgact gtgtatctac acgtggttat    20520
gtttatatct aatcagatat gaatttcttc atattgttgc gtttgtgtgt accaatccga    20580
aatcgttgat ttttttcatt taatcgtgta gctaattgta cgtatacata tggatctacg    20640
tatcaattgt tcatctgttt gtgtttgtat gtatacagat ctgaaaacat cacttctctc    20700
```

```
atctgattgt gttgttacat acatagatat agatctgtta tatcatttt  tttattaatt  20760
gtgtatatat atatgtgcat agatctggat tacatgattg tgattattta catgattttg  20820
ttatttacgt atgtatatat gtagatctgg acttttgga  gttgttgact tgattgtatt  20880
tgtgtgtgta tatgtgtgtt ctgatcttga tatgttatgt atgtgcagct gaaccatggc  20940
ggcggcaaca acaacaacaa caacatcttc ttcgatctcc ttctccacca aaccatctcc  21000
ttcctcctcc aaatcaccat taccaatctc cagattctcc ctccattct  ccctaaaccc  21060
caacaaatca tcctcctcct cccgccgccg cggtatcaaa tccagctctc cctcctccat  21120
ctccgccgtg ctcaacacaa ccaccaatgt cacaaccact ccctctccaa ccaaacctac  21180
caaacccgaa acattcatct cccgattcgc tccagatcaa ccccgcaaag cgctgatat   21240
cctcgtcgaa gctttagaac gtcaaggcgt agaaaccgta ttcgcttacc ctggaggtac  21300
atcaatggag attcaccaag ccttaacccg ctcttcctca atccgtaacg tccttcctcg  21360
tcacgaacaa ggaggtgtat tcgcagcaga aggatacgct cgatcctcag gtaaaccagg  21420
tatctgtata gccacttcag gtcccggagc tacaaatctc gttagcggat tagccgatgc  21480
gttgttagat agtgttcctc ttgtagcaat cacaggacaa gtccctcgtc gtatgattgg  21540
tacagatgcg tttcaagaga ctccgattgt tgaggtaacg cgttcgatta cgaagcataa  21600
ctatcttgtg atggatgttg aagatatccc taggattatt gaggaagctt tcttttagc   21660
tacttctggt agacctggac ctgttttggt tgatgttcct aaagatattc aacaacagct  21720
tgcgattcct aattgggaac aggctatgag attacctggt tatatgtcta ggatgcctaa  21780
acctccggaa gattctcatt tggagcagat tgttaggttg atttctgagt ctaagaagcc  21840
tgtgttgtat gttggtggtg gttgtttgaa ttctagcgat gaattgggta ggtttgttga  21900
gcttacgggg atccctgttg cgagtacgtt gatgggctg  ggatcttatc cttgtgatga  21960
tgagttgtcg ttacatatgc ttggaatgca tgggactgtg tatgcaaatt acgctgtgga  22020
gcatagtgat ttgttgttgg cgtttgggt  aaggtttgat gatcgtgtca cgggtaagct  22080
tgaggctttt gctagtaggg ctaagattgt tcatattgat attgactcgg ctgagattgg  22140
gaagaataag actcctcatg tgtctgtgtg tggtgatgtt aagctggctt tgcaagggat  22200
gaataaggtt cttgagaacc gagcggagga gcttaagctt gattttggag tttggaggaa  22260
tgagttgaac gtacagaaac agaagtttcc gttgagcttt aagacgtttg gggaagctat  22320
tcctccacag tatgcgatta aggtccttga tgagttgact gatggaaaag ccataataag  22380
tactggtgtc gggcaacatc aaatgtgggc ggcgcagttc tacaattaca agaaaccaag  22440
gcagtggcta tcatcaggag gccttggagc tatgggattt ggacttcctg ctgcgattgg  22500
agcgtctgtt gctaaccctg atgcgatagt tgtggatatt gacggagatg gaagctttat  22560
aatgaatgtg caagagctag ccactattcg tgtagagaat cttccagtga aggtactttt  22620
attaaacaac cagcatcttg gcatggttat gcaatgggaa gatcggttct acaaagctaa  22680
ccgagctcac acatttctcg gggatccggc tcaggaggac gagatattcc cgaacatgtt  22740
gctgtttgca gcagcttgcg ggattccagc ggcgagggtg acaaagaaag cagatctccg  22800
agaagctatt cagacaatgc tggatacacc aggaccttac ctgttggatg tgatttgtcc  22860
gcaccaagaa catgtgttgc cgatgatccc gaatggtggc actttcaacg atgtcataac  22920
ggaaggagat ggccggatta aatactgata gggataacag ggtaatctcg acgagatgaa  22980
accggtgatt atcagaacct tttatggtct ttgtatgcat atggtaaaaa aacttagttt  23040
gcaatttcct gtttgttttg gtaatttgag tttctttag  ttgttgatct gcctgctttt  23100
```

```
tggtttacgt cagactacta ctgctgttgt tgtttggttt cctttctttc attttataaa    23160
taaataatcc ggttcggttt actccttgtg actggctcag tttggttatt gcgaaatgcg    23220
aatggtaaat tgagtaattg aaattcgtta ttagggttct aagctgtttt aacagtcact    23280
gggttaatat ctctcgaatc ttgcatggaa aatgctctta ccattggttt ttaattgaaa    23340
tgtgctcata tgggccgtgg tttccaaatt aaataaaact acgatgtcat cgagaagtaa    23400
aatcaactgt gtccacatta tcagttttgt gtatacgatg aaatagggta attcaaaatc    23460
tagcttgata tgccttttgg ttcattttaa ccttctgtaa acatttttc agattttgaa    23520 caagtaaatc caaaaaaaaa aaaaaaaat ctcaactcaa cactaaatta ttttaatgta    23580
taaaagatgc ttaaaacatt tggcttaaaa gaaagaagct aaaaacatag agaactcttg    23640
taaattgaag tatgaaaata tactgaattg ggtattatat gaattttct gatttaggat    23700 tcacatgatc caaaaaggaa atccagaagc actaatcaga cattggaagt aggaatattt    23760
caaaaagttt ttttttttta agtaagtgac aaaagctttt aaaaaataga aagaaacta    23820 gtattaaagt tgtaaattta ataaacaaaa gaatttttt atatttttc atttcttttt    23880 ccagcatgag gttatgatgg caggatgtgg atttcatttt tttccttttg atagcctttt    23940
aattgatcta ttataattga cgaaaaaata ttagttaatt atagatatat tttaggtagt    24000
attagcaatt tacacttcca aaagactatg taagttgtaa atatgatgcg ttgatctctt    24060
catcattcaa tggttagtca aaaaataaa agcttaacta gtaaactaaa gtagtcaaaa    24120
attgtacttt agtttaaaat attacatgaa taatccaaaa cgacatttat gtgaaacaaa    24180
aacaatatgt cgaggcgatc gcagtactta atcagtgatc agtaactaaa ttcagtacat    24240
taaagacgtc cgcaatgtgt tattaagttg tctaagcgtc aatttgttta caccacaata    24300
tatcctgcca ccagccagcc aacagctccc cgaccggcag ctcggcacaa aatcac       24356
```

<210> SEQ ID NO 40
<211> LENGTH: 27539
<212> TYPE: DNA
<213> ORGANISM: Artificial Sequence
<220> FEATURE:
<223> OTHER INFORMATION: Plant Expression Plasmid

<400> SEQUENCE: 40

```
aaaagttgcc atgattacgc caagcttggc cactaaggcc aatttcgcgc cctgcagcaa      60
atttacacat tgccactaaa cgtctaaacc cttgtaattt gttttgtttt tactatgtgt     120
gttatgtatt tgatttgcga taaattttta tatttggtac taaatttata acaccttta     180 tgctaacgtt tgccaacact tagcaatttg caagttgatt aattgattct aaaattatttt    240 tgtcttctaa atacatatac taatcaactg gaaatgtaaa tatttgctaa tatttctact    300
ataggagaat taaagtgagt gaatatggta ccacaaggtt tggagattta attgttgcaa    360
tgctgcatgg atggcatata caccaaacat tcaataattc ttgaggataa taatggtacc    420
acacaagatt tgaggtgcat gaacgtcacg tggacaaaag gtttagtaat ttttcaagac    480
aacaatgtta ccacacacaa gttttgaggt gcatgcatgg atgccctgtg gaaagtttaa    540
aaatattttg gaaatgattt gcatggaagc catgtgtaaa accatgacat ccacttggag    600
gatgcaataa tgaagaaaac tacaaattta catgcaacta gttatgcatg tagtctatat    660
aatgaggatt ttgcaaatact ttcattcata cacactcact aagttttaca cgattataat    720
ttcttcatag ccagtactgt ttaagcttca ctgtctctga atcggcaaag gtaaacgtat    780
```

```
caattattct acaaaccctt ttattttttct tttgaattac cgtcttcatt ggttatatga    840
taacttgata agtaaagctt caataattga atttgatctg tgttttttttg gccttaatac    900
taaatcctta cataagcttt gttgcttctc ctcttgtgag ttgagtgtta agttgtaata    960
atggttcact ttcagcttta gaagaaacca tggaagttgt tgagaggttc tacggagagt   1020
tggatggaaa ggtttcccaa ggagtgaacg ctttgttggg atctttcgga gttgagttga   1080
ctgataccccc aactactaag ggattgccac tcgttgattc tccaactcca attgtgttgg   1140
gagtgtctgt ttacttgacc atcgtgatcg gaggattgct ttggatcaag gctagagatc   1200
tcaagccaag agcttctgag ccattcttgt tgcaagcttt ggtgttggtg cacaacttgt   1260
tctgcttcgc tttgtctctt tacatgtgcg tgggtatcgc ttaccaagct atcacctgga   1320
gatattcctt gtggggaaac gcttataacc caaagcacaa ggagatggct atcctcgttt   1380
acctcttcta catgtccaag tacgtggagt tcatggatac cgtgatcatg atcctcaaga   1440
gatccaccag acagatttct ttcctccacg tgtaccacca ctcttctatc tcccttatct   1500
ggtgggctat tgctcaccac gctccaggag agaggcttaa ttggagtgct gctctcaact   1560
ctggagtgca cgtgttgatg tacgcttact acttcttggc tgcttgcttg agatcttccc   1620
caaagctcaa gaacaagtac ctcttctggg aagatacct cacccaattc cagatgttcc    1680
agttcatgct caacttggtg caagcttact acgatatgaa aaccaacgct ccatatccac   1740
aatggctcat caagatcctc ttctactaca tgatctccct cttgttcctc ttcggaaact   1800
tctacgtgca aaagtacatc aagccatccg atggaaagca aaagggagct aagaccgagt   1860
gatcgacaag ctcgagtttc tccataataa tgtgtgagta gttcccagat aagggaatta   1920
gggttcctat agggtttcgc tcatgtgttg agcatataag aaacccttag tatgtatttg   1980
tatttgtaaa atacttctat caataaaatt tctaattcct aaaaccaaaa tccagtacta   2040
aaatccagat cccccgaatt aattcggcgt taattcaggg ccggccaaag taggcgccta   2100
ctaccggtaa ttccccgggat tagccggccgc tagtctgtgc gcacttgtat cctgcaggtt   2160
aggccggcca ttagcagata tttggtgtct aaatgtttat tttgtgatat gttcatgttt   2220
gaaatggtgg tttcgaaacc agggacaacg ttgggatctg ataggggtgtc aaagagtatt   2280
atggattggg acaatttcgg tcatgagttg caaattcaag tatatcgttc gattatgaaa   2340
attttcgaag aatatcccat ttgagagagt ctttacctca ttaatgtttt tagattatga   2400
aatttttatca tagttcatcg tagtcttttt ggtgtaaagg ctgtaaaaag aaattgttca   2460
cttttgttttt cgtttatgtg aaggctgtaa aagattgtaa aagactattt tggtgttttg   2520
gataaaatga tagttttttat agattctttt gcttttagaa gaaatacatt tgaaattttt   2580
tccatgttga gtataaaata ccgaaatcga ttgaagatca tagaaatatt ttaactgaaa   2640
acaaatttat aactgattca attctctcca tttttatacc tatttaaccg taatcgattc   2700
taatagatga tcgattttttt atataatcct aattaaccaa cggcatgtat tggataatta   2760
accgatcaac tctcaccccct aatagaatca gtattttcct tcgacgttaa ttgatcctac   2820
actatgtagg tcatatccat cgtttttaatt tttggccacc attcaattct gtcttgcctt   2880
tagggatgtg aatatgaacg gccaaggtaa gagaataaaa ataatccaaa ttaaagcaag   2940
agaggccaag taagataatc caaatgtaca cttgtcattg ccaaaattag taaaatactc   3000
ggcatattgt attcccacac attattaaaa taccgtatat gtattggctg catttgcatg   3060
aataatacta cgtgtaagcc caaaagaacc cacgtgtagc ccatgcaaag ttaacactca   3120
cgaccccatt cctcagtctc cactatataa acccaccatc cccaatctca ccaaacccac   3180
```

```
cacacaactc acaactcact ctcacacctt aaagaaccaa tcaccaccaa aaaatttcac    3240
gatttggaat ttgattcctg cgatcacagg tatgacaggt tagattttgt tttgtatagt    3300
tgtatacata cttctttgtg atgttttgtt tacttaatcg aattttggga gtgttttaag    3360
gtctctcgtt tagaaatcgt ggaaaatatc actgtgtgtg tgttcttatg attcacagtg    3420
tttatgggtt tcatgttctt tgttttatca ttgaatggga agaaatttcg ttgggataca    3480
aatttctcat gttcttactg atcgttatta ggagtttggg gaaaaaggaa gagtttttt     3540 ggttggttcg agtgattatg aggttatttc tgtatttgat ttatgagtta atggtcgttt    3600
taatgttgta gaccatggga aaaggatctg agggaagatc tgctgctaga gagatgactg    3660
ctgaggctaa cggagataag agaaagacca tcctcattga gggagtgttg tacgatgcta    3720
ccaacttcaa acacccagga ggttccatta ttaacttcct caccgaggga gaagctggag    3780
ttgatgctac ccaagcttac agagagttcc atcagagatc cggaaaggct gataagtacc    3840
tcaagtccct cccaaagttg gatgcttcta aggtggagtc taggttctct gctaaggagc    3900
aggctagaag ggacgctatg accagggatt acgctgcttt cagagaggag ttggttgctg    3960
agggatactt cgatccatct atcccacaca tgatctacag agtggtggag attgtggctt    4020
tgttcgcttt gtcttctctgg ttgatgtcta aggcttctcc aacctctttg gttttgggag    4080
tggtgatgaa cggaatcgct caaggaagat gcggatgggt tatgcacgag atgggacacg    4140
gatctttcac tggagttatc tggctcgatg ataggatgtg cgagttcttc tacgagttg     4200 gatgtggaat gtctggacac tactggaaga accagcactc taagcaccac gctgctccaa    4260
acagattgga gcacgatgtg gatttgaaca ccttgccact cgttgctttc aacgagagag    4320
ttgtgaggaa ggttaagcca ggatctttgt tggctttgtg gctcagagtt caggcttatt    4380
tgttcgctcc agtgtcttgc ttgttgatcg gattgggatg gaccttgtac ttgcacccaa    4440
gatatatgct caggaccaag agacacatgg agtttgtgtg gatcttcgct agatatatcg    4500
gatggttctc cttgatggga gctttgggat attctcctgg aacttctgtg ggaatgtacc    4560
tctgctcttt cggacttgga tgcatctaca tcttcctcca attcgctgtg tctcacaccc    4620
acttgccagt taccaaccca gaggatcaat tgcactggct tgagtacgct gctgatcaca    4680
ccgtgaacat ctctaccaag tcttggttgg ttacctggtg gatgtctaac ctcaacttcc    4740
aaatcgagca ccacttgttc ccaaccgctc cacaattcag gttcaaggag atctctccaa    4800
gagttgaggc tctcttcaag agacacaacc tcccttacta cgatttgcca tacacctctg    4860
ctgtttctac taccttcgct aacctctact ctgttggaca ctctgttgga gctgatacca    4920
agaagcagga ttgactgctt taatgagata tgcgagacgc ctatgatcgc atgatatttg    4980
ctttcaattc tgttgtgcac gttgtaaaaa acctgagcat gtgtagctca gatccttacc    5040
gccggtttcg gttcattcta atgaatatat cacccgttac tatcgtattt ttatgaataa    5100
tattctccgt tcaatttact gattgtgtcg acgcgatcgc gtgcaaacac tgtacggacc    5160
gtggcctaat aggccggtac ccaagtttgt acaaaaaagc aggctccatg attacgccaa    5220
gcttggccac taaggccaat ttaaatctac taggccggcc atcgacggcc cggactgtat    5280
ccaacttctg atctttgaat ctctctgttc aacatgttc tgaaggagtt ctaagacttt     5340
tcagaaagct tgtaacatgc tttgtagact ttctttgaat tactcttgca aactctgatt    5400
gaacctacgt gaaaactgct ccagaagttc taaccaaatt ccgtcttggg aaggcccaaa    5460
atttattgag tacttcagtt tcatggacgt gtcttcaaag atttataact tgaaatccca    5520
```

```
tcatttttaa gagaagttct gttccgcaat gtcttagatc tcattgaaat ctacaactct    5580
tgtgtcagaa gttcttccag aatcaacttg catcatggtg aaaatctggc cagaagttct    5640
gaacttgtca tatttcttaa cagttagaaa aatttctaag tgtttagaat tttgacttttt   5700 ccaaagcaaa cttgactttt gactttctta ataaaacaaa cttcatattc taacatgtct    5760
tgatgaaatg tgattcttga aatttgatgt tgatgcaaaa gtcaaagttt gacttttcag    5820
tgtgcaattg accattttgc tcttgtgcca attccaaacc taaattgatg tatcagtgct    5880
gcaaacttga tgtcatggaa gatcttatga gaaaattctt gaagactgag aggaaaaatt    5940
ttgtagtaca acacaaagaa tcctgttttt catagtcgga ctagacacat taacataaaa    6000
caccacttca ttcgaagagt gattgaagaa ggaaatgtgc agttaccttt ctgcagttca    6060
taagagcaac ttacagacac ttttactaaa atactacaaa gaggaagatt ttaacaactt    6120
agagaagtaa tgggagttaa agagcaacac attaaggggg agtgttaaaa ttaatgtgtt    6180
gtaaccacca ctacctttag taagtattat aagaaaattg taatcatcac attataatta    6240
ttgtccttat ttaaaattat gataaagttg tatcattaag attgagaaaa ccaaatagtc    6300
ctcgtcttga tttttgaatt attgttttct atgttacttt tcttcaagcc tatataaaaa    6360
ctttgtaatg ctaaattgta tgctggaaaa aaatgtgtaa tgaattgaat agaaattatg    6420
gtatttcaaa gtccaaaatc catcaataga aatttagtac aaaacgtaac tcaaaaatat    6480
tctcttattt taaattttac aacaatataa aaatattctc ttattttaaa ttttacaata    6540
atataattta tcacctgtca cctttagaat accaccaaca atattaatac ttagatattt    6600
tattcttaat aattttgaga tctctcaata tatctgatat ttatttata tttgtgtcat     6660 attttcttat gttttagagt taacccttat atcttggtca aactagtaat tcaatatatg    6720
agtttgtgaa ggacacattg acatcttgaa acattggttt taaccttgtt ggaatgttaa    6780
aggtaataaa acattcagaa ttatgaccat ctattaatat acttcctttg tcttttaaaa    6840
aagtgtgcat gaaaatgctc tatggtaagc tagagtgtct tgctggcctg tgtatatcaa    6900
ttccatttcc agatggtaga aactgccact acgaataatt agtcataaga cacgtatgtt    6960
aacacacgtc cccttgcatg ttttttgcca tatattccgt ctctttcttt tcttcacgt     7020 ataaaacaat gaactaatta atagagcgat caagctgaac tggtgcttaa acactctggt    7080
gagttctagt acttctgcta tgatcgatct cattaccatt tcttaaattt ctctccctaa    7140
atattccgag ttcttgattt ttgataactt caggttttct cttttgata aatctggtct     7200 ttccattttt ttttttttgt ggttaattta gtttcctatg ttcttcgatt gtattatgca    7260
tgatctgtgt ttggattctg ttagattatg tattggtgaa tatgtatgtg ttttttgcatg   7320 tctggttttg gtcttaaaaa tgttcaaatc tgatgatttg attgaagctt ttttagtgtt    7380
ggtttgattc ttctcaaaac tactgttaat ttactatcat gttttccaac tttgattcat    7440
gatgacactt ttgttctgct ttgttataaa attttggttg gtttgatttt gtaattatag    7500
tgtaattttg ttaggaatga acatgttttta atactctgtt ttcgatttgt cacacattcg   7560
aattattaat cgataattta actgaaaatt catggttcta gatcttgttg tcatcagatt    7620
atttgtttcg ataattcatc aaatatgtag tccttttgct gatttgcgac tgtttcattt    7680
tttctcaaaa ttgttttttg ttaagtttat ctaacagtta tcgttgtcaa agtctctttt    7740
cattttgcaa aatcttcttt tttttttttgt ttgtaacttt gttttttaag ctacacattt   7800
agtctgtaaa atagcatcga ggaacagttg tcttagtaga cttgcatgtt cttgtaactt    7860
ctatttgttt cagtttgttg atgactgctt tgattttgta ggtcaaaggc gcgcctacca    7920
```

```
tgtgtgttga gaccgagaac aacgatggaa tccctactgt ggagatcgct ttcgatggag    7980
agagagaaag agctgaggct aacgtgaagt tgtctgctga gaagatggaa cctgctgctt    8040
tggctaagac cttcgctaga agatacgtgg ttatcgaggg agttgagtac gatgtgaccg    8100
atttcaaaca tcctggagga accgtgattt tctacgctct ctctaacact ggagctgatg    8160
ctactgaggc tttcaaggag ttccaccaca gatctagaaa ggctaggaag gctttggctg    8220
cttttgcctt ctagacctgct aagaccgcta aagtggatga tgctgagatg ctccaggatt    8280
tcgctaagtg gagaaaggag ttggagaggg acggattctt caagccttct cctgctcatg    8340
ttgcttacag attcgctgag ttggctgcta tgtacgcttt gggaacctac ttgatgtacg    8400
ctagatacgt tgtgtcctct gtgttggttt acgcttgctt cttcggagct agatgtggat    8460
gggttcaaca cgagggagga cactcttctt tgaccggaaa catctggtgg gataagagaa    8520
tccaagcttt cactgctgga ttcggattgg ctggatctgg agatatgtgg aactccatgc    8580
acaacaagca ccacgctact cctcaaaaag tgaggcacga tatggatttg gataccactc    8640
ctgctgttgc tttcttcaac accgctgtgg aggataatag acctagggga ttctctaagt    8700
actggctcag attgcaagct tggaccttca ttcctgtgac ttctggattg gtgttgctct    8760
tctggatgtt cttcctccac ccttctaagg cttttgaaggg aggaaagtac gaggagcttg    8820
tgtggatgtt ggctgctcac gtgattagaa cctggaccat taaggctgtt actggattca    8880
ccgctatgca atcctacgga ctcttcttgg ctacttcttg ggtttccgga tgctacttgt    8940
tcgctcactt ctctacttct cacacccact ggatgttgt tcctgctgat gagcacttgt    9000
cttgggttag gtacgctgtg gatcacacca ttgatatcga tccttctcag ggatgggtta    9060
actggttgat gggatacttg aactgccaag tgattcacca cctcttccct tctatgcctc    9120
aattcagaca acctgaggtg tccagaagat tcgttgcttt cgctaagaag tggaacctca    9180
actacaaggt gatgacttat gctggagctt ggaaggctac tttgggaaac ctcgataatg    9240
tgggaaagca ctactacgtg cacggacaac actctggaaa gaccgcttga ttaattaact    9300
aagactccca aaaccacctt ccctgtgaca gttaaaccct gcttatacct ttcctcctaa    9360
taatgttcat ctgtcacaca aactaaaata aataaaatgg gagcaataaa taaaatggga    9420
gctcatatat ttacaccatt tacactgtct attattcacc atgccaatta ttacttcata    9480 atttttaaaat tatgtcattt ttaaaaattg cttaatgatg gaaaggatta ttataagtta    9540
aaagtataac atagataaac taaccacaaa acaaatcaat ataaactaac ttactctccc    9600
atctaatttt tatttaaatt tctttacact tctcttccat ttctatttct acaacattat    9660
ttaacatttt tattgtattt ttcttacttt ctaactctat tcatttcaaa aatcaatata    9720
tgtttatcac cacctctcta aaaaaaactt tacaatcatt ggtccagaaa agttaaatca    9780
cgagatggtc attttagcat taaaacaacg attcttgtat cactattttt cagcatgtag    9840
tccattctct tcaaacaaag acagcggcta tataatcgtt gtgttatatt cagtctaaaa    9900
caaggcgcct actaccggta attcccggga ttagcggccg ctagtctgtg cgcacttgta    9960
tcctgcaggt taggccggcc acacgggcag gacataggga ctactacaag catagtatgc   10020
ttcagacaaa gagctaggaa agaactcttg atggaggtta agagaaaaaa gtgctagagg   10080
ggcatagtaa tcaaacttgt caaaaccgtc atcatgatga gggatgacat aatataaaaa   10140
gttgactaag gtcttggtag tactcttttga ttagtattat atattggtga gaacatgagt   10200
caagaggaga caagaaaccg aggaaccata gtttagcaac aagatggaag ttgcaaagtt   10260
```

```
gagctagccg ctcgattagt tacatctcct aagcagtact acaaggaatg gtctctatac   10320
tttcatgttt agcacatggt agtgcggatt gacaagttag aaacagtgct taggagacaa   10380
agagtcagta aaggtattga aagagtgaag ttgatgctcg acaggtcagg agaagtccct   10440
ccgccagatg gtgactacca aggggttggt atcagctgag acccaaataa gattcttcgg   10500
ttgaaccagt ggttcgaccg agactcttag ggtgggattt cactgtaaga tttgtgcatt   10560
ttgttgaata taaattgaca attttttttta tttaattata gattatttag aatgaattac   10620
atatttagtt tctaacaagg atagcaatgg atgggtatgg gtacaggtta aacatatcta   10680
ttacccaccc atctagtcgt cgggttttac acgtacccac ccgtttacat aaaccagacc   10740
ggaattttaa accgtacccg tccgttagcg ggtttcagat ttacccgttt aatcgggtaa   10800
aacctgatta ctaaatatat attttttatt tgataaacaa aacaaaaatg ttaatatttt   10860
catattggat gcaattttaa gaaacacata ttcataaatt tccatatttg taggaaaata   10920
aaaagaaaaa tatattcaag aacacaaatt tcaccgacat gacttttatt acagagttgg   10980
aattagatct aacaattgaa aaattaaaat taagatagaa tatgttgagg aacatgacat   11040
agtataatgc tgggttaccc gtcgggtagg tatcgaggcg gatactacta aatccatccc   11100
actcgctatc cgataatcac tggtttcggg tatacccatt cccgtcaaca ggccttttta   11160
accggataat ttcaacttat agtgaatgaa ttttgaataa atagttagaa taccaaaatc   11220
ctggattgca tttgcaatca aattttgtga accgttaaat tttgcatgta cttgggatag   11280
atataataga accgaatttt cattagttta atttataact tactttgttc aaagaaaaaa   11340
aatatctatc caatttactt ataataaaaa ataatctatc caagttactt attataatca   11400
acttgtaaaa aggtaagaat acaaatgtgg tagcgtacgt gtgattatat gtgacgaaat   11460
gttatatcta acaaaagtcc aaattcccat ggtaaaaaaa atcaaaatgc atggcaggct   11520
gtttgtaacc ttggaataag atgttggcca attctggagc cgccacgtac gcaagactca   11580
gggccacgtt ctcttcatgc aaggatagta gaacaccact ccacccacct cctatattag   11640
acctttgccc aaccctcccc aactttccca tcccatccac aaagaaaccg acattttat   11700 cataaatcag ggtttcgttt ttgtttcatc gataaactca aaggtgatga ttttagggtc   11760
ttgtgagtgt gctttttttgt ttgattctac tgtagggttt atgttcttta gctcataggt   11820
tttgtgtatt tcttagaaat gtggcttctt taatctctgg gtttgtgact ttttgtgtgg   11880
tttctgtgtt tttcatatca aaaacctatt ttttccgagt ttttttttac aaattcttac   11940
tctcaagctt gaatacttca catgcagtgt tcttttgtag attttagagt taatgtgtta   12000
aaaagtttgg atttttcttg cttatagagc ttcttcacttt tgattttgtg ggttttttttg   12060 ttttaaaggt gagattttttg atgaggtttt tgcttcaaag atgtcacctt tctgggtttg   12120
tcttttgaat aaagctatga actgtcacat ggctgacgca atttttgttac tatgtcatga   12180 aagctgacgt ttttccgtgt tatacatgtt gcttacact tgcatgcgtc aaaaaaattg   12240
gggcttttta gttttagtca aagattttac ttctcttttg ggatttatga aggaaagttg   12300
caaactttct caaattttac cattttttgct ttgatgtttg tttagattgc gacagaacaa   12360
actcatatat gttgaaattt tgcttggtt ttgtatagga ttgtgtcttt tgcttataaa   12420
tgttgaaatc tgaactttttt ttttgtttgg tttctttgag caggagataa ggcgcgccct   12480
accatggatg cttataacgc tgctatggat aagattggag ctgctatcat cgattggagt   12540
gatccagatg gaaagttcag agctgatagg gaggattggt ggttgtgcga tttcagatcc   12600
gctatcacca ttgctctcat ctacatcgct ttcgtgatct tgggatctgc tgtgatgcaa   12660
```

```
tctctcccag ctatggaccc ataccctatc aagttcctct acaacgtgtc tcaaatcttc    12720
ctctgcgctt acatgactgt tgaggctgga ttcctcgctt ataggaacgg ataccgtt     12780 atgccatgca accacttcaa cgtgaacgat ccaccagttg ctaacttgct ctggctcttc    12840
tacatctcca aagtgtggga tttctgggat accatcttca ttgtgctcgg aaagaagtgg    12900
agacaactct ctttcttgca cgtgtaccac cacaccacca tcttcctctt ctactggttg    12960
aacgctaacg tgctctacga tggagatatc ttcttgacca tcctcctcaa cggattcatt    13020
cacaccgtga tgtacaccta ctacttcatc tgcatgcaca ccaaggattc taagaccgga    13080
aagtctttgc caatctggtg gaagtcatct ttgaccgctt tccaactctt gcaattcacc    13140
atcatgatgt cccaagctac ctacttggtt ttccacggat gcgataaggt ttccctcaga    13200
atcaccatcg tgtacttcgt gtacattctc tcccttttct tcctcttcgc tcagttcttc    13260
gtgcaatcct acatggctcc aaagaagaag aagtccgctt gatgttaatt aaggccgcag    13320
atatcagatc tggtcgacct agaggatccc cggccgcaaa gataataaca aaagcctact    13380
atataacgta catgcaagta ttgtatgata ttaatgtttt tacgtacgtg taaacaaaaa    13440
taattacgtt tgtaacgtat ggtgatgatg tggtgcacta ggtgtaggcc ttgtattaat    13500
aaaaagaagt ttgttctata tagagtggtt tagtacgacg atttatttac tagtcggatt    13560
ggaatagaga accgaattct tcaatccttg cttttgatca agaattgaaa ccgaatcaaa    13620
tgtaaaagtt gatatatttg aaaaacgtat tgagcttatg aaaatgctaa tactctcatc    13680
tgtatggaaa agtgacttta aaaccgaact taaaagtgac aaaaggggaa tatcgcatca    13740
aaccgaatga aaccgatggc gcctaccggt atcggtccga ttgcggccgc ttaaagggcg    13800
aattcgttta aacactgtac ggaccgtggc ctaataggcc ggtaccaccc agctttcttg    13860
tacaaagtgg ccatgattac gccaagcttg gccactaagg ccaatttaaa tctactaggc    13920
cggccataag gatgacctac ccattcttga gacaaatgtt acattttagt atcagagtaa    13980
aatgtgtacc tataactcaa attcgattga catgtatcca ttcaacataa aattaaacca    14040
gcctgcacct gcatccacat ttcaagtatt ttcaaaccgt tcggctccta tccaccgggt    14100
gtaacaagac ggattccgaa tttggaagat tttgactcaa attcccaatt tatattgacc    14160
gtgactaaat caactttaac ttctataatt ctgattaagc tcccaattta tattcccaac    14220
ggcactacct ccaaaattta tagactctca tcccctttta aaccaactta gtaaacgttt    14280 ttttttaat tttatgaagt taagttttta ccttgttttt aaaaagaatc gttcataaga    14340
tgccatgcca gaacattagc tacacgttac acatagcatg cagccgcgga gaattgtttt    14400
tcttcgccac ttgtcactcc cttcaaacac ctaagagctt ctctctcaca gcacacacat    14460
acaatcacat gcgtgcatgc attattacac gtgatcgcca tgcaaatctc ctttatagcc    14520
tataaattaa ctcatcggct tcactcttta ctcaaaccaa aactcatcaa tacaaacaag    14580
attaaaaaca agttctttgc tttcgaagtt gccgcaacct aaacaggttt ttccttcttc    14640
tttcttctta ttaactacga ccttgtcctt tgcctatgta aaattactag gttttcatca    14700
gttacactga ttaagttcgt tatagtggaa gataaaatgc cctcaaagca ttttgcagga    14760
tatctttgat ttttcaaaga tatggaactg tagagtttga tagtgttctt gaatgtggtt    14820
gcatgaagtt ttttggtct gcatgttatt ttttcctcga aatatgtttt gagtccaaca    14880
agtgattcac ttgggattca gaaagttgtt ttctcaatat gtaacagttt ttttctatgg    14940
agaaaaatca tagggaccgt tggttttggc ttctttaatt ttgagctcag attaaaccca    15000
```

```
ttttacccgg tgttcttggc agaattgaaa acagtacgta gtaccgccat ggctattttg    15060
aaccctgagg ctgattctgc tgctaacctc gctactgatt ctgaggctaa gcaaagacaa    15120
ttggctgagg ctggatacac tcatgttgag ggtgctcctg ctcctttgcc tttggagttg    15180
cctcatttct ctctcagaga tctcagagct gctattccta agcactgctt cgagagatct    15240
ttcgtgacct ccacctacta catgatcaag aacgtgttga cttgcgctgc tttgttctac    15300
gctgctacct tcattgatag agctggagct gctgcttatg ttttgtggcc tgtgtactgg    15360
ttcttccagg gatcttactt gactggagtg tgggttatcg ctcatgagtg tggacatcag    15420
gcttattgct cttctgaggt ggtgaacaac ttgattggac tcgtgttgca ttctgctttg    15480
ttggtgcctt accactcttg gagaatctct cacagaaagc accattccaa cactggatct    15540
tgcgagaacg atgaggtttt cgttcctgtg accagatctg tgttggcttc ttcttggaac    15600
gagaccttgg aggattctcc tctctaccaa ctctaccgta tcgtgtacat gttggttgtt    15660
ggatggatgc ctggatacct cttcttcaac gctactggac ctactaagta ctggggaaag    15720
tctaggtctc acttcaaccc ttactccgct atctatgctg ataggagag atggatgatc      15780 gtgctctccg atattttctt ggtggctatg ttggctgttt tggctgcttt ggtgcacact    15840
ttctccttca acaccatggt gaagttctac gtggtgcctt acttcattgt gaacgcttac    15900
ttggtgttga ttacctacct ccaacacacc gatacctaca tccctcattt cagagaggga    15960
gagtggaatt ggttgagagg agctttgtgc actgtggata gatcatttgg tccattcctc    16020
gattctgtgg tgcatagaat cgtggatacc catgtttgcc accacatctt ctccaagatg    16080
cctttctatc attgcgagga ggctaccaac gctattaagc ctctcctcgg aaagttctac    16140
ttgaaggata ccactcctgt tcctgttgct ctctggagat cttacaccca ttgcaagttc    16200
gttgaggatg atggaaaggt ggtgttctac aagaacaagc tctagttaat taataattga    16260
ttggttcgag tattatggca ttgggaaaac tgttttctct gtaccatttg ttgtgcttgt    16320
aatttactgt gttttttatt cggttttcgc tatcgaactg tgaaatggaa atggatggag    16380
aagagttaat gaatgatatg gtccttttgt tcattctcaa attaatatta tttgttttt      16440 ctcttatttg ttgtgtgttg aatttgaaat tataagagat atgcaaacat tttgttttga    16500
gtaaaaatgt gtcaaatcgt ggcctctaat gaccgaagtt aatatgagga gtaaaacact    16560
tgtagttgta ccattatgct tattcactag gcaacaaata tattttcaga cctagaaaag    16620
ctgcaaatgt tactgaatac aagtatgtcc tcttgtgttt tagacattta tgaactttcc    16680
tttatgtaat tttccagaat ccttgtcaga ttctaatcat tgctttataa ttatagttat    16740
actcatggat ttgtagttga gtatgaaaat attttttaat gcattttatg acttgccaat    16800
tgattgacaa catgcatcaa tggcgcctac taccggtaat tcccgggatt agcggccgct    16860
agtctgtgcg cacttgtatc ctgcaggtca atcgtttaaa cactgtacgg accgtggcct    16920
aataggccgg tacccaactt tattatacat agttgataat tcactggccg gatgtaccga    16980
attcgcggcc gcaagcttgt acactagtac gcgtcaattg gcgatcgcgg atctgagatg    17040
aaaccggtga ttatcagaac cttttatggt ctttgtatgc atatggtaaa aaacttagt     17100 ttgcaatttc ctgtttgttt tggtaatttg agtttctttt agttgttgat ctgcctgctt    17160
tttggtttac gtcagactac tactgctgtt gttgtttggt ttccttttctt tcattttata   17220 aataaataat ccggttcggt ttactccttg tgactggctc agtttggtta ttgcgaaatg    17280
cgaatggtaa attgagtaat tgaaattcgt tattagggt ctaagctgtt ttaacagtca      17340
ctgggttaat atctctcgaa tcttgcatgg aaaatgctct taccattggt ttttaattga    17400
```

```
aatgtgctca tatgggccgt ggtttccaaa ttaaataaaa ctacgatgtc atcgagaagt  17460
aaaatcaact gtgtccacat tatcagtttt gtgtatacga tgaaataggg taattcaaaa  17520
tctagcttga tatgccttt ggttcatttt aaccttctgt aaacatttt tcagattttg   17580
aacaagtaaa tccaaaaaaa aaaaaaaaaa atctcaactc aacactaaat tattttaatg  17640
tataaagat gcttaaaaca tttggcttaa aagaagaag ctaaaaacat agagaactct   17700
tgtaaattga agtatgaaaa tatactgaat tgggtattat atgaattttt ctgatttagg  17760
attcacatga tccaaaaagg aaatccagaa gcactaatca gacattggaa gtaggaatat  17820
ttcaaaaagt ttttttttt taagtaagtg acaaaagctt ttaaaaaata gaaagaaac    17880
tagtattaaa gttgtaaatt taataaacaa agaaatttt ttatatttt tcatttcttt   17940
ttccagcatg aggttatgat ggcaggatgt ggatttcatt ttttccttt tgatagcctt   18000
ttaattgatc tattataatt gacgaaaaaa tattagttaa ttatagatat attttaggta  18060
gtattagcaa tttacacttc caaaagacta tgtaagttgt aaatatgatg cgttgatctc  18120
ttcatcattc aatggttagt caaaaaaata aaagcttaac tagtaaacta agtagtcaa   18180
aaattgtact ttagtttaaa atattacatg aataatccaa aacgacattt atgtgaaaca  18240
aaaacaatat agatccatta ccctgttatc cctagagggg aaaattcgaa tccaaaaatt  18300
acggatatga atataggcat atccgtatcc gaattatccg tttgacagct agcaacgatt  18360
gtacaattgc ttcttaaaa aaggaagaaa gaaagaaaga aaagaatcaa catcagcgtt   18420
aacaaacggc cccgttacgg cccaaacggt catatagagt aacggcgtta agcgttgaaa  18480
gactcctatc gaaatacgta accgcaaacg tgtcatagtc agatcccctc ttccttcacc   18540
gcctcaaaca caaaaataat cttctacagc ctatatatac aaccccccct tctatctctc  18600
ctttctcaca attcatcatc tttctttctc tacccccaat tttaagaaat cctctcttct  18660
cctcttcatt ttcaaggtaa atctctctct ctctctctct ctctgttatt ccttgtttta  18720
attaggtatg tattattgct agtttgttaa tctgcttatc ttatgtatgc cttatgtgaa  18780
tatctttatc ttgttcatct catccgttta gaagctataa atttgttgat ttgactgtgt  18840
atctacacgt ggttatgttt atatctaatc agatatgaat ttcttcatat tgttgcgttt  18900
gtgtgtacca atccgaaatc gttgattttt ttcatttaat cgtgtagcta attgtacgta  18960
tacatatgga tctacgtatc aattgttcat ctgtttgtgt ttgtatgtat acagatctga  19020
aaacatcact tctctcatct gattgtgttg ttacatacat agatatagat ctgttatatc  19080
atttttttta ttaattgtgt atatatatat gtgcatagat ctggattaca tgattgtgat  19140
tatttacatg attttgttat ttacgtatgt atatatgtag atctggactt tttggagttg  19200
ttgacttgat tgtatttgtg tgtgtatatg tgtgttctga tcttgatatg ttatgtatgt  19260
gcagctgaac catggcggcg gcaacaacaa caacaacaac atcttcttcg atctccttct  19320
ccaccaaacc atctccttcc tcctccaaat caccattacc aatctccaga ttctccctcc  19380
cattctccct aaacccaac aaatcatcct cctcctcccg ccgccgcggt atcaaatcca   19440
gctctccctc ctccatctcc gccgtgctca acacaaccac caatgtcaca accactccct  19500
ctccaaccaa acctaccaaa cccgaaacat tcatctcccg attcgctcca gatcaacccc  19560
gcaaaggcgc tgatatcctc gtcgaagctt tagaacgtca aggcgtagaa accgtattcg  19620
cttaccctgg aggtacatca atggagattc accaagcctt aacccgctct tcctcaatcc  19680
gtaacgtcct tcctcgtcac gaacaaggag gtgtattcgc agcagaagga tacgctcgat  19740
```

```
cctcaggtaa accaggtatc tgtatagcca cttcaggtcc cggagctaca aatctcgtta    19800
gcggattagc cgatgcgttg ttagatagtg ttcctcttgt agcaatcaca ggacaagtcc    19860
ctcgtcgtat gattggtaca gatgcgtttc aagagactcc gattgttgag gtaacgcgtt    19920
cgattacgaa gcataactat cttgtgatgg atgttgaaga tatccctagg attattgagg    19980
aagctttctt tttagctact tctggtagac ctggacctgt tttggttgat gttcctaaag    20040
atattcaaca acagcttgcg attcctaatt gggaacaggc tatgagatta cctggttata    20100
tgtctaggat gcctaaacct ccggaagatt ctcatttgga gcagattgtt aggttgattt    20160
ctgagtctaa gaagcctgtg ttgtatgttg gtggtggttg tttgaattct agcgatgaat    20220
tgggtaggtt tgttgagctt acggggatcc ctgttgcgag tacgttgatg gggctgggat    20280
cttatccttg tgatgatgag ttgtcgttac atatgcttgg aatgcatggg actgtgtatg    20340
caaattacgc tgtggagcat agtgatttgt tgttggcgtt tggggtaagg tttgatgatc    20400
gtgtcacggg taagcttgag cttttgcta gtagggctaa gattgttcat attgatattg    20460
actcggctga gattgggaag aataagactc ctcatgtgtc tgtgtgtggt gatgttaagc    20520
tggctttgca agggatgaat aaggttcttg agaaccgagc ggaggagctt aagcttgatt    20580
ttggagtttg gaggaatgag ttgaacgtac agaaacagaa gtttccgttg agctttaaga    20640
cgtttgggga agctattcct ccacagtatg cgattaaggt ccttgatgag ttgactgatg    20700
gaaaagccat aataagtact ggtgtcgggc aacatcaaat gtgggcggcg cagttctaca    20760
attacaagaa accaaggcag tggctatcat caggaggcct tggagctatg ggatttggac    20820
ttcctgctgc gattggagcg tctgttgcta accctgatgc gatagttgtg gatattgacg    20880
gagatggaag ctttataatg aatgtgcaag agctagccac tattcgtgta gagaatcttc    20940
cagtgaaggt actttatta aacaaccagc atcttggcat ggttatgcaa tgggaagatc    21000
ggttctacaa agctaaccga gctcacacat ttctcgggga tccggctcag gaggacgaga    21060
tattcccgaa catgttgctg tttgcagcag cttgcgggat tccagcggcg agggtgacaa    21120
agaaagcaga tctccgagaa gctattcaga caatgctgga tacaccagga ccttacctgt    21180
tggatgtgat ttgtccgcac caagaacatg tgttgccgat gatcccgaat ggtggcactt    21240
tcaacgatgt cataacggaa ggagatggcc ggattaaata ctgatagga taacagggta    21300 atctcgacga gatgaaaccg gtgattatca gaaccttta tggtctttgt atgcatatgg    21360
taaaaaaact tagtttgcaa tttcctgttt gttttggtaa tttgagttc ttttagttgt    21420 tgatctgcct gcttttggt ttacgtcaga ctactactgc tgttgttgtt tggtttcctt    21480
tctttcattt tataaataaa taatccggtt cggtttactc cttgtgactg gctcagtttg    21540
gttattgcga aatgcgaatg gtaaattgag taattgaaat tcgttattag ggttctaagc    21600
tgttttaaca gtcactgggt taatatctct cgaatcttgc atggaaaatg ctcttaccat    21660 tggttttttaa ttgaaatgtg ctcatatggg ccgtggtttc caaattaaat aaaactacga    21720
tgtcatcgag aagtaaaatc aactgtgtcc acattatcag ttttgtgtat acgatgaaat    21780
agggtaattc aaaatctagc ttgatatgcc ttttggttca ttttaacctt ctgtaaacat    21840
tttttcagat tttgaacaag taaatccaaa aaaaaaaaaa aaaatctca actcaacact    21900 aaattatttt aatgtataaa agatgcttaa acatttggc ttaaagaaa gaagctaaaa    21960 acatagagaa ctcttgtaaa ttgaagtatg aaaatatact gaattgggta ttatatgaat    22020
ttttctgatt taggattcac atgatccaaa aaggaaatcc agaagcacta atcagacatt    22080
ggaagtagga atatttcaaa aagtttttttt ttttttaagta agtgacaaaa gctttttaaaa    22140
```

```
aatagaaaag aaactagtat taaagttgta aatttaataa acaaaagaaa tttttttatat    22200 tttttcattt cttttttccag catgaggtta tgatggcagg atgtggattt catttttttc    22260
cttttgatag cctttttaatt gatctattat aattgacgaa aaaatattag ttaattatag    22320
atatatttta ggtagtatta gcaatttaca cttccaaaag actatgtaag ttgtaaatat    22380
gatgcgttga tctcttcatc attcaatggt tagtcaaaaa aataaaagct taactagtaa    22440
actaaagtag tcaaaaattg tactttagtt taaaatatta catgaataat ccaaaacgac    22500
atttatgtga aacaaaaaca atatgtcgag gcgatcgcag tacttaatca gtgatcagta    22560
actaaattca gtacattaaa gacgtccgca atgtgttatt aagttgtcta agcgtcaatt    22620
tgtttacacc acaatatatc ctgccaccag ccagccaaca gctccccgac cggcagctcg    22680
gcacaaaatc actgatcatc taaaaaggtg atgtgtattt gagtaaaaca gcttgcgtca    22740
tgcggtcgct gcgtatatga tgcgatgagt aaataaacaa atacgcaagg ggaacgcatg    22800
aaggttatcg ctgtacttaa ccagaaaggc gggtcaggca agacgaccat cgcaacccat    22860
ctagcccgcg ccctgcaact cgccggggcc gatgttctgt tagtcgattc cgatccccag    22920
ggcagtgccc gcgattgggc ggccgtgcgg gaagatcaac cgctaaccgt tgtcggcatc    22980
gaccgcccga cgattgaccg cgacgtgaag gccatcggcc ggcgcgactt cgtagtgatc    23040
gacggagcgc cccaggcggc ggacttggct gtgtccgcga tcaaggcagc cgacttcgtg    23100
ctgattccgg tgcagccaag cccttacgac atttgggcca ccgccgacct ggtggagctg    23160
gttaagcagc gcattgaggt cacggatgga aggctacaag cggcctttgt cgtgtcgcgg    23220
gcgatcaaag gcacgcgcat cggcggtgag gttgccgagg cgctggccgg gtacgagctg    23280
cccattcttg agtcccgtat cacgcagcgc gtgagctacc caggcactgc cgccgccggc    23340
acaaccgttc ttgaatcaga acccgagggc gacgctgccc gcgaggtcca ggcgctggcc    23400
gctgaaatta aatcaaaact catttgagtt aatgaggtaa agagaaaatg agcaaaagca    23460
caaacacgct aagtgccggc cgtccgagcg cacgcagcag caaggctgca acgttggcca    23520
gcctggcaga cacgccagcc atgaagcggg tcaactttca gttgccggcg gaggatcaca    23580
ccaagctgaa gatgtacgcg gtacgccaag gcaagaccat taccgagctg ctatctgaat    23640
acatcgcgca gctaccagag taaatgagca aatgaataaa tgagtagatg aattttagcg    23700
gctaaaggag gcggcatgga aaatcaagaa caaccaggca ccgacgccgt ggaatgcccc    23760
atgtgtggag gaacgggcgg ttggccaggc gtaagcggct gggttgtctg ccggccctgc    23820
aatggcactg gaacccccaa gcccgaggaa tcggcgtgag cggtcgcaaa ccatccggcc    23880
cggtacaaat cggcgcggcg ctgggtgatg acctggtgga gaagttgaag gccgcgcagg    23940
ccgcccagcg gcaacgcatc gaggcagaag cacgccccgg tgaatcgtgg caaggggccg    24000
ctgatcgaat ccgcaaagaa tcccggcaac cgccggcagc cggtgcgccg tcgattagga    24060
agccgcccaa gggcgacgag caaccagatt ttttcgttcc gatgctctat gacgtgggca    24120
cccgcgatag tcgcagcatc atggacgtgg ccgttttccg tctgtcgaag cgtgaccgac    24180
gagctggcga ggtgatccgc tacgagcttc cagacgggca cgtagaggtt ccgcaggcc    24240 ccgccggcat ggccagtgtg tgggattacg acctggtact gatggcggtt tcccatctaa    24300
ccgaatccat gaaccgatac cgggaaggga agggagacaa gcccggccgc gtgttccgtc    24360
cacacgttgc ggacgtactc aagttctgcc ggcgagccga tggcggaaag cagaaagacg    24420
acctggtaga aacctgcatt cggttaaaca ccacgcacgt tgccatgcag cgtaccaaga    24480
```

-continued

```
aggccaagaa cggccgcctg gtgacggtat ccgagggtga agccttgatt agccgctaca   24540
agatcgtaaa gagcgaaacc gggcggccgg agtacatcga gatcgagctt gctgattgga   24600
tgtaccgcga gatcacagaa ggcaagaacc cggacgtgct gacggttcac cccgattact   24660
ttttgatcga ccccggcatc ggccgttttc tctaccgcct ggcacgccgc gccgcaggca   24720
aggcagaagc cagatggttg ttcaagacga tctacgaacg cagtggcagc gccggagagt   24780
tcaagaagtt ctgtttcacc gtgcgcaagc tgatcgggtc aaatgacctg ccggagtacg   24840
atttgaagga ggaggcgggg caggctggcc cgatcctagt catgcgctac cgcaacctga   24900
tcgagggcga agcatccgcc ggttcctaat gtacggagca gatgctaggg caaattgccc   24960
tagcagggga aaaggtcga aaggtctct ttcctgtgga tagcacgtac attgggaacc   25020
caaagccgta cattgggaac cggaacccgt acattgggaa cccaaagccg tacattggga   25080
accggtcaca catgtaagtg actgatataa aagagaaaaa aggcgatttt ccgcctaaa   25140
actctttaaa acttattaaa actcttaaaa cccgcctggc ctgtgcataa ctgtctggcc   25200
agcgcacagc cgaagagctg caaaaagcgc ctacccttcg gtcgctgcgc tcctacgcc   25260
ccgccgcttc gcgtcggcct atcgcggcct atgcggtgtg aaataccgca cagatgcgta   25320
aggagaaaat accgcatcag gcgctcttcc gcttcctcgc tcactgactc gctgcgctcg   25380
gtcgttcggc tgcggcgagc ggtatcagct cactcaaagg cggtaatacg gttatccaca   25440
gaatcagggg ataacgcagg aaagaacatg tgagcaaaag gccagcaaaa ggccaggaac   25500
cgtaaaaagg ccgcgttgct ggcgtttttc cataggctcc gcccccctga cgagcatcac   25560
aaaaatcgac gctcaagtca gaggtggcga acccgacag gactataaag ataccaggcg   25620
tttccccctg gaagctccct cgtgcgctct cctgttccga ccctgccgct taccggatac   25680
ctgtccgcct ttctcccttc gggaagcgtg gcgctttctc atagctcacg ctgtaggtat   25740
ctcagttcgg tgtaggtcgt tcgctccaag ctgggctgtg tgcacgaacc ccccgttcag   25800
cccgaccgct gcgccttatc cggtaactat cgtcttgagt ccaacccggt aagacacgac   25860
ttatcgccac tggcagcagc cactggtaac aggattagca gagcgaggta tgtaggcggt   25920
gctacagagt tcttgaagtg gtggcctaac tacggctaca ctagaaggac agtatttggt   25980
atctgcgctc tgctgaagcc agttaccttc ggaaaaagag ttggtagctc ttgatccggc   26040
aaacaaacca ccgctggtag cggtggtttt tttgtttgca agcagcagat tacgcgcaga   26100
aaaaaaggat ctcaagaaga tcctttgatc ttttctacgg ggtccttcaa ctcatcgata   26160
gtttggctgt gagcaattat gtgcttagtg catctaacgc ttgagttaag ccgcgccgcg   26220
aagcggcgtc ggcttgaacg aatttctagc tagacattat ttgccaacga ccttcgtgat   26280
ctcgcccttg acatagtgga caaattcttc gagctggtcg gcccgggacg cgagacggtc   26340
ttcttcttgg cccagatagg cttggcgcgc ttcgaggatc acgggctggt attgcgccgg   26400
aaggcgctcc atcgcccagt cggcggcgac atccttcggc gcgatcttgc cggtaaccgc   26460
cgagtaccaa atccggctca gcgtaaggac cacattgcgc tcatcgcccg cccaatccgg   26520
cggggagttc cacagggtca gcgtctcgtt cagtgcttcg aacagatcct gttccggcac   26580
cgggtcgaaa agttcctcgg ccgcggggcc gacgagggcc acgctatgct cccgggcctt   26640
ggtgagcagg atcgccagat caatgtcgat ggtggccggt tcaaagatac ccgccagaat   26700
atcattacgc tgccattcgc cgaactggag ttcgcgtttg ccggatagc gccaggggat   26760
gatgtcatcg tgcaccacaa tcgtcacctc aaccgcgcgc aggatttcgc tctcgccggg   26820
ggaggcggac gtttccagaa ggtcgttgat aagcgcgcgg cgcgtggtct cgtcgagacg   26880
```

-continued

```
gacggtaacg gtgacaagca ggtcgatgtc cgaatggggc ttaaggccgc cgtcaacggc    26940
gctaccatac agatgcacgg cgaggagggt cggttcgagg tggcgctcga tgacacccac    27000
gacttccgac agctgggtgg acacctcggc gatgaccgct tcacccatga tgttttaactt   27060 tgttttaggg cgactgccct gctgcgtaac atcgttgctg ctccataaca tcaaacatcg    27120
acccacggcg taacgcgctt gctgcttgga tgcccgaggc atagactgta ccccaaaaaa    27180
acagtcataa caagccatga aaaccgccac tgcgttccat gaatattcaa acaaacacat    27240
acagcgcgac ttatcatgga tattgacata caaatggacg aacggataaa ccttttcacg    27300 ccctttttaaa tatccgatta ttctaataaa cgctcttttc tcttaggttt acccgccaat   27360
atatcctgtc aaacactgat agtttaaact gaaggcggga aacgacaatc tgatcactga    27420
ttagtaacta aggcctttaa ttaatctaga ggcgcgccgg gccccctgca gggagctcgg    27480
ccggccaatt taaattgata tcggtacatc gattacgcca agctatcaac tttgtatag    27539
```

```
<210> SEQ ID NO 41
<211> LENGTH: 161
<212> TYPE: DNA
<213> ORGANISM: Artificial Sequence
<220> FEATURE:
<223> OTHER INFORMATION: Primer

<400> SEQUENCE: 41
aagcttggcc actaaggcca atttaaatct actaggccgg ccaaagtagg cgcctactac      60
cggtaattcc cgggattagc ggccgctagt ctgtgcgcac ttgtatcctg caggtcaatc    120
gtttaaacac tgtacggacc gtggcctaat aggccggtac c                        161

<210> SEQ ID NO 42
<211> LENGTH: 24
<212> TYPE: DNA
<213> ORGANISM: Artificial Sequence
<220> FEATURE:
<223> OTHER INFORMATION: Primer

<400> SEQUENCE: 42
tggtgcttaa acactctggt gagt                                            24

<210> SEQ ID NO 43
<211> LENGTH: 26
<212> TYPE: DNA
<213> ORGANISM: Artificial Sequence
<220> FEATURE:
<223> OTHER INFORMATION: Primer

<400> SEQUENCE: 43
tttgacctac aaaatcaaag cagtca                                          26

<210> SEQ ID NO 44
<211> LENGTH: 22
<212> TYPE: DNA
<213> ORGANISM: Artificial Sequence
<220> FEATURE:
<223> OTHER INFORMATION: Primer

<400> SEQUENCE: 44
agttctttgc tttcgaagtt gc                                              22

<210> SEQ ID NO 45
<211> LENGTH: 23
<212> TYPE: DNA
```

```
<213> ORGANISM: Artificial Sequence
<220> FEATURE:
<223> OTHER INFORMATION: Primer

<400> SEQUENCE: 45
tactacgtac tgttttcaat tct                                          23

<210> SEQ ID NO 46
<211> LENGTH: 25
<212> TYPE: DNA
<213> ORGANISM: Artificial Sequence
<220> FEATURE:
<223> OTHER INFORMATION: Primer

<400> SEQUENCE: 46
atttccacac gctttctatc atttc                                        25

<210> SEQ ID NO 47
<211> LENGTH: 30
<212> TYPE: DNA
<213> ORGANISM: Artificial Sequence
<220> FEATURE:
<223> OTHER INFORMATION: Primer

<400> SEQUENCE: 47
ttatctctct ctaaaaaata aaaacgaatc                                   30

<210> SEQ ID NO 48
<211> LENGTH: 21
<212> TYPE: DNA
<213> ORGANISM: Artificial Sequence
<220> FEATURE:
<223> OTHER INFORMATION: Primer

<400> SEQUENCE: 48
gtccagaatt ttctccattg a                                            21

<210> SEQ ID NO 49
<211> LENGTH: 22
<212> TYPE: DNA
<213> ORGANISM: Artificial Sequence
<220> FEATURE:
<223> OTHER INFORMATION: Primer

<400> SEQUENCE: 49
tcttcactat ccaaagctct ca                                           22

<210> SEQ ID NO 50
<211> LENGTH: 25
<212> TYPE: DNA
<213> ORGANISM: Artificial Sequence
<220> FEATURE:
<223> OTHER INFORMATION: Primer

<400> SEQUENCE: 50
gtctactttc attacagtga ctctg                                        25

<210> SEQ ID NO 51
<211> LENGTH: 27
<212> TYPE: DNA
<213> ORGANISM: Artificial Sequence
<220> FEATURE:
<223> OTHER INFORMATION: Primer

<400> SEQUENCE: 51
ttatatttta cctgcaacac aattcaa                                      27
```

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
cactcgaata ctgcatgcaa                                              20

<210> SEQ ID NO 53
<211> LENGTH: 26
<212> TYPE: DNA
<213> ORGANISM: Artificial Sequence
<220> FEATURE:
<223> OTHER INFORMATION: Primer

<400> SEQUENCE: 53
ttatgtagcc tttacacaga aaacaa                                       26

<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
aacaactatg gcctgagggt                                              20

<210> SEQ ID NO 55
<211> LENGTH: 32
<212> TYPE: DNA
<213> ORGANISM: Artificial Sequence
<220> FEATURE:
<223> OTHER INFORMATION: Primer

<400> SEQUENCE: 55
ttatcttact gttttttaacc aaaaaataaa at                               32

<210> SEQ ID NO 56
<211> LENGTH: 24
<212> TYPE: DNA
<213> ORGANISM: Artificial Sequence
<220> FEATURE:
<223> OTHER INFORMATION: Primer

<400> SEQUENCE: 56
atcttagggt ttcgcgagat ctca                                         24

<210> SEQ ID NO 57
<211> LENGTH: 30
<212> TYPE: DNA
<213> ORGANISM: Artificial Sequence
<220> FEATURE:
<223> OTHER INFORMATION: Primer

<400> SEQUENCE: 57
tgctaagcta tctctgttaa tataaaattg                                   30

<210> SEQ ID NO 58
<211> LENGTH: 22
<212> TYPE: DNA
<213> ORGANISM: Artificial Sequence
<220> FEATURE:

<223> OTHER INFORMATION: Primer

<400> SEQUENCE: 58
atttttgttg gtgaaaggta ga                                        22

<210> SEQ ID NO 59
<211> LENGTH: 25
<212> TYPE: DNA
<213> ORGANISM: Artificial Sequence
<220> FEATURE:
<223> OTHER INFORMATION: Primer

<400> SEQUENCE: 59
ttacgttttt gtctctgctt cttct                                     25

<210> SEQ ID NO 60
<211> LENGTH: 24
<212> TYPE: DNA
<213> ORGANISM: Artificial Sequence
<220> FEATURE:
<223> OTHER INFORMATION: Primer

<400> SEQUENCE: 60
tctgggaaat atcgattttg atct                                      24

<210> SEQ ID NO 61
<211> LENGTH: 21
<212> TYPE: DNA
<213> ORGANISM: Artificial Sequence
<220> FEATURE:
<223> OTHER INFORMATION: Primer

<400> SEQUENCE: 61
tctcaccaca tcccaaagct c                                         21

<210> SEQ ID NO 62
<211> LENGTH: 23
<212> TYPE: DNA
<213> ORGANISM: Artificial Sequence
<220> FEATURE:
<223> OTHER INFORMATION: Primer

<400> SEQUENCE: 62
gcacaatctt agcttacctt gaa                                       23

<210> SEQ ID NO 63
<211> LENGTH: 25
<212> TYPE: DNA
<213> ORGANISM: Artificial Sequence
<220> FEATURE:
<223> OTHER INFORMATION: Primer

<400> SEQUENCE: 63
ttatttaatc cacaagcctt gcctc                                     25

<210> SEQ ID NO 64
<211> LENGTH: 17
<212> TYPE: DNA
<213> ORGANISM: Artificial Sequence
<220> FEATURE:
<223> OTHER INFORMATION: Primer

<400> SEQUENCE: 64
tgtcggagaa gtgggcg                                              17

```
<210> SEQ ID NO 65
<211> LENGTH: 15
<212> TYPE: DNA
<213> ORGANISM: Artificial Sequence
<220> FEATURE:
<223> OTHER INFORMATION: Primer

<400> SEQUENCE: 65
agaagtgggc ggacg                                                    15

<210> SEQ ID NO 66
<211> LENGTH: 25
<212> TYPE: DNA
<213> ORGANISM: Artificial Sequence
<220> FEATURE:
<223> OTHER INFORMATION: Primer

<400> SEQUENCE: 66
tagcttaatc tcagattcga atcgt                                         25

<210> SEQ ID NO 67
<211> LENGTH: 28
<212> TYPE: DNA
<213> ORGANISM: Artificial Sequence
<220> FEATURE:
<223> OTHER INFORMATION: Primer

<400> SEQUENCE: 67
tagtatctac ataccaatca tacaaatg                                      28

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
tttcacgatt tggaatttga                                               20

<210> SEQ ID NO 69
<211> LENGTH: 24
<212> TYPE: DNA
<213> ORGANISM: Artificial Sequence
<220> FEATURE:
<223> OTHER INFORMATION: Primer

<400> SEQUENCE: 69
tctacaacat taaaacgacc atta                                          24

<210> SEQ ID NO 70
<211> LENGTH: 20
<212> TYPE: DNA
<213> ORGANISM: Artificial Sequence
<220> FEATURE:
<223> OTHER INFORMATION: Primer

<400> SEQUENCE: 70
agggtttcgt ttttgtttca                                               20

<210> SEQ ID NO 71
<211> LENGTH: 23
<212> TYPE: DNA
<213> ORGANISM: Artificial Sequence
<220> FEATURE:
<223> OTHER INFORMATION: Primer
```

```
<400> SEQUENCE: 71
ttatctcctg ctcaaagaaa cca                                            23

<210> SEQ ID NO 72
<211> LENGTH: 21
<212> TYPE: DNA
<213> ORGANISM: Artificial Sequence
<220> FEATURE:
<223> OTHER INFORMATION: Primer

<400> SEQUENCE: 72
agaagctcat ttcttcgata c                                              21

<210> SEQ ID NO 73
<211> LENGTH: 20
<212> TYPE: DNA
<213> ORGANISM: Artificial Sequence
<220> FEATURE:
<223> OTHER INFORMATION: Primer

<400> SEQUENCE: 73
tctctgcgca aaaattcacc                                                20

<210> SEQ ID NO 74
<211> LENGTH: 19
<212> TYPE: DNA
<213> ORGANISM: Artificial Sequence
<220> FEATURE:
<223> OTHER INFORMATION: Primer

<400> SEQUENCE: 74
tctaaaaata cagggcacc                                                 19

<210> SEQ ID NO 75
<211> LENGTH: 23
<212> TYPE: DNA
<213> ORGANISM: Artificial Sequence
<220> FEATURE:
<223> OTHER INFORMATION: Primer

<400> SEQUENCE: 75
ttactcttcg ttgcagaagc cta                                            23

<210> SEQ ID NO 76
<211> LENGTH: 21
<212> TYPE: DNA
<213> ORGANISM: Artificial Sequence
<220> FEATURE:
<223> OTHER INFORMATION: Primer

<400> SEQUENCE: 76
actgtttaag cttcactgtc t                                              21

<210> SEQ ID NO 77
<211> LENGTH: 20
<212> TYPE: DNA
<213> ORGANISM: Artificial Sequence
<220> FEATURE:
<223> OTHER INFORMATION: Primer

<400> SEQUENCE: 77
tttcttctaa agctgaaagt                                                20

<210> SEQ ID NO 78
<211> LENGTH: 27
```

```
<212> TYPE: DNA
<213> ORGANISM: Artificial Sequence
<220> FEATURE:
<223> OTHER INFORMATION: Primer

<400> SEQUENCE: 78
ttaagctttt aagaatctct actcaca                                        27

<210> SEQ ID NO 79
<211> LENGTH: 29
<212> TYPE: DNA
<213> ORGANISM: Artificial Sequence
<220> FEATURE:
<223> OTHER INFORMATION: Primer

<400> SEQUENCE: 79
ttaaatttta cctgtcatca aaaacaaca                                      29

<210> SEQ ID NO 80
<211> LENGTH: 24
<212> TYPE: DNA
<213> ORGANISM: Artificial Sequence
<220> FEATURE:
<223> OTHER INFORMATION: Primer

<400> SEQUENCE: 80
tcgacggccc ggactgtatc caac                                           24

<210> SEQ ID NO 81
<211> LENGTH: 48
<212> TYPE: DNA
<213> ORGANISM: Artificial Sequence
<220> FEATURE:
<223> OTHER INFORMATION: Primer

<400> SEQUENCE: 81
actcaccaga gtgtttaagc accagttcag cttgatcgct ctattaat                 48

<210> SEQ ID NO 82
<211> LENGTH: 48
<212> TYPE: DNA
<213> ORGANISM: Artificial Sequence
<220> FEATURE:
<223> OTHER INFORMATION: Primer

<400> SEQUENCE: 82
attaatagag cgatcaagct gaactggtgc ttaaacactc tggtgagt                 48

<210> SEQ ID NO 83
<211> LENGTH: 24
<212> TYPE: DNA
<213> ORGANISM: Artificial Sequence
<220> FEATURE:
<223> OTHER INFORMATION: Primer

<400> SEQUENCE: 83
taaggatgac ctacccattc ttga                                           24

<210> SEQ ID NO 84
<211> LENGTH: 46
<212> TYPE: DNA
<213> ORGANISM: Artificial Sequence
<220> FEATURE:
<223> OTHER INFORMATION: Primer

<400> SEQUENCE: 84
```
gcaacttcga aagcaaagaa cttgttttta atcttgtttg tattga　　　　　　46

<210> SEQ ID NO 85
<211> LENGTH: 46
<212> TYPE: DNA
<213> ORGANISM: Artificial Sequence
<220> FEATURE:
<223> OTHER INFORMATION: Primer

<400> SEQUENCE: 85
tcaatacaaa caagattaaa aacaagttct tgctttcga agttgc　　　　　　46

<210> SEQ ID NO 86
<211> LENGTH: 24
<212> TYPE: DNA
<213> ORGANISM: Artificial Sequence
<220> FEATURE:
<223> OTHER INFORMATION: Primer

<400> SEQUENCE: 86
ttagcagata tttggtgtct aaat　　　　　　24

<210> SEQ ID NO 87
<211> LENGTH: 44
<212> TYPE: DNA
<213> ORGANISM: Artificial Sequence
<220> FEATURE:
<223> OTHER INFORMATION: Primer

<400> SEQUENCE: 87
tcaaattcca aatcgtgaaa tttttggtg gtgattggtt cttt　　　　　　44

<210> SEQ ID NO 88
<211> LENGTH: 44
<212> TYPE: DNA
<213> ORGANISM: Artificial Sequence
<220> FEATURE:
<223> OTHER INFORMATION: Primer

<400> SEQUENCE: 88
aaagaaccaa tcaccaccaa aaaatttcac gatttggaat ttga　　　　　　44

<210> SEQ ID NO 89
<211> LENGTH: 24
<212> TYPE: DNA
<213> ORGANISM: Artificial Sequence
<220> FEATURE:
<223> OTHER INFORMATION: Primer

<400> SEQUENCE: 89
cacgggcagg acatagggac tact　　　　　　24

<210> SEQ ID NO 90
<211> LENGTH: 44
<212> TYPE: DNA
<213> ORGANISM: Artificial Sequence
<220> FEATURE:
<223> OTHER INFORMATION: Primer

<400> SEQUENCE: 90
tgaaacaaaa acgaaaccct gatttatgat aaaaatgtcg gttt　　　　　　44

<210> SEQ ID NO 91
<211> LENGTH: 44
<212> TYPE: DNA
<213> ORGANISM: Artificial Sequence

```
<220> FEATURE:
<223> OTHER INFORMATION: Primer

<400> SEQUENCE: 91
aaaccgacat ttttatcata aatcagggtt tcgttttttgt ttca                   44

<210> SEQ ID NO 92
<211> LENGTH: 24
<212> TYPE: DNA
<213> ORGANISM: Artificial Sequence
<220> FEATURE:
<223> OTHER INFORMATION: Primer

<400> SEQUENCE: 92
ctgcagcaaa tttacacatt gcca                                          24

<210> SEQ ID NO 93
<211> LENGTH: 45
<212> TYPE: DNA
<213> ORGANISM: Artificial Sequence
<220> FEATURE:
<223> OTHER INFORMATION: Primer

<400> SEQUENCE: 93
agacagtgaa gcttaaacag tactggctat gaagaaatta taatc                   45

<210> SEQ ID NO 94
<211> LENGTH: 45
<212> TYPE: DNA
<213> ORGANISM: Artificial Sequence
<220> FEATURE:
<223> OTHER INFORMATION: Primer

<400> SEQUENCE: 94
gattataatt tcttcatagc cagtactgtt taagcttcac tgtct                   45

<210> SEQ ID NO 95
<211> LENGTH: 1197
<212> TYPE: DNA
<213> ORGANISM: Phytophtora sojae

<400> SEQUENCE: 95
atggctattt tgaaccctga ggctgattct gctgctaacc tcgctactga ttctgaggct    60
aagcaaagac aattggctga ggctggatac actcatgttg agggtgctcc tgctcctttg   120
cctttggagt tgcctcattt ctctctcaga gatctcagag ctgctattcc taagcactgc   180
ttcgagagat cttccgtgac ctccacctac tacatgatca agaacgtgtt gacttgcgct   240
gctttgttct acgctgctac cttcattgat agagctggag ctgctgctta tgttttgtgg   300
cctgtgtact ggttcttcca gggatcttac ttgactggag tgtgggttat cgctcatgag   360
tgtggacatc aggcttattg ctcttctgag gtggtgaaca acttgattgg actcgtgttg   420
cattctgctt tgttggtgcc ttaccactct tggagaatct ctcacagaaa gcaccattcc   480
aacactggat cttgcgagaa cgatgaggtt ttcgttcctg tgaccagatc tgtgttggct   540
tcttcttgga acgagacctt ggaggattct cctctctacc aactctaccg tatcgtgtac   600
atgttggttg ttggatggat gcctggatac ctcttcttca acgctactgg acctactaag   660
tactggggaa agtctaggtc tcacttcaac ccttactccg ctatctatgc tgatagggag   720
agatggatga tcgtgctctc cgatatttc ttggtggcta tgttggctgt tttggctgct   780
ttggtgcaca cttctccctt caacaccatg gtgaagttct acgtggtgcc ttacttcatt   840
```

```
gtgaacgctt acttggtgtt gattacctac ctccaacaca ccgataccta catccctcat    900
ttcagagagg gagagtggaa ttggttgaga ggagctttgt gcactgtgga tagatcattt    960
ggtccattcc tcgattctgt ggtgcataga atcgtggata cccatgtttg ccaccacatc   1020
ttctccaaga tgcctttcta tcattgcgag gaggctacca acgctattaa gcctctcctc   1080
ggaaagttct acttgaagga taccactcct gttcctgttg ctctctggag atcttacacc   1140
cattgcaagt tcgttgagga tgatggaaag gtggtgttct acaagaacaa gctctag      1197
```

<210> SEQ ID NO 96
<211> LENGTH: 1371
<212> TYPE: DNA
<213> ORGANISM: Ostreococcus tauri

<400> SEQUENCE: 96

```
atgtgtgttg agaccgagaa caacgatgga atccctactg tggagatcgc tttcgatgga     60
gagagagaaa gagctgaggc taacgtgaag ttgtctgctg agaagatgga acctgctgct    120
ttggctaaga ccttcgctag aagatacgtg gttatcgagg gagttgagta cgatgtgacc    180
gatttcaaac atcctggagg aaccgtgatt ttctacgctc tctctaacac tggagctgat    240
gctactgagg ctttcaagga gttccaccac agatctagaa aggctaggaa ggctttggct    300
gctttgcctt ctagacctgc taagaccgct aaagtggatg atgctgagat gctccaggat    360
ttcgctaagt ggagaaagga gttggagagg gacggattct tcaagccttc tcctgctcat    420
gttgcttaca gattcgctga gttggctgct atgtacgctt gggaaccta cttgatgtac    480 gctagatacg ttgtgtcctc tgtgttggtt tacgcttgct tcttcggagc tagatgtgga    540
tgggttcaac acgagggagg acactcttct ttgaccggaa acatctggtg ggataagaga    600
atccaagctt tcactgctgg attcggattg gctggatctg gagatatgtg gaactccatg    660
cacaacaagc accacgctac tcctcaaaaa gtgaggcacg atatggattt ggataccact    720
cctgctgttg ctttcttcaa caccgctgtg gaggataata gacctagggg attctctaag    780
tactggctca gattgcaagc ttggaccttc attcctgtga cttctggatt ggtgttgctc    840
ttctggatgt tcttcctcca cccttctaag gcttttgaagg gaggaaagta cgaggagctt    900
gtgtggatgt tggctgctca cgtgattaga acctggacca ttaaggctgt tactggattc    960
accgctatgc aatcctacgg actcttcttg gctacttctt gggtttccgg atgctacttg   1020
ttcgctcact tctctacttc tcacacccac ttggatgttg ttcctgctga tgagcacttg   1080
tcttgggtta ggtacgctgt ggatcacacc attgatatcg atccttctca gggatgggtt   1140
aactggttga tgggatactt gaactgccaa gtgattcacc acctcttccc ttctatgcct   1200
caattcagac aacctgaggt gtccagaaga ttcgttgctt tcgctaagaa gtggaacctc   1260
aactacaagg tgatgactta tgctggagct tggaaggcta ctttgggaaa cctcgataat   1320
gtgggaaagc actactacgt gcacggacaa cactctggaa agaccgcttg a             1371
```

<210> SEQ ID NO 97
<211> LENGTH: 1371
<212> TYPE: DNA
<213> ORGANISM: Ostreococcus tauri

<400> SEQUENCE: 97

```
atgtgtgttg agaccgagaa caacgatgga atccctactg tggagatcgc tttcgatgga     60
gagagagaaa gagctgaggc taacgtgaag ttgtctgctg agaagatgga acctgctgct    120
ttggctaaga ccttcgctag aagatacgtg gttatcgagg gagttgagta cgatgtgacc    180
```

```
gatttcaaac atcctggagg aaccgtgatt ttctacgctc tctctaacac tggagctgat      240
gctactgagg ctttcaagga gttccaccac agatctagaa aggctaggaa ggctttggct      300
gctttgcctt ctagacctgc taagaccgct aaagtggatg atgctgagat gctccaggat      360
ttcgctaagt ggagaaagga gttggagagg acggattct tcaagccttc tcctgctcat       420
gttgcttaca gattcgctga gttggctgct atgtacgctt tgggaaccta cttgatgtac      480
gctagatacg ttgtgtcctc tgtgttggtt tacgcttgct tcttcggagc tagatgtgga      540
tgggttcaac atgagggagg acattcttct ttgaccggaa acatctggtg ggataagaga      600
atccaagctt tcactgctgg attcggattg gctggatctg gagatatgtg gaactccatg      660
cacaacaagc accatgctac tcctcaaaaa gtgaggcacg atatggattt ggataccact      720
cctgctgttg ctttcttcaa caccgctgtg gaggataata gacctagggg attctctaag      780
tactggctca gattgcaagc ttggaccttc attcctgtga cttctggatt ggtgttgctc      840
ttctggatgt tcttcctcca tccttctaag gctttgaagg gaggaaagta cgaggagctt      900
gtgtggatgt tggctgctca tgtgattaga acctggacca ttaaggctgt tactggattc      960
accgctatgc aatcctacgg actcttcttg gctacttctt gggtttccgg atgctacttg     1020
ttcgctcact tctctacttc tcacacccat ttggatgttg ttcctgctga tgagcatttg     1080
tcttgggtta ggtacgctgt ggatcacacc attgatatcg atccttctca gggatgggtt     1140
aactggttga tgggatactt gaactgccaa gtgattcatc acctcttccc ttctatgcct     1200
caattcagac aacctgaggt gtccagaaga ttcgttgctt tcgctaagaa gtggaacctc     1260
aactacaagg tgatgactta tgctggagct tggaaggcta ctttgggaaa cctcgataat     1320
gtgggaaagc actactacgt gcacggacaa cattctggaa agaccgcttg a              1371

<210> SEQ ID NO 98
<211> LENGTH: 1569
<212> TYPE: DNA
<213> ORGANISM: Pythium irregulare

<400> SEQUENCE: 98
atggttgatt tgaagccagg agtgaagaga ttggtttcct ggaaggagat tagagagcac       60
gctactccag ctactgcttg gattgtgatc caccacaagg tgtacgatat ctccaagtgg      120
gattctcatc aggtggaag tgtgatgttg actcaggctg agaggatgc tactgatgct       180 ttcgctgtgt ccatccatc ttccgctttg aagctcttgg agcagttcta cgtaagtttc      240
tgcttctacc tttgatatat atataataat tatcattaat tagtagtaat ataatatttc      300
aaatattttt ttcaaaataa agaatgtag tatatagcaa ttgctttttct gtagtttata     360 agtgtgtata ttttaattta taacttttct aatatatgac caaaatttgt tgatgtgcag      420
gtaggagatg tggatgagac ttccaaggct gagattgagg agaaccagc ttctgatgag      480 gagagagcta aagagagag gatcaacgag ttcatcgctc ttacagaag gctcagggtt       540 aaggttaagg gaatgggact ctacgatgct tctgctcttt actacgcttg gaagctcgtt      600
tctaccttcg gaattgctgt gctctctatg gctatctgct tcttcttcaa ctccttcgct      660
atgtacatgg tggctggagt tattatggga ctcttctacc aacaatctgg atggcttgct      720
cacgatttct tgcacaacca ggtgtgcgag aacagaactt tgggaaactt gatcggatgc      780
cttgttggaa atgcttggca gggattctct atgcaatggt ggaagaacaa gcacaacttg      840
caccacgctg tgccaaactt gcactccgct aaggatgagg gattcatcgg agatccagat      900
```

```
atcgatacca tgccattgct tgcttggtct aaggagatgg ctagaaaggc tttcgagtct      960
gctcacggac cattcttcat caggaaccag gctttcttgt acttcccatt gctcttgttg     1020
gctagattgt cttggctcgc tcagtctttc ttctacgtgt tcaccgagtt ctcattcgga     1080
atcttcgata aggtggagtt cgatggacca gaaaaggctg gattgatcgt gcactacatc     1140
tggcaactcg ctattccata cttctgcaac atgtccttgt tcgagggagt tgcttacttc     1200
ttgatgggac aagcttcttg cggattgctt tggctctcg tgttctctat ggacacaac      1260
ggaatgtctg tgtacgagag agagaccaag ccagatttct ggcaattgca agtgactacc     1320
accagaaaca ttagggcttc cgtgttcatg gattggttca ccggaggact caactaccaa     1380
atcgatcacc acttgttccc attggtgcca agacacaact tgccaaaggt gaacgtgttg     1440
atcaagtctc tctgcaagga gttcgatatc ccattccacg agactggatt ctgggaggga     1500
atctacgagg ttgtggatca cctcgctgat atctctaagg agttcatcac tgagttccca     1560
gctatgtga                                                             1569
```

<210> SEQ ID NO 99
<211> LENGTH: 873
<212> TYPE: DNA
<213> ORGANISM: Physcomitrella patens

<400> SEQUENCE: 99

```
atggaagttg ttgagaggtt ctacggagag ttggatggaa aggtttccca aggagtgaac       60
gctttgttgg atctttcgg agttgagttg actgataccc aactactaa gggattgcca       120
ctcgttgatt ctccaactcc aattgtgttg ggagtgtctg tttacttgac catcgtgatc      180
ggaggattgc tttggatcaa ggctagagat ctcaagccaa gagcttctga gccattcttg      240
ttgcaagctt tggtgttggt gcacaacttg ttctgcttcg ctttgtctct ttacatgtgc      300
gtgggtatcg cttaccaagc tatcacctgg agatattcct tgtggggaaa cgcttataac      360
ccaaagcaca aggagatggc tatcctcgtt tacctcttct acatgtccaa gtacgtggag      420
ttcatggata ccgtgatcat gatcctcaag agatccacca gacagatttc tttcctccac      480
gtgtaccacc actcttctat ctcccttatc tggtgggcta ttgctcacca cgctccagga      540
ggagaggctt attggagtgc tgctctcaac tctggagtgc acgtgttgat gtacgcttac      600
tacttcttgg ctgcttgctt gagatcttcc ccaaagctca agaacaagta cctcttctgg      660
ggaagatacc tcacccaatt ccagatgttc cagttcatgc tcaacttggt gcaagcttac      720
tacgatatga aaaccaacgc tccatatcca caatggctca tcaagatcct cttctactac      780
atgatctccc tcttgttcct cttcggaaac ttctacgtgc aaaagtacat caagccatcc      840
gatggaaagc aaaagggagc taagaccgag tga                                   873
```

<210> SEQ ID NO 100
<211> LENGTH: 819
<212> TYPE: DNA
<213> ORGANISM: Thalassiosira pseudonana

<400> SEQUENCE: 100

```
atggatgctt ataacgctgc tatggataag attggagctg ctatcatcga ttggagtgat       60
ccagatggaa agttcagagc tgataggag gattggtggt tgtgcgattt cagatccgct       120
atcaccattg ctctcatcta catcgctttc gtgatcttgg atctgctgt gatgcaatct       180
ctcccagcta tggacccata ccctatcaag ttcctctaca cgtgtctca aatcttcctc      240
tgcgcttaca tgactgttga ggctggattc ctcgcttata ggaacggata caccgttatg      300
```

```
ccatgcaacc acttcaacgt gaacgatcca ccagttgcta acttgctctg gctcttctac        360
atctccaaag tgtgggattt ctgggatacc atcttcattg tgctcggaaa gaagtggaga        420
caactctctt tcttgcacgt gtaccaccac accaccatct tcctcttcta ctggttgaac        480
gctaacgtgc tctacgatgg agatatcttc ttgaccatcc tcctcaacgg attcattcac        540
accgtgatgt acacctacta cttcatctgc atgcacacca aggattctaa gaccggaaag        600
tctttgccaa tctggtggaa gtcatctttg accgctttcc aactcttgca attcaccatc        660
atgatgtccc aagctaccta cttggttttc cacggatgcg ataaggtttc cctcagaatc        720
accatcgtgt acttcgtgta cattctctcc cttttcttcc tcttcgctca gttcttcgtg        780
caatcctaca tggctccaaa gaagaagaag tccgcttga                                819

<210> SEQ ID NO 101
<211> LENGTH: 1320
<212> TYPE: DNA
<213> ORGANISM: Thraustochytrium ssp.

<400> SEQUENCE: 101
atgggaaaag gatctgaggg aagatctgct gctagagaga tgactgctga ggctaacgga         60
gataagagaa agaccatcct cattgaggga gtgttgtacg atgctaccaa cttcaaacac        120
ccaggaggtt ccattattaa cttcctcacc gagggagaag ctggagttga tgctacccaa        180
gcttacagag agttccatca gagatccgga aaggctgata agtacctcaa gtccctccca        240
aagttggatg cttctaaggt ggagtctagg ttctctgcta aggagcaggc tagaagggac        300
gctatgacca gggattacgc tgcttttcaga gaggagttgg ttgctgaggg atacttcgat        360
ccatctatcc cacacatgat ctacagagtg gtggagattg tggctttgtt cgctttgtct        420
ttctggttga tgtctaaggc ttctccaacc tctttggttt tgggagtggt gatgaacgga        480
atcgctcaag gaagatgcgg atgggttatg cacgagatgg gacacggatc tttcactgga        540
gttatctggc tcgatgatag gatgtgcgag ttcttctacg gagttggatg tggaatgtct        600
ggacactact ggaagaacca gcactctaag caccacgctg ctccaaacag attggagcac        660
gatgtggatt tgaacaccct gccactcgtt gctttcaacg agagagttgt gaggaaggtt        720
aagccaggat ctttgttggc tttgtggctc agagttcagg cttatttgtt cgctccagtg        780
tcttgcttgt tgatcggatt gggatggacc ttgtacttgc acccaagata tatgctcagg        840
accaagagac acatggagtt tgtgtggatc ttcgctagat atatcggatg gttctccttg        900
atgggagctt tgggatattc tcctggaact tctgtgggaa tgtacctctg ctctttcgga        960
cttggatgca tctacatctt cctccaattc gctgtgtctc acccacactt gccagttacc       1020
aacccagagg atcaattgca ctggcttgag tacgctgctg atcacaccgt gaacatctct       1080
accaagtctt ggttggttac ctggtggatg tctaacctca acttccaaat cgagcaccac       1140
ttgttcccaa ccgctccaca attcaggttc aaggagatct ctccaagagt tgaggctctc       1200
ttcaagagac acaacctccc ttactacgat ttgccataca cctctgctgt ttctactacc       1260
ttcgctaacc tctactctgt tggacactct gttggagctg ataccaagaa gcaggattga       1320

<210> SEQ ID NO 102
<211> LENGTH: 903
<212> TYPE: DNA
<213> ORGANISM: Ostreococcus tauri

<400> SEQUENCE: 102
```

```
atgtctgcta gcggagcttt gttgcctgct atagctttcg ctgcttacgc ttacgctacc    60
tacgcttatg ctttcgagtg gagccacgct aacggaatcg ataacgtgga tgctagagag   120
tggattggag ctttgtcttt gagactccct gcaattgcaa ccacaatgta cctcttgttc   180
tgccttgtgg gacctagatt gatggctaag agggaggctt ttgatcctaa gggatttatg   240
ctcgcttaca acgcttacca aaccgctttc aacgttgtgg tgctcggaat gttcgctaga   300
gagatctctg gattgggaca acctgttggg ggatctacta tgccttggag cgataggaag   360
tccttcaaga ttttgttggg agtgtggctc cactacaaca ataagtacct cgagttgttg   420
gatactgtgt tcatggtggc taggaaaaag accaagcagc tctctttctt gcacgtgtac   480
caccacgctt tgttgatttg ggcttggtgg cttgtttgtc acctcatggc taccaacgat   540
tgcatcgatg cttatttcgg agctgcttgc aactcttttca tccacatcgt gatgtactcc   600
tactacctca tgtctgcttt gggaattagg tgcccttgga agagatatat cacccaggct   660
cagatgttgc aattcgtgat cgtgttcgct cacgctgttt tcgtgctcag acaaaagcac   720
tgccctgtta ctttgccttg ggcacaaatg ttcgtgatga caaatatgtt ggtgctcttc   780
ggaaacttct acctcaaggc ttactctaac aagtctaggg gagatggagc ttcttctgtt   840
aagcctgctg agactactag agcaccttct gtgagaagaa ccaggtcaag gaagatcgat   900
tga                                                                 903

<210> SEQ ID NO 103
<211> LENGTH: 1560
<212> TYPE: DNA
<213> ORGANISM: Traustochytrium ssp.

<400> SEQUENCE: 103
atgactgttg gatacgacga ggagatccca ttcgagcaag ttagggctca taacaagcca    60
gacgacgctt ggtgtgctat tcacggacac gtgtacgacg ttaccaagtt cgcttcagtt   120
cacccaggag gagatattat cttgctcgct gctggaaagg aagctactgt cctctacgag   180
acctaccatg ttagaggagt gtctgacgct gtgctcagaa agtacagaat aggaaagttg   240
ccagacggac aaggaggagc taacgagaag gagaagagaa ccttgtctgg attgtcctct   300
gcttcttact acacctggaa ctccgatttc tacagagtga tgagggagag agttgtggct   360
agattgaagg agagaggaaa ggctagaaga ggaggatacg aactctggat caaggctttc   420
ttgctccttg ttggattctg gtcctctctt tactggatgt gcaccctcga tccatctttc   480
ggagctatct tggctgctat gtcttttggga gtgttcgctg cttttgttgg aacctgcatc   540
caacacgatg gaaaccacgg agctttcgct caatctagat gggttaacaa ggtggcagga   600 tggacttttgg atatgatcgg agcttctgga atgacttggg agttccaaca cgtgttggga   660
caccacccat acactaactt gatcgaggag agaacggat tgcaaaaggt gtccggaaag   720
aagatggata ccaagttggc tgatcaagag tctgatccag atgtgttctc cacctaccca   780
atgatgagat tgcaccccttg gcaccagaag aggtggtatc acaggttcca gcacatctac   840 ggaccttttca tcttcggatt catgaccatc aacaaggtgg tgactcaaga tgttggagtg   900
gtgttgagaa agagactctt ccaaatcgat gctgagtgca gatatgcttc cccaatgtac   960
gttgctaggt tctggattat gaaggctttg accgtgttgt atatggttgc tttgccttgt  1020
tatatgcaag gaccttggca cggattgaaa ctcttcgcta tcgctcactt cacttgcgga  1080
gaggttttgg ctaccatgtt catcgtgaac cacattatcg agggagtgtc ttacgcttct  1140
aaggatgctg ttaagggaac tatggctcca ccaaagacta tgcacggagt gaccccaatg  1200
```

```
aacaacacta gaaaggaggt tgaggctgag gcttctaagt ctggagctgt ggttaagtct   1260
gtgccattgg atgattgggc tgctgttcag tgccaaacct ctgtgaactg gtctgttgga   1320
tcttggtttt ggaaccactt ctctggagga ctcaaccacc aaatcgagca ccacctcttc   1380
ccaggattgt ctcacgagac ctactaccac atccaagacg tggttcaatc tacctgtgct   1440
gagtacggag ttccatacca acacgagcca tctttgtgga ctgcttactg aagatgctc    1500 gaacacctta gacaattggg aaacgaggag actcacgagt catggcagag agctgcttga   1560
```

<210> SEQ ID NO 104
<211> LENGTH: 1563
<212> TYPE: DNA
<213> ORGANISM: Phythophtora infestance

<400> SEQUENCE: 104

```
atgaactgcc agcgtcatcc aacacacgtc gcacatgaca tcaccttcgg cagcatcctt     60
gccatcctcg ccgcgcagcc tcccattcct gtttctgcct cgcatttggc actcatggct    120
tctcacgttg tctcgtcgct gagtaatgca gccactccgc tgcgattcac cttgttaaac    180
cagcagctca cacaactctc ggagctcgta ggggttccag tggaccaact acgttgcgtc    240
gcttgcctgt tagctgtcta cccattggca cttatcgtgc gcaagttgcc gtcggtcaca    300
gctaagcatt ggctgcacat ttgcgctggt gtgagcatcg cccaattcgt ctatggaaca    360
ggatggctac actcgcttct atcctcgctg gtcacgtacg cgttggtgtg cgtgctgccg    420
cccaaacgcg caccgttcgt ggtgtttctc gccaatatgt tgtttgtggc ggcactgcac    480
atccaccgta tgcgagtcaa ctatatgggc tggagtatgg actcgacagc gagtcagatg    540
ctgctgctca tcaagctcac gagcttcgcc ttcaactacc acgatggtgt tgttcccagt    600
gccacagcag tgcagaacgg cgactcagag cacacgaaaa gagtcaagca gttgcgtaaa    660
caactggcga tcccacagat cccgtcactg ctggagtttt tgggcttcgt ctactgcttc    720
acgacgttcc tggccggtcc ggcatttgag tacaaagagt acagcgacgc tattcaccag    780
gctaggttcg tcgacaacaa cggtgtccga cgtaatgtgt cccctgcgcg tgcggcaatg    840
tccaagttgg tattgggtct tggacttatg ggacttttgg tgcagttcgg agctctagcc    900
gacttgaatc agattttgaa cgatgagaat cagtccatgc tcatgaagtg ggggcgacta    960
tttgtcgcgt tgttcttgac tcgtgccaag tattacgtgg cgtggaaact ggcggagggg   1020
gcgactgtgc tgaccggaac gggattcgaa ggattcgacg agcagaacaa ccccaaaggc   1080
tgggatggtg tcagtaatgt ggacatcctg gccttcgaac tcggcgccaa cgtgcgtgag   1140
atctcgcgtg cttggaacaa gggcacgcag aactggctgg agcgttatgt gtacacacgc   1200
acgggcaact cgttgcttgc cacgtactct gtatcggctc tgtggcacgg attctaccct   1260
ggttactatc tcttcttcct cacggtgccg cttgcgacgt ctgtgaatcg cctggcgcga   1320
cgtcacgtgc gtccgtacgt tgtggacagc ccgctgaagc cactctacga cctcgtcggt   1380
atgatctgta ctgctttggt cgtcaactac ttggccgtct cgttcgtagt gctgtcgtgg   1440
gaggacgcag ttgctggttt ccgctccatg cgctttactg ccacgtcgg gcttgtgggc    1500 tgctacttgt tgctcacctt tgtgcctatc aagaagactg cgaacagtaa gaagaccttg   1560
taa                                                                 1563
```

<210> SEQ ID NO 105
<211> LENGTH: 1371
<212> TYPE: DNA

<213> ORGANISM: Phythophtora infestance

<400> SEQUENCE: 105

| | |
|---|---|
| atggaccgcg tcgtggactt tgtggagcac ctgcagccgt acacggagct tgccactcct | 60 |
| ttggacttca gtttcctcca tgcaaaagtg gacgagctgt ccgtgtcgct cggtctgggc | 120 |
| agcgaccagc tctgctacgt cctctgccta ttcgctgcgt atccgctggc tgttgtgtac | 180 |
| aaactgctac ccggtgccag cctcaagcac gtgtttgatg tggtgctagg tgtgagcatc | 240 |
| gctcagttcg tgctgggctc cggctgggtg cactcgttca tctcgagctt cctgacgtac | 300 |
| ctgatcgtta agttcgggcc atccaagcac gcgccaggca tcgtgttcct cttcaacatg | 360 |
| ctatacatgt cagcgtcaca catctaccgt ttgtatgtgg actacatggg ttggacgctg | 420 |
| gacttcaccg gcccgcagat gctgctggtc atcaagctca ccagcttcgc ctacaactac | 480 |
| tacgacggcg tggtggacaa gacgtttgag aagaaaggtg ccgagatgtc ccccggcata | 540 |
| aagaaagtgt acgaaggacg tcagaagctc gctatccagg gatcccgtc tctgctcgag | 600 |
| ttcttcggct acgtgtacag cttcaccacc ttcctggccg gccggcgtt cgagatccgc | 660 |
| gagtatttgg acgtgacgag cggcaaaaag ttccttatgg acggcaagaa caaagagccg | 720 |
| tcgagtgtgc tcgctgcgtt ctctaaattc ctggtgggat cgctgttgat ggctgcgttc | 780 |
| gctgtgtatg gccccatgta cccgctgtcg aacctgcacg accccaagat cgctgcgcag | 840 |
| ccgttgctgt accagatccg cgacctgtac atcgcgctga tcttctgcaa ggccaagtat | 900 |
| tactccgcct ggaagattgc cgagggcgcc accgtgctgt gtggcttcgg attcgagggc | 960 |
| ttcaacaagg acgaaccag tcgcggctgg aacggtgtga gcaacatgga catcttgggc | 1020 |
| tttgagttct cgcagagcat ccgtgcggcc tcgcgagcct ggaacaaggg gacgcagaac | 1080 |
| tggctggaac gctacgtgta cacgcgcacg ggcaactcgc tgatggccac gtacttcatc | 1140 |
| tcagccttct ggcacggatt ctacccgggc tactacattt tcttcatgag tctgccgctg | 1200 |
| gctacggcgg tgaaccgttt ggcttttcaag cgtcttcgtc cacgtttcat cgaggccgac | 1260 |
| ggatcgttcg gagccaagaa gaaaattttac gacgtgctca gctacttgtt gacgctcttc | 1320 |
| gctatgcact acttcgtcat gccgttccag gtacttaata agtatttgtg a | 1371 |

<210> SEQ ID NO 106
<211> LENGTH: 1458
<212> TYPE: DNA
<213> ORGANISM: Phythophtora infestance

<400> SEQUENCE: 106

| | |
|---|---|
| atgcgtgtca ctcgccgcat tcgaagactt gccgaagcgt ggatcgtgtt tcgctatcga | 60 |
| gcagcagagc agagcatgga gatactgcgt ggccccgtgg acggcatcgc cctaagcgag | 120 |
| aacttccctg ttgatggatt ccgcctcatg gtggcgcttg cgggttgcag cctcatcgca | 180 |
| ccgctcatcc acctcacacg cggcgagaca tctcgtcact tgttcaatgt tgcggtggga | 240 |
| ctattcgccg gcgtcttcgt gttcgacttg gccgtgttgc acactatcgg gacggccgtt | 300 |
| gttgtgtatt tgctcatgat ggtggctcca agcttgtggg gcgcattgtg ctgccgctgc | 360 |
| tgttggcgta cctctcacta ttaccgtgaa ttctacagcc cagacattgt gtgggactcg | 420 |
| gcccaaatga tcctaacgct taagctcagc agcgtcgcga tcaactacag tgacggcggg | 480 |
| ctgcccacgg agaagaagac gcccacaatg cttaagaacg agctgcaaga aatcccagag | 540 |
| ctgatcccgt acttttggctt cgttttcttc ttcccgacct acttggctgg tcctgcgttc | 600 |
| gagtacaagg actacattta ctggatgaag gacgttcgcg ttgctccttt catggtccat | 660 |

```
ctccgcaatc tcgtcatttc cgctgctggt ttcttcgtct cgctccaatt ccccgtcgag      720
gaaatcgact cccccgactt cttcccgaaa tcgtcgtggg ctgtgcgctg cctccgtatg      780
tgcatccctg tcgtgttgtt ccgtttccgc tactatctgg cctggtcgct ggccgaggcg      840
gcgagtgctg ctgcgggcgt gggctacgtg caagctactg gaaaatggaa cggcatcacg      900
aacaacgatc tcctgtgtgt ggagcttccg acgaatttcc gagtggccat caacagctgg      960
aacattggag ttgcgcgctg gattaacact tacatttacc agcgcgtcgg tctgaccaag     1020
tctgggaagt ccacgatgct ctccacgatg gcgtcattct tgtcagcgc tctgtggcat      1080 ggactgtcgc ctggttacta cctgttcttc ctcttgggtg gcatctacat cgaagttggc     1140
aagcaacttc gtcgtcgtct gcgtccatac ttccactaca cggaggaccg taaggctcac     1200
tcgcatgcca ttttcctctc gtactttagc ggcacgtctc atccactggc cttcttgtac     1260
gacatctcgg gcatgttctt cacgtgggtg gcgatgcagt acgctggtgt cgccttcgag     1320
atcctggacg tgcgtcgttg cctcgccatt tggagctcgt ggtacttcct cccgcacctt     1380
gtgagcatcg gcttgctggt tttctttaac ctcttcccgc aacgtcgctc cactcccacc     1440
gacaagaaga cgcagtaa                                                    1458
```

<210> SEQ ID NO 107
<211> LENGTH: 1677
<212> TYPE: DNA
<213> ORGANISM: Phythophtora infestance

<400> SEQUENCE: 107

```
atgagcacca ccgcgctatt acaagcctcc acttctcctc ctccttcgcg agagccggaa       60
tacgcagcat tggagcagct cgagccgcct ctgtcccatg caatcgacat ggggtcaaa       120 gtctcaccgt ccgagtcagc ggcgatagca ggtgggtct acgtgaccgc ctcgtccagt       180 tgtgggcct ccactatcaa gcacaatccg ttcacgtaca cgacaccggt ggacacgtac       240
gagaaggcca agatgaccat cttgtgtctc ttaggagtcc cattcattcg tttcgtactg       300
ctactctgtg tgggcattct actcgtcatc gtaagtcact tggctctcat tgggtacaaa       360
ccattggacg ctcactctgg agctcgtcca cctctgccac gttggagacg tatcgtcggt       420
tcgcctgtgc cgtatctgct acggtcactg atgctcatcg tgggttacta ctgggttcca       480
gtgaaatacc ctccgaattt taatcgtcat gccatgccac cgtcatcgt aagcaaccat       540 ttgaccttct tcgacggact ctacatcttc acgttgctat cgcccagtat cgccatgaag       600
acggacgtag ctaacctccc attgatcagt cgaatcgtgc agatgattca accgattctg       660
atcgacagag gaacacccga aggacgtaga agagcgatga atgacatcac gtcacatgtt       720
gctgatccca gtaagcctcc gcttcttgta ttcccggaag gcactacatc gaatcaaacg       780
gtactgtgta aattcaaggt cgggtctttc gtctcaggtg taccgtgtca gccggttgta       840
ctacggtacc cctacaaaca cttcgatttg agttggccac ctggggtttc tgggttgtac       900
ttggcgttac gtgtgttgtg tcaggtgtac aaccgattgg aagtggagat ctaccagcg       960 tactacccgt cggagcgaga acggaaagac cctcaattat acgctattaa tgtgcgtgag     1020
gtaatggcca aagcgctggg agttcccaca acgaaccacg cttttgaaga tgtagccatg     1080
ttgatgcgtg tcggagacta cgccacaaaa cacgtcgtac cactgacaga cgtgggtgaa     1140
gtgatctcgc taacggcact aaagcgaggt gacgtagatc gcctggtggg ctacttccgt     1200
cgccacgacc ttgataagga cggccactta tctatgcagg agctacgtgc actgttccct     1260
```

| | |
|---|---|
| aatgacgatc ctgtgatcgt tgatcagctc ttcgacctcg ttgatttaga cgacagtggg | 1320 |
| ctcatcgatt tccgggaatt gtgcttggct ctacgtgcac taaacccgca gaatatcaac | 1380 |
| gagggagacg acgccttggc gaaattcgct ttccgtctct atgatcttga taacaacgga | 1440 |
| gtcatcgacg cctctgaact ggaacaacta cttcgcttcc aacgcaactt ctacggcgtt | 1500 |
| tctgaagcga gtgttgcagc cgcgttacgt caagctcagg cagaaaacac gaccggtatc | 1560 |
| acttataaca gattcgagca gctggtatta caaaaccccg aagttttgtg gtacgtccgc | 1620 |
| gacaaactcg aagtcctacg tggctccatg cgagaaagca gtctcgagat tccgtag | 1677 |

<210> SEQ ID NO 108
<211> LENGTH: 1047
<212> TYPE: DNA
<213> ORGANISM: Phythophtora infestance

<400> SEQUENCE: 108

| | |
|---|---|
| atggagaagt atagtcggtg gtcggatctg acgacaggca tcaacccgtt cgtgccgcag | 60 |
| cgtcggcgct tcacgtccgg atggcccgtg accatcttgc aggtcatatc tggctccgct | 120 |
| ttggcgctcg tacgcttccc gttggtgcta gtagccttcg tcgcgctatt tctagtcaac | 180 |
| ctagtggtgt ccattctcgc cgtaatcccg ttcctaggac gtctgcttaa gcgcatcaca | 240 |
| gaatggttgc tgtgctcact cctcctcctg cttttcggtg tgttcacctc gaacggctca | 300 |
| actcgcgttg gatctggcga cgtgctggtt tgcaactaca cgagcttttt ggagatatta | 360 |
| tacctggcca cgcgcttctc accagttttt gtatttgcta cagagaccaa gagtaacgac | 420 |
| gaaggattgg tacacgtatg tggcctactc gaggcgctgt acaggtcgtt ggcaatgcct | 480 |
| gtgagtgttg aacgtgtcaa acccacaagg aagatcgcag acgtagtgcg tcgagctgct | 540 |
| gggccagtag tcgtgcttcc cgagggggct agaagcaatg gtaaggctgt gctgaagttc | 600 |
| atccccgtgc tacagaacct gccggtcaag accgcgtac acctcgtggc cttccgctac | 660 |
| gagttcaagc gcttcagtcc gagtcaaagt gccggtggtg cctggtctca cctcttctgg | 720 |
| actgccttcc acgtgtacca caccatgcgt gtgacggtat tgagtgctaa agacttgaat | 780 |
| ctagacgact taacgccgac taaactaccg agtaacaaga gcagtaagaa gcaggagaac | 840 |
| tccaagacac tgtcgactga tcaggtcgag aaactacgca cacttctagc cgctatgtta | 900 |
| cgcaccaaga ccgttgactt gggaccagag gactctgtgt cttttcaataa ttactggaag | 960 |
| cacgtcaaca gcggaggacg tcaaccagcg tcccaattca cggaccgcaa ggctcctcat | 1020 |
| gaacacgccc aatgggccaa gagatag | 1047 |

<210> SEQ ID NO 109
<211> LENGTH: 1275
<212> TYPE: DNA
<213> ORGANISM: Phythophtora infestance

<400> SEQUENCE: 109

| | |
|---|---|
| atgtcgttcg ctacacctgc gcaggtgctg caggatgtgc gcttcgaaga gcgttttgct | 60 |
| gagattgagt cgaggttgcc ggccacgttg gctttggcca aggagggatc tttagccaaa | 120 |
| cgcaatcaga ccaagcgcaa gctttaccac gacagcgagc tcatccgtat cgagctggaa | 180 |
| gagcgtctga atgaactagg tatcgaaagt cagtgggtca ctgccccgga gatgaaggaa | 240 |
| gccaatgaga agctggacgc agtgcgtaag cagctcaaac tggacgtgct gcccgccagt | 300 |
| tcctctcctc tggagaagat ctacatggtc gtgcgcatgc ttacaatggt gctggtgctc | 360 |
| gtgggttggc tcagctgtgt gacagtgctg atcccactca aatggctcaa cccagtactc | 420 |

```
aagaagatgg gagtcaagaa gaactacctt cccatggaca ttgtgtcatg gggtacggcc    480
ttcatggtct gtgtcacggc ctgtaccgac atgaaggccg agggcgtcga aaacctgctc    540
aaccttaagg actctgtcgt ctgcatgttc agccactcgt ccaacttgga cggcttcatt    600
gtcaatggat catcgccgat tgccttcaag tttgccgcca agaaaagcat ttttctagtc    660
ccgttcctcg gctggtcgtc tcgttggggc ttcgactttg tggccatcga ccgctcgcac    720
cgtaaatcag cgctgaagag tttaaaggaa cttgcagtgt cggtaaacga gcatggcaat    780
tcagtctgca tctcgcctga aggcacacgc tcgaaggacg gactgcttca agaattcaag    840
aaggggccat tctacctgcg tgaggacacg aagaagaacg tggtgccctc catcgtgttc    900
ggcgcgtacg agctgtggcc tcctggacga ttgttcagca tccccggaca cacgttggtg    960
cgttacctgc ccgagtacaa gtcagatccg aacttgaacc gtaaccagaa ccggttggcg   1020
ctgcgtcgca tctatctcaa ggcgttcacg gaggatgttc cggactacat tggcactcgc   1080
gtgagcacca acttcatcct gaagaacatg ttctatcact atcttgcgtg ggcgatcacg   1140
ttcaaagtga cttcgtgggc actcacagtg atcagcctcg tcttgtactg gctcaacatc   1200
acatatggca cctttatgct gttctcgctg gtcatgatgg tggcgggaga agccctcatg   1260
ttcttcacct gctaa                                                    1275

<210> SEQ ID NO 110
<211> LENGTH: 1278
<212> TYPE: DNA
<213> ORGANISM: Phythophtora infestance

<400> SEQUENCE: 110
atgagtcaaa gtgacgagtg ccaagcaacc caaacctccg tgtatccaac caagcgctgc     60
gtgtcaggag gccccgtagt cgagcccgac gctgagccag tgctcaatcg cgtcatccat    120
ccgagtacaa agtttgagac tgcatggacg tggtccggat gcatcatcgg ctgcagctac    180
ctgctccttc tcgtagtatg tgccttcctg aacaccactt tcgtgctgtg gccactgacg    240
ctgctgcaat ggagccacct cctctcaacg cgcagctgcc gatggatatg tcgctttctg    300
gaggataaat acttcgctat gttaagtgga tatttggaac tagttggcgg cgtcaagatt    360
atcatcactg gagacgaaga gctgcagttc gcacaccacg agcacgtgct cttgatctgc    420
aatcatcgca gtgaagtcga ctggatcttc ttctggaatc tggcgctgcg tctcaatgtt    480
catgaccgta ttcgagtcat gatgaagagt gtcattcgat acgcccctgg cgtcggctgg    540
accatgatgc tgctgcgata cccgtacgtt aaccggaact gggccacgga ccaggacaga    600
ttgaccaagg tgattgagtc gtacaaggac gtggacatgg gcacgtggct agccatgttt    660
ccggaaggaa cggcgttgta tgacaagacg ctcaagaaaa gccacgagtt tgctagcaag    720
caaggagaag cgaaatggaa ctacgtgttg cagcccagag tcaagggctt tgagctgtgt    780
atggacaaga tggaccccgga ctatgtcgtg gacctcacgg tggcgtatcc ggagctcatg    840
gagggcgtga gaccgtcacc ggtgcgattt gtgagaggac agttcccgac tgaagtacac    900
atgcacgtgc agcggtatca ccggtcaacg ctgctgaagc acaaggaccg catgggtcaa    960
tggctgaaag atcgatttgc agaaaaagag gagcgtcttg aacatttcta cgagactggc   1020
gcgtttcaag gcgaacagca gacgagcggc cagcatgcga gccgtgtcgc tctgttgccc   1080
gcgcaacaga ttctcctctt cgttggtgaa aactacctca cttactttg gtcgagaaga    1140 cgcctgtctg tatacctgcg tgctttccag gttgctggtg cgtccatcca ctcgatggat   1200
```
agccacaaga ttcacaacga gaagcaccaa gacaaacttc atactcgatc ggcagatgag    1260
ttgcgcctct tcacgtga                                                  1278

<210> SEQ ID NO 111
<211> LENGTH: 1173
<212> TYPE: DNA
<213> ORGANISM: Phythophtora infestance

<400> SEQUENCE: 111
atggcggtgt tccacctgta ctcggcgctg aatctgctgt ggatcctatg caacagcgcg     60
tgtatcaatt tcctgcaatt ctgtctttgg tgccttgtgc ggccgtttaa caaggcactt    120
tatcgccgac ttatgggctc cgtggcacaa tcactctggg tagacgtcac atccacgagc    180
ttcccacaga ccaagctctc ggtcactggc gagctgccgt cagacccac gaagcccgtg     240 atcatcatag cgaaccacca agttgacgcg gactggtggt atatttggca ggccgcgcgt    300
caccaacacg cagctgggaa catcaagatc gtgctcaaag accaactcaa gtacctgccc    360
atcatcggct ggggcatgcg cctctttcag ttcctcttcc tacgacgccg catcgaccag    420
gatgcagagc acatcaagaa gtacatgggc ggactcatca gcgataattt cccttttttgg    480 ctcgtgttat tccccgaggg aacgaccatc caccgtgaat acgtggtcaa gtcacaggct    540
tttgcggctc gagaagctcg tcccaagttc gagcgagtgt tgctgccacg cacgaccggg    600
atgcggatca ttctggacgc tgtggcggat gccaaacccg atatttacga cctcactgtg    660
gccttcccgt cgtactcggg tgaagtcccg acgttcgaca tgggatatgg acgcagagtt    720
gacaccgaag tgccgtcgat gaagtcgcta ctggcaggga gcagcctgt gggccgagtg     780 gctttacact caaggaagtt taagtacgag gacgctgcga cagacttgca gggattcttg    840
gatgctcgct ggacggagaa ggaggagcgg atgaactatt tcatcaagca tcagcagttc    900
ccggaaacgg agagcacagt ggagatgcaa ctatcgacct cgatgggagc agttttccgg    960
ctgtggatgg gcatcttgct gtcgtgtgtt gtgcttcccg tcgtcatgat gctcttcttc   1020
ccattgtact tcacgtgggt cgtctactgc ttcgtgtact cggtgtacga ccgcaccacg   1080
aacttctggt ggccgtacat tttcaatctc ttcgtggagc gcgccactaa gacgcacgaa   1140
cactttaagc gtcaccaggc taagtatctg tga                                1173

<210> SEQ ID NO 112
<211> LENGTH: 1110
<212> TYPE: DNA
<213> ORGANISM: Phythophtora infestance

<400> SEQUENCE: 112
atgggcgtgg ctgttgtggg cgtcgtgttc ctgacgtcgc tagtggtcac gggttggaca     60
ggtgtggcct ggatattgac cccatgtttc ttgctggcgg ctctcccact gccggcgttt    120
ctacagacca aacgcttcta tcgccgcgtc actcgcttca tacaatgggc gtggatgggc    180
caagtgaaat tgtttggaat ccaggttcga gtgctcggcg atgcggagac gaaagctcgt    240
gagagcgaat tatcgaagga tcgagcgcta tggctgtcaa accaccgcac tcgtatcgac    300
tggatgctgc tgtggagcgt cgcgtggcgg acgcggacgc tgcatcagtt gcggatcgtc    360
ttgaaggccc cattacggaa aatgcccatc ttcgggtggg ccatgcagca cttcatcttc    420
atctttctgc aacgccgttg ggctgatgac caagtgaatt tgcgcaagtt gttgccattc    480
ctcacgtcga cagaaccgga ggcttcctat ctccttttcc ccgaaggcac cgatctgagc    540
gagagtaacc tcgaaaagag tgctgtattt gcagagaaga aaagcctttc acctcgtcag    600

```
tactcgctgt acccacgcac gacgggttgg acatttatgt tcccactgct gcgctcacaa    660
cttaccgctg tgtacgatgt caccatgttc tacgtggact atgccgctaa cgaacgtcca    720
tcggagtcgt cactgcttac cggtcgtatg ccgcgaatga tccatttcta catcgagcga    780
gtggacatct cggttttgcg tgacaaaagt gagactgact tagcggcctg gttggaaaag    840
cgcttcgaac gtaaggagtc tttgctcaag gccttttacg aggacaacgg caagcttcct    900
catggagccg aacctctctt tcaagagaat caaggtactg cgatggtgat gctggtggcg    960
ttttggctca tatccattgg tgctgccaca ctccttggat tgattggcaa cttcatctcg   1020
gtcattgctg cgctggcggt tgtagttgga tacgccacca acacggcata tgggcctggc   1080
gtggacgggt ttctcataaa caactcgtag                                    1110
```

<210> SEQ ID NO 113
<211> LENGTH: 1344
<212> TYPE: DNA
<213> ORGANISM: Phythophtora infestance

<400> SEQUENCE: 113

```
atgggacccc gagtggaacc tccaaacagc gggcgctcgc ccacagcgag caagaggcgc     60
atgaagaagt tccgtgacgt tgtgtccccg ttggacccgg cggatgcgcg ctccggtgtg    120
cacagctccg agttccgcgg cttgtacaac ctggcgatgc tgtctggggt gctctacgtg    180
ttcacgacgc tcttcacgaa cctgctaatg acgaacgaac ccatcgactc gaagcttctg    240
ctgtcggtgt tttactcgac gcatttactc gaggtattgg ctacattcgt gtgtcaagct    300
ctgtatgcct acacggccct gatcccagtg tacatggcgg gcacggacaa gccgaaccgc    360
ctgctcatca acatcgtgca ccacacgctt caaagtctgc tcttcttctt cacaatcgtc    420
ttcatcgtct ggcgcgactg gaacctcatc cacgccgtgt cagcgttcat tgaaggtctc    480
gtactattga tgaagatgca ctcctacatc cgcaccaagc tggagatctc acgcactgag    540
aacaaaccgc ccattcctga catcaaggac tttactatgt atttactgat cccgtcgctg    600
gtgtacgaac ctaacttccc acgtacctgt cggattcgct gggcttacct tgctgagaag    660
actttctcgg ttatcatggg gatttcgatg ctatacatca tcgtcacgac ccatgtgatg    720
cctcgcctgg aggattccgg gactgtgaac cctgtgctat cggtcgtgag tcttctgctc    780
cctttcctgg gatgctactt gctcacatgg ttcatcatct ttgagtgcat ctgcaatggc    840
ttcgctgaag tgacttactc agccgaccgg gacttttatg gtgactggtg gaacagcaca    900
acgttcgacg agtttgcgcg caagtggaac aaaccggtgc atgagtttct actacgacat    960
gtatacttgg agacgttgga ctcgtacaag atctcgaaga cttacgccac tatgttcacc   1020
ttcttcatgt ctgctgcact ccacgaatgc gtcttcatcc tcatgttccg cacagtcaga   1080
atgtacttct ttactcttca gatggtccag ttggttacca tcgtgtacgg acgtggcttg   1140
cgtggctcgc ggatgggaaa tatcaccttc tggctcggta tgatcctcgg actcccactt   1200
caagctgtca tttacagtcg cgaatatcac ggtggtgagc ccatctttat ggtcatcatg   1260
atgccagcaa tgatcttcgg gttcggtgga gttctcgttg cttcactgat gcatctaagt   1320
cgtttgagga agaaacaagc ctaa                                          1344
```

<210> SEQ ID NO 114
<211> LENGTH: 927
<212> TYPE: DNA
<213> ORGANISM: Phythophtora infestance

```
<400> SEQUENCE: 114
atgacaggcc agcaacacac ttggctgctt ggtgtcggcc tcgcagtggc gacaatctcc      60
ctttgcgtcg ccattcatgc aagcgcctta ataacgattg caactgcatg tgtagctgct    120
tatctcccctt catacttgga cggctcagag tacacggggg agcgctactg gccatggttt    180
gccaccttca tcggacacgg catggcgcac attccgggga cgctggaatt cgaggagccc    240
attgacgcct ccaagcaaca catcttttgt tcgcatccac atggactgct ttccacccac    300
cacggacttc tcatgtctgg gcagactgtt cctccattct acgagacggt accgctgtct    360
acacgacgcc acttggctgc gtccgttttgt ttccggatac cattctaccg tgaatatgta    420
ctctggtctg gatgtgttga tgcacgccgt agtgtggcgg aaaagatgct tcgaaatggc    480
aagagtctgg tgatcttagt cggggggtatt gcggagcaga tgctctctca gcgtggagac    540
cacacgatct acgtcaaaaa gcgcaagggg cacattcgct tagcactgaa atacggggta    600
cccatcgttc ccggctacgc gtttggagag accgacctgt tcacccactc aagtgtgctg    660
ttgtcgttcc gccaaacgat tgcgaagaag ttttctgtgg cgttgctgct tggacgtgga    720
tactccaagt ggttgttttg gctacctcat aaaggagtga ccatcaacca ggtctttggc    780
aaacccattc cagtcttgaa gaaggacgac ccgagttcgg acgacatcga aaagctgcat    840
caccagtacg agcgcgagct agtgcgcatt tttgacaagt acaaggagaa acatggatac    900
ggaaactgta cgctgcatgt gcgctag                                         927

<210> SEQ ID NO 115
<211> LENGTH: 1179
<212> TYPE: DNA
<213> ORGANISM: Phythophtora infestance

<400> SEQUENCE: 115
atgtcggcag cccaagtgct caacaatgct gcttacggcc gcacatcggc gtggcctgat      60
tcgaataccc gtccggatct gcagacacta cgaggacgct ttctacgacg acttcatctt    120
tcgcttattt atggtctctg ggtgcttggt acgcttttca atgcagcgat gtgggttttc    180
tcgctcgtct gtgtagctca gtgggtttgg agtaccctca tcggtgctaa tgaagctccg    240
attccacttg ccgtgcaagt atttctaagt ctcgtcgcac tctatgagag ttaccatttc    300
gtgactcggc cttcgcatca cccctggcca ttcatgcggc gcttgattcg ctactcgctc    360
cttcactacc cgtacttccg cctcaatgcc acggtcttcg acgagcgcga gcgggccaag    420
caattaagtc aagatggtgc taccaatgac actagcgctt caacacgga gatcgctagc    480
aagaccatcg tggagaacga tatttctcca tttgtgaaac ccaacgagag cgccatgttt    540
gcttttcatc cgcacagcgt tctctccaat ggctgggtag ccaatggcgc gaatcacatg    600
agtttcgaac aagctgactg tcgatggctc gtagctgaaa atctctttgg ggtcccccctc    660
atgagagact tgctaaactg gatggacttt agtagcgttg ccaagtcaac gttccaacag    720
cgtatgtctg cccgtcaaaa tgtgtgtttg atccctggtg gcttcgaaga agcaacactc    780
tacgaacgag gcaaacatcg tgtgtacatc aagaaacgct ttggcttcat caagctggct    840
ttgcagtatg ggtacaaggt gcacccagtg tacacgttcg gggaggagta cgcttatcac    900
acctttcctt atctgctcaa gttgcgtctc aagctgaacg agttcaagat tcctggagta    960
tttttcttcg tcttccgca ttgtttcttt ctgcctcgca ccgacgtgga ccttatcact   1020
gtcgttggag aaccccttggt cctaccgcgt atcgaacaac cgaccaagga agacgtgcag   1080
aaatatcaag gtcagtacgt cgaggctctg caaaagctgt tcaacaagta caagtctgtg   1140
```

```
tacgccgtcg atccgcaagc gcagttggaa atatactaa                          1179
```

<210> SEQ ID NO 116
<211> LENGTH: 1146
<212> TYPE: DNA
<213> ORGANISM: Phythophtora infestance

<400> SEQUENCE: 116

```
atggcgaagc tcacgaatgc ggcttgcggt cgcacatctg cgtggccgga ctttgatact    60
cgcccagagt tgcgaacgct acgagggcga ttcatgcgac gcttcgatct cttcattctc   120
tacggtctct gggtcgtcgg cctcctgttt ctcgcagtaa tgtgggtctt ctcactcttc   180
tgtttggtgc aatggagttg gagacgagct acacacgacc atgctcctcc gatggcattt   240
tcagcccaga tacctgggg tttcatcgtg ctgcacgaaa gctaccacta cctcacaaaa    300
ccttcgttgc atcagtggcc atttatgaga cgttttttc gacaagtttt tcttcattac    360
ccatacttcc gcctcaacgt cttggttttt gaagagcgtt cgaaaacttc aagtgaaaat   420
ggcaaatgca acaaagaaat tgccagcaag gccgttgaag agaacaatct gtcgccattc   480
gtgaccccg atgatcgcgc tctatttgcc ttccatccgc acggtgtcct ctccagtgga    540
ttcgccttca cggcgcgca ccacatggga ttcttgcatg cccattgtcg ctggctcgta    600
tcggagaatc tcttctggtt ccccgtcatg cgcgacctgt tgaactggat ggacttcagt   660
tgcgtatctc gatcgacttt ccatcgtttc atggccacag gtcaaaatgt gtgtttgatc   720
cctggcggct tcgaagacgc aacactctac gaacgaggca acatcgtgt gtacatcaag    780
aaacgctttg gctttatcaa gttggctttg cagtatgggt acaaggtgca cccagtgtac   840
acgttcgggg aggagtacgc ttatcacacc tttccttatc tgctcaagtt gcgtctcaag   900
ctgaacgagt tcaagattcc tggagtcttt ttcttcggtc ttccgcattg tttctttctg   960
cctcgcaccg acgtggacct tatcactgtc gttggagaac ccttggtcct gccgcgtatc  1020
gaacaaccga ccaaggaaga cgtgcagaaa taccatggtc agtacgtcga ggctctgcaa  1080
aagctgttca acaagtacaa gtctgtgtac gcagtcgacc cagacgctga acttgaatta  1140
tactga                                                             1146
```

<210> SEQ ID NO 117
<211> LENGTH: 852
<212> TYPE: DNA
<213> ORGANISM: Phythophtora infestance

<400> SEQUENCE: 117

```
atggaggctt tcgtcccagt gctgctcctc actatcacag cttacatgta cgagttcacg    60
tatcgcggac acccgcacca aacgggctgt agagagcgtc ttgattggat atatggtcac   120
agctttctca ttgagaccgt caagcggtac tttagcgaaa agataattcg catggcaccc   180
ctggatccca agaagcaata tgtactgggc tttcatccac acggcatcac accgacctca   240
gttatgtggc tccagttcag cgcagaatgg cgaaggttgt tcccgaactt ctacgcgcac   300
atttaactg ccggcattat gcatgcactg ccacttgctc gggacatcct tcagttcttg    360
gggtcacgag aagttacccg acaagccttc acatatactc ttcagcacaa cgagagtgtg   420
ttgctggtgc cgggtggcca agccgagatg ttagagcagc gatctggtca gaaggaggtt   480
cgggtgtaca cacatcacaa aggtttcatc cgcctcgcaa tcgagcatgg agtaccgttg   540
gtccccgtcc tcagcttcaa cgagggcgag atgctggaca acatccaggc tcccatgctc   600
```

| | |
|---|---|
| cagcgctggt tcgttataaa gctcgcgttc ccattcccat ttttccccta cggtcgtgca | 660 |
| ttgctgccga tcccgcgcaa agtacaaatt cctatcgtgg tgggagcacc tctggaggtg | 720 |
| ccacacatga agaaacccag ccatgaagat atcgataaag tccacgccag atactttgat | 780 |
| gagcttcgtg acatgttcgc aaagtacaag gatgaagctg gatgcggcga ctacaagctc | 840 |
| atttacgtct ga | 852 |

```
<210> SEQ ID NO 118
<211> LENGTH: 1050
<212> TYPE: DNA
<213> ORGANISM: Phythophtora infestance

<400> SEQUENCE: 118
```

| | |
|---|---|
| atggcgagcg aaactcaggc tgatcctgtc cagacagaca agggcctctt tgtctatgag | 60 |
| cctcttggat tcttcgcgga tgatagcaaa gtacccaagt ggatgcagct cctaattact | 120 |
| gacgtgttta gcttcgtgac tacgcactac ttcgtgtgga gcttgccatt cctcgcgctg | 180 |
| ttctgctacc tacaccagca cgaactcgac tacgtatcgg tcgctatgat tgctctgtat | 240 |
| ctgccctcat tcttcagtgg ggcgcagaag acagggaagg caacgagtg ggaagccgcg | 300 |
| cggacgtcga gtttatgggg cctcatgaac aaatttcttc gcgtcaagat tattcgggag | 360 |
| caagagctgg atccgaagaa gaagttcatt ttcggattcc accctcacgg aatcctcgta | 420 |
| ctctctcgaa tcgcaggctt cggtcgaaac ttcattgacg tgtgtccggg catcacgact | 480 |
| cggttccttg agcctcggc aatgtattat attccgctag acgtgaaat gtgtctgtgg | 540 |
| atgggtggag tcgatgcctc acgctccaca ggtgaaaagg tgctgaaaga aggcaacagc | 600 |
| atcatcgtct accctggcgg cgtacccgag attttcctca cggatccgaa tttaaaggag | 660 |
| acccagctcg tgctgaaaaa gcgtctcggg tttatcaagc tcgccatgcg tcagggcgca | 720 |
| cagctcgtcc cgacgttcgt ctttggtgaa aagtggctgt acaacatgtg gaccccgccc | 780 |
| gaaagtgtga ctaacttttt ccgcaagaca ctcggcatcc tgttctggt cttctggggg | 840 |
| aaattctggt ggatgcccaa ggctccaggc gaaggaaaac gctacggact tgtgtacggg | 900 |
| aagcctattg cgacgaagca cgattcaaac ccgagcgacg aagaaatccg tgctgttcat | 960 |
| gccgaatacg ttagcgaaat cgagcgcatc ttcagccagt acaaatcgga attcggctac | 1020 |
| gacgaggacg agacgctggc catcatttag | 1050 |

```
<210> SEQ ID NO 119
<211> LENGTH: 1212
<212> TYPE: DNA
<213> ORGANISM: Phythophtora infestance

<400> SEQUENCE: 119
```

| | |
|---|---|
| atgccgcaag cttgtggacg gacgtctgcg tggctggaca atgacgcgcg tccagagcta | 60 |
| cagacgctac atggacgcat tcttcggttt gtgctgctgt ggtacctgtt cggactgtgg | 120 |
| attgtcgggc tggcatcgtt cataggtatg tggctcttct cggggctctg cacgatacgg | 180 |
| tcgttgttga gtttcctaca caatggaggc agttggactg cagccacgcc gctacctgtt | 240 |
| cttgtccaag tgtatctggt tggtatgatc gcgtacgaaa gttatcatta tgtgacgcgg | 300 |
| aacgcgctgc atgaatggcc gctaattcga cgcgtggtgc gctacgtgtt cctgcattac | 360 |
| ccgtattttc gactgaacgc tgtggttttc gaagagcgag aggatgcgaa gcagaacgtc | 420 |
| gagatccaag agccagagca ggagaaggat ggcaacgata gcactaccaa caagagcgac | 480 |
| gacgctagat acttcagctc gaaggctgca gctgcagcta tcgaagaaaa cgatgtgacc | 540 |

```
ccgtacgtcg agccggacaa gcgcgcgtta tttactttcc acccacacgg agtactgacc      600
tgcgggttct cgttcaacgg tgctcatcac atggccttcc agcgtgcggc gtgccgctgg      660
atctcggctg agaacctctt ctacttcccg ataatgcgtg acattttgca ttggatggag      720
ttcagcagta gcaccaaaac cagcatggag aacaccatgc gtacaggtca gaacttatgt      780
ctactgcccg gaggcttcga agaagctacg ctctatcagc gaggcaagca ccgcgtgtac      840
attcagaagc gcttcggatt catcaaactg gcgcttcagc atggctacga catctacccg      900
gcgtacacat tcggcgaaga gtacacctat cacgcgtttc cttatctgca gtggctacgc      960
ttgcaattga accggttccg aatcccgggc gttatcttct tcgggattcc gttctgcttc     1020
ttcatgccac gctcggacgt ggacctcatt accgtcatcg gtaagccgct gcgccttcca     1080
cacattgaca acccgagcag agatgaggtg aaggagaacc acgacaagta cgtcgaggct     1140
ctgcgtgacc tatttgacag gtacaaatgt gtctacgctg ctgaccctga cgccgaatta     1200
gaaattttct ga                                                        1212
```

<210> SEQ ID NO 120  
<211> LENGTH: 1221  
<212> TYPE: DNA  
<213> ORGANISM: Phythophtora infestance

<400> SEQUENCE: 120

```
atggtcggcg ttgcgcacgc tgctacaggg cgcacgccct tgtggcccaa caataatgct       60
gttcctgagc tgcagacgct gcgcggatac gtggggcggc gcttcttgct gtggtcgctc      120
ttcggtctct ggatctttgg actcggggca tacatcctta tgtggctgta ctccggctgg      180
tgcgttggtc actgggcttg gacagcgctg caaaccaaaa gttgggcgct tgcaacacca      240
ccgccaatta gtgtgcaggt atatctagcg ttcacggcgc tgtacgagag ctaccactac      300
atcacgcgcg attcgctgca tttgtggccg cgcatgaggc gtctggcgcg gcacatcctg      360
ctgcgctacc cgtacttccg tctgaacgtg accattttcg aggaacgcga gcttgagaaa      420
caaaagcagc ggctaaagga cgagcagacc aacaacagcg acgacgccac agtagacacg      480
gagcaggatg aaagtgaaca cctcagtccc gctgcagcta tcaaggctgt tgaagagaac      540
gatatctcac cgtatgtgga gacaggaacc aagaacctgt tcgctttcca tccgcatgga      600
atactgacct gtggcttctc tttcaacggc gcatatcaca tgagcttcga gcgctctgcg      660
tgtcgatggc tgtcggctga gaacctcttc tggttccctc tcgtccgtga ccttctcaac      720
tggatggagt acagcagctg cgcgaaagcc aacatgctca gttcatgcg cagagatcaa      780 aacgtcagca tcattcctgg cggctttgaa gaagccacac tctaccagag aggcaaacat      840
cgcttgtatc ttaaaaagcg cttcgggttc atcaaaattg cattgcaaca tggctacaat      900
gtccatccag tatacacttt cggcgaggaa tacacgtacc acgcgttccc gtacctgcag      960
tcgctgcggc tgcaattgaa ccgacttcag attcctggca caatcttctt cggagaggcc     1020
tcgtgctttt acttgccacg caacgatatc gacctcatca ctgtcgttgg caagtctctg     1080
cgattcccac gaatcgagca cccatcgaag gaagatgtac aaaagtatca agcgcagtac     1140
atagaggcgc tgaggagtct attcgacagc tacaagggcg tgtacgctgt tgatcccaac     1200
gccaccctgg agatttttta a                                              1221
```

<210> SEQ ID NO 121  
<211> LENGTH: 1551  
<212> TYPE: DNA

<213> ORGANISM: Phythophtora infestance

<400> SEQUENCE: 121

```
atggacgtgg agaacagtct tttgacgcgg ctagcggcca acgggccgac aatgagcgac     60
gctcccatgc ttctgatggc tgtggtgctg gtgctggcgc tatctggcgt tgtgtccacc    120
gtctcgcagc agcgtcaaaa gcccagcgag gacgagacgc tgcagggccg taagctcacg    180
cgtaagctta gcagcatggg gctatcgacg ttggtgacag agacacctac aaacttgtcc    240
atcccagtgt ctgtattaac tgtcgaaggt catctggcta aggaagacta cgtcgagcgc    300
ctacgtgcgc gtatactaca cgacgccttc ttcctacgct ggcgcagcgt cgtacgtggt    360
gactacaaga caggcgtcta caagtatgtg gaagttcctg gctacgacgt ggcacagaac    420
gtggtggagc acacagttga agagggagag accacgatgt cgtacgttga gtcggcgtta    480
gtaaacaccc cgctggactt tgacaagccg ctctgggaga tgcatgtgat ccacgacccc    540
aagggcaatc ctggtaacac tagcgtcggc tggaaagtgc atcattgtct cggtgacggt    600
gcttcgctgg ctacagccat ggccaagctc agtgaccaga gtgagctctt cgacgccatg    660
gtcgagaagc gcctacaagc caagaagagc ccaaagaccc ccaagccacg caaacccgtg    720
actcagatca ttaaagacat tttggtcttc ctgtacgtct gcatctggtc ggtctacgtg    780
atctcctatc acatgttcgc actcgtgact cgtcgtgaac cggccaccgt ctttaaacgt    840
cccggcggca agcaaaaacg tctgtcgtac aacatgatct actctgtgaa tgccactaag    900
gccgtaggta aacacttccg cgccacagtg aacgacgtga tgcttaatgt cgtagctggt    960
gccatgcgga agaccatgtt gtctgtgggc gagtctgtgg ctccaacact caaggtacgc   1020
tgcgctatcc cagtggacat gcgctccagt acagaagtga tccgccacac tagcaaccgc   1080
ttctcctctc tcgtcattga cctgcccatc ggcgttgagg actctgctca gcgtctgctc   1140
caagtcacgg ctgctatgaa cgatgccaag aattcacttg agaagttctt cgtgtactgg   1200
tcgacccacc tcgtgtcgat gttgccagcg ccgcttatgc gcttgatcgt acactttact   1260
accagtcgta tctctgtggc aacgagcaat gtgcgtgcta gtgtcgtgga agtgagtcta   1320
tgcaagagtc cagtgtcggg cttctacggg ttcgtgcctc caccgccata tgtgaacctt   1380
ggagtagcca tcttgtcaat gggcgatgat ctcggtctta acgttcttgt ggacccatgt   1440
gtcggtgtca acgcgaagca attcctggag tttgcgaagg aagagttcac tgcactgcaa   1500
gaatcggtcg ctgctatgga ggcaaatgcc ggtgacaaga agacaaaata a            1551
```

<210> SEQ ID NO 122
<211> LENGTH: 2028
<212> TYPE: DNA
<213> ORGANISM: Phythophtora infestance

<400> SEQUENCE: 122

```
atgacactgg acgacgattc ctcagcctcg ggcgtgcgcc agcgcaagcc acacggcggc     60
acctccagtg acaggccatc atcccccgag gccttggcgg aggaggccgt cgcttcggcc    120
ttctcggccc ccaaggatga gcagtctcga accaaggaaa cgtttcaaca tgccgctcgc    180
tcgctcggcc ggacacaaag ttggcacgcg cgggcggccg accacgtggc caggaagcgc    240
atctactcca tcatggccgg cgtcattatt ggtgtcgcgg ccgttatcaa ttttcagaga    300
ttttacctgg agaagcctct gatcagcgaa gactcattgc tcatggtccg ggagatgttt    360
gacaacttta actggtccgt gaacgttaag gaagagctca tggctgcctt cgataaccgg    420
ccacctctta tgggtgcagc cgagattcgg cccggtgtcc agttgttcca agagaacgtg    480
```

```
acggccaact cgcctgttgt attggtgccc ggcttcacat ctacgggcct cgagatctgg    540
aacggtagcg aatgcagcaa ggcctatttc agacaacgta tgtggggcac atccaggatg    600
ttgcagcagt ttatgatgaa ccaaaagtgc tggttagagc acatgatgct caaccggtcg    660
tcaggtatgg acccgacgg catcaagtta cgcgcggcca aaggcttaga agcggccgac     720
tatttgatcg gcggcttctg ggtctgggga agatggtgg agaacttggc cgagatcgga     780
tacgacagca acaatctgta catggccgcg tacgactgga ggctcatgcc gcatcttttg    840
gagaagcgcg acgggtattt tacgaaactc aaatacacta tcgagatggc gcgaatgtcg    900
gccggcggcc acaaggtgat gctggtcacg cactcgtatg ctacgcaagt gttttccac    960 tttttgaagt gggtagagag tgagaacgga ggcaaaggtg gcgaccagtg ggtggagacc   1020
aaccttgagt ccttcgttaa tattgccggc ccgaccttgg gcgtggtcaa gacgatcagt   1080
gcgttgatgt cgggcgagat gaaggatacg gccgagctgg gcgggctgtc caagttcctc   1140
ggctactttt tcagtgtgtc ggcgcgtacg caactggccc gctcgtggtc gagtgtgttc   1200
tcgatgatgc ctatcggtgg tgaccgtatc tggggcacgg ccgactcggc ccccgacgat   1260
gtggtagcgg cctccccgtt atcgaccgga aagaactcga cgatcgaccc aaggaaggtc   1320
aaagagcacg tggcacgcta cggatcgaat ggccacgtcg ttcggttcgt caatacttca   1380
cacgagaacg tcactatcgg aggcgtacag aagatgctgg gcaaattaga cccgtacctt   1440
gaccagttcc gttcgtggct gagtaccggt attgccgaag atctgtcctt gcctgaatac   1500
gatcaatcca agtactggac gaacccgttg gaggctgctc tacccaaagc tccgagcctc   1560
aatgtgttct gcttttacgg tgtcggcaaa cctgttgagc gaggatacac gtacggagac   1620
aacccgcccg atgaagataa cgcgacagtg aacggcaaac gtgttgctcc gtacgtgttc   1680
aacacggata ccgacgatct tccgtacatc aagggtgggc tcagatactc ggacggagac   1740
ggcacggtgc cgctgatctc tctgggcctc atgtgtgcca gtggctggcg gacgaagaag   1800
ttcaaccccg gcaacgtcga cgtacgtgtt cgtgaatacc gacacaaccc cgtgtccatg   1860
ctgttcgacg cgcgtggcgg acctgagacg gccgatcacg tcgacatcat gggcaaccac   1920
ggtctcatcc gggacgttct actcgtcgcc gctagggcgt acgaccgcgt gcctgaaaac   1980
attacgtcca gcatcatgga gattgccgaa cgtgtcggag agctctaa                2028
```

<210> SEQ ID NO 123
<211> LENGTH: 2187
<212> TYPE: DNA
<213> ORGANISM: Phythophtora infestance

<400> SEQUENCE: 123

```
atgaagttcg acgacaagaa ggtgctcaat gacacatgga cgcagttcct ggcgctgtgt     60
ctgctgctca tgctggctgt cgactcgctc aaccccatca aggctgtaag taagtttcta    120
ggcgttccgt cgtattactg gggcgctctg tccgtgggta ttatgctagg gctgctgttc    180
cacaacgccg ccgacgtcat ctaccgttcc acacgcgtct tcctcaacag tatcctcagt    240
atctcattta agagtgtgga tctcatcggt ctggataacg taccgaccga cgggcccgtc    300
atcttcaccg gtaaccacgc caaccagttc gtagacggtt tgtagtcat gatgactagt     360 cctcgtaaag taggcttcat gatcgcagaa aagtcgtggc atttgcctgt cgtgggccac    420
ttggctcgta tcatgggctg catccccgtg gtgcgtcctc aggactctgt agcttctggt    480
gttggcagca tgaagctcgc cagtgaagat cccgtgactg tagctagctc gtccagtggt    540
```

| | |
|---|---|
| ggcgctagca gtagtacgcc tcagtggctc gtgcagggcg acggcaccag tttcactaag | 600 |
| caggtgacgc ctggagacca gatccgcttc caagggcaga gcgtcaagga ctcggggtcg | 660 |
| cctgtgaaga tcgtacaggt tctagacgac acgcagttgc tactgaacgc gccgttgaag | 720 |
| agcggcgaag gcaaattagt gcttgagagt gcaccgtttg gtattctcaa gcgtgtggac | 780 |
| caatccgtga cgtttgccaa ggtgtacacg cacttgaagc gtgggaactg catcggtatc | 840 |
| ttcccggaag gaggctcaca cgaccgtacg gacttgttac cactaaaagc tggtgttgcc | 900 |
| gtcatggctc ttggagttaa ggacaagtac aacatcaacg tgccggtggt gcctgtgggc | 960 |
| ttgaactact ccgtggcca tcgcttccgt ggccgcgtga cggtggaatt cggcactccg | 1020 |
| atcactgtgg accaagcgtt gatggccaag taccaggaag acaagcgtac agcgtgtaac | 1080 |
| acgctcttac atcgtgtgga ggagagtatg cgctccgtga tcgtgactac gcccagctac | 1140 |
| ggcgtcatgc aggaggtgtt gactgcgcgt cgtctcttcc agcgctctgg agtgcggctg | 1200 |
| tcggcaaaag agacacaaga cttgaaccgc cgctttgcag aaggctacaa ggtgttgcag | 1260 |
| gatgtgccag aagcccaaga agatctcgta atcttgcaac ataagctgga taactactac | 1320 |
| aagacgctgc agaagatggg actcaaggac catcaagtgc cgtatatccc gtggtggaca | 1380 |
| attcacgacg tgttgggctc cgcactgtac ggcacgttga tccttctact gtcctccatt | 1440 |
| ccgtcgttca tcctgaatgc accggtgggg cttctagctc gttatgtggc gaattcagcg | 1500 |
| cagaagaagg cgctggaagg ctccaaggtc aaggtgttgg ctcgcgacgt tattcttagc | 1560 |
| aagaagatcc agttctcgat tgtagctgtg cccgtgctgt ggttcattta ttttacgatc | 1620 |
| gccgcggtgt tcacggattg gtactggtcg tcaatcatgc tgctgatggt gtcgttcccg | 1680 |
| ctattttctt tcttcggtgt acgctcggta gaggctggaa tgatcgagct gaagacggtc | 1740 |
| cgtccgttgt tctaccgtct gctaccgacg tacaaggcta cacaggatga gcttcctcgg | 1800 |
| caacgtgctg agttgcagaa ggaagtgcgt gagtttgtga agaaatactc gcagtatctg | 1860 |
| ggaaaactgg ccgagccaaa gaagctcgac tggagcgagt acatgcacga gcgctcgttg | 1920 |
| gtattggctg agaagactga gcaggccgag tcgatcccgt cgcctcctcc ggtacatgag | 1980 |
| gaggacgagg agccgcggga aggcgaggct gaagatgata tcggctctcc tgtgcctacg | 2040 |
| atcaccaagt tccacgacat cagtatcctg gcaagtcgg agaactcggt gctggactta | 2100 |
| gcaggtctcg aacgctccat gtcttgcccg ccaggatacc aagagctagc ggaggagata | 2160 |
| gccaagcaac gtaaagggtc cgtgtag | 2187 |

<210> SEQ ID NO 124
<211> LENGTH: 1533
<212> TYPE: DNA
<213> ORGANISM: Phythophtora infestance

<400> SEQUENCE: 124

| | |
|---|---|
| atgctgtcta cgctactatg gcttgcgctg gccgtcgtgg tccttgctac acagggctac | 60 |
| aagatggtgg cgcgcttcct gcgactattg ctacacactt acttccgcaa atcgtggtt | 120 |
| tacggactca acaacttccc gcgtgagggg cctgtgatcc tgtgcccgaa ccaccccaac | 180 |
| atgcttgtgg acgccattct cgtcatgacc gaggccgtaa gtcacggtcg caatccgtac | 240 |
| gtatgggcca agggttcgct gttcagcaac cctgtcgccg ccttcttcct caagaaattc | 300 |
| ggcgccgtgc cggtctatcg tccgcggcgc aaagaggaca gtctcgccga cgtggactca | 360 |
| gataagactc ccgagcaact ggaggcggcc aaccgcaaaa tgttcgagca tacgtggcat | 420 |
| gtacttgctg ggggcaacgt catggtgctt ttccctgaag gaacatcgta cacggctcca | 480 |

```
aagatgctgt cactgcgtac gggtgttgtg cgtgtcgcga cgggtttcgc taagcattat      540
gaccaaccta tcccgatcat cccgctaggt ctcaactact tcaacaaaga ccacttcagg      600
agccagatga cgctggaatt cggtccaccg atggtgatca cgcccgacat ggtgcaaact      660
gaagctttcc aacaggacga acatggcgag gtgaagcgtc tgaccctgga gctagaggag      720
cgcatgcacg atgtgacttt gaatgcatct gacttcagca ctatccacgc tgcgcgaatg      780
atgcgacgcc tctatctaaa cactcctggc cccattgaca ccaacaaaga agtccgtttg      840
acacagtaca ttatcaatat gctggagaag gagccccaag acgacgagca aaaggagcga      900
atcgctacga tccgtgaaaa agttcttcga tacaaagagc aattggaaaa gctgcggttg      960
aaagaccaag aggtgaattt gccgatgccc aaagagaaat cgcttttgca actgttttg      1020
gagcggattc tgtacctgct tgtgctgctg ccactggcca cgcccgggct tttgttgaat     1080
ttaccctact atttattgg aacgaagatg aacagcctcg caggattcgt ggaatccaag      1140
tcgatgttca agatcttcgc tgctgctgtg ttggtgcctg tacattggct cgtactgatc     1200
cttgcaactt ggtatttcct cggatcatcg tatgcgtatg tgctggctgt tggtttgccg     1260
ctgctgctgt actcgcacat ccgcgtactg gaagagagcc gctccatcgc cgagaacgtg    1320
tatttcctct tcaacatcac agctcacgcc gataaggtgg cggtgcttcg aacggaacgg    1380
gagctgctag cgcaagaagt ccacgagctt gtgactaagt acgtcgatgc caagtttctc    1440
tcagccatac acaagtctct agcgagctcg cccgtgaaca gacgattgcg ccaccgtgcc    1500
tcctccacca gcgacacact gcttactaca tag                                 1533
```

<210> SEQ ID NO 125
<211> LENGTH: 520
<212> TYPE: PRT
<213> ORGANISM: Phythophtora infestance

<400> SEQUENCE: 125

```
Met Asn Cys Gln Arg His Pro Thr His Val Ala His Asp Ile Thr Phe
1               5                   10                  15

Gly Ser Ile Leu Ala Ile Leu Ala Ala Gln Pro Pro Ile Pro Val Ser
            20                  25                  30

Ala Ser His Leu Ala Leu Met Ala Ser His Val Val Ser Ser Leu Ser
        35                  40                  45

Asn Ala Ala Thr Pro Leu Arg Phe Thr Leu Leu Asn Gln Gln Leu Thr
    50                  55                  60

Gln Leu Ser Glu Leu Val Gly Val Pro Val Asp Gln Leu Arg Cys Val
65                  70                  75                  80

Ala Cys Leu Leu Ala Val Tyr Pro Leu Ala Leu Ile Val Arg Lys Leu
                85                  90                  95

Pro Ser Val Thr Ala Lys His Trp Leu His Ile Cys Ala Gly Val Ser
            100                 105                 110

Ile Ala Gln Phe Val Tyr Gly Thr Gly Trp Leu His Ser Leu Leu Ser
        115                 120                 125

Ser Leu Val Thr Tyr Ala Leu Val Cys Val Leu Pro Pro Lys Arg Ala
    130                 135                 140

Pro Phe Val Val Phe Leu Ala Asn Met Leu Phe Val Ala Ala Leu His
145                 150                 155                 160

Ile His Arg Met Arg Val Asn Tyr Met Gly Trp Ser Met Asp Ser Thr
                165                 170                 175

Ala Ser Gln Met Leu Leu Leu Ile Lys Leu Thr Ser Phe Ala Phe Asn
```

```
            180                 185                 190
Tyr His Asp Gly Val Pro Ser Ala Thr Ala Val Gln Asn Gly Asp
            195                 200                 205

Ser Glu His Thr Lys Arg Val Lys Gln Leu Arg Lys Gln Leu Ala Ile
    210                 215                 220

Pro Gln Ile Pro Ser Leu Leu Glu Phe Leu Gly Phe Val Tyr Cys Phe
225                 230                 235                 240

Thr Thr Phe Leu Ala Gly Pro Ala Phe Glu Tyr Lys Glu Tyr Ser Asp
                245                 250                 255

Ala Ile His Gln Ala Arg Phe Val Asp Asn Asn Gly Val Arg Arg Asn
            260                 265                 270

Val Ser Pro Ala Arg Ala Ala Met Ser Lys Leu Val Leu Gly Leu Gly
        275                 280                 285

Leu Met Gly Leu Leu Val Gln Phe Gly Ala Leu Ala Asp Leu Asn Gln
    290                 295                 300

Ile Leu Asn Asp Glu Asn Gln Ser Met Leu Met Lys Trp Gly Arg Leu
305                 310                 315                 320

Phe Val Ala Leu Phe Leu Thr Arg Ala Lys Tyr Tyr Val Ala Trp Lys
                325                 330                 335

Leu Ala Glu Gly Ala Thr Val Leu Thr Gly Thr Gly Phe Glu Gly Phe
            340                 345                 350

Asp Glu Gln Asn Asn Pro Lys Gly Trp Asp Gly Val Ser Asn Val Asp
        355                 360                 365

Ile Leu Gly Phe Glu Leu Gly Ala Asn Val Arg Glu Ile Ser Arg Ala
    370                 375                 380

Trp Asn Lys Gly Thr Gln Asn Trp Leu Glu Arg Tyr Val Tyr Thr Arg
385                 390                 395                 400

Thr Gly Asn Ser Leu Leu Ala Thr Tyr Ser Val Ser Ala Leu Trp His
                405                 410                 415

Gly Phe Tyr Pro Gly Tyr Tyr Leu Phe Phe Leu Thr Val Pro Leu Ala
            420                 425                 430

Thr Ser Val Asn Arg Leu Ala Arg Arg His Val Arg Pro Tyr Val Val
        435                 440                 445

Asp Ser Pro Leu Lys Pro Leu Tyr Asp Leu Val Gly Met Ile Cys Thr
450                 455                 460

Ala Leu Val Val Asn Tyr Leu Ala Val Ser Phe Val Leu Ser Trp
465                 470                 475                 480

Glu Asp Ala Val Ala Gly Phe Arg Ser Met Arg Phe Thr Gly His Val
                485                 490                 495

Gly Leu Val Gly Cys Tyr Leu Leu Leu Thr Phe Val Pro Ile Lys Lys
            500                 505                 510

Thr Ala Asn Ser Lys Lys Thr Leu
        515                 520

<210> SEQ ID NO 126
<211> LENGTH: 456
<212> TYPE: PRT
<213> ORGANISM: Phythophtora infestance

<400> SEQUENCE: 126

Met Asp Arg Val Val Asp Phe Val Glu His Leu Gln Pro Tyr Thr Glu
1               5                   10                  15

Leu Ala Thr Pro Leu Asp Phe Ser Phe Leu His Ala Lys Val Asp Glu
            20                  25                  30
```

Leu Ser Val Ser Leu Gly Leu Gly Ser Asp Gln Leu Cys Tyr Val Leu
            35                  40                  45

Cys Leu Phe Ala Ala Tyr Pro Leu Ala Val Val Tyr Lys Leu Leu Pro
 50                  55                  60

Gly Ala Ser Leu Lys His Val Phe Asp Val Val Leu Gly Val Ser Ile
 65                  70                  75                  80

Ala Gln Phe Val Leu Gly Ser Gly Trp Val His Ser Phe Ile Ser Ser
                 85                  90                  95

Phe Leu Thr Tyr Leu Ile Val Lys Phe Gly Pro Ser Lys His Ala Pro
            100                 105                 110

Gly Ile Val Phe Leu Phe Asn Met Leu Tyr Met Ser Ala Ser His Ile
            115                 120                 125

Tyr Arg Leu Tyr Val Asp Tyr Met Gly Trp Thr Leu Asp Phe Thr Gly
130                 135                 140

Pro Gln Met Leu Leu Val Ile Lys Leu Thr Ser Phe Ala Tyr Asn Tyr
145                 150                 155                 160

Tyr Asp Gly Val Val Asp Lys Thr Phe Glu Lys Lys Gly Ala Glu Met
                165                 170                 175

Ser Pro Gly Ile Lys Lys Val Tyr Glu Gly Arg Gln Lys Leu Ala Ile
            180                 185                 190

Gln Glu Ile Pro Ser Leu Leu Glu Phe Phe Gly Tyr Val Tyr Ser Phe
            195                 200                 205

Thr Thr Phe Leu Ala Gly Pro Ala Phe Glu Ile Arg Glu Tyr Leu Asp
            210                 215                 220

Val Thr Ser Gly Lys Lys Phe Leu Met Asp Gly Lys Asn Lys Glu Pro
225                 230                 235                 240

Ser Ser Val Leu Ala Ala Phe Ser Lys Phe Leu Val Gly Ser Leu Leu
                245                 250                 255

Met Ala Ala Phe Ala Val Tyr Gly Pro Met Tyr Pro Leu Ser Asn Leu
            260                 265                 270

His Asp Pro Lys Ile Ala Ala Gln Pro Leu Leu Tyr Gln Ile Arg Asp
            275                 280                 285

Leu Tyr Ile Ala Leu Ile Phe Cys Lys Ala Lys Tyr Tyr Ser Ala Trp
290                 295                 300

Lys Ile Ala Glu Gly Ala Thr Val Leu Cys Gly Phe Gly Phe Glu Gly
305                 310                 315                 320

Phe Asn Lys Asp Gly Thr Ser Arg Gly Trp Asn Gly Val Ser Asn Met
                325                 330                 335

Asp Ile Leu Gly Phe Glu Phe Ser Gln Ser Ile Arg Ala Ala Ser Arg
            340                 345                 350

Ala Trp Asn Lys Gly Thr Gln Asn Trp Leu Glu Arg Tyr Val Tyr Thr
            355                 360                 365

Arg Thr Gly Asn Ser Leu Met Ala Thr Tyr Phe Ile Ser Ala Phe Trp
370                 375                 380

His Gly Phe Tyr Pro Gly Tyr Tyr Ile Phe Phe Met Ser Leu Pro Leu
385                 390                 395                 400

Ala Thr Ala Val Asn Arg Leu Ala Phe Lys Arg Leu Arg Pro Arg Phe
                405                 410                 415

Ile Glu Ala Asp Gly Ser Phe Gly Ala Lys Lys Ile Tyr Asp Val
            420                 425                 430

Leu Ser Tyr Leu Leu Thr Leu Phe Ala Met His Tyr Phe Val Met Pro
435                 440                 445

Phe Gln Val Leu Asn Lys Tyr Leu

<210> SEQ ID NO 127
<211> LENGTH: 485
<212> TYPE: PRT
<213> ORGANISM: Phythophtora infestance

<400> SEQUENCE: 127

| Met | Arg | Val | Thr | Arg | Arg | Ile | Arg | Arg | Leu | Ala | Glu | Ala | Trp | Ile | Val |
|-----|-----|-----|-----|-----|-----|-----|-----|-----|-----|-----|-----|-----|-----|-----|-----|
| 1 | | | | 5 | | | | | 10 | | | | | 15 | |

| Phe | Arg | Tyr | Arg | Ala | Ala | Glu | Gln | Ser | Met | Glu | Ile | Leu | Arg | Gly | Pro |
| | | | 20 | | | | | 25 | | | | | 30 | | |

| Val | Asp | Gly | Ile | Ala | Leu | Ser | Glu | Asn | Phe | Pro | Val | Asp | Gly | Phe | Arg |
| | | 35 | | | | | 40 | | | | | 45 | | | |

| Leu | Met | Val | Ala | Leu | Ala | Gly | Cys | Ser | Leu | Ile | Ala | Pro | Leu | Ile | His |
| | 50 | | | | | 55 | | | | | 60 | | | | |

| Leu | Thr | Arg | Gly | Glu | Thr | Ser | Arg | His | Leu | Phe | Asn | Val | Ala | Val | Gly |
| 65 | | | | | 70 | | | | | 75 | | | | | 80 |

| Leu | Phe | Ala | Gly | Val | Phe | Val | Phe | Asp | Leu | Ala | Val | Leu | His | Thr | Ile |
| | | | | 85 | | | | | 90 | | | | | 95 | |

| Gly | Thr | Ala | Val | Val | Val | Tyr | Leu | Leu | Met | Met | Val | Ala | Pro | Ser | Leu |
| | | | | 100 | | | | | 105 | | | | | 110 | |

| Trp | Gly | Ala | Leu | Cys | Cys | Arg | Cys | Cys | Trp | Arg | Thr | Ser | His | Tyr | Tyr |
| | | 115 | | | | | 120 | | | | | 125 | | | |

| Arg | Glu | Phe | Tyr | Ser | Pro | Asp | Ile | Val | Trp | Asp | Ser | Ala | Gln | Met | Ile |
| | 130 | | | | | 135 | | | | | 140 | | | | |

| Leu | Thr | Leu | Lys | Leu | Ser | Ser | Val | Ala | Ile | Asn | Tyr | Ser | Asp | Gly | Gly |
| 145 | | | | | 150 | | | | | 155 | | | | | 160 |

| Leu | Pro | Thr | Glu | Lys | Lys | Thr | Pro | Thr | Met | Leu | Lys | Asn | Glu | Leu | Gln |
| | | | | 165 | | | | | 170 | | | | | 175 | |

| Glu | Ile | Pro | Glu | Leu | Ile | Pro | Tyr | Phe | Gly | Phe | Val | Phe | Phe | Phe | Pro |
| | | | 180 | | | | | 185 | | | | | 190 | | |

| Thr | Tyr | Leu | Ala | Gly | Pro | Ala | Phe | Glu | Tyr | Lys | Asp | Tyr | Ile | Tyr | Trp |
| | | 195 | | | | | 200 | | | | | 205 | | | |

| Met | Lys | Asp | Val | Arg | Val | Ala | Pro | Phe | Met | Val | His | Leu | Arg | Asn | Leu |
| | 210 | | | | | 215 | | | | | 220 | | | | |

| Val | Ile | Ser | Ala | Ala | Gly | Phe | Phe | Val | Ser | Leu | Gln | Phe | Pro | Val | Glu |
| 225 | | | | | 230 | | | | | 235 | | | | | 240 |

| Glu | Ile | Asp | Ser | Pro | Asp | Phe | Phe | Pro | Lys | Ser | Ser | Trp | Ala | Val | Arg |
| | | | | 245 | | | | | 250 | | | | | 255 | |

| Cys | Leu | Arg | Met | Cys | Ile | Pro | Val | Val | Leu | Phe | Arg | Phe | Arg | Tyr | Tyr |
| | | | 260 | | | | | 265 | | | | | 270 | | |

| Leu | Ala | Trp | Ser | Leu | Ala | Glu | Ala | Ala | Ser | Ala | Ala | Ala | Gly | Val | Gly |
| | | 275 | | | | | 280 | | | | | 285 | | | |

| Tyr | Val | Gln | Ala | Thr | Gly | Lys | Trp | Asn | Gly | Ile | Thr | Asn | Asn | Asp | Leu |
| | 290 | | | | | 295 | | | | | 300 | | | | |

| Leu | Cys | Val | Glu | Leu | Pro | Thr | Asn | Phe | Arg | Val | Ala | Ile | Asn | Ser | Trp |
| 305 | | | | | 310 | | | | | 315 | | | | | 320 |

| Asn | Ile | Gly | Val | Ala | Arg | Trp | Ile | Asn | Thr | Tyr | Ile | Tyr | Gln | Arg | Val |
| | | | | 325 | | | | | 330 | | | | | 335 | |

| Gly | Leu | Thr | Lys | Ser | Gly | Lys | Ser | Thr | Met | Leu | Ser | Thr | Met | Ala | Ser |
| | | | 340 | | | | | 345 | | | | | 350 | | |

| Phe | Phe | Val | Ser | Ala | Leu | Trp | His | Gly | Leu | Ser | Pro | Gly | Tyr | Tyr | Leu |
| | | | 355 | | | | | 360 | | | | | 365 | | |

```
Phe Phe Leu Leu Gly Gly Ile Tyr Ile Glu Val Gly Lys Gln Leu Arg
            370                 375                 380

Arg Arg Leu Arg Pro Tyr Phe His Tyr Thr Glu Asp Arg Lys Ala His
385                 390                 395                 400

Ser His Ala Ile Phe Leu Ser Tyr Phe Ser Gly Thr Ser His Pro Leu
                405                 410                 415

Ala Phe Leu Tyr Asp Ile Ser Gly Met Phe Phe Thr Trp Val Ala Met
                420                 425                 430

Gln Tyr Ala Gly Val Ala Phe Glu Ile Leu Asp Val Arg Arg Cys Leu
                435                 440                 445

Ala Ile Trp Ser Ser Trp Tyr Phe Leu Pro His Leu Val Ser Ile Gly
            450                 455                 460

Leu Leu Val Phe Phe Asn Leu Phe Pro Gln Arg Arg Ser Thr Pro Thr
465                 470                 475                 480

Asp Lys Lys Thr Gln
                485

<210> SEQ ID NO 128
<211> LENGTH: 558
<212> TYPE: PRT
<213> ORGANISM: Phythophtora infestance

<400> SEQUENCE: 128

Met Ser Thr Thr Ala Leu Leu Gln Ala Ser Thr Ser Pro Pro Pro Ser
1               5                   10                  15

Arg Glu Pro Glu Tyr Ala Ala Leu Glu Gln Leu Glu Pro Pro Leu Ser
                20                  25                  30

His Ala Ile Asp Met Gly Val Lys Val Ser Pro Ser Glu Ser Ala Ala
            35                  40                  45

Ile Ala Gly Gly Val Tyr Val Thr Ala Ser Ser Ser Cys Gly Ala Ser
        50                  55                  60

Thr Ile Lys His Asn Pro Phe Thr Tyr Thr Thr Pro Val Asp Thr Tyr
65                  70                  75                  80

Glu Lys Ala Lys Met Thr Ile Leu Cys Leu Leu Gly Val Pro Phe Ile
                85                  90                  95

Arg Phe Val Leu Leu Cys Val Gly Ile Leu Val Ile Val Ser
                100                 105                 110

His Leu Ala Leu Ile Gly Tyr Lys Pro Leu Asp Ala His Ser Gly Ala
            115                 120                 125

Arg Pro Pro Leu Pro Arg Trp Arg Arg Ile Val Gly Ser Pro Val Pro
        130                 135                 140

Tyr Leu Leu Arg Ser Leu Met Leu Ile Val Gly Tyr Tyr Trp Val Pro
145                 150                 155                 160

Val Lys Tyr Pro Pro Asn Phe Asn Arg His Ala Met Pro Arg Val Ile
                165                 170                 175

Val Ser Asn His Leu Thr Phe Phe Asp Gly Leu Tyr Ile Phe Thr Leu
            180                 185                 190

Leu Ser Pro Ser Ile Ala Met Lys Thr Asp Val Ala Asn Leu Pro Leu
        195                 200                 205

Ile Ser Arg Ile Val Gln Met Ile Gln Pro Ile Leu Ile Asp Arg Gly
        210                 215                 220

Thr Pro Glu Gly Arg Arg Ala Met Asn Asp Ile Thr Ser His Val
225                 230                 235                 240

Ala Asp Pro Ser Lys Pro Pro Leu Leu Val Phe Pro Glu Gly Thr Thr
                245                 250                 255
```

```
Ser Asn Gln Thr Val Leu Cys Lys Phe Lys Val Gly Ser Phe Val Ser
            260                 265                 270

Gly Val Pro Cys Gln Pro Val Val Leu Arg Tyr Pro Tyr Lys His Phe
        275                 280                 285

Asp Leu Ser Trp Pro Pro Gly Val Ser Gly Leu Tyr Leu Ala Leu Arg
    290                 295                 300

Val Leu Cys Gln Val Tyr Asn Arg Leu Glu Val Glu Ile Leu Pro Ala
305                 310                 315                 320

Tyr Tyr Pro Ser Glu Arg Glu Arg Lys Asp Pro Gln Leu Tyr Ala Ile
                325                 330                 335

Asn Val Arg Glu Val Met Ala Lys Ala Leu Gly Val Pro Thr Thr Asn
            340                 345                 350

His Ala Phe Glu Asp Val Ala Met Leu Met Arg Val Gly Asp Tyr Ala
        355                 360                 365

Thr Lys His Val Val Pro Leu Thr Asp Val Gly Glu Val Ile Ser Leu
    370                 375                 380

Thr Ala Leu Lys Arg Gly Asp Val Asp Arg Leu Val Gly Tyr Phe Arg
385                 390                 395                 400

Arg His Asp Leu Asp Lys Asp Gly His Leu Ser Met Gln Glu Leu Arg
                405                 410                 415

Ala Leu Phe Pro Asn Asp Asp Pro Val Ile Val Asp Gln Leu Phe Asp
            420                 425                 430

Leu Val Asp Leu Asp Asp Ser Gly Leu Ile Asp Phe Arg Glu Leu Cys
        435                 440                 445

Leu Ala Leu Arg Ala Leu Asn Pro Gln Asn Ile Asn Glu Gly Asp Asp
    450                 455                 460

Ala Leu Ala Lys Phe Ala Phe Arg Leu Tyr Asp Leu Asp Asn Asn Gly
465                 470                 475                 480

Val Ile Asp Ala Ser Glu Leu Glu Gln Leu Leu Arg Phe Gln Arg Asn
                485                 490                 495

Phe Tyr Gly Val Ser Glu Ala Ser Val Ala Ala Ala Leu Arg Gln Ala
            500                 505                 510

Gln Ala Glu Asn Thr Thr Gly Ile Thr Tyr Asn Arg Phe Glu Gln Leu
        515                 520                 525

Val Leu Gln Asn Pro Glu Val Leu Trp Tyr Val Arg Asp Lys Leu Glu
    530                 535                 540

Val Leu Arg Gly Ser Met Arg Glu Ser Ser Leu Glu Ile Pro
545                 550                 555
```

<210> SEQ ID NO 129
<211> LENGTH: 348
<212> TYPE: PRT
<213> ORGANISM: Phythophtora infestance

<400> SEQUENCE: 129

```
Met Glu Lys Tyr Ser Arg Trp Ser Asp Leu Thr Thr Gly Ile Asn Pro
1               5                   10                  15

Phe Val Pro Gln Arg Arg Arg Phe Thr Ser Gly Trp Pro Val Thr Ile
            20                  25                  30

Leu Gln Val Ile Ser Gly Ser Ala Leu Ala Leu Val Arg Phe Pro Leu
        35                  40                  45

Val Leu Val Ala Phe Val Ala Leu Phe Leu Val Asn Leu Val Val Ser
    50                  55                  60

Ile Leu Ala Val Ile Pro Phe Leu Gly Arg Leu Leu Lys Arg Ile Thr
```

-continued

```
65                  70                  75                  80

Glu Trp Leu Leu Cys Ser Leu Leu Leu Leu Leu Phe Gly Val Phe Thr
                85                  90                  95
Ser Asn Gly Ser Thr Arg Val Gly Ser Gly Asp Val Leu Val Cys Asn
            100                 105                 110

Tyr Thr Ser Phe Leu Glu Ile Leu Tyr Leu Ala Thr Arg Phe Ser Pro
        115                 120                 125

Val Phe Val Phe Ala Thr Glu Thr Lys Ser Asn Asp Glu Gly Leu Val
    130                 135                 140

His Val Cys Gly Leu Leu Glu Ala Leu Tyr Arg Ser Leu Ala Met Pro
145                 150                 155                 160
Val Ser Val Glu Arg Val Lys Pro Thr Arg Lys Ile Ala Asp Val Val
                165                 170                 175

Arg Arg Ala Ala Gly Pro Val Val Val Leu Pro Glu Gly Ala Arg Ser
            180                 185                 190

Asn Gly Lys Ala Val Leu Lys Phe Ile Pro Val Leu Gln Asn Leu Pro
        195                 200                 205

Val Lys Thr Arg Val His Leu Val Ala Phe Arg Tyr Glu Phe Lys Arg
    210                 215                 220

Phe Ser Pro Ser Gln Ser Ala Gly Gly Ala Trp Ser His Leu Phe Trp
225                 230                 235                 240
Thr Ala Phe His Val Tyr His Thr Met Arg Val Thr Val Leu Ser Ala
                245                 250                 255
Lys Asp Leu Asn Leu Asp Asp Leu Thr Pro Thr Lys Leu Pro Ser Asn
            260                 265                 270

Lys Ser Ser Lys Lys Gln Glu Asn Ser Lys Thr Leu Ser Thr Asp Gln
        275                 280                 285

Val Glu Lys Leu Arg Thr Leu Leu Ala Ala Met Leu Arg Thr Lys Thr
    290                 295                 300

Val Asp Leu Gly Pro Glu Asp Ser Val Ser Phe Asn Asn Tyr Trp Lys
305                 310                 315                 320
His Val Asn Ser Gly Gly Arg Gln Pro Ala Ser Gln Phe Thr Asp Arg
                325                 330                 335
Lys Ala Pro His Glu His Ala Gln Trp Ala Lys Arg
            340                 345

<210> SEQ ID NO 130
<211> LENGTH: 424
<212> TYPE: PRT
<213> ORGANISM: Phythophtora infestance

<400> SEQUENCE: 130

Met Ser Phe Ala Thr Pro Ala Gln Val Leu Gln Asp Val Arg Phe Glu
1               5                   10                  15

Glu Arg Phe Ala Glu Ile Glu Ser Arg Leu Pro Ala Thr Leu Ala Leu
            20                  25                  30

Ala Lys Glu Gly Ser Leu Ala Lys Arg Asn Gln Thr Lys Arg Lys Leu
        35                  40                  45

Tyr His Asp Ser Glu Leu Ile Arg Ile Glu Leu Glu Glu Arg Leu Asn
    50                  55                  60

Glu Leu Gly Ile Glu Ser Gln Trp Val Thr Ala Pro Glu Met Lys Glu
65                  70                  75                  80

Ala Asn Glu Lys Leu Asp Ala Val Arg Lys Gln Leu Lys Leu Asp Val
                85                  90                  95
```

Leu Pro Ala Ser Ser Pro Leu Glu Lys Ile Tyr Met Val Val Arg
            100                 105                 110

Met Leu Thr Met Val Leu Val Leu Val Gly Trp Leu Ser Cys Val Thr
        115                 120                 125

Val Leu Ile Pro Leu Lys Trp Leu Asn Pro Val Leu Lys Lys Met Gly
        130                 135                 140

Val Lys Lys Asn Tyr Leu Pro Met Asp Ile Val Ser Trp Gly Thr Ala
145                 150                 155                 160

Phe Met Val Cys Val Thr Ala Cys Thr Asp Met Lys Ala Glu Gly Val
                165                 170                 175

Glu Asn Leu Leu Asn Leu Lys Asp Ser Val Val Cys Met Phe Ser His
            180                 185                 190

Ser Ser Asn Leu Asp Gly Phe Ile Val Asn Gly Ser Ser Pro Ile Ala
        195                 200                 205

Phe Lys Phe Ala Ala Lys Lys Ser Ile Phe Leu Val Pro Phe Leu Gly
        210                 215                 220

Trp Ser Ser Arg Trp Gly Phe Asp Phe Val Ala Ile Asp Arg Ser His
225                 230                 235                 240

Arg Lys Ser Ala Leu Lys Ser Leu Lys Glu Leu Ala Val Ser Val Asn
                245                 250                 255

Glu His Gly Asn Ser Val Cys Ile Ser Pro Glu Gly Thr Arg Ser Lys
            260                 265                 270

Asp Gly Leu Leu Gln Glu Phe Lys Lys Gly Pro Phe Tyr Leu Arg Glu
        275                 280                 285

Asp Thr Lys Lys Asn Val Val Pro Ser Ile Val Phe Gly Ala Tyr Glu
        290                 295                 300

Leu Trp Pro Pro Gly Arg Leu Phe Ser Ile Pro Gly His Thr Leu Val
305                 310                 315                 320

Arg Tyr Leu Pro Glu Tyr Lys Ser Asp Pro Asn Leu Asn Arg Asn Gln
                325                 330                 335

Asn Arg Leu Ala Leu Arg Arg Ile Tyr Leu Lys Ala Phe Thr Glu Asp
            340                 345                 350

Val Pro Asp Tyr Ile Gly Thr Arg Val Ser Thr Asn Phe Ile Leu Lys
        355                 360                 365

Asn Met Phe Tyr His Tyr Leu Ala Trp Ala Ile Thr Phe Lys Val Thr
        370                 375                 380

Ser Trp Ala Leu Thr Val Ile Ser Leu Val Leu Tyr Trp Leu Asn Ile
385                 390                 395                 400

Thr Tyr Gly Thr Phe Met Leu Phe Ser Leu Val Met Met Val Ala Gly
                405                 410                 415

Glu Ala Leu Met Phe Phe Thr Cys
            420

<210> SEQ ID NO 131
<211> LENGTH: 425
<212> TYPE: PRT
<213> ORGANISM: Phythophtora infestance

<400> SEQUENCE: 131

```
Met Ser Gln Ser Asp Glu Cys Gln Ala Thr Gln Thr Ser Val Tyr Pro
1               5                   10                  15

Thr Lys Arg Cys Val Ser Gly Gly Pro Val Val Glu Pro Asp Ala Glu
            20                  25                  30

Pro Val Leu Asn Arg Val Ile His Pro Ser Thr Lys Phe Glu Thr Ala
        35                  40                  45
```

Trp Thr Trp Ser Gly Cys Ile Ile Gly Cys Ser Tyr Leu Leu Leu
    50                  55                  60

Val Val Cys Ala Phe Leu Asn Thr Thr Phe Val Leu Trp Pro Leu Thr
65                  70                  75                  80

Leu Leu Gln Trp Ser His Leu Leu Ser Thr Arg Ser Cys Arg Trp Ile
                85                  90                  95

Cys Arg Phe Leu Glu Asp Lys Tyr Phe Ala Met Leu Ser Gly Tyr Leu
            100                 105                 110

Glu Leu Val Gly Gly Val Lys Ile Ile Ile Thr Gly Asp Glu Glu Leu
        115                 120                 125

Gln Phe Ala His His Glu His Val Leu Leu Ile Cys Asn His Arg Ser
    130                 135                 140

Glu Val Asp Trp Ile Phe Phe Trp Asn Leu Ala Leu Arg Leu Asn Val
145                 150                 155                 160

His Asp Arg Ile Arg Val Met Met Lys Ser Val Ile Arg Tyr Ala Pro
                165                 170                 175

Gly Val Gly Trp Thr Met Met Leu Leu Arg Tyr Pro Tyr Val Asn Arg
            180                 185                 190

Asn Trp Ala Thr Asp Gln Asp Arg Leu Thr Lys Val Ile Glu Ser Tyr
        195                 200                 205

Lys Asp Val Asp Met Gly Thr Trp Leu Ala Met Phe Pro Glu Gly Thr
210                 215                 220

Ala Leu Tyr Asp Lys Thr Leu Lys Lys Ser His Glu Phe Ala Ser Lys
225                 230                 235                 240

Gln Gly Glu Ala Lys Trp Asn Tyr Val Leu Gln Pro Arg Val Lys Gly
                245                 250                 255

Phe Glu Leu Cys Met Asp Lys Met Asp Pro Asp Tyr Val Val Asp Leu
            260                 265                 270

Thr Val Ala Tyr Pro Glu Leu Met Glu Gly Val Arg Pro Ser Pro Val
        275                 280                 285

Arg Phe Val Arg Gly Gln Phe Pro Thr Glu Val His Met His Val Gln
290                 295                 300

Arg Tyr His Arg Ser Thr Leu Leu Lys His Lys Asp Arg Met Gly Gln
305                 310                 315                 320

Trp Leu Lys Asp Arg Phe Ala Glu Lys Glu Arg Leu Glu His Phe
                325                 330                 335

Tyr Glu Thr Gly Ala Phe Gln Gly Glu Gln Thr Ser Gly Gln His
            340                 345                 350

Ala Ser Arg Val Ala Leu Leu Pro Ala Gln Gln Ile Leu Leu Phe Val
        355                 360                 365

Gly Glu Asn Tyr Leu Thr Tyr Phe Trp Ser Arg Arg Leu Ser Val
370                 375                 380

Tyr Leu Arg Ala Phe Gln Val Ala Gly Ala Ser Ile His Ser Met Asp
385                 390                 395                 400

Ser His Lys Ile His Asn Glu Lys His Gln Asp Lys Leu His Thr Arg
                405                 410                 415

Ser Ala Asp Glu Leu Arg Leu Phe Thr
            420                 425

<210> SEQ ID NO 132
<211> LENGTH: 390
<212> TYPE: PRT
<213> ORGANISM: Phythophtora infestance

<400> SEQUENCE: 132

Met Ala Val Phe His Leu Tyr Ser Ala Leu Asn Leu Leu Trp Ile Leu
1               5                   10                  15

Cys Asn Ser Ala Cys Ile Asn Phe Leu Gln Phe Cys Leu Trp Cys Leu
            20                  25                  30

Val Arg Pro Phe Asn Lys Ala Leu Tyr Arg Arg Leu Met Gly Ser Val
        35                  40                  45

Ala Gln Ser Leu Trp Val Asp Val Thr Ser Thr Ser Phe Pro Gln Thr
    50                  55                  60

Lys Leu Ser Val Thr Gly Glu Leu Pro Ser Asp Pro Thr Lys Pro Val
65                  70                  75                  80

Ile Ile Ile Ala Asn His Gln Val Asp Ala Asp Trp Trp Tyr Ile Trp
                85                  90                  95

Gln Ala Ala Arg His Gln His Ala Ala Gly Asn Ile Lys Ile Val Leu
            100                 105                 110

Lys Asp Gln Leu Lys Tyr Leu Pro Ile Ile Gly Trp Gly Met Arg Leu
        115                 120                 125

Phe Gln Phe Leu Phe Leu Arg Arg Arg Ile Asp Gln Asp Ala Glu His
    130                 135                 140

Ile Lys Lys Tyr Met Gly Gly Leu Ile Ser Asp Asn Phe Pro Phe Trp
145                 150                 155                 160

Leu Val Leu Phe Pro Glu Gly Thr Thr Ile His Arg Glu Tyr Val Val
                165                 170                 175

Lys Ser Gln Ala Phe Ala Ala Arg Glu Ala Arg Pro Lys Phe Glu Arg
            180                 185                 190

Val Leu Leu Pro Arg Thr Thr Gly Met Arg Ile Ile Leu Asp Ala Val
        195                 200                 205

Ala Asp Ala Lys Pro Asp Ile Tyr Asp Leu Thr Val Ala Phe Pro Ser
    210                 215                 220

Tyr Ser Gly Glu Val Pro Thr Phe Asp Met Gly Tyr Gly Arg Arg Val
225                 230                 235                 240

Asp Thr Glu Val Pro Ser Met Lys Ser Leu Leu Ala Gly Lys Gln Pro
                245                 250                 255

Val Gly Arg Val Ala Leu His Ser Arg Lys Phe Lys Tyr Glu Asp Ala
            260                 265                 270

Ala Thr Asp Leu Gln Gly Phe Leu Asp Ala Arg Trp Thr Glu Lys Glu
        275                 280                 285

Glu Arg Met Asn Tyr Phe Ile Lys His Gln Gln Phe Pro Glu Thr Glu
    290                 295                 300

Ser Thr Val Glu Met Gln Leu Ser Thr Ser Met Gly Ala Val Phe Arg
305                 310                 315                 320

Leu Trp Met Gly Ile Leu Leu Ser Cys Val Val Leu Pro Val Val Met
                325                 330                 335

Met Leu Phe Phe Pro Leu Tyr Phe Thr Trp Val Val Tyr Cys Phe Val
            340                 345                 350

Tyr Ser Val Tyr Asp Arg Thr Thr Asn Phe Trp Trp Pro Tyr Ile Phe
        355                 360                 365

Asn Leu Phe Val Glu Arg Ala Thr Lys Thr His Glu His Phe Lys Arg
    370                 375                 380

His Gln Ala Lys Tyr Leu
385                 390

<210> SEQ ID NO 133

<211> LENGTH: 369
<212> TYPE: PRT
<213> ORGANISM: Phythophtora infestance

<400> SEQUENCE: 133

```
Met Gly Val Ala Val Val Gly Val Val Phe Leu Thr Ser Leu Val Val
1               5                   10                  15

Thr Gly Trp Thr Gly Val Ala Trp Ile Leu Thr Pro Cys Phe Leu Leu
            20                  25                  30

Ala Ala Leu Pro Leu Pro Ala Phe Leu Gln Thr Lys Arg Phe Tyr Arg
        35                  40                  45

Arg Val Thr Arg Phe Ile Gln Trp Ala Trp Met Gly Gln Val Lys Leu
    50                  55                  60

Phe Gly Ile Gln Val Arg Val Leu Gly Asp Ala Glu Thr Lys Ala Arg
65                  70                  75                  80

Glu Ser Glu Leu Ser Lys Asp Arg Ala Leu Trp Leu Ser Asn His Arg
                85                  90                  95

Thr Arg Ile Asp Trp Met Leu Leu Trp Ser Val Ala Trp Arg Thr Arg
            100                 105                 110

Thr Leu His Gln Leu Arg Ile Val Leu Lys Ala Pro Leu Arg Lys Met
        115                 120                 125

Pro Ile Phe Gly Trp Ala Met Gln His Phe Ile Phe Ile Phe Leu Gln
    130                 135                 140

Arg Arg Trp Ala Asp Asp Gln Val Asn Leu Arg Lys Leu Leu Pro Phe
145                 150                 155                 160

Leu Thr Ser Thr Glu Pro Glu Ala Ser Tyr Leu Leu Phe Pro Glu Gly
                165                 170                 175

Thr Asp Leu Ser Glu Ser Asn Leu Glu Lys Ser Ala Val Phe Ala Glu
            180                 185                 190

Lys Lys Ser Leu Ser Pro Arg Gln Tyr Ser Leu Tyr Pro Arg Thr Thr
        195                 200                 205

Gly Trp Thr Phe Met Phe Pro Leu Leu Arg Ser Gln Leu Thr Ala Val
    210                 215                 220

Tyr Asp Val Thr Met Phe Tyr Val Asp Tyr Ala Ala Asn Glu Arg Pro
225                 230                 235                 240

Ser Glu Ser Ser Leu Leu Thr Gly Arg Met Pro Arg Met Ile His Phe
                245                 250                 255

Tyr Ile Glu Arg Val Asp Ile Ser Val Leu Arg Asp Lys Ser Glu Thr
            260                 265                 270

Asp Leu Ala Ala Trp Leu Glu Lys Arg Phe Glu Arg Lys Glu Ser Leu
        275                 280                 285

Leu Lys Ala Phe Tyr Glu Asp Asn Gly Lys Leu Pro His Gly Ala Glu
    290                 295                 300

Pro Leu Phe Gln Glu Asn Gln Gly Thr Ala Met Val Met Leu Val Ala
305                 310                 315                 320

Phe Trp Leu Ile Ser Ile Gly Ala Ala Thr Leu Leu Gly Leu Ile Gly
                325                 330                 335

Asn Phe Ile Ser Val Ile Ala Ala Leu Ala Val Val Val Gly Tyr Ala
            340                 345                 350

Thr Asn Thr Ala Tyr Gly Pro Gly Val Asp Gly Phe Leu Ile Asn Asn
        355                 360                 365

Ser
```

<210> SEQ ID NO 134

<211> LENGTH: 447
<212> TYPE: PRT
<213> ORGANISM: Phythophtora infestance

<400> SEQUENCE: 134

```
Met Gly Pro Arg Val Glu Pro Pro Asn Ser Gly Arg Ser Pro Thr Ala
1               5                   10                  15

Ser Lys Arg Arg Met Lys Lys Phe Arg Asp Val Val Ser Pro Leu Asp
            20                  25                  30

Pro Ala Asp Ala Arg Ser Gly Val His Ser Ser Glu Phe Arg Gly Leu
        35                  40                  45

Tyr Asn Leu Ala Met Leu Ser Gly Val Leu Tyr Val Phe Thr Thr Leu
    50                  55                  60

Phe Thr Asn Leu Leu Met Thr Asn Glu Pro Ile Asp Ser Lys Leu Leu
65                  70                  75                  80

Leu Ser Val Phe Tyr Ser Thr His Leu Leu Glu Val Leu Ala Thr Phe
                85                  90                  95

Val Cys Gln Ala Leu Tyr Ala Tyr Thr Ala Leu Ile Pro Val Tyr Met
            100                 105                 110

Ala Gly Thr Asp Lys Pro Asn Arg Leu Leu Ile Asn Ile Val His His
        115                 120                 125

Thr Leu Gln Ser Leu Leu Phe Phe Phe Thr Ile Val Phe Ile Val Trp
    130                 135                 140

Arg Asp Trp Asn Leu Ile His Ala Val Ser Ala Phe Ile Glu Gly Leu
145                 150                 155                 160

Val Leu Leu Met Lys Met His Ser Tyr Ile Arg Thr Lys Leu Glu Ile
                165                 170                 175

Ser Arg Thr Glu Asn Lys Pro Pro Ile Pro Asp Ile Lys Asp Phe Thr
            180                 185                 190

Met Tyr Leu Leu Ile Pro Ser Leu Val Tyr Glu Pro Asn Phe Pro Arg
        195                 200                 205

Thr Cys Arg Ile Arg Trp Ala Tyr Leu Ala Glu Lys Thr Phe Ser Val
    210                 215                 220

Ile Met Gly Ile Ser Met Leu Tyr Ile Ile Val Thr Thr His Val Met
225                 230                 235                 240

Pro Arg Leu Glu Asp Ser Gly Thr Val Asn Pro Val Leu Ser Val Val
                245                 250                 255

Ser Leu Leu Leu Pro Phe Leu Gly Cys Tyr Leu Leu Thr Trp Phe Ile
            260                 265                 270

Ile Phe Glu Cys Ile Cys Asn Gly Phe Ala Glu Val Thr Tyr Ser Ala
        275                 280                 285

Asp Arg Asp Phe Tyr Gly Asp Trp Trp Asn Ser Thr Thr Phe Asp Glu
    290                 295                 300

Phe Ala Arg Lys Trp Asn Lys Pro Val His Glu Phe Leu Leu Arg His
305                 310                 315                 320

Val Tyr Leu Glu Thr Leu Asp Ser Tyr Lys Ile Ser Lys Thr Tyr Ala
                325                 330                 335

Thr Met Phe Thr Phe Phe Met Ser Ala Ala Leu His Glu Cys Val Phe
            340                 345                 350

Ile Leu Met Phe Arg Thr Val Arg Met Tyr Phe Phe Thr Leu Gln Met
        355                 360                 365

Val Gln Leu Val Thr Ile Val Tyr Gly Arg Gly Leu Arg Gly Ser Arg
    370                 375                 380

Met Gly Asn Ile Thr Phe Trp Leu Gly Met Ile Leu Gly Leu Pro Leu
```

```
385                 390                 395                 400

Gln Ala Val Ile Tyr Ser Arg Glu Tyr His Gly Gly Glu Pro Ile Phe
                405                 410                 415

Met Val Ile Met Met Pro Ala Met Ile Phe Gly Phe Gly Gly Val Leu
            420                 425                 430

Val Ala Ser Leu Met His Leu Ser Arg Leu Arg Lys Lys Gln Ala
        435                 440                 445

<210> SEQ ID NO 135
<211> LENGTH: 308
<212> TYPE: PRT
<213> ORGANISM: Phythophtora infestance

<400> SEQUENCE: 135

Met Thr Gly Gln Gln His Thr Trp Leu Leu Gly Val Gly Leu Ala Val
1               5                   10                  15

Ala Thr Ile Ser Leu Cys Val Ala Ile His Ala Ser Ala Leu Ile Thr
            20                  25                  30

Ile Ala Thr Ala Cys Val Ala Ala Tyr Leu Pro Ser Tyr Leu Asp Gly
        35                  40                  45

Ser Glu Tyr Thr Gly Glu Arg Tyr Trp Pro Trp Phe Ala Thr Phe Ile
    50                  55                  60

Gly His Gly Met Ala His Ile Pro Gly Thr Leu Glu Phe Glu Glu Pro
65                  70                  75                  80

Ile Asp Ala Ser Lys Gln His Ile Phe Cys Ser His Pro His Gly Leu
                85                  90                  95

Leu Ser Thr His His Gly Leu Leu Met Ser Gly Gln Thr Val Pro Pro
            100                 105                 110

Phe Tyr Glu Thr Val Pro Leu Ser Thr Arg Arg His Leu Ala Ala Ser
        115                 120                 125

Val Cys Phe Arg Ile Pro Phe Tyr Arg Glu Tyr Val Leu Trp Ser Gly
    130                 135                 140

Cys Val Asp Ala Arg Arg Ser Val Ala Glu Lys Met Leu Arg Asn Gly
145                 150                 155                 160

Lys Ser Leu Val Ile Leu Val Gly Gly Ile Ala Glu Gln Met Leu Ser
                165                 170                 175

Gln Arg Gly Asp His Thr Ile Tyr Val Lys Lys Arg Lys Gly His Ile
            180                 185                 190

Arg Leu Ala Leu Lys Tyr Gly Val Pro Ile Val Pro Gly Tyr Ala Phe
        195                 200                 205

Gly Glu Thr Asp Leu Phe Thr His Ser Ser Val Leu Leu Ser Phe Arg
    210                 215                 220

Gln Thr Ile Ala Lys Lys Phe Ser Val Ala Leu Leu Leu Gly Arg Gly
225                 230                 235                 240

Tyr Ser Lys Trp Leu Phe Trp Leu Pro His Lys Gly Val Thr Ile Asn
                245                 250                 255

Gln Val Phe Gly Lys Pro Ile Pro Val Leu Lys Lys Asp Asp Pro Ser
            260                 265                 270

Ser Asp Asp Ile Glu Lys Leu His His Gln Tyr Glu Arg Glu Leu Val
        275                 280                 285

Arg Ile Phe Asp Lys Tyr Lys Glu Lys His Gly Tyr Gly Asn Cys Thr
    290                 295                 300

Leu His Val Arg
305
```

<210> SEQ ID NO 136
<211> LENGTH: 392
<212> TYPE: PRT
<213> ORGANISM: Phythophtora infestance

<400> SEQUENCE: 136

```
Met Ser Ala Ala Gln Val Leu Asn Asn Ala Ala Tyr Gly Arg Thr Ser
1               5                   10                  15

Ala Trp Pro Asp Ser Asn Thr Arg Pro Asp Leu Gln Thr Leu Arg Gly
            20                  25                  30

Arg Phe Leu Arg Arg Leu His Leu Ser Leu Ile Tyr Gly Leu Trp Val
        35                  40                  45

Leu Gly Thr Leu Phe Asn Ala Ala Met Trp Val Phe Ser Leu Val Cys
    50                  55                  60

Val Ala Gln Trp Val Trp Ser Thr Leu Ile Gly Ala Asn Glu Ala Pro
65                  70                  75                  80

Ile Pro Leu Ala Val Gln Val Phe Leu Ser Leu Val Ala Leu Tyr Glu
                85                  90                  95

Ser Tyr His Phe Val Thr Arg Pro Ser His His Pro Trp Pro Phe Met
            100                 105                 110

Arg Arg Leu Ile Arg Tyr Ser Leu Leu His Tyr Pro Tyr Phe Arg Leu
        115                 120                 125

Asn Ala Thr Val Phe Asp Glu Arg Glu Arg Ala Lys Gln Leu Ser Gln
    130                 135                 140

Asp Gly Ala Thr Asn Asp Thr Ser Ala Phe Asn Thr Glu Ile Ala Ser
145                 150                 155                 160

Lys Thr Ile Val Glu Asn Asp Ile Ser Pro Phe Val Lys Pro Asn Glu
                165                 170                 175

Ser Ala Met Phe Ala Phe His Pro His Ser Val Leu Ser Asn Gly Trp
            180                 185                 190

Val Ala Asn Gly Ala Asn His Met Ser Phe Glu Gln Ala Asp Cys Arg
        195                 200                 205

Trp Leu Val Ala Glu Asn Leu Phe Gly Val Pro Leu Met Arg Asp Leu
    210                 215                 220

Leu Asn Trp Met Asp Phe Ser Ser Val Ala Lys Ser Thr Phe Gln Gln
225                 230                 235                 240

Arg Met Ser Ala Arg Gln Asn Val Cys Leu Ile Pro Gly Gly Phe Glu
                245                 250                 255

Glu Ala Thr Leu Tyr Glu Arg Gly Lys His Arg Val Tyr Ile Lys Lys
            260                 265                 270

Arg Phe Gly Phe Ile Lys Leu Ala Leu Gln Tyr Gly Tyr Lys Val His
        275                 280                 285

Pro Val Tyr Thr Phe Gly Glu Glu Tyr Ala Tyr His Thr Phe Pro Tyr
    290                 295                 300

Leu Leu Lys Leu Arg Leu Lys Leu Asn Glu Phe Lys Ile Pro Gly Val
305                 310                 315                 320

Phe Phe Phe Gly Leu Pro His Cys Phe Phe Leu Pro Arg Thr Asp Val
                325                 330                 335

Asp Leu Ile Thr Val Val Gly Glu Pro Leu Val Leu Pro Arg Ile Glu
            340                 345                 350

Gln Pro Thr Lys Glu Asp Val Gln Lys Tyr Gln Gly Gln Tyr Val Glu
        355                 360                 365

Ala Leu Gln Lys Leu Phe Asn Lys Tyr Lys Ser Val Tyr Ala Val Asp
    370                 375                 380
```

Pro Gln Ala Gln Leu Glu Ile Tyr
385                 390

<210> SEQ ID NO 137
<211> LENGTH: 381
<212> TYPE: PRT
<213> ORGANISM: Phythophtora infestance

<400> SEQUENCE: 137

Met Ala Lys Leu Thr Asn Ala Ala Cys Gly Arg Thr Ser Ala Trp Pro
1               5                   10                  15

Asp Phe Asp Thr Arg Pro Glu Leu Arg Thr Leu Arg Gly Arg Phe Met
            20                  25                  30

Arg Arg Phe Asp Leu Phe Ile Leu Tyr Gly Leu Trp Val Val Gly Leu
        35                  40                  45

Leu Phe Leu Ala Val Met Trp Val Phe Ser Leu Phe Cys Leu Val Gln
    50                  55                  60

Trp Ser Trp Arg Arg Ala Thr His Asp His Ala Pro Pro Met Ala Phe
65                  70                  75                  80

Ser Ala Gln Ile Tyr Leu Gly Phe Ile Val Leu His Glu Ser Tyr His
                85                  90                  95

Tyr Leu Thr Lys Pro Ser Leu His Gln Trp Pro Phe Met Arg Arg Phe
            100                 105                 110

Phe Arg Gln Val Phe Leu His Tyr Pro Tyr Phe Arg Leu Asn Val Leu
        115                 120                 125

Val Phe Glu Glu Arg Ser Lys Thr Ser Ser Glu Asn Gly Lys Cys Asn
130                 135                 140

Lys Glu Ile Ala Ser Lys Ala Val Glu Glu Asn Asn Leu Ser Pro Phe
145                 150                 155                 160

Val Thr Pro Asp Asp Arg Ala Leu Phe Ala Phe His Pro His Gly Val
                165                 170                 175

Leu Ser Ser Gly Phe Ala Phe Asn Gly Ala His His Met Gly Phe Leu
            180                 185                 190

His Ala His Cys Arg Trp Leu Val Ser Glu Asn Leu Phe Trp Phe Pro
        195                 200                 205

Val Met Arg Asp Leu Leu Asn Trp Met Asp Phe Ser Cys Val Ser Arg
210                 215                 220

Ser Thr Phe His Arg Phe Met Ala Thr Gly Gln Asn Val Cys Leu Ile
225                 230                 235                 240

Pro Gly Gly Phe Glu Asp Ala Thr Leu Tyr Glu Arg Gly Lys His Arg
                245                 250                 255

Val Tyr Ile Lys Lys Arg Phe Gly Phe Ile Lys Leu Ala Leu Gln Tyr
            260                 265                 270

Gly Tyr Lys Val His Pro Val Tyr Thr Phe Gly Glu Glu Tyr Ala Tyr
        275                 280                 285

His Thr Phe Pro Tyr Leu Leu Lys Leu Arg Leu Lys Leu Asn Glu Phe
    290                 295                 300

Lys Ile Pro Gly Val Phe Phe Gly Leu Pro His Cys Phe Phe Leu
305                 310                 315                 320

Pro Arg Thr Asp Val Asp Leu Ile Thr Val Val Gly Glu Pro Leu Val
                325                 330                 335

Leu Pro Arg Ile Glu Gln Pro Thr Lys Glu Asp Val Gln Lys Tyr His
            340                 345                 350

Gly Gln Tyr Val Glu Ala Leu Gln Lys Leu Phe Asn Lys Tyr Lys Ser

```
                   355                 360                 365
Val Tyr Ala Val Asp Pro Asp Ala Glu Leu Glu Leu Tyr
    370                 375                 380

<210> SEQ ID NO 138
<211> LENGTH: 283
<212> TYPE: PRT
<213> ORGANISM: Phythophtora infestance

<400> SEQUENCE: 138

Met Glu Ala Phe Val Pro Val Leu Leu Leu Thr Ile Thr Ala Tyr Met
1               5                   10                  15

Tyr Glu Phe Thr Tyr Arg Gly His Pro His Gln Thr Gly Cys Arg Glu
            20                  25                  30

Arg Leu Asp Trp Ile Tyr Gly His Ser Phe Leu Ile Glu Thr Val Lys
        35                  40                  45

Arg Tyr Phe Ser Glu Lys Ile Ile Arg Met Ala Pro Leu Asp Pro Lys
    50                  55                  60

Lys Gln Tyr Val Leu Gly Phe His Pro His Gly Ile Thr Pro Thr Ser
65                  70                  75                  80

Val Met Trp Leu Gln Phe Ser Ala Glu Trp Arg Arg Leu Phe Pro Asn
                85                  90                  95

Phe Tyr Ala His Ile Leu Thr Ala Gly Ile Met His Ala Leu Pro Leu
            100                 105                 110

Ala Arg Asp Ile Leu Gln Phe Leu Gly Ser Arg Glu Val Thr Arg Gln
        115                 120                 125

Ala Phe Thr Tyr Thr Leu Gln His Asn Glu Ser Val Leu Leu Val Pro
    130                 135                 140

Gly Gly Gln Ala Glu Met Leu Glu Gln Arg Ser Gly Gln Lys Glu Val
145                 150                 155                 160

Arg Val Tyr Thr His His Lys Gly Phe Ile Arg Leu Ala Ile Glu His
                165                 170                 175

Gly Val Pro Leu Val Pro Val Leu Ser Phe Asn Glu Gly Glu Met Leu
            180                 185                 190

Asp Asn Ile Gln Ala Pro Met Leu Gln Arg Trp Phe Val Ile Lys Leu
        195                 200                 205

Ala Phe Pro Phe Pro Phe Phe Pro Tyr Gly Arg Ala Leu Leu Pro Ile
    210                 215                 220

Pro Arg Lys Val Gln Ile Pro Ile Val Val Gly Ala Pro Leu Glu Val
225                 230                 235                 240

Pro His Met Lys Lys Pro Ser His Glu Asp Ile Asp Lys Val His Ala
                245                 250                 255

Arg Tyr Phe Asp Glu Leu Arg Asp Met Phe Ala Lys Tyr Lys Asp Glu
            260                 265                 270

Ala Gly Cys Gly Asp Tyr Lys Leu Ile Tyr Val
        275                 280

<210> SEQ ID NO 139
<211> LENGTH: 349
<212> TYPE: PRT
<213> ORGANISM: Phythophtora infestance

<400> SEQUENCE: 139

Met Ala Ser Glu Thr Gln Ala Asp Pro Val Gln Thr Asp Lys Gly Leu
1               5                   10                  15

Phe Val Tyr Glu Pro Leu Gly Phe Phe Ala Asp Asp Ser Lys Val Pro
```

```
                20                  25                  30
Lys Trp Met Gln Leu Leu Ile Thr Asp Val Phe Ser Phe Val Thr Thr
            35                  40                  45
His Tyr Phe Val Trp Ser Leu Pro Phe Leu Ala Leu Phe Cys Tyr Leu
 50                  55                  60
His Gln His Glu Leu Asp Tyr Val Ser Val Ala Met Ile Ala Leu Tyr
 65                  70                  75                  80
Leu Pro Ser Phe Phe Ser Gly Ala Gln Lys Thr Gly Lys Gly Asn Glu
                85                  90                  95
Trp Glu Ala Ala Arg Thr Ser Ser Leu Trp Gly Leu Met Asn Lys Phe
            100                 105                 110
Leu Arg Val Lys Ile Ile Arg Glu Gln Glu Leu Asp Pro Lys Lys Lys
        115                 120                 125
Phe Ile Phe Gly Phe His Pro His Gly Ile Leu Val Leu Ser Arg Ile
    130                 135                 140
Ala Gly Phe Gly Arg Asn Phe Ile Asp Val Cys Pro Gly Ile Thr Thr
145                 150                 155                 160
Arg Phe Leu Gly Ala Ser Ala Met Tyr Tyr Ile Pro Leu Gly Arg Glu
                165                 170                 175
Met Cys Leu Trp Met Gly Gly Val Asp Ala Ser Arg Ser Thr Gly Glu
            180                 185                 190
Lys Val Leu Lys Glu Gly Asn Ser Ile Ile Val Tyr Pro Gly Gly Val
        195                 200                 205
Pro Glu Ile Phe Leu Thr Asp Pro Asn Leu Lys Glu Thr Gln Leu Val
    210                 215                 220
Leu Lys Lys Arg Leu Gly Phe Ile Lys Leu Ala Met Arg Gln Gly Ala
225                 230                 235                 240
Gln Leu Val Pro Thr Phe Val Phe Gly Glu Lys Trp Leu Tyr Asn Met
                245                 250                 255
Trp Thr Pro Pro Glu Ser Val Thr Asn Phe Phe Arg Lys Thr Leu Gly
            260                 265                 270
Ile Pro Val Leu Val Phe Trp Gly Lys Phe Trp Met Pro Lys Ala
        275                 280                 285
Pro Gly Glu Gly Lys Arg Tyr Gly Leu Val Tyr Gly Lys Pro Ile Ala
    290                 295                 300
Thr Lys His Asp Ser Asn Pro Ser Asp Glu Glu Ile Arg Ala Val His
305                 310                 315                 320
Ala Glu Tyr Val Ser Glu Ile Glu Arg Ile Phe Ser Gln Tyr Lys Ser
                325                 330                 335
Glu Phe Gly Tyr Asp Glu Asp Glu Thr Leu Ala Ile Ile
            340                 345

<210> SEQ ID NO 140
<211> LENGTH: 403
<212> TYPE: PRT
<213> ORGANISM: Phythophtora infestance

<400> SEQUENCE: 140

Met Pro Gln Ala Cys Gly Arg Thr Ser Ala Trp Leu Asp Asn Asp Ala
1               5                   10                  15
Arg Pro Glu Leu Gln Thr Leu His Gly Arg Ile Leu Arg Phe Val Leu
            20                  25                  30
Leu Trp Tyr Leu Phe Gly Leu Trp Ile Val Gly Leu Ala Ser Phe Ile
        35                  40                  45
```

```
Gly Met Trp Leu Phe Ser Gly Leu Cys Thr Ile Arg Ser Leu Leu Ser
        50                  55                  60

Phe Leu His Asn Gly Gly Ser Trp Thr Ala Ala Thr Pro Leu Pro Val
 65                  70                  75                  80

Leu Val Gln Val Tyr Leu Val Gly Met Ile Ala Tyr Glu Ser Tyr His
                 85                  90                  95

Tyr Val Thr Arg Asn Ala Leu His Glu Trp Pro Leu Ile Arg Arg Val
            100                 105                 110

Val Arg Tyr Val Phe Leu His Tyr Pro Tyr Phe Arg Leu Asn Ala Val
        115                 120                 125

Val Phe Glu Glu Arg Glu Asp Ala Lys Gln Asn Val Glu Ile Gln Glu
130                 135                 140

Pro Glu Gln Glu Lys Asp Gly Asn Asp Ser Thr Thr Asn Lys Ser Asp
145                 150                 155                 160

Asp Ala Arg Tyr Phe Ser Ser Lys Ala Ala Ala Ala Ile Glu Glu
                165                 170                 175

Asn Asp Val Thr Pro Tyr Val Glu Pro Asp Lys Arg Ala Leu Phe Thr
            180                 185                 190

Phe His Pro His Gly Val Leu Thr Cys Gly Phe Ser Phe Asn Gly Ala
        195                 200                 205

His His Met Ala Phe Gln Arg Ala Ala Cys Arg Trp Ile Ser Ala Glu
210                 215                 220

Asn Leu Phe Tyr Phe Pro Ile Met Arg Asp Ile Leu His Trp Met Glu
225                 230                 235                 240

Phe Ser Ser Ser Thr Lys Thr Ser Met Glu Asn Thr Met Arg Thr Gly
                245                 250                 255

Gln Asn Leu Cys Leu Leu Pro Gly Gly Phe Glu Glu Ala Thr Leu Tyr
            260                 265                 270

Gln Arg Gly Lys His Arg Val Tyr Ile Gln Lys Arg Phe Gly Phe Ile
        275                 280                 285

Lys Leu Ala Leu Gln His Gly Tyr Asp Ile Tyr Pro Ala Tyr Thr Phe
290                 295                 300

Gly Glu Glu Tyr Thr Tyr His Ala Phe Pro Tyr Leu Gln Trp Leu Arg
305                 310                 315                 320

Leu Gln Leu Asn Arg Phe Arg Ile Pro Gly Val Ile Phe Gly Ile
                325                 330                 335

Pro Phe Cys Phe Phe Met Pro Arg Ser Asp Val Asp Leu Ile Thr Val
            340                 345                 350

Ile Gly Lys Pro Leu Arg Leu Pro His Ile Asp Asn Pro Ser Arg Asp
        355                 360                 365

Glu Val Lys Glu Asn His Asp Lys Tyr Val Glu Ala Leu Arg Asp Leu
370                 375                 380

Phe Asp Arg Tyr Lys Cys Val Tyr Ala Ala Asp Pro Asp Ala Glu Leu
385                 390                 395                 400

Glu Ile Phe

<210> SEQ ID NO 141
<211> LENGTH: 406
<212> TYPE: PRT
<213> ORGANISM: Phythophtora infestance

<400> SEQUENCE: 141

Met Val Gly Val Ala His Ala Ala Thr Gly Arg Thr Pro Leu Trp Pro
 1               5                  10                  15
```

```
Asn Asn Asn Ala Val Pro Glu Leu Gln Thr Leu Arg Gly Tyr Val Gly
             20                  25                  30

Arg Arg Phe Leu Leu Trp Ser Leu Phe Gly Leu Trp Ile Phe Gly Leu
         35                  40                  45

Gly Ala Tyr Ile Leu Met Trp Leu Tyr Ser Gly Trp Cys Val Gly His
     50                  55                  60

Trp Ala Trp Thr Ala Leu Gln Thr Lys Ser Trp Ala Leu Ala Thr Pro
 65                  70                  75                  80

Pro Pro Ile Ser Val Gln Val Tyr Leu Ala Phe Thr Ala Leu Tyr Glu
                 85                  90                  95

Ser Tyr His Tyr Ile Thr Arg Asp Ser Leu His Leu Trp Pro Arg Met
            100                 105                 110

Arg Arg Leu Ala Arg His Ile Leu Leu Arg Tyr Pro Tyr Phe Arg Leu
        115                 120                 125

Asn Val Thr Ile Phe Glu Glu Arg Glu Leu Glu Lys Gln Lys Gln Arg
    130                 135                 140

Leu Lys Asp Glu Gln Thr Asn Asn Ser Asp Asp Ala Thr Val Asp Thr
145                 150                 155                 160

Glu Gln Asp Glu Ser Glu His Leu Ser Pro Ala Ala Ile Lys Ala
                165                 170                 175

Val Glu Glu Asn Asp Ile Ser Pro Tyr Val Glu Thr Gly Thr Lys Asn
                180                 185                 190

Leu Phe Ala Phe His Pro His Gly Ile Leu Thr Cys Gly Phe Ser Phe
            195                 200                 205

Asn Gly Ala Tyr His Met Ser Phe Glu Arg Ser Ala Cys Arg Trp Leu
        210                 215                 220

Ser Ala Glu Asn Leu Phe Trp Phe Pro Leu Val Arg Asp Leu Leu Asn
225                 230                 235                 240

Trp Met Glu Tyr Ser Ser Cys Ala Lys Ala Asn Met Leu Lys Phe Met
                245                 250                 255

Arg Arg Asp Gln Asn Val Ser Ile Ile Pro Gly Gly Phe Glu Glu Ala
            260                 265                 270

Thr Leu Tyr Gln Arg Gly Lys His Arg Leu Tyr Leu Lys Lys Arg Phe
        275                 280                 285

Gly Phe Ile Lys Ile Ala Leu Gln His Gly Tyr Asn Val His Pro Val
    290                 295                 300

Tyr Thr Phe Gly Glu Glu Tyr Thr Tyr His Ala Phe Pro Tyr Leu Gln
305                 310                 315                 320

Ser Leu Arg Leu Gln Leu Asn Arg Leu Gln Ile Pro Gly Thr Ile Phe
                325                 330                 335

Phe Gly Glu Ala Ser Cys Phe Tyr Leu Pro Arg Asn Asp Ile Asp Leu
            340                 345                 350

Ile Thr Val Val Gly Lys Ser Leu Arg Phe Pro Arg Ile Glu His Pro
        355                 360                 365

Ser Lys Glu Asp Val Gln Lys Tyr Gln Ala Gln Tyr Ile Glu Ala Leu
    370                 375                 380

Arg Ser Leu Phe Asp Ser Tyr Lys Gly Val Tyr Ala Val Asp Pro Asn
385                 390                 395                 400

Ala Thr Leu Glu Ile Phe
                405

<210> SEQ ID NO 142
<211> LENGTH: 516
<212> TYPE: PRT
```

<213> ORGANISM: Phythophtora infestance

<400> SEQUENCE: 142

```
Met Asp Val Glu Asn Ser Leu Leu Thr Arg Leu Ala Ala Asn Gly Pro
1               5                   10                  15

Thr Met Ser Asp Ala Pro Met Leu Leu Met Ala Val Val Leu Val Leu
            20                  25                  30

Ala Leu Ser Gly Val Val Ser Thr Val Ser Gln Gln Arg Gln Lys Pro
        35                  40                  45

Ser Glu Asp Glu Thr Leu Gln Gly Arg Lys Leu Thr Arg Lys Leu Ser
    50                  55                  60

Ser Met Gly Leu Ser Thr Leu Val Thr Glu Thr Pro Thr Asn Leu Ser
65                  70                  75                  80

Ile Pro Val Ser Val Leu Thr Val Glu Gly His Leu Ala Lys Glu Asp
                85                  90                  95

Tyr Val Glu Arg Leu Arg Ala Arg Ile Leu His Asp Ala Phe Phe Leu
            100                 105                 110

Arg Trp Arg Ser Val Val Arg Gly Asp Tyr Lys Thr Gly Val Tyr Lys
        115                 120                 125

Tyr Val Glu Val Pro Gly Tyr Asp Val Ala Gln Asn Val Val Glu His
    130                 135                 140

Thr Val Glu Glu Gly Glu Thr Thr Met Ser Tyr Val Glu Ser Ala Leu
145                 150                 155                 160

Val Asn Thr Pro Leu Asp Phe Asp Lys Pro Leu Trp Glu Met His Val
                165                 170                 175

Ile His Asp Pro Lys Gly Asn Pro Gly Asn Thr Ser Val Gly Trp Lys
            180                 185                 190

Val His His Cys Leu Gly Asp Gly Ala Ser Leu Ala Thr Ala Met Ala
        195                 200                 205

Lys Leu Ser Asp Gln Ser Glu Leu Phe Asp Ala Met Val Glu Lys Arg
    210                 215                 220

Leu Gln Ala Lys Lys Ser Pro Lys Thr Pro Lys Pro Arg Lys Pro Val
225                 230                 235                 240

Thr Gln Ile Ile Lys Asp Ile Leu Val Phe Leu Tyr Val Cys Ile Trp
                245                 250                 255

Ser Val Tyr Val Ile Ser Tyr His Met Phe Ala Leu Val Thr Arg Arg
            260                 265                 270

Glu Pro Ala Thr Val Phe Lys Arg Pro Gly Gly Lys Gln Lys Arg Leu
        275                 280                 285

Ser Tyr Asn Met Ile Tyr Ser Val Asn Ala Thr Lys Ala Val Gly Lys
    290                 295                 300

His Phe Arg Ala Thr Val Asn Asp Val Met Leu Asn Val Val Ala Gly
305                 310                 315                 320

Ala Met Arg Lys Thr Met Leu Ser Val Gly Glu Ser Val Ala Pro Thr
                325                 330                 335

Leu Lys Val Arg Cys Ala Ile Pro Val Asp Met Arg Ser Ser Thr Glu
            340                 345                 350

Val Ile Arg His Thr Ser Asn Arg Phe Ser Ser Leu Val Ile Asp Leu
        355                 360                 365

Pro Ile Gly Val Glu Asp Ser Ala Gln Arg Leu Leu Gln Val Thr Ala
    370                 375                 380

Ala Met Asn Asp Ala Lys Asn Ser Leu Glu Lys Phe Phe Val Tyr Trp
385                 390                 395                 400
```

```
Ser Thr His Leu Val Ser Met Leu Pro Ala Pro Leu Met Arg Leu Ile
            405                 410                 415

Val His Phe Thr Thr Ser Arg Ile Ser Val Ala Thr Ser Asn Val Arg
            420                 425                 430

Ala Ser Val Val Glu Val Ser Leu Cys Lys Ser Pro Val Ser Gly Phe
            435                 440                 445

Tyr Gly Phe Val Pro Pro Pro Tyr Val Asn Leu Gly Val Ala Ile
            450                 455                 460

Leu Ser Met Gly Asp Asp Leu Gly Leu Asn Val Leu Val Asp Pro Cys
465                 470                 475                 480

Val Gly Val Asn Ala Lys Gln Phe Leu Glu Phe Ala Lys Glu Glu Phe
                485                 490                 495

Thr Ala Leu Gln Glu Ser Val Ala Ala Met Glu Ala Asn Ala Gly Asp
            500                 505                 510

Lys Lys Thr Lys
            515

<210> SEQ ID NO 143
<211> LENGTH: 675
<212> TYPE: PRT
<213> ORGANISM: Phythophtora infestance

<400> SEQUENCE: 143

Met Thr Leu Asp Asp Ser Ser Ala Ser Gly Val Arg Gln Arg Lys
1               5                   10                  15

Pro His Gly Gly Thr Ser Ser Asp Arg Pro Ser Ser Pro Glu Ala Leu
                20                  25                  30

Ala Glu Glu Ala Val Ala Ser Ala Phe Ser Ala Pro Lys Asp Glu Gln
            35                  40                  45

Ser Arg Thr Lys Glu Thr Phe Gln His Ala Ala Arg Ser Leu Gly Arg
        50                  55                  60

Thr Gln Ser Trp His Ala Arg Ala Ala Asp His Val Ala Arg Lys Arg
65              70                  75                  80

Ile Tyr Ser Ile Met Ala Gly Val Ile Gly Val Ala Ala Val Ile
                85                  90                  95

Asn Phe Gln Arg Phe Tyr Leu Glu Lys Pro Leu Ile Ser Glu Asp Ser
            100                 105                 110

Leu Leu Met Val Arg Glu Met Phe Asp Asn Phe Asn Trp Ser Val Asn
            115                 120                 125

Val Lys Glu Glu Leu Met Ala Ala Phe Asp Asn Arg Pro Pro Leu Met
        130                 135                 140

Gly Ala Ala Glu Ile Arg Pro Gly Val Gln Leu Phe Gln Glu Asn Val
145                 150                 155                 160

Thr Ala Asn Ser Pro Val Val Leu Val Pro Gly Phe Thr Ser Thr Gly
                165                 170                 175

Leu Glu Ile Trp Asn Gly Ser Glu Cys Ser Lys Ala Tyr Phe Arg Gln
            180                 185                 190

Arg Met Trp Gly Thr Ser Arg Met Leu Gln Gln Phe Met Met Asn Gln
        195                 200                 205

Lys Cys Trp Leu Glu His Met Met Leu Asn Arg Ser Ser Gly Met Asp
    210                 215                 220

Pro Asp Gly Ile Lys Leu Arg Ala Ala Lys Gly Leu Glu Ala Ala Asp
225                 230                 235                 240

Tyr Leu Ile Gly Gly Phe Trp Val Trp Gly Lys Met Val Glu Asn Leu
                245                 250                 255
```

```
Ala Glu Ile Gly Tyr Asp Ser Asn Asn Leu Tyr Met Ala Ala Tyr Asp
            260                 265                 270

Trp Arg Leu Met Pro His Leu Leu Glu Lys Arg Asp Gly Tyr Phe Thr
            275                 280                 285

Lys Leu Lys Tyr Thr Ile Glu Met Ala Arg Met Ser Ala Gly Gly His
            290                 295                 300

Lys Val Met Leu Val Thr His Ser Tyr Ala Thr Gln Val Phe Phe His
305                 310                 315                 320

Phe Leu Lys Trp Val Ser Glu Asn Gly Lys Gly Gly Asp Gln
                325                 330                 335

Trp Val Glu Thr Asn Leu Glu Ser Phe Val Asn Ile Ala Gly Pro Thr
            340                 345                 350

Leu Gly Val Val Lys Thr Ile Ser Ala Leu Met Ser Gly Glu Met Lys
            355                 360                 365

Asp Thr Ala Glu Leu Gly Gly Leu Ser Lys Phe Leu Gly Tyr Phe Phe
            370                 375                 380

Ser Val Ser Ala Arg Thr Gln Leu Ala Arg Ser Trp Ser Ser Val Phe
385                 390                 395                 400

Ser Met Met Pro Ile Gly Gly Asp Arg Ile Trp Gly Thr Ala Asp Ser
                405                 410                 415

Ala Pro Asp Asp Val Val Ala Ala Ser Pro Leu Ser Thr Gly Lys Asn
            420                 425                 430

Ser Thr Ile Asp Pro Arg Lys Val Lys Glu His Val Ala Arg Tyr Gly
            435                 440                 445

Ser Asn Gly His Val Val Arg Phe Val Asn Thr Ser His Glu Asn Val
            450                 455                 460

Thr Ile Gly Gly Val Gln Lys Met Leu Gly Lys Leu Asp Pro Tyr Leu
465                 470                 475                 480

Asp Gln Phe Arg Ser Trp Leu Ser Thr Gly Ile Ala Glu Asp Leu Ser
                485                 490                 495

Leu Pro Glu Tyr Asp Gln Ser Lys Tyr Trp Thr Asn Pro Leu Glu Ala
            500                 505                 510

Ala Leu Pro Lys Ala Pro Ser Leu Asn Val Phe Cys Phe Tyr Gly Val
            515                 520                 525

Gly Lys Pro Val Glu Arg Gly Tyr Thr Tyr Gly Asp Asn Pro Pro Asp
            530                 535                 540

Glu Asp Asn Ala Thr Val Asn Gly Lys Arg Val Ala Pro Tyr Val Phe
545                 550                 555                 560

Asn Thr Asp Thr Asp Leu Pro Tyr Ile Lys Gly Gly Leu Arg Tyr
                565                 570                 575

Ser Asp Gly Asp Gly Thr Val Pro Leu Ile Ser Leu Gly Leu Met Cys
                580                 585                 590

Ala Ser Gly Trp Arg Thr Lys Lys Phe Asn Pro Gly Asn Val Asp Val
                595                 600                 605

Arg Val Arg Glu Tyr Arg His Asn Pro Val Ser Met Leu Phe Asp Ala
            610                 615                 620

Arg Gly Gly Pro Glu Thr Ala Asp His Val Asp Ile Met Gly Asn His
625                 630                 635                 640

Gly Leu Ile Arg Asp Val Leu Leu Val Ala Ala Arg Ala Tyr Asp Arg
                645                 650                 655

Val Pro Glu Asn Ile Thr Ser Ser Ile Met Glu Ile Ala Glu Arg Val
            660                 665                 670
```

Gly Glu Leu
        675

<210> SEQ ID NO 144
<211> LENGTH: 728
<212> TYPE: PRT
<213> ORGANISM: Phythophtora infestance

<400> SEQUENCE: 144

Met Lys Phe Asp Asp Lys Lys Val Leu Asn Asp Thr Trp Thr Gln Phe
1               5                   10                  15

Leu Ala Leu Cys Leu Leu Leu Met Leu Ala Val Asp Ser Leu Asn Pro
            20                  25                  30

Ile Lys Ala Val Ser Lys Phe Leu Gly Val Pro Ser Tyr Tyr Trp Gly
        35                  40                  45

Ala Leu Ser Val Gly Ile Met Leu Gly Leu Leu Phe His Asn Ala Ala
    50                  55                  60

Asp Val Ile Tyr Arg Ser Thr Arg Val Phe Leu Asn Ser Ile Leu Ser
65                  70                  75                  80

Ile Ser Phe Lys Ser Val Asp Leu Ile Gly Leu Asp Asn Val Pro Thr
                85                  90                  95

Asp Gly Pro Val Ile Phe Thr Gly Asn His Ala Asn Gln Phe Val Asp
            100                 105                 110

Gly Leu Val Val Met Met Thr Ser Pro Arg Lys Val Gly Phe Met Ile
        115                 120                 125

Ala Glu Lys Ser Trp His Leu Pro Val Val Gly His Leu Ala Arg Ile
    130                 135                 140

Met Gly Cys Ile Pro Val Val Arg Pro Gln Asp Ser Val Ala Ser Gly
145                 150                 155                 160

Val Gly Ser Met Lys Leu Ala Ser Glu Asp Pro Val Thr Val Ala Ser
                165                 170                 175

Ser Ser Ser Gly Gly Ala Ser Ser Ser Thr Pro Gln Trp Leu Val Gln
            180                 185                 190

Gly Asp Gly Thr Ser Phe Thr Lys Gln Val Thr Pro Gly Asp Gln Ile
        195                 200                 205

Arg Phe Gln Gly Gln Ser Val Lys Asp Ser Gly Ser Pro Val Lys Ile
    210                 215                 220

Val Gln Val Leu Asp Asp Thr Gln Leu Leu Asn Ala Pro Leu Lys
225                 230                 235                 240

Ser Gly Glu Gly Lys Leu Val Leu Glu Ser Ala Pro Phe Gly Ile Leu
                245                 250                 255

Lys Arg Val Asp Gln Ser Val Thr Phe Ala Lys Val Tyr Thr His Leu
            260                 265                 270

Lys Arg Gly Asn Cys Ile Gly Ile Phe Pro Glu Gly Gly Ser His Asp
        275                 280                 285

Arg Thr Asp Leu Leu Pro Leu Lys Ala Gly Val Ala Val Met Ala Leu
    290                 295                 300

Gly Val Lys Asp Lys Tyr Asn Ile Asn Val Pro Val Val Pro Val Gly
305                 310                 315                 320

Leu Asn Tyr Phe Arg Gly His Arg Phe Arg Gly Arg Thr Val Glu
                325                 330                 335

Phe Gly Thr Pro Ile Thr Val Asp Gln Ala Leu Met Ala Lys Tyr Gln
            340                 345                 350

Glu Asp Lys Arg Thr Ala Cys Asn Thr Leu Leu His Arg Val Glu Glu
        355                 360                 365

Ser Met Arg Ser Val Ile Val Thr Thr Pro Ser Tyr Gly Val Met Gln
370                 375                 380

Glu Val Leu Thr Ala Arg Arg Leu Phe Gln Arg Ser Gly Val Arg Leu
385                 390                 395                 400

Ser Ala Lys Glu Thr Gln Asp Leu Asn Arg Arg Phe Ala Glu Gly Tyr
                405                 410                 415

Lys Val Leu Gln Asp Val Pro Glu Ala Gln Glu Asp Leu Val Ile Leu
                420                 425                 430

Gln His Lys Leu Asp Asn Tyr Tyr Lys Thr Leu Gln Lys Met Gly Leu
                435                 440                 445

Lys Asp His Gln Val Pro Tyr Ile Pro Trp Trp Thr Ile His Asp Val
450                 455                 460

Leu Gly Ser Ala Leu Tyr Gly Thr Leu Ile Leu Leu Ser Ser Ile
465                 470                 475                 480

Pro Ser Phe Ile Leu Asn Ala Pro Val Gly Leu Leu Ala Arg Tyr Val
                485                 490                 495

Ala Asn Ser Ala Gln Lys Lys Ala Leu Glu Gly Ser Lys Val Lys Val
                500                 505                 510

Leu Ala Arg Asp Val Ile Leu Ser Lys Lys Ile Gln Phe Ser Ile Val
                515                 520                 525

Ala Val Pro Val Leu Trp Phe Ile Tyr Phe Thr Ile Ala Ala Val Phe
530                 535                 540

Thr Asp Trp Tyr Trp Ser Ser Ile Met Leu Leu Met Val Ser Phe Pro
545                 550                 555                 560

Leu Phe Ser Phe Phe Gly Val Arg Ser Val Glu Ala Gly Met Ile Glu
                565                 570                 575

Leu Lys Thr Val Arg Pro Leu Phe Tyr Arg Leu Leu Pro Thr Tyr Lys
                580                 585                 590

Ala Thr Gln Asp Glu Leu Pro Arg Gln Arg Ala Glu Leu Gln Lys Glu
                595                 600                 605

Val Arg Glu Phe Val Lys Lys Tyr Ser Gln Tyr Leu Gly Lys Leu Ala
610                 615                 620

Glu Pro Lys Lys Leu Asp Trp Ser Glu Tyr Met His Glu Arg Ser Leu
625                 630                 635                 640

Val Leu Ala Glu Lys Thr Glu Gln Ala Glu Ser Ile Pro Ser Pro Pro
                645                 650                 655

Pro Val His Glu Glu Asp Glu Glu Pro Arg Glu Gly Glu Ala Glu Asp
                660                 665                 670

Asp Ile Gly Ser Pro Val Pro Thr Ile Thr Lys Phe His Asp Ile Ser
                675                 680                 685

Ile Leu Gly Lys Ser Glu Asn Ser Val Leu Asp Leu Ala Gly Leu Glu
                690                 695                 700

Arg Ser Met Ser Cys Pro Pro Gly Tyr Gln Glu Leu Ala Glu Glu Ile
705                 710                 715                 720

Ala Lys Gln Arg Lys Gly Ser Val
                725

<210> SEQ ID NO 145
<211> LENGTH: 510
<212> TYPE: PRT
<213> ORGANISM: Phythophtora infestance

<400> SEQUENCE: 145

Met Leu Ser Thr Leu Leu Trp Leu Ala Leu Ala Val Val Val Leu Ala

-continued

```
  1               5                   10                  15
Thr Gln Gly Tyr Lys Met Val Ala Arg Phe Leu Arg Leu Leu Leu His
                 20                  25                  30
Thr Tyr Phe Arg Lys Ile Val Val Tyr Gly Leu Asn Asn Phe Pro Arg
                 35                  40                  45
Glu Gly Pro Val Ile Leu Cys Pro Asn His Pro Asn Met Leu Val Asp
 50                  55                  60
Ala Ile Leu Val Met Thr Glu Ala Val Ser His Gly Arg Asn Pro Tyr
 65                  70                  75                  80
Val Trp Ala Lys Gly Ser Leu Phe Ser Asn Pro Val Ala Ala Phe Phe
                 85                  90                  95
Leu Lys Lys Phe Gly Ala Val Pro Val Tyr Arg Pro Arg Arg Lys Glu
                100                 105                 110
Asp Ser Leu Ala Asp Val Asp Ser Asp Lys Thr Pro Glu Gln Leu Glu
                115                 120                 125
Ala Ala Asn Arg Lys Met Phe Glu His Thr Trp His Val Leu Ala Gly
                130                 135                 140
Gly Asn Val Met Val Leu Phe Pro Glu Gly Thr Ser Tyr Thr Ala Pro
145                 150                 155                 160
Lys Met Leu Ser Leu Arg Thr Gly Val Val Arg Val Ala Thr Gly Phe
                165                 170                 175
Ala Lys His Tyr Asp Gln Pro Ile Pro Ile Pro Leu Gly Leu Asn
                180                 185                 190
Tyr Phe Asn Lys Asp His Phe Arg Ser Gln Met Thr Leu Glu Phe Gly
                195                 200                 205
Pro Pro Met Val Ile Thr Pro Asp Met Val Gln Thr Glu Ala Phe Gln
                210                 215                 220
Gln Asp Glu His Gly Glu Val Lys Arg Leu Thr Leu Glu Leu Glu Glu
225                 230                 235                 240
Arg Met His Asp Val Thr Leu Asn Ala Ser Asp Phe Ser Thr Ile His
                245                 250                 255
Ala Ala Arg Met Met Arg Arg Leu Tyr Leu Asn Thr Pro Gly Pro Ile
                260                 265                 270
Asp Thr Asn Lys Glu Val Arg Leu Thr Gln Tyr Ile Ile Asn Met Leu
                275                 280                 285
Glu Lys Glu Pro Gln Asp Asp Glu Gln Lys Arg Ile Ala Thr Ile
                290                 295                 300
Arg Glu Lys Val Leu Arg Tyr Lys Glu Gln Leu Glu Lys Leu Arg Leu
305                 310                 315                 320
Lys Asp Gln Glu Val Asn Leu Pro Met Pro Lys Glu Lys Ser Leu Leu
                325                 330                 335
Gln Leu Phe Leu Glu Arg Ile Leu Tyr Leu Leu Val Leu Leu Pro Leu
                340                 345                 350
Ala Thr Pro Gly Leu Leu Leu Asn Leu Pro Tyr Tyr Phe Ile Gly Thr
                355                 360                 365
Lys Met Asn Ser Leu Ala Gly Phe Val Glu Ser Lys Ser Met Phe Lys
                370                 375                 380
Ile Phe Ala Ala Ala Val Leu Val Pro Val His Trp Leu Val Leu Ile
385                 390                 395                 400
Leu Ala Thr Trp Tyr Phe Leu Gly Ser Ser Tyr Ala Tyr Val Leu Ala
                405                 410                 415
Val Gly Leu Pro Leu Leu Leu Tyr Ser His Ile Arg Val Leu Glu Glu
                420                 425                 430
```

```
Ser Arg Ser Ile Ala Glu Asn Val Tyr Phe Leu Phe Asn Ile Thr Ala
        435                 440                 445

His Ala Asp Lys Val Ala Val Leu Arg Thr Glu Arg Glu Leu Leu Ala
    450                 455                 460

Gln Glu Val His Glu Leu Val Thr Lys Tyr Val Asp Ala Lys Phe Leu
465                 470                 475                 480

Ser Ala Ile His Lys Ser Leu Ala Ser Ser Pro Val Asn Arg Arg Leu
                485                 490                 495

Arg His Arg Ala Ser Ser Thr Ser Asp Thr Leu Leu Thr Thr
            500                 505                 510

<210> SEQ ID NO 146
<211> LENGTH: 26802
<212> TYPE: DNA
<213> ORGANISM: Artificial Sequence
<220> FEATURE:
<223> OTHER INFORMATION: Plant Expression Plasmid

<400> SEQUENCE: 146
ttgacataca aatggacgaa cggataaacc ttttcacgcc cttttaaata tccgattatt      60
ctaataaacg ctcttttctc ttaggtttac ccgccaatat atcctgtcaa acactgatag     120
tttaaactga aggcgggaaa cgacaatctg atcactgatt agtaactaag gcctttaatt     180
aatctagagg cgcgccgggc ccctgcagg gagctcggcc ggccaattta aattgatatc     240
ggtacatcga ttacgccaag ctatcaactt tgtatagaaa agttgccatg attacgccaa     300
gcttggccac taaggccaat ttcgcgccct gcagcaaatt tacacattgc cactaaacgt     360
ctaaaccctt gtaatttgtt tttgttttac tatgtgtgtt atgtatttga tttgcgataa     420
atttttatat ttggtactaa atttataaca cctttttatgc taacgtttgc caacacttag    480
caatttgcaa gttgattaat tgattctaaa ttattttttgt cttctaaata catatactaa    540
tcaactggaa atgtaaatat ttgctaatat ttctactata ggagaattaa agtgagtgaa    600
tatggtacca caaggtttgg agatttaatt gttgcaatgc tgcatggatg gcatatacac    660
caaacattca ataattcttg aggataataa tggtaccaca caagatttga ggtgcatgaa    720
cgtcacgtgg acaaaaggtt tagtaatttt tcaagacaac aatgttacca cacacaagtt    780
ttgaggtgca tgcatggatg ccctgtggaa agtttaaaaa tattttggaa atgatttgca    840
tggaagccat gtgtaaaacc atgacatcca cttggaggat gcaataatga agaaaactac    900
aaatttacat gcaactagtt atgcatgtag tctatataat gaggattttg caatactttc    960
attcatacac actcactaag ttttacacga ttataatttc ttcatagcca gtactgttta   1020
agcttcactg tctctgaatc ggcaaaggta aacgtatcaa ttattctaca acccttttta   1080
tttttctttt gaattaccgt cttcattggt tatatgataa cttgataagt aaagcttcaa   1140
taattgaatt tgatctgtgt tttttttggcc ttaatactaa atccttacat aagctttgtt   1200
gcttctcctc ttgtgagttg agtgttaagt tgtaataatg gttcactttc agctttagaa   1260
gaaaccatgg aagttgttga gaggttctac ggagagttgg atggaaaggt tcccaagga    1320 gtgaacgctt tgttgggatc tttcggagtt gagttgactg ataccccaac tactaaggga   1380
ttgccactcg ttgattctcc aactccaatt gtgttgggag tgtctgttta cttgaccatc   1440
gtgatcggag gattgctttg gatcaaggct agagatctca agccaagagc ttctgagcca   1500
ttcttgttgc aagctttggt gttggtgcac aacttgttct gcttcgcttt gtctctttac   1560
atgtgcgtgg gtatcgctta ccaagctatc acctggagat attccttgtg gggaaacgct   1620
```

```
tataacccaa agcacaagga gatggctatc ctcgtttacc tcttctacat gtccaagtac   1680
gtggagttca tggataccgt gatcatgatc ctcaagagat ccaccagaca gatttctttc   1740
ctccacgtgt accaccactc ttctatctcc cttatctggt gggctattgc tcaccacgct   1800
ccaggaggag aggcttattg gagtgctgct ctcaactctg gagtgcacgt gttgatgtac   1860
gcttactact tcttggctgc ttgcttgaga tcttccccaa agctcaagaa caagtacctc   1920
ttctggggaa gatacctcac ccaattccag atgttccagt tcatgctcaa cttggtgcaa   1980
gcttactacg atatgaaaac caacgctcca tatccacaat ggctcatcaa gatcctcttc   2040
tactacatga tctccctctt gttcctcttc ggaaacttct acgtgcaaaa gtacatcaag   2100
ccatccgatg aaagcaaaa gggagctaag accgagtgat cgacaagctc gagtttctcc   2160
ataataatgt gtgagtagtt cccagataag ggaattaggg ttcctatagg gtttcgctca   2220
tgtgttgagc atataagaaa cccttagtat gtatttgtat ttgtaaaata cttctatcaa   2280
taaaatttct aattcctaaa accaaaatcc agtactaaaa tccagatccc ccgaattaat   2340
tcggcgttaa ttcagggccg gccaaagtag gcgcctacta ccggtaattc ccgggattag   2400
cggccgctag tctgtgcgca cttgtatcct gcaggttagg ccggccatta gcagatattt   2460
ggtgtctaaa tgtttatttt gtgatatgtt catgtttgaa atggtggttt cgaaaccagg   2520
gacaacgttg ggatctgata gggtgtcaaa gagtattatg gattgggaca atttcggtca   2580
tgagttgcaa attcaagtat atcgttcgat tatgaaaatt ttcgaagaat atcccatttg   2640
agagagtctt tacctcatta atgttttttag attatgaaat tttatcatag ttcatcgtag   2700
tcttttttggt gtaaaggctg taaaagaaa ttgttcactt ttgttttcgt ttatgtgaag   2760
gctgtaaaag attgtaaaag actattttgg tgttttggat aaaatgatag tttttataga   2820
ttcttttgct tttagaagaa atacatttga aattttttcc atgttgagta taaaataccg   2880
aaatcgattg aagatcatag aaatatttta actgaaaaca aatttataac tgattcaatt   2940
ctctccattt ttatacctat ttaaccgtaa tcgattctaa tagatgatcg attttttata   3000
taatcctaat taaccaacgg catgtattgg ataattaacc gatcaactct caccctaat   3060
agaatcagta ttttccttcg acgttaattg atcctacact atgtaggtca tatccatcgt   3120
tttaattttt ggccaccatt caattctgtc ttgcctttag ggatgtgaat atgaacggcc   3180
aaggtaagag aataaaaata atccaaatta aagcaagaga ggccaagtaa gataatccaa   3240
atgtacactt gtcattgcca aaattagtaa aatactcggc atattgtatt cccacacatt   3300
attaaaatac cgtatatgta ttggctgcat ttgcatgaat aatactacgt gtaagcccaa   3360
aagaacccac gtgtagccca tgcaaagtta acactcacga ccccattcct cagtctccac   3420
tatataaacc caccatcccc aatctcacca aacccaccac acaactcaca actcactctc   3480
acaccttaaa gaaccaatca ccaccaaaaa atttcacgat ttggaatttg attcctgcga   3540
tcacaggtat gacaggttag attttgtttt gtatagttgt atacatactt ctttgtgatg   3600
ttttgtttac ttaatcgaat ttttggagtg ttttaaggtc tctcgtttag aaatcgtgga   3660
aaatatcact gtgtgtgtgt tcttatgatt cacagtgttt atgggtttca tgttctttgt   3720
tttatcattg aatgggaaga aatttcgttg ggatacaaat ttctcatgtt cttactgatc   3780
gttattagga gtttggggaa aaaggaagag tttttttggt tggttcgagt gattatgagg   3840
ttatttctgt atttgattta tgagttaatg gtcgttttaa tgttgtagac catgggaaaa   3900
ggatctgagg gaagatctgc tgctagagag atgactgctg aggctaacgg agataagaga   3960
```

```
aagaccatcc tcattgaggg agtgttgtac gatgctacca acttcaaaca cccaggaggt    4020
tccattatta acttcctcac cgagggagaa gctggagttg atgctaccca agcttacaga    4080
gagttccatc agagatccgg aaaggctgat aagtacctca agtccctccc aaagttggat    4140
gcttctaagg tggagtctag gttctctgct aaggagcagg ctagaaggga cgctatgacc    4200
agggattacg ctgctttcag agaggagttg gttgctgagg gatacttcga tccatctatc    4260
ccacacatga tctacagagt ggtggagatt gtggctttgt tcgctttgtc tttctggttg    4320
atgtctaagg cttctccaac ctctttggtt ttgggagtgg tgatgaacgg aatcgctcaa    4380
ggaagatgcg gatgggttat gcacgagatg ggacacggat cttccactgg agttatctgg    4440
ctcgatgata ggatgtgcga gttcttctac ggagttggat gtggaatgtc tggacactac    4500
tggaagaacc agcactctaa gcaccacgct gctccaaaca gattggagca cgatgtggat    4560
ttgaacacct tgccactcgt tgctttcaac gagagagttg tgaggaaggt taagccagga    4620
tctttgttgg ctttgtggct cagagttcag gcttatttgt tcgctccagt gtcttgcttg    4680
ttgatcggat tgggatggac cttgtacttg cacccaagat atatgctcag gaccaagaga    4740
cacatggagt ttgtgtggat cttcgctaga tatatcggat ggttctcctt gatgggagct    4800
ttgggatatt ctcctggaac ttctgtggga atgtacctct gctctttcgg acttggatgc    4860
atctacatct tcctccaatt cgctgtgtct cacacccact tgccagttac caacccagag    4920
gatcaattgc actggcttga gtacgctgct gatcacaccg tgaacatctc taccaagtct    4980
tggttggtta cctggtggat gtctaacctc aacttccaaa tcgagcacca cttgttccca    5040
accgctccac aattcaggtt caaggagatc tctccaagag ttgaggctct cttcaagaga    5100
cacaacctcc cttactacga tttgccatac acctctgctg tttctactac cttcgctaac    5160
ctctactctg ttggacactc tgttggagct gataccaaga agcaggattg actgctttaa    5220
tgagatatgc gagacgccta tgatcgcatg atatttgctt tcaattctgt tgtgcacgtt    5280
gtaaaaaacc tgagcatgtg tagctcagat ccttaccgcc ggtttcggtt cattctaatg    5340
aatatatcac ccgttactat cgtatttta tgaataatat tctccgttca atttactgat    5400
tgtgtcgacg cgatcgcgtg caaacactgt acggaccgtg gcctaatagg ccggtaccca    5460
agtttgtaca aaaaagcagg ctccatgatt acgccaagct tggccactaa ggccaattta    5520
aatctactag gccggccatc gacggcccgg actgtatcca acttctgatc tttgaatctc    5580
tctgttccaa catgttctga aggagttcta agacttttca gaaagcttgt aacatgcttt    5640
gtagactttc tttgaattac tcttgcaaac tctgattgaa cctacgtgaa aactgctcca    5700
gaagttctaa ccaaattccg tcttgggaag gcccaaaatt tattgagtac ttcagtttca    5760
tggacgtgtc ttcaaagatt tataacttga aatcccatca tttttaagag aagttctgtt    5820
ccgcaatgtc ttagatctca ttgaaatcta caactcttgt gtcagaagtt cttccagaat    5880
caacttgcat catggtgaaa atctggccag aagttctgaa cttgtcatat ttcttaacag    5940
ttagaaaaat ttctaagtgt ttagaatttt gacttttcca aagcaaactt gacttttgac    6000
tttcttaata aaacaaactt catattctaa catgtcttga tgaaatgtga ttcttgaaat    6060
ttgatgttga tgcaaaagtc aaagtttgac ttttcagtgt gcaattgacc attttgctct    6120
tgtgccaatt ccaaacctaa attgatgtat cagtgctgca aacttgatgt catggaagat    6180
cttatgagaa aattcttgaa gactgagagg aaaaattttg tagtacaaca caaagaatcc    6240
tgtttttcat agtcggacta gacacattaa cataaaacac cacttcattc gaagagtgat    6300
tgaagaagga aatgtgcagt tacctttctg cagttcataa gagcaactta cagacacttt    6360
```

```
tactaaaata ctacaaagag gaagatttta acaacttaga gaagtaatgg gagttaaaga   6420
gcaacacatt aaggggagt gttaaaatta atgtgttgta accaccacta cctttagtaa    6480
gtattataag aaaattgtaa tcatcacatt ataattattg tccttattta aaattatgat   6540
aaagttgtat cattaagatt gagaaaacca aatagtcctc gtcttgattt ttgaattatt   6600
gttttctatg ttactttct tcaagcctat ataaaaactt tgtaatgcta aattgtatgc    6660
tggaaaaaaa tgtgtaatga attgaataga aattatggta tttcaaagtc caaaatccat   6720
caatagaaat ttagtacaaa acgtaactca aaaatattct cttattttaa attttacaac   6780
aatataaaaa tattctctta ttttaaattt tacaataata taatttatca cctgtcacct   6840
ttagaatacc accaacaata ttaatactta gatattttat tcttaataat tttgagatct   6900
ctcaatatat ctgatattta tttatattt gtgtcatatt ttcttatgtt ttagagttaa    6960
cccttatatc ttggtcaaac tagtaattca atatatgagt ttgtgaagga cacattgaca   7020
tcttgaaaca ttggttttaa ccttgttgga atgttaaagg taataaaaca ttcagaatta   7080
tgaccatcta ttaatatact tcctttgtct tttaaaaaag tgtgcatgaa aatgctctat   7140
ggtaagctag agtgtcttgc tggcctgtgt atatcaattc catttccaga tggtagaaac   7200
tgccactacg aataattagt cataagacac gtatgttaac acacgtcccc ttgcatgttt   7260
tttgccatat attccgtctc tttcttttc ttcacgtata aaacaatgaa ctaattaata    7320
gagcgatcaa gctgaacagt tctttgcttt cgaagttgcc gcaacctaaa caggttttc    7380 cttcttcttt cttcttatta actacgacct tgtcctttgc ctatgtaaaa ttactaggtt   7440
ttcatcagtt acactgatta agttcgttat agtggaagat aaaatgccct caaagcattt   7500
tgcaggatat ctttgatttt tcaaagatat ggaactgtag agtttgatag tgttcttgaa   7560
tgtggttgca tgaagttttt ttggtctgca tgttattttt tcctcgaaat atgttttgag   7620
tccaacaagt gattcacttg ggattcagaa agttgttttc tcaatatgta acagtttttt   7680
tctatggaga aaaatcatag ggaccgttgg ttttggcttc tttaattttg agctcagatt   7740
aaacccattt tacccggtgt tcttggcaga attgaaaaca gtacgtagta ccgcgcctac   7800
catgtgtgtt gagaccgaga acaacgatgg aatccctact gtggagatcg ctttcgatgg   7860
agagagagaa agagctgagg ctaacgtgaa gttgtctgct gagaagatgg aacctgctgc   7920
tttggctaag accttcgcta gaagatacgt ggttatcgag ggagttgagt acgatgtgac   7980
cgatttcaaa catcctggag gaaccgtgat tttctacgct ctctctaaca ctggagctga   8040
tgctactgag gctttcaagg agttccacca cagatctaga aaggctagga aggctttggc   8100
tgctttgcct tctagacctg ctaagaccgc taaagtggat gatgctgaga tgctccagga   8160
tttcgctaag tggagaaagg agttggagag ggacggattc ttcaagcctt ctcctgctca   8220
tgttgcttac agattcgctg agttggctgc tatgtacgct ttgggaacct acttgatgta   8280
cgctagatac gttgtgtcct ctgtgttggt ttacgcttgc ttcttcggag ctagatgtgg   8340
atgggttcaa cacgagggag gacactcttc tttgaccgga acatctggt gggataagag   8400 aatccaagct ttcactgctg gattcggatt ggctggatct ggagatatgt ggaactccat   8460
gcacaacaag caccacgcta ctcctcaaaa agtgaggcac gatatggatt tggataccac   8520
tcctgctgtt gctttcttca acaccgctgt ggaggataat agacctaggg gattctctaa   8580
gtactggctc agattgcaag cttggacctt cattcctgtg acttctggat tggtgttgct   8640
cttctggatg ttcttcctcc acccttctaa ggctttgaag ggaggaaagt acgaggagct   8700
```

```
tgtgtggatg ttggctgctc acgtgattag aacctggacc attaaggctg ttactggatt    8760
caccgctatg caatcctacg gactcttctt ggctacttct tgggtttccg gatgctactt    8820
gttcgctcac ttctctactt ctcacaccca cttggatgtt gttcctgctg atgagcactt    8880
gtcttgggtt aggtacgctg tggatcacac cattgatatc gatccttctc agggatgggt    8940
taactggttg atgggatact tgaactgcca agtgattcac cacctcttcc cttctatgcc    9000
tcaattcaga caacctgagg tgtccagaag attcgttgct ttcgctaaga agtgaaacct    9060
caactacaag gtgatgactt atgctggagc ttggaaggct actttgggaa acctcgataa    9120
tgtgggaaag cactactacg tgcacggaca acactctgga aagaccgctt gattaattaa    9180
ggccgcctcg accgtacccc ctgcagatag actatactat gttttagcct gcctgctggc    9240
tagctactat gttatgttat gttgtaaaat aaacacctgc taaggtatat ctatctatat    9300
tttagcatgg ctttctcaat aaattgtctt tccttatcgt ttactatctt atacctaata    9360
atgaaataat aatatcacat atgaggaacg gggcaggttt aggcatatat atacgagtgt    9420
agggcggagt gggggcgcc tactaccggt aattcccggg attagcggcc gctagtctgt    9480
gcgcacttgt atcctgcagg ttaggccggc cacacgggca ggacataggg actactacaa    9540
gcatagtatg cttcagacaa agagctagga aagaactctt gatggaggtt aagagaaaaa    9600
agtgctagag gggcatagta atcaaacttg tcaaaaccgt catcatgatg agggatgaca    9660
taatataaaa agttgactaa ggtcttggta gtactctttg attagtatta tatattggtg    9720
agaacatgag tcaagaggag acaagaaacc gaggaaccat agtttagcaa caagatggaa    9780
gttgcaaagt tgagctagcc gctcgattag ttacatctcc taagcagtac tacaaggaat    9840
ggtctctata ctttcatgtt tagcacatgg tagtgcggat tgacaagtta gaaacagtgc    9900
ttaggagaca aagagtcagt aaaggtattg aaagagtgaa gttgatgctc gacaggtcag    9960
gagaagtccc tccgccagat ggtgactacc aaggggttgg tatcagctga gacccaaata   10020
agattcttcg gttgaaccag tggttcgacc gagactctta gggtgggatt tcactgtaag   10080
atttgtgcat tttgttgaat ataaattgac aattttttt atttaattat agattattta   10140
gaatgaatta catatttagt ttctaacaag gatagcaatg gatgggtatg ggtacaggtt   10200
aaacatatct attacccacc catctagtcg tcgggtttta cacgtaccca cccgtttaca   10260
taaaccagac cggaatttta aaccgtaccc gtccgttagc gggtttcaga tttacccgtt   10320
taatcgggta aaacctgatt actaaatata tattttttat ttgataaaca aaacaaaaat   10380
gttaatattt tcatattgga tgcaatttta agaaacacat attcataaat ttccatattt   10440
gtaggaaaat aaaagaaaa atatattcaa gaacacaaat ttcaccgaca tgacttttat   10500
tacagagttg gaattagatc taacaattga aaaattaaaa ttaagataga atatgttgag   10560
gaacatgaca tagtataatg ctgggttacc cgtcgggtag gtatcgaggc ggatactact   10620
aaatccatcc cactcgctat ccgataatca ctggtttcgg gtatacccat tcccgtcaac   10680
aggccttttt aaccggataa tttcaactta tagtgaatga attttgaata aatagttaga   10740
ataccaaaat cctggattgc atttgcaatc aaattttgtg aaccgttaaa ttttgcatgt   10800
acttgggata gatataatag aaccgaattt tcattagttt aatttataac ttactttgtt   10860
caaagaaaaa aaatatctat ccaatttact tataataaaa aataatctat ccaagttact   10920
tattataatc aacttgtaaa aaggtaagaa tacaaatgtg gtagcgtacg tgtgattata   10980
tgtgacgaaa tgttatatct aacaaaagtc caaattccca tggtaaaaaa aatcaaaatg   11040
catggcaggc tgtttgtaac cttggaataa gatgttggcc aattctggag ccgccacgta   11100
```

```
cgcaagactc agggccacgt tctcttcatg caaggatagt agaacaccac tccacccacc   11160
tcctatatta gacctttgcc caaccctccc caactttccc atcccatcca caaagaaacc   11220
gacattttta tcataaatct ggtgcttaaa cactctggtg agttctagta cttctgctat   11280
gatcgatctc attaccattt cttaaatttc tctccctaaa tattccgagt tcttgatttt   11340
tgataacttc aggttttctc tttttgataa atctggtctt tccattttt ttttttgtg    11400 gttaatttag tttcctatgt tcttcgattg tattatgcat gatctgtgtt tggattctgt   11460
tagattatgt attggtgaat atgtatgtgt ttttgcatgt ctggttttgg tcttaaaaat   11520
gttcaaatct gatgatttga ttgaagcttt tttagtgttg gtttgattct tctcaaaact   11580
actgttaatt tactatcatg ttttccaact ttgattcatg atgacacttt tgttctgctt   11640
tgttataaaa ttttggttgg tttgatttg taattatagt gtaattttgt taggaatgaa    11700
catgttttaa tactctgttt tcgatttgtc acacattcga attattaatc gataaattaa   11760
ctgaaaattc atggttctag atcttgttgt catcagatta tttgtttcga taattcatca   11820
aatatgtagt cctttgctg atttgcgact gtttcatttt ttctcaaaat tgttttttgt    11880
taagtttatc taacagttat cgttgtcaaa agtctctttc attttgcaaa atcttctttt   11940 ttttttttgtt tgtaactttg tttttaagc tacacattta gtctgtaaaa tagcatcgag   12000
gaacagttgt cttagtagac ttgcatgttc ttgtaacttc tatttgtttc agttgttga    12060 tgactgcttt gattttgtag gtcaaaggcg cgccctacca tggatgctta taacgctgct   12120
atggataaga ttggagctgc tatcatcgat tggagtgatc cagatggaaa gttcagagct   12180
gatagggagg attggtggtt gtgcgatttc agatccgcta tcaccattgc tctcatctac   12240
atcgctttcg tgatcttggg atctgctgtg atgcaatctc tcccagctat ggacccatac   12300
cctatcaagt tcctctacaa cgtgtctcaa atcttcctct gcgcttacat gactgttgag   12360
gctggattcc tcgcttatag gaacggatac accgttatgc catgcaacca cttcaacgtg   12420
aacgatccac cagttgctaa cttgctctgg ctcttctaca tctccaaagt gtgggatttc   12480
tgggatacca tcttcattgt gctcggaaag aagtggagac aactctcttt cttgcacgtg   12540
taccaccaca ccaccatctt cctcttctac tggttgaacg ctaacgtgct ctacgatgga   12600
gatatcttct tgaccatcct cctcaacgga ttcattcaca ccgtgatgta cacctactac   12660
ttcatctgca tgcacaccaa ggattctaag accggaaagt ctttgccaat ctggtggaag   12720
tcatctttga ccgctttcca actcttgcaa ttcaccatca tgatgtccca agctacctac   12780
ttggttttcc acgatgcga taaggttcc ctcagaatca ccatcgtgta cttcgtgtac    12840
attctctccc ttttcttcct cttcgctcag ttcttcgtgc aatcctacat ggctccaaag   12900
aagaagaagt ccgcttgatg ttaattaagg ccgcagatat cagatctggt cgacctagag   12960
gatccccggc cgcaaagata ataacaaaag cctactatat aacgtacatg caagtattgt   13020
atgatattaa tgtttttacg tacgtgtaaa caaaaataat tacgtttgta acgtatggtg   13080
atgatgtggt gcactaggtg taggccttgt attaataaaa agaagtttgt tctatataga   13140
gtggtttagt acgacgattt atttactagt cggattggaa tagagaaccg aattcttcaa   13200
tccttgcttt tgatcaagaa ttgaaaccga atcaaatgta aaagttgata tatttgaaaa   13260
acgtattgag cttatgaaaa tgctaatact ctcatctgta tggaaaagtg acttaaaaac   13320
cgaacttaaa agtgacaaaa ggggaatatc gcatcaaacc gaatgaaacc gatggcgcct   13380
accggtatcg gtccgattgc ggccgcttaa agggcgaatt cgtttaaaca ctgtacggac   13440
```

```
cgtggcctaa taggccggta ccacccagct ttcttgtaca aagtggccat gattacgcca   13500
agcttggcca ctaaggccaa tttaaatcta ctaggccggc cataaggatg acctacccat   13560
tcttgagaca aatgttacat tttagtatca gagtaaaatg tgtacctata actcaaattc   13620
gattgacatg tatccattca acataaaatt aaaccagcct gcacctgcat ccacatttca   13680
agtattttca aaccgttcgg ctcctatcca ccgggtgtaa caagacggat tccgaatttg   13740
gaagattttg actcaaattc ccaatttata ttgaccgtga ctaaatcaac tttaacttct   13800
ataattctga ttaagctccc aatttatatt cccaacggca ctacctccaa aatttataga   13860
ctctcatccc cttttaaacc aacttagtaa acgttttttt tttaatttta tgaagttaag   13920 ttttttacctt gttttttaaaa agaatcgttc ataagatgcc atgccagaac attagctaca   13980
cgttacacat agcatgcagc cgcggagaat tgttttttctt cgccacttgt cactcccttc   14040
aaacacctaa gagcttctct ctcacagcac acacatacaa tcacatgcgt gcatgcatta   14100
ttacacgtga tcgccatgca aatctccttt atagcctata aattaactca tcggcttcac   14160
tctttactca aaccaaaact catcaataca aacaagatta aaaacatttc acgatttgga   14220
atttgattcc tgcgatcaca ggtatgacag gttagatttt gttttgtata gttgtataca   14280
tacttctttg tgatgttttg tttacttaat cgaattttg gagtgttta aggtctctcg   14340 tttagaaatc gtggaaaata tcactgtgtg tgtgttctta tgattcacag tgttatggg   14400 tttcatgttc tttgttttat cattgaatgg gaagaaattt cgttgggata caaatttctc   14460
atgttcttac tgatcgttat taggagtttg gggaaaaagg aagagttttt ttggttggtt   14520
cgagtgatta tgaggttatt tctgtatttg atttatgagt taatggtcgt tttaatgttg   14580
tagaccgcca tggctatttt gaaccctgag gctgattctg ctgctaacct cgctactgat   14640
tctgaggcta agcaaagaca attggctgag gctggataca ctcatgttga gggtgctcct   14700
gctcctttgc ctttggagtt gcctcatttc tctctcagag atctcagagc tgctattcct   14760
aagcactgct tcgagagatc tttcgtgacc tccacctact acatgatcaa gaacgtgttg   14820
acttgcgctg ctttgttcta cgctgctacc ttcattgata gagctggagc tgctgcttat   14880
gttttgtggc ctgtgtactg gttcttccag ggatcttact tgactggagt gtgggttatc   14940
gctcatgagt gtggacatca ggcttattgc tcttctgagg tggtgaacaa cttgattgga   15000
ctcgtgttgc attctgcttt gttggtgcct taccactctt ggagaatctc tcacagaaag   15060
caccattcca acactggatc ttgcgagaac gatgaggttt tcgttcctgt gaccagatct   15120
gtgttggctt cttcttggaa cgagaccttg gaggattctc ctctctacca actctaccgt   15180
atcgtgtaca tgttggttgt tggatggatg cctggatacc tcttcttcaa cgctactgga   15240
cctactaagt actggggaaa gtctaggtct cacttcaacc cttactccgc tatctatgct   15300
gatagggaga gatggatgat cgtgctctcc gatatttct tggtggctat gttggctgtt   15360
ttggctgctt tggtgcacac tttctccttc aacaccatgg tgaagttcta cgtggtgcct   15420
tacttcattg tgaacgctta cttggtgttg attacctacc tccaacacac cgataccac   15480 atccctcatt tcagagaggg agagtggaat tggttgagag gagctttgtg cactgtggat   15540
agatcatttg gtccattcct cgattctgtg gtgcatagaa tcgtggatac ccatgtttgc   15600
caccacatct tctccaagat gcctttctat cattgcgagg aggctaccaa cgctattaag   15660
cctctcctcg gaaagttcta cttgaaggat accactcctg ttcctgttgc tctctggaga   15720
tcttacaccc attgcaagtt cgttgaggat gatggaaagg tggtgttcta caagaacaag   15780
ctctagttaa ttaataattg attggttcga gtattatggc attgggaaaa ctgttttct   15840
```

```
tgtaccattt gttgtgcttg taatttactg tgttttttat tcggttttcg ctatcgaact   15900
gtgaaatgga aatggatgga gaagagttaa tgaatgatat ggtcctttg ttcattctca    15960
aattaatatt atttgttttt tctcttattt gttgtgtgtt gaatttgaaa ttataagaga   16020
tatgcaaaca ttttgttttg agtaaaaatg tgtcaaatcg tggcctctaa tgaccgaagt   16080
taatatgagg agtaaaacac ttgtagttgt accattatgc ttattcacta ggcaacaaat   16140
atattttcag acctagaaaa gctgcaaatg ttactgaata caagtatgtc ctcttgtgtt   16200
ttagacattt atgaactttc ctttatgtaa ttttccagaa tccttgtcag attctaatca   16260
ttgctttata attatagtta tactcatgga tttgtagttg agtatgaaaa tattttttaa   16320
tgcattttat gacttgccaa ttgattgaca acatgcatca atggcgccta ctaccggtaa   16380
ttcccgggat tagcggccgc tagtctgtgc gcacttgtat cctgcaggtc aatcgtttaa   16440
acactgtacg gaccgtggcc taataggccg gtacccaact ttattataca tagttgataa   16500
ttcactggcc ggatgtaccg aattcgcggc cgcaagcttg tacactagta cgcgtcaatt   16560
ggcgatcgcg gatctgagat gaaaccggtg attatcagaa cctttatgg tctttgtatg    16620
catatggtaa aaaaacttag tttgcaattt cctgtttgtt ttggtaattt gagtttcttt   16680
tagttgttga tctgcctgct ttttggttta cgtcagacta ctactgctgt tgttgtttgg   16740
tttcctttct ttcattttat aaataaataa tccggttcgg tttactcctt gtgactggct   16800
cagtttggtt attgcgaaat gcgaatggta aattgagtaa ttgaaattcg ttattagggt   16860
tctaagctgt tttaacagtc actgggttaa tatctctcga atcttgcatg gaaaatgctc   16920
ttaccattgg tttttaattg aaatgtgctc atatgggccg tggtttccaa attaaataaa   16980
actacgatgt catcgagaag taaaatcaac tgtgtccaca ttatcagttt tgtgtatacg   17040
atgaaatagg gtaattcaaa atctagcttg atatgccttt tggttcattt taaccttctg   17100
taaacatttt ttcagatttt gaacaagtaa atccaaaaaa aaaaaaaaaa aatctcaact   17160
caacactaaa ttattttaat gtataaaaga tgcttaaaac atttggctta aaagaaagaa   17220
gctaaaaaca tagagaactc ttgtaaattg aagtatgaaa atatactgaa ttgggtatta   17280
tatgaatttt tctgatttag gattcacatg atccaaaaag gaaatccaga agcactaatc   17340
agacattgga agtaggaata tttcaaaaag tttttttttt taagtaagtg acaaaagctt   17400
ttaaaaaata gaaaagaaac tagtattaaa gttgtaaatt taataaacaa agaaattttt   17460
ttatatttt tcatttctt ttccagcatg aggttatgat ggcaggatgt ggatttcatt     17520
tttttcctt tgatagcctt ttaattgatc tattataatt gacgaaaaaa tattagttaa    17580
ttatagatat attttaggta gtattagcaa tttacacttc caaaagacta tgtaagttgt   17640
aaatatgatg cgttgatctc ttcatcattc aatggttagt caaaaaaata aaagcttaac   17700
tagtaaacta aagtagtcaa aaattgtact ttagtttaaa atattacatg aataatccaa   17760
aacgacattt atgtgaaaca aaaacaatat agatccatta ccctgttatc cctagagggg   17820
aaaattcgaa tccaaaaatt acggatatga atataggcat atccgtatcc gaattatccg   17880
tttgacagct agcaacgatt gtacaattgc ttctttaaaa aaggaagaaa gaaagaaaga   17940
aaagaatcaa catcagcgtt aacaaacggc ccgttacgg cccaaacggt catatagagt     18000
aacggcgtta agcgttgaaa gactcctatc gaaatacgta accgcaaacg tgtcatagtc   18060
agatcccctc ttccttcacc gcctcaaaca caaaataat cttctacagc ctatatatac    18120
aaccccccct tctatctctc ctttctcaca attcatcatc tttctttctc tacccccaat   18180
```

```
tttaagaaat cctctcttct cctcttcatt ttcaaggtaa atctctctct ctctctctct   18240
ctctgttatt ccttgtttta attaggtatg tattattgct agtttgttaa tctgcttatc   18300
ttatgtatgc cttatgtgaa tatctttatc ttgttcatct catccgttta gaagctataa   18360
atttgttgat ttgactgtgt atctacacgt ggttatgttt atatctaatc agatatgaat   18420
ttcttcatat tgttgcgttt gtgtgtacca atccgaaatc gttgattttt ttcatttaat   18480
cgtgtagcta attgtacgta tacatatgga tctacgtatc aattgttcat ctgtttgtgt   18540
ttgtatgtat acagatctga aaacatcact tctctcatct gattgtgttg ttacatacat   18600
agatatagat ctgttatatc attttttta ttaattgtgt atatatatat gtgcatagat   18660
ctggattaca tgattgtgat tatttacatg attttgttat ttacgtatgt atatatgtag   18720
atctggactt tttggagttg ttgacttgat tgtatttgtg tgtgtatatg tgtgttctga   18780
tcttgatatg ttatgtatgt gcagctgaac catggcggcg gcaacaacaa caacaacaac   18840
atcttcttcg atctccttct ccaccaaacc atctccttcc tcctccaaat caccattacc   18900
aatctccaga ttctccctcc cattctccct aaacccaac aaatcatcct cctcctcccg   18960
ccgccgcggt atcaaatcca gctctccctc ctccatctcc gccgtgctca acacaaccac   19020
caatgtcaca accactccct ctccaaccaa acctaccaaa cccgaaacat tcatctcccg   19080
attcgctcca gatcaacccc gcaaaggcgc tgatatcctc gtcgaagctt tagaacgtca   19140
aggcgtagaa accgtattcg cttaccctgg aggtacatca atggagattc accaagcctt   19200
aacccgctct tcctcaatcc gtaacgtcct tcctcgtcac gaacaaggag gtgtattcgc   19260
agcagaagga tacgctcgat cctcaggtaa accaggtatc tgtatagcca cttcaggtcc   19320
cggagctaca aatctcgtta gcggattagc cgatgcgttg ttagatagtg ttcctcttgt   19380
agcaatcaca ggacaagtcc ctcgtcgtat gattggtaca gatgcgtttc aagagactcc   19440
gattgttgag gtaacgcgtt cgattacgaa gcataactat cttgtgatgg atgttgaaga   19500
tatccctagg attattgagg aagctttctt tttagctact tctggtagac ctggacctgt   19560
tttggttgat gttcctaaag atattcaaca acagcttgcg attcctaatt gggaacaggc   19620
tatgagatta cctggttata tgtctaggat gcctaaacct ccggaagatt ctcatttgga   19680
gcagattgtt aggttgattt ctgagtctaa gaagcctgtg ttgtatgttg gtggtggttg   19740
tttgaattct agcgatgaat tgggtaggtt tgttgagctt acggggatcc ctgttgcgag   19800
tacgttgatg gggctgggat cttatccttg tgatgatgag ttgtcgttac atatgcttgg   19860
aatgcatggg actgtgtatg caaattacgc tgtggagcat agtgatttgt tgttggcgtt   19920
tggggtaagg tttgatgatc gtgtcacggg taagcttgag gcttttgcta gtagggctaa   19980
gattgttcat attgatattg actcggctga gattgggaag aataagactc tcatgtgtc    20040 tgtgtgtggt gatgttaagc tggctttgca agggatgaat aaggttcttg agaaccgagc   20100
ggaggagctt aagcttgatt ttggagtttg gaggaatgag ttgaacgtac agaaacagaa   20160
gtttccgttg agctttaaga cgtttgggga agctattcct ccacagtatg cgattaaggt   20220
ccttgatgag ttgactgatg gaaaagccat aataagtact ggtgtcgggc aacatcaaat   20280
gtgggcggcg cagttctaca attacaagaa accaaggcag tggctatcat caggaggcct   20340
tggagctatg ggatttggac ttcctgctgc gattggagcg tctgttgcta accctgatgc   20400
gatagttgtg gatattgacg gagatggaag ctttataatg aatgtgcaag agctagccac   20460
tattcgtgta gagaatcttc cagtgaaggt acttttatta aacaaccagc atcttggcat   20520
ggttatgcaa tgggaagatc ggttctacaa agctaaccga gctcacacat ttctcgggga   20580
```

```
tccggctcag gaggacgaga tattcccgaa catgttgctg tttgcagcag cttgcgggat   20640
tccagcggcg agggtgacaa agaaagcaga tctccgagaa gctattcaga caatgctgga   20700
tacaccagga ccttacctgt tggatgtgat ttgtccgcac caagaacatg tgttgccgat   20760
gatcccgaat ggtggcactt tcaacgatgt cataacggaa ggagatggcc ggattaaata   20820
ctgataggga taacagggta atctcgacga gatgaaaccg gtgattatca gaacctttta   20880
tggtctttgt atgcatatgg taaaaaaact tagtttgcaa tttcctgttt gttttggtaa   20940
tttgagtttc ttttagttgt tgatctgcct gcttttttggt ttacgtcaga ctactactgc   21000
tgttgttgtt tggtttcctt tctttcattt tataaataaa taatccggtt cggtttactc   21060
cttgtgactg gctcagtttg gttattgcga aatgcgaatg gtaaattgag taattgaaat   21120
tcgttattag ggttctaagc tgttttaaca gtcactgggt taatatctct cgaatcttgc   21180
atggaaaatg ctcttaccat tggttttttaa ttgaaatgtg ctcatatggg ccgtggtttc   21240
caaattaaat aaaactacga tgtcatcgag aagtaaaatc aactgtgtcc acattatcag   21300
ttttgtgtat acgatgaaat agggtaattc aaaatctagc ttgatatgcc ttttggttca   21360
ttttaacctt ctgtaaacat tttttcagat tttgaacaag taaatccaaa aaaaaaaaaa   21420
aaaaatctca actcaacact aaattatttt aatgtataaa agatgcttaa aacatttggc   21480
ttaaaagaaa gaagctaaaa acatagagaa ctccttgtaaa ttgaagtatg aaaatatact   21540
gaattgggta ttatatgaat ttttctgatt taggattcac atgatccaaa aaggaaatcc   21600
agaagcacta atcagacatt ggaagtagga atatttcaaa aagttttttt tttttaagta   21660
agtgacaaaa gcttttaaaa aatagaaaag aaactagtat taaagttgta aatttaataa   21720
acaaagaaa ttttttatat tttttcattt ctttttccag catgaggtta tgatggcagg   21780
atgtggattt catttttttc cttttgatag ccttttaatt gatctattat aattgacgaa   21840
aaaatattag ttaattatag atatatttta ggtagtatta gcaatttaca cttccaaaag   21900
actatgtaag ttgtaaatat gatgcgttga tctcttcatc attcaatggt tagtcaaaaa   21960
aataaaagct taactagtaa actaaagtag tcaaaaattg tactttagtt taaaatatta   22020
catgaataat ccaaaacgac atttatgtga aacaaaaaca atatgtcgag gcgatcgcag   22080
tacttaatca gtgatcagta actaaattca gtacattaaa gacgtccgca atgtgttatt   22140
aagttgtcta agcgtcaatt tgtttacacc acaatatatc ctgccaccag ccagccaaca   22200
gctcccccgac cggcagctcg gcacaaaatc actgatcatc taaaaaggtg atgtgtattt   22260
gagtaaaaca gcttgcgtca tgcggtcgct gcgtatatga tgcgatgagt aaataaacaa   22320
atacgcaagg ggaacgcatg aaggttatcg ctgtacttaa ccagaaaggc gggtcaggca   22380
agacgaccat cgcaacccat ctagcccgcg ccctgcaact cgccggggcc gatgttctgt   22440
tagtcgattc cgatccccag ggcagtgccc gcgattgggc ggccgtgcgg gaagatcaac   22500
cgctaaccgt tgtcggcatc gaccgcccga cgattgaccg cgacgtgaag gccatcggcc   22560
ggcgcgactt cgtagtgatc gacggagcgc cccaggcggc ggacttggct gtgtccgcga   22620
tcaaggcagc cgacttcgtg ctgattccgg tgcagccaag cccttacgac atttgggcca   22680
ccgccgacct ggtggagctg gttaagcagc gcattgaggt cacggatgga aggctacaag   22740
cggcctttgt cgtgtcgcgg gcgatcaaag gcacgcgcat cggcggtgag gttgccgagg   22800
cgctggccgg gtacgagctg cccattcttg agtcccgtat cacgcagcgc gtgagctacc   22860
caggcactgc cgccgccggc acaaccgttc ttgaatcaga acccgagggc gacgctgccc   22920
```

```
gcgaggtcca ggcgctggcc gctgaaatta aatcaaaact catttgagtt aatgaggtaa    22980
agagaaaatg agcaaaagca caaacacgct aagtgccggc cgtccgagcg cacgcagcag    23040
caaggctgca acgttggcca gcctggcaga cacgccagcc atgaagcggg tcaactttca    23100
gttgccggcg gaggatcaca ccaagctgaa gatgtacgcg gtacgccaag gcaagaccat    23160
taccgagctg ctatctgaat acatcgcgca gctaccagag taaatgagca atgaataaa     23220 tgagtagata aattttagcg gctaaaggag gcggcatgga aaatcaagaa caaccaggca    23280
ccgacgccgt ggaatgcccc atgtgtggag gaacgggcgg ttggccaggc gtaagcggct    23340
gggttgtctg ccggccctgc aatggcactg gaacccccaa gcccgaggaa tcggcgtgag    23400
cggtcgcaaa ccatccggcc cggtacaaat cggcgcggcg ctgggtgatg acctggtgga    23460
gaagttgaag gccgcgcagg ccgcccagcg gcaacgcatc gaggcagaag cacgccccgg    23520
tgaatcgtgg caaggggccg ctgatcgaat ccgcaaagaa tcccggcaac cgccggcagc    23580
cggtgcgccg tcgattagga agccgcccaa gggcgacgag caaccagatt ttttcgttcc    23640
gatgctctat gacgtgggca cccgcgatag tcgcagcatc atggacgtgg ccgttttccg    23700
tctgtcgaag cgtgaccgac gagctggcga ggtgatccgc tacgagcttc cagacgggca    23760
cgtagaggtt tccgcaggcc ccgccggcat ggccagtgtg tgggattacg acctggtact    23820
gatggcggtt tcccatctaa ccgaatccat gaaccgatac cgggaaggga agggagacaa    23880
gcccggccgc gtgttccgtc cacacgttgc ggacgtactc aagttctgcc ggcgagccga    23940
tggcggaaag cagaaagacg acctggtaga aacctgcatt cggttaaaca ccacgcacgt    24000
tgccatgcag cgtaccaaga aggccaagaa cggccgcctg gtgacggtat ccgagggtga    24060
agccttgatt agccgctaca agatcgtaaa gagcgaaacc gggcggccgg agtacatcga    24120
gatcgagctt gctgattgga tgtaccgcga gatcacagaa ggcaagaacc cggacgtgct    24180
gacggttcac cccgattact tttgatcga ccccggcatc ggccgttttc tctaccgcct     24240
ggcacgccgc gccgcaggca aggcagaagc cagatggttg ttcaagacga tctacgaacg    24300
cagtggcagc gccggagagt tcaagaagtt ctgtttcacc gtgcgcaagc tgatcgggtc    24360
aaatgacctg ccggagtacg atttgaagga ggaggcgggg caggctggcc cgatcctagt    24420
catgcgctac cgcaacctga tcgagggcga agcatccgcc ggttcctaat gtacggagca    24480
gatgctaggg caaattgccc tagcagggga aaaaggtcga aaaggtctct ttcctgtgga    24540
tagcacgtac attgggaacc caaagccgta cattgggaac cggaacccgt acattgggaa    24600
cccaaagccg tacattggga accggtcaca catgtaagtg actgatataa aagagaaaaa    24660
aggcgatttt tccgcctaaa actctttaaa acttattaaa actcttaaaa cccgcctggc    24720
ctgtgcataa ctgtctggcc agcgcacagc cgaagagctg caaaaagcgc ctaccctcg    24780 gtcgctgcgc tccctacgcc ccgccgcttc gcgtcggcct atcgcggcct atgcggtgtg    24840
aaataccgca cagatgcgta aggagaaaat accgcatcag gcgctcttcc gcttcctcgc    24900
tcactgactc gctgcgctcg tcgttcggc tgcggcgagc ggtatcagct cactcaaagg     24960
cggtaatacg gttatccaca gaatcagggg ataacgcagg aaagaacatg tgagcaaaag    25020
gccagcaaaa ggccaggaac cgtaaaaagg ccgcgttgct ggcgtttttc cataggctcc    25080
gcccccctga cgagcatcac aaaaatcgac gctcaagtca gaggtggcga aacccgacag    25140
gactataaag ataccaggcg tttccccctg gaagctccct cgtgcgctct cctgttccga    25200
ccctgccgct taccggatac ctgtccgcct ttctcccttc gggaagcgtg gcgctttctc    25260
atagctcacg ctgtaggtat ctcagttcgg tgtaggtcgt tcgctccaag ctgggctgtg    25320
```

```
tgcacgaacc cccgttcag cccgaccgct gcgccttatc cggtaactat cgtcttgagt   25380
ccaacccggt aagacacgac ttatcgccac tggcagcagc cactggtaac aggattagca   25440
gagcgaggta tgtaggcggt gctacagagt tcttgaagtg gtggcctaac tacggctaca   25500
ctagaaggac agtatttggt atctgcgctc tgctgaagcc agttaccttc ggaaaaagag   25560
ttggtagctc ttgatccggc aaacaaacca ccgctggtag cggtggtttt tttgtttgca   25620
agcagcagat tacgcgcaga aaaaaaggat ctcaagaaga tcctttgatc ttttctacgg   25680
ggtccttcaa ctcatcgata gtttggctgt gagcaattat gtgcttagtg catctaacgc   25740
ttgagttaag ccgcgccgcg aagcggcgtc ggcttgaacg aatttctagc tagacattat   25800
ttgccaacga ccttcgtgat ctcgcccttg acatagtgga caaattcttc gagctggtcg   25860
gcccgggacg cgagacggtc ttcttcttgg cccagatagg cttggcgcgc ttcgaggatc   25920
acgggctggt attgcgccgg aaggcgctcc atcgcccagt cggcggcgac atccttcggc   25980
gcgatcttgc cggtaaccgc cgagtaccaa atccggctca gcgtaaggac acattgcgc   26040 tcatcgcccg cccaatccgg cggggagttc cacagggtca gcgtctcgtt cagtgcttcg   26100
aacagatcct gttccggcac cgggtcgaaa agttcctcgg ccgcggggcc gacgagggcc   26160
acgctatgct cccgggcctt ggtgagcagg atcgccagat caatgtcgat ggtggccggt   26220
tcaaagatac ccgccagaat atcattacgc tgccattcgc cgaactggag ttcgcgtttg   26280
gccggatagc gccaggggat gatgtcatcg tgcaccacaa tcgtcacctc aaccgcgcgc   26340
aggatttcgc tctcgccggg ggaggcggac gtttccagaa ggtcgttgat aagcgcgcgg   26400
cgcgtggtct cgtcgagacg gacggtaacg gtgacaagca ggtcgatgtc cgaatggggc   26460
ttaaggccgc cgtcaacggc gctaccatac agatgcacgg cgaggagggt cggttcgagg   26520
tggcgctcga tgacacccac gacttccgac agctgggtgg cacctcggc gatgaccgct   26580 tcacccatga tgtttaactt tgttttaggg cgactgccct gctgcgtaac atcgttgctg   26640
ctccataaca tcaaacatcg acccacggcg taacgcgctt gctgcttgga tgcccgaggc   26700
atagactgta ccccaaaaaa acagtcataa caagccatga aaaccgccac tgcgttccat   26760
gaatattcaa acaaacacat acagcgcgac ttatcatgga ta                     26802
```

<210> SEQ ID NO 147
<211> LENGTH: 2254
<212> TYPE: DNA
<213> ORGANISM: Artificial Sequence
<220> FEATURE:
<223> OTHER INFORMATION: p-VfSBP-NEENAss2 expression element

<400> SEQUENCE: 147

```
tcgacggccc ggactgtatc caacttctga tctttgaatc tctctgttcc aacatgttct      60
gaaggagttc taagactttt cagaaagctt gtaacatgct ttgtagactt tctttgaatt     120
actcttgcaa actctgattg aacctacgtg aaaactgctc cagaagttct aaccaaattc     180
cgtcttggga aggcccaaaa tttattgagt acttcagttt catggacgtg tcttcaaaga     240
tttataactt gaaatcccat cattttttaag agaagttctg ttccgcaatg tcttagatct     300
cattgaaatc tacaactctt gtgtcagaag ttcttccaga atcaacttgc atcatggtga     360
aaatctggcc agaagttctg aacttgtcat atttcttaac agttagaaaa atttctaagt     420
gtttagaatt ttgacttttc caaagcaaac ttgacttttg actttcttaa taaacaaac      480 ttcatattct aacatgtctt gatgaaatgt gattcttgaa atttgatgtt gatgcaaaag     540
```

```
tcaaagtttg acttttcagt gtgcaattga ccattttgct cttgtgccaa ttccaaacct      600
aaattgatgt atcagtgctg caaacttgat gtcatggaag atcttatgag aaaattcttg      660
aagactgaga ggaaaaattt tgtagtacaa cacaaagaat cctgttttc atagtcggac       720 tagacacatt aacataaaac accacttcat tcgaagagtg attgaagaag gaatgtgca       780 gttacctttc tgcagttcat aagagcaact tacagacact tttactaaaa tactacaaag      840
aggaagattt taacaactta gagaagtaat gggagttaaa gagcaacaca ttaaggggga      900
gtgttaaaat taatgtgttg taaccaccac tacctttagt aagtattata agaaaattgt      960
aatcatcaca ttataattat tgtccttatt taaaattatg ataaagttgt atcattaaga    1020
ttgagaaaac caaatagtcc tcgtcttgat ttttgaatta ttgttttcta tgttacttt     1080 cttcaagcct atataaaaac tttgtaatgc taaattgtat gctggaaaaa aatgtgtaat    1140
gaattgaata gaaattatgg tatttcaaag tccaaaatcc atcaatagaa atttagtaca    1200
aaacgtaact caaaaatatt ctcttatttt aaattttaca acaatataaa aatattctct    1260
tattttaaat tttacaataa tataatttat cacctgtcac ctttagaata ccaccaacaa    1320
tattaatact tagatatttt attcttaata attttgagat ctctcaatat atctgatatt    1380
tattttatat ttgtgtcata ttttcttatg ttttagagtt aacccttata tcttggtcaa    1440
actagtaatt caatatatga gtttgtgaag gacacattga catcttgaaa cattggtttt    1500
aaccttgttg gaatgttaaa ggtaataaaa cattcagaat tatgaccatc tattaatata    1560
cttcctttgt cttttaaaaa agtgtgcatg aaaatgctct atggtaagct agagtgtctt    1620
gctggcctgt gtatatcaat tccatttcca gatggtagaa actgccacta cgaataatta    1680
gtcataagac acgtatgtta acacacgtcc ccttgcatgt tttttgccat atattccgtc    1740
tctttctttt tcttcacgta taaaacaatg aactaattaa tagagcgatc aagctgaaca    1800
gttctttgct ttcgaagttg ccgcaaccta acaggttttt tccttcttct ttcttcttat    1860
taactacgac cttgtccttt gcctatgtaa aattactagg ttttcatcag ttacactgat    1920
taagttcgtt atagtggaag ataaaatgcc ctcaaagcat tttgcaggat atctttgatt    1980
tttcaaagat atggaactgt agagtttgat agtgttcttg aatgtggttg catgaagttt    2040
ttttggtctg catgttattt tttcctcgaa atatgttttg agtccaacaa gtgattcact    2100
tgggattcag aaagttgttt tctcaatatg taacagtttt tttctatgga gaaaaatcat    2160
agggaccgtt ggttttggct tctttaattt tgagctcaga ttaaacccat tttacccggt    2220
gttcttggca gaattgaaaa cagtacgtag tacc                                  2254
```

<210> SEQ ID NO 148
<211> LENGTH: 2568
<212> TYPE: DNA
<213> ORGANISM: Artificial Sequence
<220> FEATURE:
<223> OTHER INFORMATION: p-LuPxr-NEENAss1 expression element

<400> SEQUENCE: 148

```
cacgggcagg acatagggac tactacaagc atagtatgct tcagacaaag agctaggaaa       60
gaactcttga tggaggttaa gagaaaaaag tgctagaggg gcatagtaat caaacttgtc      120
aaaaccgtca tcatgatgag ggatgacata atataaaaag ttgactaagg tcttggtagt      180
actctttgat tagtattata tattggtgag aacatgagtc aagaggagac aagaaaccga      240
ggaaccatag tttagcaaca agatggaagt tgcaaagttg agctagccgc tcgattagtt      300
acatctccta agcagtacta caaggaatgg tctctatact ttcatgttta gcacatggta      360
```

```
gtgcggattg acaagttaga aacagtgctt aggagacaaa gagtcagtaa aggtattgaa      420
agagtgaagt tgatgctcga caggtcagga gaagtccctc cgccagatgg tgactaccaa      480
ggggttggta tcagctgaga cccaaataag attcttcggt tgaaccagtg gttcgaccga      540
gactcttagg gtgggatttc actgtaagat ttgtgcattt tgttgaatat aaattgacaa      600 tttttttttat ttaattatag attatttaga atgaattaca tatttagttt ctaacaagga    660
tagcaatgga tgggtatggg tacaggttaa acatatctat tacccaccca tctagtcgtc     720
gggttttaca cgtacccacc cgtttacata aaccagaccg gaattttaaa ccgtacccgt     780
ccgttagcgg gtttcagatt tacccgttta atcgggtaaa acctgattac taaatatata     840 tttttttattt gataaacaaa acaaaaatgt taatattttc atattggatg caattttaag    900
aaacacatat tcataaattt ccatatttgt aggaaaataa aaagaaaaat atattcaaga     960
acacaaattt caccgacatg acttttatta cagagttgga attagatcta acaattgaaa    1020
aattaaaatt aagatagaat atgttgagga acatgacata gtataatgct gggttacccg    1080
tcgggtaggt atcgaggcgg atactactaa atccatccca ctcgctatcc gataatcact    1140
ggtttcgggt atacccattc ccgtcaacag gccttttttaa ccggataatt tcaacttata   1200
gtgaatgaat tttgaataaa tagttagaat accaaaatcc tggattgcat ttgcaatcaa    1260
attttgtgaa ccgttaaatt ttgcatgtac ttgggataga tataatagaa ccgaattttc    1320
attagtttaa tttataactt actttgttca agaaaaaaaa atatctatcc aatttactta    1380
taataaaaaa taatctatcc aagttactta ttataatcaa cttgtaaaaa ggtaagaata    1440
caaatgtggt agcgtacgtg tgattatatg tgacgaaatg ttatatctaa caaaagtcca    1500
aattcccatg gtaaaaaaaa tcaaaatgca tggcaggctg tttgtaacct tggaataaga    1560
tgttggccaa ttctggagcc gccacgtacg caagactcag ggccacgttc tcttcatgca    1620
aggatagtag aacaccactc cacccacctc ctatattaga cctttgccca accctcccca    1680
actttcccat cccatccaca aagaaaccga cattttttatc ataaatctgg tgcttaaaca    1740
ctctggtgag ttctagtact tctgctatga tcgatctcat taccatttct taaatttctc    1800 tccctaaaata ttccgagttc ttgattttttg ataacttcag gttttctctt tttgataaat   1860
ctggtctttc catttttttt tttttgtggt taatttagtt tcctatgttc ttcgattgta    1920
ttatgcatga tctgtgtttg gattctgtta gattatgtat tggtgaatat gtatgtgttt    1980
ttgcatgtct ggttttggtc ttaaaaatgt tcaaatctga tgatttgatt gaagcttttt    2040
tagtgttggt ttgattcttc tcaaaactac tgttaatttta ctatcatgtt ttccaactttt   2100 gattcatgat gacacttttg ttctgctttg ttataaaatt tggttggtt tgattttgta    2160 attatagtgt aatttttgtta ggaatgaaca tgttttaata ctctgttttc gatttgtcac   2220
acattcgaat tattaatcga taatttaact gaaaattcat ggttctagat cttgttgtca    2280
tcagattatt tgtttcgata attcatcaaa tatgtagtcc ttttgctgat ttgcgactgt    2340
ttcatttttt ctcaaaattg tttttttgtta agtttatcta acagttatcg ttgtcaaaag    2400
tctctttcat tttgcaaaat cttcttttttt ttttgtttg taactttgtt ttttaagcta    2460
cacatttagt ctgtaaaata gcatcgagga acagttgtct tagtagactt gcatgttctt    2520
gtaacttcta tttgtttcag tttgttgatg actgctttga ttttgtag               2568
```

<210> SEQ ID NO 149
<211> LENGTH: 1041
<212> TYPE: DNA

```
<213> ORGANISM: Artificial Sequence
<220> FEATURE:
<223> OTHER INFORMATION: p-BnNapin-NEENAss14 expression element

<400> SEQUENCE: 149
taaggatgac ctacccattc ttgagacaaa tgttacattt tagtatcaga gtaaaatgtg      60
tacctataac tcaaattcga ttgacatgta tccattcaac ataaaattaa accagcctgc     120
acctgcatcc acatttcaag tattttcaaa ccgttcggct cctatccacc gggtgtaaca     180
agacggattc cgaatttgga agattttgac tcaaattccc aatttatatt gaccgtgact     240
aaatcaactt taacttctat aattctgatt aagctcccaa tttatattcc caacggcact     300
acctccaaaa tttatagact ctcatcccct tttaaaccaa cttagtaaac gtttttttt      360
taattttatg aagttaagtt tttaccttgt ttttaaaaag aatcgttcat aagatgccat     420
gccagaacat tagctacacg ttacacatag catgcagccg cggagaattg tttttcttcg     480
ccacttgtca ctcccttcaa acacctaaga gcttctctct cacagcacac acatacaatc     540
acatgcgtgc atgcattatt acacgtgatc gccatgcaaa tctcctttat agcctataaa     600
ttaactcatc ggcttcactc tttactcaaa ccaaaactca tcaatacaaa caagattaaa     660
aacatttcac gatttggaat tgattcctg cgatcacagg tatgacaggt tagattttgt      720
tttgtatagt tgtatacata cttctttgtg atgttttgtt tacttaatcg aattttgga      780
gtgttttaag gtctctcgtt tagaaatcgt ggaaaatatc actgtgtgtg tgttcttatg     840
attcacagtg tttatgggtt tcatgttctt tgttttatca ttgaatggga agaaatttcg     900
ttgggataca aatttctcat gttcttactg atcgttatta ggagtttggg gaaaaaggaa     960
gagtttttt ggttggttcg agtgattatg aggttatttc tgtatttgat ttatgagtta    1020
atggtcgttt taatgttgta g                                              1041

<210> SEQ ID NO 150
<211> LENGTH: 46
<212> TYPE: DNA
<213> ORGANISM: Artificial Sequence
<220> FEATURE:
<223> OTHER INFORMATION: Primer

<400> SEQUENCE: 150
gcaacttcga aagcaaagaa ctgttcagct tgatcgctct attaat                    46

<210> SEQ ID NO 151
<211> LENGTH: 46
<212> TYPE: DNA
<213> ORGANISM: Artificial Sequence
<220> FEATURE:
<223> OTHER INFORMATION: Primer

<400> SEQUENCE: 151
attaatagag cgatcaagct gaacagttct ttgctttcga agttgc                    46

<210> SEQ ID NO 152
<211> LENGTH: 48
<212> TYPE: DNA
<213> ORGANISM: Artificial Sequence
<220> FEATURE:
<223> OTHER INFORMATION: Primer

<400> SEQUENCE: 152
actcaccaga gtgtttaagc accagattta tgataaaaat gtcggttt                  48
```

```
<210> SEQ ID NO 153
<211> LENGTH: 48
<212> TYPE: DNA
<213> ORGANISM: Artificial Sequence
<220> FEATURE:
<223> OTHER INFORMATION: Primer

<400> SEQUENCE: 153
aaaccgacat ttttatcata aatctggtgc ttaaacactc tggtgagt                 48

<210> SEQ ID NO 154
<211> LENGTH: 44
<212> TYPE: DNA
<213> ORGANISM: Artificial Sequence
<220> FEATURE:
<223> OTHER INFORMATION: Primer

<400> SEQUENCE: 154
tcaaattcca aatcgtgaaa tgtttttaat cttgtttgta ttga                     44

<210> SEQ ID NO 155
<211> LENGTH: 44
<212> TYPE: DNA
<213> ORGANISM: Artificial Sequence
<220> FEATURE:
<223> OTHER INFORMATION: Primer

<400> SEQUENCE: 155
tcaatacaaa caagattaaa aacatttcac gatttggaat ttga                     44
```

REGULATORY NUCLEIC ACID MOLECULES FOR ENHANCING SEED-SPECIFIC GENE EXPRESSION IN PLANTS PROMOTING ENHANCED POLYUNSATURATED FATTY ACID SYNTHESIS

RELATED APPLICATIONS

This application is a national stage application (under 35 U.S.C. §371) of PCT/EP2010/062561, filed Aug. 27, 2010 which claims benefit of U.S. Provisional Application No. 61/238,254, filed Aug. 31, 2009 and European Application No. 09169079.2, filed Aug. 31, 2009.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Revised_Sequence_List_13987_00173_US. The size of the text file is 318 KB and the text file was created on Mar. 23, 2012.

The invention in principle pertains to the field of recombinant manufacture of fatty acids. It provides novel nucleic acid molecules comprising nucleic acid sequences encoding fatty acid desaturases, elongases, acyltransferases, terminator sequences and high expressing seed-specific promoters operatively linked to the said nucleic acid sequences wherein nucleic acid expression enhancing nucleic acids (NEENAs) are functionally linked to said promoters.

The invention also provides recombinant expression vectors containing the nucleic acid molecules, host cells or host cell cultures into which the expression vectors have been introduced, and methods for large-scale production of long chain polyunsaturated fatty acids (LCPUFAs), e.g. arachidonic acid (ARA), eicosapentaenoic acid (EPA) or docosahexaenoic acid (DHA).

DESCRIPTION OF THE INVENTION

Expression of transgenes in plants is strongly affected by various external and internal factors resulting in a variable and unpredictable level of transgene expression. Often a high number of transformants have to be produced and analyzed in order to identify lines with desirable expression strength. As transformation and screening for lines with desirable expression strength is costly and labor intensive there is a need for high expression of one or more transgenes in a plant. This problem is especially pronounced, when several genes have to be coordinately expressed in a transgenic plant in order to achieve a specific effect as a plant has to be identified in which each and every gene is strongly expressed.

For example, expression of a transgene can vary significantly, depending on construct design and positional effects of the T-DNA insertion locus in individual transformation events. Strong promoters can partially overcome these challenges. However, availability of suitable promoters showing strong expression with the desired specificity is often limited. In order to ensure availability of sufficient promoters with desired expression specificity, the identification and characterization of additional promoters can help to close this gap. However, natural availability of promoters of the respective specificity and strength and the time consuming characterization of promoter candidates impedes the identification of suitable new promoters.

In order to overcome these challenges, diverse genetic elements and/or motifs have been shown to positively affect gene expression. Among these, some introns have been recognized as genetic elements with a strong potential for improving gene expression. Although the mechanism is largely unknown, it has been shown that some introns positively affect the steady state amount of mature mRNA, possibly by enhanced transcriptional activity, improved mRNA maturation, enhanced nuclear mRNA export and/or improved translation initiation (e.g. Huang and Gorman, 1990; Le Hir et al., 2003; Nott et al., 2004). Since only selected introns were shown to increase expression, splicing as such is likely not accountable for the observed effects.

The increase of gene expression observed upon functionally linking introns to promoters is called intron mediated enhancement (IME) of gene expression and has been shown in various monocotyledonous (e.g. Callis et al., 1987; Vasil et al., 1989; Bruce et al., 1990; Lu et al., 2008) and dicotyledonous plants (e.g. Chung et al., 2006; Kim et al., 2006; Rose et al., 2008). In this respect, the position of the intron in relation to the translational start site (ATG) was shown to be crucial for intron mediated enhancement of gene expression (Rose et al., 2004).

Next to their potential for enhancing gene expression, few introns were shown to also affect the tissue specificity in their native nucleotide environment in plants. Reporter gene expression was found to be dependent on the presence of genomic regions containing up to two introns (Sieburth et al., 1997; Wang et al., 2004). 5' UTR introns have also been reported to be of importance for proper functionality of promoter elements, likely due to tissue specific gene control elements residing in the introns (Fu et al., 1995a; Fu et al., 1995b; Vitale et al., 2003; Kim et al., 2006). However, these studies also show that combination of introns with heterologous promoters can have strong negative impacts on strength and/or specificity of gene expression (Vitale et al., 2003; Kim et al., 2006, WO2006/003186, WO2007/098042). For example the strong constitutive Cauliflower Mosaic Virus CaMV35S promoter is negatively affected through combination with the sesame SeFAD2 5' UTR intron (Kim et al., 2006). In contrast to these observations, some documents show enhanced expression of a nucleic acid by IME without affecting the tissue specificity of the respective promoter (Schünemann et al., 2004). Introns or NEENAs that enhance seed-specific expression when functionally linked to a heterologous promoter have not been shown in the art.

In the present application further nucleic acid molecules are described that enhance the expression of said promoters without affecting their specificity upon functionally linkage to seed-specific promoters. These nucleic acid molecules are in the present application described as "nucleic acid expression enhancing nucleic acids" (NEENA). Introns have the intrinsic feature to be spliced out of the respective pre-mRNA. In contrast to that the nucleic acids presented in the application at hand, do not necessarily have to be included in the mRNA or, if present in the mRNA, have not necessarily to be spliced out of the mRNA in order to enhance the expression derived from the promoter the NEENAs are functionally linked to.

DETAILED DESCRIPTION OF THE INVENTION

A first embodiment of the invention pertains to a polynucleotide that promotes enhancing of polyunsaturated fatty acid synthesis, therefore it pertains in generally in the recombinant manufacture of polyunsaturated fatty acids.

Fatty acids are carboxylic acids with long-chain hydrocarbon side groups that play a fundamental role in many biological processes. Fatty acids are rarely found free in nature but, rather, occur in esterified form as the major component of lipids. As such, lipids/fatty acids are sources of energy (e.g., b-oxidation). In addition, lipids/fatty acids are an integral part of cell membranes and, therefore, are indispensable for processing biological or biochemical information.

Fatty acids can be divided into two groups: saturated fatty acids formed of single carbon bonds and the unsaturated fatty acids which contain one or more carbon double bonds in cis-configuration. Unsaturated fatty acids are produced by terminal desaturases that belong to the class of nonheme-iron enzymes. Each of these enzymes are part of an electron-transport system that involves one or two other proteins, namely cytochrome $b_5$ and NADH-cytochrome $b_5$ reductase. The cytochrome b5 functionality can also be n-terminally fused to the desaturase moiety of one single protein. Specifically, such enzymes catalyze the formation of double bonds between the carbon atoms of a fatty acid molecule, for example, by catalyzing the oxygen-dependent dehydrogenation of fatty acids (Sperling et al., 2003). Human and other mammals have a limited spectrum of desaturases that are required for the formation of particular double bonds in unsaturated fatty acids and thus, have a limited capacity for synthesizing essential fatty acids, e.g., long chain polyunsaturated fatty acids (LCPUFAs). Thus, humans have to take up some fatty acids through their diet. Such essential fatty acids include, for example, linoleic acid (C18:2), linolenic acid (C18:3). In contrast, insects, microorganisms and plants are able to synthesize a much larger variety of unsaturated fatty acids and their derivatives. Indeed, the biosynthesis of fatty acids is a major activity of plants and microorganisms.

Long chain polyunsaturated fatty acids (LCPUFAs) such as docosahexaenoic acid (DHA, 22:6(4,7,10,13,16,19)) are essential components of cell membranes of various tissues and organelles in mammals (nerve, retina, brain and immune cells). For example, over 30% of fatty acids in brain phospholipid are 22:6 (n-3) and 20:4 (n-6) (Crawford, M. A., et al., (1997) Am. J. Clin. Nutr. 66:1032 S-1041S). In retina, DHA accounts for more than 60% of the total fatty acids in the rod outer segment, the photosensitive part of the photoreceptor cell (Giusto, N. M., et al. (2000) Prog. Lipid Res. 39:315-391). Clinical studies have shown that DHA is essential for the growth and development of the brain in infants, and for maintenance of normal brain function in adults (Martinetz, M. (1992) J. Pediatr. 120:S129-S138). DHA also has significant effects on photoreceptor function involved in the signal transduction process, rhodopsin activation, and rod and cone development (Giusto, N. M., et al. (2000) Prog. Lipid Res. 39:315-391). In addition, some positive effects of DHA were also found on diseases such as hypertension, arthritis, atherosclerosis, depression, thrombosis and cancers (Horrocks, L. A. and Yeo, Y. K. (1999) Pharmacol. Res. 40:211-215). Therefore, appropriate dietary supply of the fatty acid is important for human health. Because such fatty acids cannot be efficiently synthesized by infants, young children and senior citizens, it is particularly important for these individuals to adequately intake these fatty acids from the diet (Spector, A. A. (1999) Lipids 34:S1-S3).

Currently the major sources of DHA are oils from fish and algae. Fish oil is a major and traditional source for this fatty acid, however, it is usually oxidized by the time it is sold. In addition, the supply of fish oil is highly variable, particularly in view of the shrinking fish populations. Moreover, the algal source of oil is expensive due to low yield and the high costs of extraction.

EPA and ARA are both Δ5 essential fatty acids. They form a unique class of food and feed constituents for humans and animals. EPA belongs to the n-3 series with five double bonds in the acyl chain. EPA is found in marine food and is abundant in oily fish from North Atlantic. ARA belongs to the n-6 series with four double bonds. The lack of a double bond in the ω-3 position confers on ARA different properties than those found in EPA. The eicosanoids produced from ARA have strong inflammatory and platelet aggregating properties, whereas those derived from EPA have anti-inflammatory and anti-platelet aggregating properties. ARA can be obtained from some foods such as meat, fish and eggs, but the concentration is low.

Gamma-linolenic acid (GLA) is another essential fatty acid found in mammals. GLA is the metabolic intermediate for very long chain n-6 fatty acids and for various active molecules. In mammals, formation of long chain polyunsaturated fatty acids is rate-limited by Δ6 desaturation. Many physiological and pathological conditions such as aging, stress, diabetes, eczema, and some infections have been shown to depress the Δ6 desaturation step. In addition, GLA is readily catabolized by the oxidation and rapid cell division associated with certain disorders, e.g., cancer or inflammation. Therefore, dietary supplementation with GLA can reduce the risks of these disorders. Clinical studies have shown that dietary supplementation with GLA is effective in treating some pathological conditions such as atopic eczema, premenstrual syndrome, diabetes, hypercholesterolemia, and inflammatory and cardiovascular disorders.

A large number of beneficial health effects have been shown for DHA or mixtures of EPA/DHA. DHA is a n-3 very long chain fatty acid with six double bonds.

Although biotechnology offers an attractive route for the production of specialty fatty acids, current techniques fail to provide an efficient means for the large scale production of unsaturated fatty acids. Accordingly, there exists a need for an improved and efficient method of producing unsaturated fatty acids, such as DHA, EPA and ARA.

Thus, the present invention relates to a polynucleotide comprising:
 a) at least one nucleic acid sequence encoding a polypeptide having desaturase or elongase activity;
 b) at least one seed-specific and/or a seed-preferential plant promoter operatively linked to the said nucleic acid sequence;
 c) at least one terminator sequence operatively linked to the said nucleic acid sequence and
 d) one or more nucleic acid expression enhancing nucleic acid (NEENA) molecule functionally linked to said promoter and which is/are heterologous to said promoter and to said polypeptide defined in a).

In one embodiment the term "polynucleotide" as used in accordance with the present invention relates to a polynucleotide comprising a nucleic acid sequence which encodes a polypeptide having desaturase or elongase activity. Preferably, the polypeptide encoded by the polynucleotide of the present invention having desaturase, or elongase activity upon expression in a plant shall be capable of increasing the amount of PUFA and, in particular, LCPUFA in, e.g., seed oils or the entire plant or parts thereof. Such an increase is, preferably, statistically significant when compared to a LCPUFA producing transgenic control plant which expresses the present state of the art set of desaturases and elongases required for LCPUFA synthesis but does not express the polynucleotide of the present invention. Whether an increase is significant can be determined by statistical tests well known in the art including, e.g., Student's t-test. More preferably, the increase is an increase of the amount of triglycerides containing LCPUFA of at least 5%, at least 10%, at least 15%, at least 20% or at least 30% compared to the said control. Preferably, the LCPUFA referred to before is a polyunsaturated fatty acid having a C-20 or C-22 fatty acid body, more preferably, ARA, EPA or DHA. Suitable assays for measuring the activities mentioned before are described in the accompanying Examples.

The term "desaturase" or "elongase" as used herein refers to the activity of a desaturase, introducing a double bond into the carbon chain of a fatty acid, preferably into fatty acids with 18, 20 or 22 carbon molecules, or an elongase, introducing two carbon molecules into the carbon chain of a fatty acid, preferably into fatty acids with 18, 20 or 22 carbon molecules Preferred polynucleotides are those having a nucleic acid sequence as shown in SEQ ID NOs: 95, 96, 97, 98, 99, 100 or 101 encoding for polypeptides exhibit desaturase or elongase activity (see table 3)

Other preferred polynucleotides are those having a nucleic acid sequence as shown in SEQ ID NOs: 102 or 103 encoding a polypeptide having desaturase or elongase activity (see table 4, also), that are especially used in addition to the polynucleotides listed in table 3 for synthesis of 22:6n-3 (DHA), i.e. in rapeseed.

A preferred seed-specific promoter as meant herein is selected from the group consisting of Napin, USP, Conlinin, SBP, Fae, Arc and LuPXR. Other most preferred seed-specific promoter as meant herein are encoded by a nucleic acid sequence as shown in SEQ ID NOs: 25, 26, 27, 28, 29 or 30. A person skilled in the art is aware of methods for rendering a unidirectional to a bidirectional promoter and of methods to use the complement or reverse complement of a promoter sequence for creating a promoter having the same promoter specificity as the original sequence. Such methods are for example described for constitutive as well as inducible promoters by Xie et al. (2001) "Bidirectionalization of polar promoters in plants" (Nature Biotechnology 19, pages 677-679). The authors describe that it is sufficient to add a minimal promoter to the 5' prime end of any given promoter to receive a promoter controlling expression in both directions with same promoter specificity.

The term "NEENA" as described below is used for the expression "nucleic acid expression enhancing nucleic acid" referring to a sequence and/or a nucleic acid molecule of a specific sequence having the intrinsic property to enhance expression of a nucleic acid under the control of a promoter to which the NEENA is functionally linked. Hence a high expression promoter functionally linked to a NEENA as claimed is functional in complement or reverse complement and therefore the NEENA is functional in complement or reverse complement too.

In principal the NEENA may be functionally linked to any promoter such as tissue specific, inducible, developmental specific or constitutive promoters. The respective NEENA will lead to an enhanced seed-specific expression of the heterologous nucleic acid under the control of the respective promoter to which the one or more NEENA is functionally linked to. The enhancement of expression of promoters other than seed-specific promoters, for example constitutive promoters or promoters with differing tissue specificity, will influence the specificity of these promoters. Expression of the nucleic acid under control of the respective promoter will be significantly increased in seeds, where the transcript of said nucleic acid may have not or only weakly been detected without the NEENA functionally linked to its promoter. Hence, tissue- or developmental specific or any other promoter may be rendered to seed-specific promoters by functionally linking one or more of the NEENA molecules as described above to said promoter. Preferred NEENAs as for the present invention are encoded by the sequences shown in SEQ ID NOs: 11, 12, 13, 14, 15, 16, 17, 18, 19, 10, 21, 22, 23 or 24. More preferred NEENAs as for the present invention are encoded by the sequences shown in SEQ ID NOs: 6, 7, 8, 9 or 10. Also (i) nucleic acid molecule having a sequence with an identity of 80% or more to any of the sequences as defined by SEQ ID NO: 6 to 24, preferably, the identity is 85% or more, more preferably the identity is 90% or more, even more preferably, the identity is 95% or more, 96% or more, 97% or more, 98% or more or 99% or more, in the most preferred embodiment, the identity is 100% to any of the sequences as defined by SEQ ID NO: 6 to 24 or (ii) a fragment of 100 bases or more consecutive bases, preferably 150 or more consecutive bases, more preferably 200 consecutive bases or more even more preferably 250 or more consecutive bases of a nucleic acid molecule of i) or ii) which has an expressing enhancing activity, for example 65% or more, preferably 70% or more, more preferably 75% or more, even more preferably 80% or more, 85% or more or 90% or more, in a most preferred embodiment it has 95% or more of the expression enhancing activity as the corresponding nucleic acid molecule having the sequence of any of the sequences as defined by SEQ ID NO: 6 to 24, or iii) a nucleic acid molecule which is the complement or reverse complement of any of the previously mentioned nucleic acid molecules under i) to ii) or iv) a nucleic acid molecule which is obtainable by PCR using oligonucleotide primers as shown in Table 6 or v) a nucleic acid molecule of 100 nucleotides or more, 150 nucleotides or more, 200 nucleotides or more or 250 nucleotides or more, hybridizing under conditions equivalent to hybridization in 7% sodium dodecyl sulfate (SDS), 0.5 M NaPO4, 1 mM EDTA at 50° C. with washing in 2×SSC, 0.1% SDS at 50° C. or 65° C., preferably 65° C. to a nucleic acid molecule comprising at least 50, preferably at least 100, more preferably at least 150, even more preferably at least 200, most preferably at least 250 consecutive nucleotides of a transcription enhancing nucleotide sequence described by SEQ ID NO: 6 to 24 or the complement thereof are encompassed by the present invention. Preferably, said nucleic acid molecule is hybridizing under conditions equivalent to hybridization in 7% sodium dodecyl sulfate (SDS), 0.5 M NaPO4, 1 mM EDTA at 50° C. with washing in 1×SSC, 0.1% SDS at 50° C. or 65° C., preferably 65° C. to a nucleic acid molecule comprising at least 50, preferably at least 100, more preferably at least 150, even more preferably at least 200, most preferably at least 250 consecutive nucleotides of a transcription enhancing nucleotide sequence described by SEQ ID NO: 6 to 24 or the complement thereof, more preferably, said nucleic acid molecule is hybridizing under conditions equivalent to hybridization in 7% sodium dodecyl sulfate (SDS), 0.5 M NaPO4, 1 mM EDTA at 50° C. with washing in 0.1×SSC, 0.1% SDS at 50° C. or 65° C., preferably 65° C. to a nucleic acid molecule comprising at least 50, preferably at least 100, more preferably at least 150, even more preferably at least 200, most preferably at least 250 consecutive nucleotides of a transcription enhancing nucleotide sequence described by any of the sequences as defined by SEQ ID NO:1 to 15 or the complement thereof.

As described above under iv) the nucleic acid molecule obtainable by PCR using oligonucleotides shown in table 6 is obtainable for example from genomic DNA from *Arabidopsis* plants such as *A. thaliana* using the conditions as described in Example 3.2 below.

Preferably, the one or more NEENA is functionally linked to seed-specific promoters and will enhance expression of the nucleic acid molecule under control of said promoter. Seed-specific promoters to be used in any method of the invention may be derived from plants, for example monocotyledonous or dicotyledonous plants, from bacteria and/or viruses or may be synthetic promoters. Seed specific promoters to be used functionally linked to a NEENA are in a preferred embodiment the seed-specific promoter linked to NEENAs shown in SEQ ID NOs: 1, 2, 3, 4 or 5, table 5.

The high expression seed-specific promoters functionally linked to a NEENA may be employed in any plant comprising for example moss, fern, gymnosperm or angiosperm, for example monocotyledonous or dicotyledonous plant. In a preferred embodiment said promoter of the invention functionally linked to a NEENA may be employed in monocotyledonous or dicotyledonous plants, preferably crop plant such as corn, soy, canola, cotton, potato, sugar beet, rice, wheat, *sorghum*, barley, *musa*, sugarcane, miscanthus and the like. In a preferred embodiment of the invention, said promoter which is functionally linked to a NEENA may be employed in monocotyledonous crop plants such as corn, rice, wheat, *sorghum*, barley, *musa*, miscanthus or sugarcane. In an especially preferred embodiment the promoter functionally linked to a NEENA may be employed in dicotyledonous crop plants such as soy, canola, cotton or potato.

A high expressing seed-specific promoter as used in the application means for example a promoter which is functionally linked to a NEENA causing enhanced seed-specific expression of the promoter in a plant seed or part thereof wherein the accumulation of RNA or rate of synthesis of RNA in seeds derived from the nucleic acid molecule under the control of the respective promoter functionally linked to a NEENA is higher, preferably significantly higher than the expression in seeds caused by the same promoter lacking a NEENA of the invention. Preferably the amount of RNA of the respective nucleic acid and/or the rate of RNA synthesis and/or the RNA stability in a plant is increased 50% or more, for example 100% or more, preferably 200% or more, more preferably 5 fold or more, even more preferably 10 fold or more, most preferably 20 fold or more for example 50 fold compared to a control plant of same age grown under the same conditions comprising the same seed-specific promoter the latter not being functionally linked to a NEENA of the invention.

When used herein, significantly higher refers to statistical significance the skilled person is aware how to determine, for example by applying statistical tests such as the t-test to the respective data sets.

Methods for detecting expression conferred by a promoter are known in the art. For example, the promoter may be functionally linked to a marker gene such as GUS, GFP or luciferase and the activity of the respective protein encoded by the respective marker gene may be determined in the plant or part thereof. As a representative example, the method for detecting luciferase is described in detail below. Other methods are for example measuring the steady state level or synthesis rate of RNA of the nucleic acid molecule controlled by the promoter by methods known in the art, for example Northern blot analysis, qPCR, run-on assays or other methods described in the art, or detecting the encoded protein using specific antibodies by methods known in the art, e.g. Western Blot and/or enzyme-linked immunosorbent assay (ELISA).

A skilled person is aware of various methods for functionally linking two or more nucleic acid molecules. Such methods may encompass restriction/ligation, ligase independent cloning, recombineering, recombination or synthesis. Other methods may be employed to functionally link two or more nucleic acid molecules.

The term "heterologous" with respect to a nucleic acid molecule or DNA refers to a nucleic acid molecule which is operably linked to, or is manipulated to become operably linked to, a second nucleic acid molecule to which it is not operably linked in nature, or to which it is operably linked at a different location in nature. For example, a NEENA of the invention is in its natural environment functionally linked to its native promoter, whereas in the present invention it is linked to another promoter which might be derived from the same organism, a different organism or might be a synthetic promoter. It may also mean that the NEENA of the present invention is linked to its native promoter but the nucleic acid molecule under control of said promoter is heterologous to the promoter comprising its native NEENA. It is in addition to be understood that the promoter and/or the nucleic acid molecule under the control of said promoter functionally linked to a NEENA of the invention are heterologous to said NEENA as their sequence has been manipulated by for example mutation such as insertions, deletions and the forth so that the natural sequence of the promoter and/or the nucleic acid molecule under control of said promoter is modified and therefore have become heterologous to a NEENA of the invention. It may also be understood that the NEENA is heterologous to the nucleic acid to which it is functionally linked when the NEENA is functionally linked to its native promoter wherein the position of the NEENA in relation to said promoter is changed so that the promoter shows higher expression after such manipulation.

A plant exhibiting enhanced seed-specific expression of a nucleic acid molecule as meant herein means a plant having a higher, preferably statistically significant higher seed-specific expression of a nucleic acid molecule compared to a control plant grown under the same conditions without the respective NEENA functionally linked to the respective nucleic acid molecule. Such control plant may be a wild-type plant or a transgenic plant comprising the same promoter controlling the same gene as in the plant of the invention wherein the promoter is not linked to a NEENA of the invention.

In generally the NEENA may be heterologous to the nucleic acid molecule which is under the control of said promoter to which the NEENA is functionally linked or it may be heterologous to both the promoter and the nucleic acid molecule under the control of said promoter.

The term "elongase activity" as meant by the present invention refers to the activity of the entire elongation complex as defined in the passage below and it is also be understood as the activity of the first component of the elongation complex with beta-ketoacyl-CoA synthase activity, which determines the substrate specificity of the entire elongation complex. By understanding the elongase activity as synthase activity only, the polypeptide of the of the present invention needs also comprising:

e) at least one nucleic acid sequence encoding a polypeptide having beta-ketoacyl reductase activity;

f) at least one nucleic acid sequence encoding a polypeptide having dehydratase activity or g) at least one nucleic acid sequence encoding a polypeptide having enoyl-CoA reductase activity, wherein the nucleic acid sequences defined in e) to g) are heterologous to said polypeptide having desaturase or elongase activity.

Preferably, the polynucleotide of the present invention comprises nucleic acid sequence encoding fatty acid dehydratase-/enoyl-CoA reductase (nECR) protein having an activity of catalyzing the dehydration and reduction of fatty acid elongated intermediates.

Fatty acid elongation is catalyzed in four steps, represented by four enzymes: KCR (β-keto-acyl-CoA-synthase), KCR (β-keto-acyl-CoA reductase), DH (dehydratase) and ECR (enoyl-CoA-reductase) forming the entire elongation complex. In the first step a fatty acid-CoA ester is condensed with malonyl-CoA producing a β-keto-acyl-CoA intermediate, which is elongated by to carbon atoms, and $CO_2$. The keto-group of the intermediate is then reduced by the KCR to a hydroxyl-group. In the next step the DH cleaves of the hydroxyl-group ($H_2O$ is produced), forming a 2-acylen-CoA ester. In the final step the double bound at position 2, 3 is reduced by the ECR forming the elongated acyl-CoA ester (Buchanan, Gruissem, Jones (2000) Biochemistry & Molecular biology of plants, American Society of Plant Physiologists). DH and ECR activity might also be confered by one single protein being a natural or artificial fusion of a DH-moiety and a ECR moiety, referred to as novel enoyl-CoA-reductase (nECR) in the present invention. In the current invention either all nucleic acid sequences defined in e) to f) could be comprised in the polynucleotide or only at least one of these nucleic acid sequences defined in e) to f) could be comprised in the polynucleotide in any combination occurred from different organisms.

A polynucleotide comprising a fragment of any of the aforementioned nucleic acid sequences is also encompassed as a nucleic acid molecule of the present invention. The fragment shall encode a polypeptide which still has nECR activity as specified above. Accordingly, the polypeptide may comprise or consist of the domains of the polypeptide of the present invention conferring the said biological activity. A fragment as meant herein, preferably, comprises at least 15, at least 20, at least 50, at least 100, at least 250 or at least 500 consecutive nucleotides of any one of the aforementioned nucleic acid sequences or encodes an amino acid sequence comprising at least 5, at least 10, at least 20, at least 30, at least 50, at least 80, at least 100 or at least 150 consecutive amino acids of any one of the aforementioned amino acid sequences.

The variant nucleic acid molecule or fragments referred to above, preferably, encode polypeptides retaining at least 10%, at least 20%, at least 30%, at least 40%, at least 50%, at least 60%, at least 70%, at least 80% or at least 90% of the nECR activity exhibited by the polypeptide encoded by the nucleotide sequences.

The term "polynucleotide" as used in accordance with the present invention also relates to a polynucleotide comprising a nucleic acid sequence which encodes a polypeptide having acyltransferase activity. Preferably, the polypeptide encoded by the polynucleotide of the present invention having acyltransferase activity upon expression in a plant shall be capable of increasing the amount of PUFA and, in particular, LCPUFA esterified to triglycerides in, e.g., seed oils or the entire plant or parts thereof. Such an increase is, preferably, statistically significant when compared to a LCPUFA producing transgenic control plant which expresses the minimal set of desaturases and elongases required for LCPUFA synthesis but does not express the polynucleotide of the present invention. Such a transgenic plant may, preferably, express desaturases and elongases comprised by the vector LJB765 listed in table 11 of example 5 in WO2009/016202 or a similar set of desaturases and elongases required for DHA synthesis. Whether an increase is significant can be determined by statistical tests well known in the art including, e.g., Student's t-test. More preferably, the increase is an increase of the amount of triglycerides containing LCPUFA of at least 5%, at least 10%, at least 15%, at least 20% or at least 30% compared to the said control. Preferably, the LCPUFA referred to before is a polyunsaturated fatty acid having a C-20, C-22 or C24 fatty acid body, more preferably, EPA or DHA, most preferably, DHA. Suitable assays for measuring the activities mentioned before are described in the accompanying Examples. Variant nucleic acid molecules as referred above may be obtained by various natural as well as artificial sources. For example, nucleic acid molecules may be obtained by in vitro and in vivo mutagenesis approaches using the above mentioned specific nucleic acid molecules as a basis. Moreover, nucleic acid molecules being homologs or orthologs may be obtained from various animal, plant or fungus species. Preferably, they are obtained from plants such as algae, for example *Isochrysis, Mantoniella, Ostreococcus* or *Crypthecodinium*, algae/diatoms such as *Phaeodactylum, Thalassiosira* or *Thraustochytrium*, mosses such as *Physcomitrella* or *Ceratodon*, or higher plants such as the *Primulaceae* such as *Aleuritia, Calendula stellate, Osteospermum spinescens* or *Osteospermum hyoseroides*, microorganisms such as fungi, such as *Aspergillus, Phytophthora, Entomophthora, Mucor* or *Mortierella*, bacteria such as *Shewanella*, yeasts or animals. Preferred animals are nematodes such as *Caenorhabditis*, insects or vertebrates. Among the vertebrates, the nucleic acid molecules may, preferably, be derived from *Euteleostomi, Actinopterygii; Neopterygii; Teleostei, Euteleostei, Protacanthopterygii, Salmoniformes; Salmonidae* or *Oncorhynchus*, more preferably, from the order of the *Salmoniformes*, most preferably, the family of the Salmonidae, such as the genus *Salmo*, for example from the genera and species *Oncorhynchus mykiss, Trutta trutta* or *Salmo trutta fario*. Moreover, the nucleic acid molecules may be obtained from the diatoms such as the genera *Thallasiosira* or *Phaeodactylum*.

Thus the present invention also relates to a polynucleotide comprising at least one nucleic acid sequence encoding a polypeptide having acyltransferase activity additionally to the abovementioned polypeptides exhibit desaturase, elongase orbeta-ketoacyl reductase, dehydratase or enoyl-CoA reductase activity. Therefore the polynucleotide of the present invention also comprising at least one nucleic acid sequence encoding a polypeptide having acyltransferase activity, wherein the nucleic acid sequence is heterologous to said polypeptide having desaturase, elongase, beta-ketoacyl reductase, dehydratase or enoyl-CoA reductase activity and wherein at least one seed-specific plant promoter and at least one terminator sequence are operatively linked to the said nucleic acid sequence and wherein one or more nucleic acid expression enhancing nucleic acid (NEENA) molecule is/are functionally linked to said promoter and which is/are heterologous to said promoter.

The term "acyltransferase activity" or "acyltransferase" as used herein encompasses all enymatic activities and enzymes which are capable of transferring or are involved in the transfer of PUFA and, in particular; LCPUFA from the acly-CoA pool or the membrane phospholipids to the triglycerides, from the acyl-CoA pool to membrane lipids and from membrane lipids to the acyl-CoA pool by a transesterification process. It will be understood that this acyltransferase activity will result in an increase of the LCPUFA esterified to triglycerides in, e.g., seed oils. In particular, it is envisaged that these acyltransferases are capable of producing triglycerides having esterified EPA or even DHA, or that these acyltransferases are capable of enhancing synthesis of desired PUFA by increasing the flux for specific intermediates of the desired PUFA between the acyl-CoA pool (the site of elongation) and membrane lipids (the predominant site of desaturation). Specifically, acyltransferase activity as used herein pertains to lysophospholipid acyltransferase (LPLAT) activity, preferably, lysophosphatidylcholine acyltransferase (LPCAT) or Lysophosphatidylethanolamine acyltransferase (LPEAT) activity, lysophosphophosphatidic acid acyltransferase (LPAAT) activity, phospholipid:diacylglycerol acyltransferase (PDAT) activity, glycerol-3-phosphate acyltransferase (GPAT) activity or diacylglycerol acyltransferase (DGAT), and, more preferably, to PLAT, LPAAT, DGAT, PDAT or GPAT activity.

A polynucleotide encoding a polypeptide having a acyltransferase activity as specified above could be obtained for example from *Phythophthora infestance*. Polynucleotides encoding a polypeptide having desaturase or elongase activity as specified above could be obtained in accordance with the present invention from *Thraustochytrium* ssp. for example. Preferred acyltransferases which shall be present in the host cell are at least one enzyme selected from the group consisting of: LPLATs, LPAATs, DGATs, PDATs and GPATs. Especially preferred are the LPLATs LPLAT(Ce) from *Caenorhabditis elegans* (WO2004076617), LPCAT (Ms) from *Mantoniella squamata* (WO2006069936) and LPCAT(Ot) from *Ostreococcus tauri* (WO2006069936), pLPLAT_01332(Pi) (SEQ-ID No.:104 encoding the polypeptide SEQ-ID No.:125) pLPLAT_01330(Pi) (SEQ-ID No.:105 encoding the polypeptide SEQ-ID No.:126), pLPLAT_07077(Pi) (SEQ-ID No.:106 encoding the polypeptide SEQ-ID No.:127), LPLAT_18374(Pi) (SEQ-ID No.: 107 encoding the polypeptide SEQ-ID No.:128), pLPLAT_14816(Pi) (SEQ-ID No.:108 encoding the polypeptide SEQ-ID No.:129), LPCAT_02075(Pi) (SEQ-ID No.: 111 encoding the polypeptide SEQ-ID No.:132), pLPAAT_06638(Pi) (SEQ-ID No.:112 encoding the polypeptide SEQ-ID No.:133) form *Phytophthora infestance*, the LPAATs LPAAT(Ma)1.1 from *Mortierella alpina* (WO2004087902), LPAAT(Ma)1.2 from *Mortierella alpina* (WO2004087902), the LPAAT_13842(Pi) (SEQ-ID No.:109 encoding the polypeptide SEQ-ID No.:130), pLPAAT_10763(Pi) (SEQ-ID No.:110 encoding the polypeptide SEQ-ID No.:131) from *Phytophthora infestance*, the DGATs DGAT2(Cc) from *Crypthecodinium cohnii* (WO2004087902), pDGAT1_12278(Pi) (SEQ-ID No.:113 encoding the polypeptide SEQ-ID No.:134), DGAT2_03074 (Pi) (SEQ-ID No.:114 encoding the polypeptide SEQ-ID No.:135), pDGAT2_08467(Pi) (SEQ-ID No.:115 encoding the polypeptide SEQ-ID No.:136), DGAT2_08470(Pi) (SEQ-ID No.:116 encoding the polypeptide SEQ-ID No.: 137), pDGAT2_03835-mod(Pi) (SEQ-ID No.:117 encoding the polypeptide SEQ-ID No.:138), DGAT2_11677-mod(Pi) (SEQ-ID No.:118 encoding the polypeptide SEQ-ID No.: 139), DGAT2_08432-mod(Pi) (SEQ-ID No.:119 encoding the polypeptide SEQ-ID No.:140), pDGAT2_08431(Pi) (SEQ-ID No.:120 encoding the polypeptide SEQ-ID No.: 141), DGAT_13152-mod(Pi) (SEQ-ID No.:121 encoding the polypeptide SEQ-ID No.:142), the PDAT pPDAT_11965-mod(Pi) (SEQ-ID No.:122 encoding the polypeptide SEQ-ID No.:143) and the GPATs pGPAT-PITG_18707 (SEQ-ID No.:123 encoding the polypeptide SEQ-ID No.:144) and pGPAT-PITG_03371 (SEQ-ID No.: 124 encoding the polypeptide SEQ-ID No.:145).

However, orthologs, paralogs or other homologs may be identified from other species. Preferably, they are obtained from plants such as algae, for example *Isochrysis, Mantoniella, Ostreococcus* or *Crypthecodinium*, algae/diatoms such as *Phaeodactylum* or *Thalassiosira* or *Thraustochytrium*, mosses such as *Physcomitrella* or *Ceratodon*, or higher plants such as the *Primulaceae* such as *Aleuritia, Calendula stellata, Osteospermum spinescens* or *Osteospermum hyoseroides*, microorganisms such as fungi, such as *Aspergillus, Phytophthora, Entomophthora, Mucor* or *Mortierella*, bacteria such as *Shewanella*, yeasts or animals. Preferred animals are nematodes such as *Caenorhabditis*, insects or vertebrates. Among the vertebrates, the nucleic acid molecules may, preferably, be derived from *Euteleostomi, Actinopterygii; Neopterygii; Teleostei, Euteleostei, Protacanthopterygii, Salmoniformes; Salmonidae* or *Oncorhynchus*, more preferably, from the order of the *Salmoniformes*, most preferably, the family of the Salmonidae, such as the genus *Salmo*, for example from the genera and species *Oncorhynchus mykiss, Trutta trutta* or *Salmo trutta fario*. Moreover, the nucleic acid molecules may be obtained from the diatoms such as the genera *Thallasiosira* or *Phaeodactylum*.

Thus, the term "polynucleotide" as used in accordance with the present invention further encompasses variants of the aforementioned specific polynucleotides representing orthologs, paralogs or other homologs of the polynucleotide of the present invention. Moreover, variants of the polynucleotide of the present invention also include artificially generated muteins. Said muteins include, e.g., enzymes which are generated by mutagenesis techniques and which exhibit improved or altered substrate specificity, or codon optimized polynucleotides. The polynucleotide variants, preferably, comprise a nucleic acid sequence characterized in that the sequence can be derived from the aforementioned specific nucleic acid sequences shown in any one of SEQ ID NOs: 95, 96, 97, 98, 99, 100, 101, 102, 103, 104, 105, 106, 107, 108, 109, 110, 111, 112, 113, 114, 115, 116, 117, 118, 119, 120, 121, 122, 123 or 124 by a polynucleotide encoding a polypeptide having an amino acid sequence (i.e. as shown in any one of SEQ ID NOs: 125, 126, 127, 128, 129, 130, 131, 132, 133, 134, 135, 136, 137, 138, 139, 140, 141, 142, 143, 144 or 145 as for acyltransferases) by at least one nucleotide substitution, addition and/or deletion, whereby the variant nucleic acid sequence shall still encode a polypeptide having a desaturase or elongase activity as specified above. Variants also encompass polynucleotides comprising a nucleic acid sequence which is capable of hybridizing to the aforementioned specific nucleic acid sequences, preferably, under stringent hybridization conditions. These stringent conditions are known to the skilled worker and can be found in Current Protocols in Molecular Biology, John Wiley & Sons, N. Y. (1989), 6.3.1-6.3.6. A preferred example for stringent hybridization conditions are hybridization conditions in 6× sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5×SSC (pH 7.2). If organic solvent is present in the above-mentioned buffer, for example 50% formamide, the temperature under standard conditions is approximately 42° C. The hybridization conditions for DNA: DNA hybrids are, preferably, 0.1×SSC and 20° C. to 45° C., preferably between 30° C. and 45° C. The hybridization conditions for DNA:RNA hybrids are, preferably, 0.1×SSC and 30° C. to 55° C., preferably between 45° C. and 55° C. The above-mentioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. Alternatively, polynucleotide variants are obtainable by PCR-based techniques such as mixed oligonucleotide primer-based amplification of DNA, i.e. using degenerated primers against conserved domains of the polypeptides of the present invention. Conserved domains of the polypeptide of the present invention may be identified by a sequence comparison of the nucleic acid sequences of the polynucleotides or the amino acid sequences of the polypeptides of the present invention. Oligonucleotides suitable as PCR primers as well as suitable PCR conditions are described in the accompanying Examples. As a template, DNA or cDNA from bacteria, fungi, plants or animals may be used. Further, variants include polynucleotides comprising nucleic acid sequences which are at least 50%, at least 55%, at least 60%, at least 65%, at least 70%, at least 75%, at least 80%, at least 85%, at least 90%, at least 95%, at least 98% or at least 99% identical to the nucleic acid sequences shown in any one of SEQ ID NOs: 95, 96, 97, 98, 99, 100, 101, 102, 103, 104, 105, 106, 107, 108, 109, 110, 111, 112, 113, 114, 115, 116, 117, 118, 119, 120, 121, 122, 123 or 124 preferably, encoding polypeptides retaining a desaturase, elongase, or acyltransferase activity as specified above. Moreover, also encompassed are polynucleotides which comprise nucleic acid sequences encoding a polypeptide having an amino acid sequences which are at least 50%, at least 55%, at least 60%, at least 65%, at least 70%, at least 75%, at least 80%, at least 85%, at least 90%, at least 95%, at least 98% or at least 99% identical to the amino acid sequences encoded by the nucleic acid sequences shown in any one of SEQ ID NOs: 95, 96, 97, 98, 99, 100, 101, 102, 103, 104, 105, 106, 107, 108, 109, 110, 111, 112, 113, 114, 115, 116, 117, 118, 119, 120, 121, 122, 123 or 124 (i.e. as shown in any one of SEQ ID NOs: 125, 126, 127, 128, 129, 130, 131, 132, 133, 134, 135, 136, 137, 138, 139, 140, 141, 142, 143, 144 or 145 as for acyltransferases), wherein the polypeptide, preferably, retains desaturase, elongase or acyltransferase activity as specified above. The percent identity values are, preferably, calculated over the entire amino acid or nucleic acid sequence region. A series of programs based on a variety of algorithms is available to the skilled worker for comparing different sequences. In a preferred embodiment, the percent identity between two amino acid sequences is determined using the Needleman and Wunsch algorithm (Needleman 1970, J. Mol. Biol. (48):444-453) which has been incorporated into the needle program in the EMBOSS software package (*EMBOSS: The European Molecular Biology Open Software Suite*, Rice, P., Longden, I., and Bleasby, A, Trends in Genetics 16(6), 276-277, 2000), using either a BLOSUM 45 or PAM250 scoring matrix for distantly related proteins, or either a BLOSUM 62 or PAM160 scoring matrix for closer related proteins, and a gap opening penalty of 16, 14, 12, 10, 8, 6, or 4 and a gap entension pentalty of 0.5, 1, 2, 3, 4, 5, or 6. Guides for local installation of the EMBOSS package as well as links to WEB-Services can be found at emboss.sourceforge.net. A preferred, non-limiting example of parameters to be used for aligning two amino acid sequences using the needle program are the default parameters, including the EBLOSUM62 scoring matrix, a gap opening penalty of 10 and a gap extension penalty of 0.5. In yet another preferred embodiment, the percent identity between two nucleotide sequences is determined using the needle program in the EMBOSS software package (*EMBOSS: The European Molecular Biology Open Software Suite*, Rice, P., Longden, I., and Bleasby, A, Trends in Genetics 16(6), 276-277, 2000), using the EDNAFULL scoring matrix and a gap opening penalty of 16, 14, 12, 10, 8, 6, or 4 and a gap extension penalty of 0.5, 1, 2, 3, 4, 5, or 6. A preferred, non-limiting example of parameters to be used in conjunction for aligning two amino acid sequences using the needle program are the default parameters, including the EDNAFULL scoring matrix, a gap opening penalty of 10 and a gap extension penalty of 0.5. The nucleic acid and protein sequences of the present invention can further be used as a "query sequence" to perform a search against public databases to, for example, identify other family members or related sequences. Such searches can be performed using the BLAST series of programs (version 2.2) of Altschul et al. (Altschul 1990, J. Mol. Biol. 215:403-10). BLAST using nucleic acid sequences of the invention as query sequence can be performed with the BLASTn, BLASTx or the tBLASTx program using default parameters to obtain either nucleotide sequences (BLASTn, tBLASTx) or amino acid sequences (BLASTx) homologous to sequences encoded by the nucleic acid sequences of the invention. BLAST using protein sequences encoded by the nucleic acid sequences of the invention as query sequence can be performed with the BLASTp or the tBLASTn program using default parameters to obtain either amino acid sequences (BLASTp) or nucleic acid sequences (tBLASTn) homologous to sequences of the invention. To obtain gapped alignments for comparison purposes, Gapped BLAST using default parameters can be utilized as described in Altschul et al. (Altschul 1997, Nucleic Acids Res. 25(17):3389-3402).

The following block diagram shows the relation of sequence types of querry and hit sequences for various BLASt programs

| Input query sequence | Converted Query | Algorithm | Converted Hit | Actual Database |
|---|---|---|---|---|
| DNA | | BLASTn | | DNA |
| PRT | | BLASTp | | PRT |
| DNA | PRT | BLASTx | | PRT |
| PRT | | tBLASTn | PRT | DNA |
| DNA | PRT | tBLASTx | PRT | DNA |

A polynucleotide comprising a fragment of any of the aforementioned nucleic acid sequences is also encompassed as a polynucleotide of the present invention. The fragment shall encode a polypeptide which still has desaturase and elongase activity as specified above. Accordingly, the polypeptide may comprise or consist of the domains of the polypeptide of the present invention conferring the said biological activity. A fragment as meant herein, preferably, comprises at least 50, at least 100, at least 250 or at least 500 consecutive nucleotides of any one of the aforementioned nucleic acid sequences or encodes an amino acid sequence comprising at least 20, at least 30, at least 50, at least 80, at least 100 or at least 150 consecutive amino acids of any one of the aforementioned amino acid sequences.

The variant polynucleotides or fragments referred to above, preferably, encode polypeptides retaining desaturase or elongase activity to a significant extent, preferably, at least 10%, at least 20%, at least 30%, at least 40%, at least 50%, at least 60%, at least 70%, at least 80% or at least 90% of the desaturase and elongase activity exhibited by any of the polypeptide encoded by the nucleic acid sequences shown in any one of SEQ ID NOs: 95, 96, 97, 98, 99, 100, 101, 102, 103, 104, 105, 106, 107, 108, 109, 110, 111, 112, 113, 114, 115, 116, 117, 118, 119, 120, 121, 122, 123 or 124 (i.e. as shown in any one of SEQ ID NOs: 125, 126, 127, 128, 129, 130, 131, 132, 133, 134, 135, 136, 137, 138, 139, 140, 141, 142, 143, 144 or 145 as for acyltransferases). The activity may be tested as described in the accompanying Examples.

The polynucleotides of the present invention either essentially consist of the aforementioned nucleic acid sequences or comprise the aforementioned nucleic acid sequences. Thus, they may contain further nucleic acid sequences as well. Preferably, the polynucleotide of the present invention may comprise in addition to an open reading frame further untranslated sequence at the 3' and at the 5' terminus of the coding gene region: at least 500, preferably 200, more preferably 100 nucleotides of the sequence upstream of the 5' terminus of the coding region and at least 100, preferably 50, more preferably 20 nucleotides of the sequence downstream of the 3' terminus of the coding gene region. Furthermore, the polynucleotides of the present invention may encode fusion proteins wherein one partner of the fusion protein is a polypeptide being encoded by a nucleic acid sequence recited above. Such fusion proteins may comprise as additional part other enzymes of the fatty acid or PUFA biosynthesis pathways, polypeptides for monitoring expression (e.g., green, yellow, blue or red fluorescent proteins, alkaline phosphatase and the like) or so called "tags" which may serve as a detectable marker or as an auxiliary measure for purification purposes. Tags for the different purposes are well known in the art and comprise FLAG-tags, 6-histidine-tags, MYC-tags and the like.

The polynucleotide of the present invention shall be provided, preferably, either as an isolated polynucleotide (i.e. purified or at least isolated from its natural context such as its natural gene locus) or in genetically modified or exogenously (i.e. artificially) manipulated form. An isolated polynucleotide can, for example, comprise less than approximately 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid is derived. The polynucleotide, preferably, is provided in the form of double or single stranded molecule. It will be understood that the present invention by referring to any of the aforementioned polynucleotides of the invention also refers to complementary or reverse complementary strands of the specific sequences or variants thereof referred to before. The polynucleotide encompasses DNA, including cDNA and genomic DNA, or RNA polynucleotides.

However, the present invention also pertains to polynucleotide variants which are derived from the polynucleotides of the present invention and are capable of interfering with the transcription or translation of the polynucleotides of the present invention. Such variant polynucleotides include antisense nucleic acids, ribozymes, siRNA molecules, morpholino nucleic acids (phosphorodiamidate morpholino oligos), triple-helix forming oligonucleotides, inhibitory oligonucleotides, or micro RNA molecules all of which shall specifically recognize the polynucleotide of the invention due to the presence of complementary or substantially complementary sequences. These techniques are well known to the skilled artisan. Suitable variant polynucleotides of the aforementioned kind can be readily designed based on the structure of the polynucleotides of this invention.

Moreover, comprised are also chemically modified polynucleotides including naturally occurring modified polynucleotides such as glycosylated or methylated polynucleotides or artificial modified ones such as biotinylated polynucleotides.

In a preferred embodiment of the polynucleotide of the present invention, said polynucleotide further comprises an expression control sequence operatively linked to the said nucleic acid sequence.

The term "expression control sequence" as used herein refers to a nucleic acid sequence which is capable of governing, i.e. initiating and controlling, transcription of a nucleic acid sequence of interest, in the present case the nucleic sequences recited above. Such a sequence usually comprises or consists of a promoter or a combination of a promoter and enhancer sequences. Expression of a polynucleotide comprises transcription of the nucleic acid molecule, preferably, into a translatable mRNA. Additional regulatory elements may include transcriptional as well as translational enhancers. The following promoters and expression control sequences may be, preferably, used in an expression vector according to the present invention. The cos, tac, trp, tet, trp-tet, lpp, lac, lpp-lac, lacIq, T7, T5, T3, gal, trc, ara, SP6, λ-PR or λ-PL promoters are, preferably, used in Gram-negative bacteria. For Gram-positive bacteria, promoters amy and SPO2 may be used. From yeast or fungal promoters ADC1, AOX1r, GAL1, MFα, AC, P-60, CYC1, GAPDH, TEF, rp28, ADH are, preferably, used. For animal cell or organism expression, the promoters CMV-, SV40-, RSV-promoter (Rous sarcoma virus), CMV-enhancer, SV40-enhancer are preferably used. From plants the promoters CaMV/35S (Franck 1980, Cell 21: 285-294], PRP1 (Ward 1993, Plant. Mol. Biol. 22), SSU, OCS, lib4, usp, STLS1, B33, nos or the ubiquitin or phaseolin promoter. Also preferred in this context are inducible promoters, such as the promoters described in EP 0 388 186 A1 (i.e. a benzylsulfonamide-inducible promoter), Gatz 1992, Plant J. 2:397-404 (i.e. a tetracyclin-inducible promoter), EP 0 335 528 A1 (i.e. a abscisic-acid-inducible promoter) or WO 93/21334 (i.e. a ethanol- or cyclohexenol-inducible promoter). Further suitable plant promoters are the promoter of cytosolic FBPase or the ST-LSI promoter from potato (Stockhaus 1989, EMBO J. 8, 2445), the phosphoribosyl-pyrophosphate amidotransferase promoter from *Glycine max* (Genbank accession No. U87999) or the node-specific promoter described in EP 0 249 676 A1. Particularly preferred are promoters which enable the expression in tissues which are involved in the biosynthesis of fatty acids. Also particularly preferred are seed-specific promoters such as the USP promoter in accordance with the practice, but also other promoters such as the LeB4, DC3, phaseolin or napin promoters. Further especially preferred promoters are seed-specific promoters which can be used for monocotyledonous or dicotyledonous plants and which are described in U.S. Pat. No. 5,608,152 (napin promoter from oilseed rape), WO 98/45461 (oleosin promoter from *Arobidopsis*, U.S. Pat. No.

5,504,200 (phaseolin promoter from *Phaseolus vulgaris*), WO 91/13980 (Bce4 promoter from *Brassica*), by Baeumlein et al., Plant J., 2, 2, 1992:233-239 (LeB4 promoter from a legume), these promoters being suitable for dicots. The following promoters are suitable for monocots: Ipt-2 or Ipt-1 promoter from barley (WO 95/15389 and WO 95/23230), hordein promoter from barley and other promoters which are suitable and which are described in WO 99/16890. In principle, it is possible to use all natural promoters together with their regulatory sequences, such as those mentioned above, for the novel process. Likewise, it is possible and advantageous to use synthetic promoters, either additionally or alone, especially when they mediate a seed-specific expression, such as, for example, as described in WO 99/16890. In a particular embodiment, seed-specific promoters are utilized to enhance the production of the desired PUFA or LCPUFA. In a preferred embodiment of the present invention promoters encoded by the nucleic acid sequences shown in any one of SEQ ID NOs: 25, 26, 27, 28, 29 or 30 are used.

The term "operatively linked" as used herein means that the expression control sequence and the nucleic acid of interest are linked so that the expression of the said nucleic acid of interest can be governed by the said expression control sequence, i.e. the expression control sequence shall be functionally linked to the said nucleic acid sequence to be expressed. Accordingly, the expression control sequence and, the nucleic acid sequence to be expressed may be physically linked to each other, e.g., by inserting the expression control sequence at the 5"end of the nucleic acid sequence to be expressed. Alternatively, the expression control sequence and the nucleic acid to be expressed may be merely in physical proximity so that the expression control sequence is capable of governing the expression of at least one nucleic acid sequence of interest. The expression control sequence and the nucleic acid to be expressed are, preferably, separated by not more than 500 bp, 300 bp, 100 bp, 80 bp, 60 bp, 40 bp, 20 bp, 10 bp or 5 bp.

In a further preferred embodiment of the polynucleotide of the present invention, said polynucleotide further comprises a terminator sequence operatively linked to the nucleic acid sequence. Preferably used terminators are encoded by the nucleotide sequences shown in SEQ ID NOs: 36 or 37. More preferably used terminators are encoded by the nucleotide sequences shown in SEQ ID NOs: 31, 32, 33, 34 or 35

The term "terminator" as used herein refers to a nucleic acid sequence which is capable of terminating transcription. These sequences will cause dissociation of the transcription machinery from the nucleic acid sequence to be transcribed. Preferably, the terminator shall be active in plants and, in particular, in plant seeds. Suitable terminators are known in the art and, preferably, include polyadenylation signals such as the SV40-poly-A site or the tk-poly-A site or one of the plant specific signals indicated in Loke et al. (Loke 2005, Plant Physiol 138, pp. 1457-1468), downstream of the nucleic acid sequence to be expressed.

The present invention also relates to a vector comprising the polynucleotide of the present invention.

The term "vector", preferably, encompasses phage, plasmid, viral vectors as well as artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homolgous or heterologous recombination as described in detail below.

The vector encompassing the polynucleotide of the present invention, preferably, further comprises selectable markers for propagation and/or selection in a host. The vector may be incorporated into a host cell by various techniques well known in the art. If introduced into a host cell, the vector may reside in the cytoplasm or may be incorporated into the genome. In the latter case, it is to be understood that the vector may further comprise nucleic acid sequences which allow for homologous recombination or heterologous insertion. Vectors can be introduced into prokaryotic or eukaryotic cells via conventional transformation or transfection techniques. The terms "transformation" and "transfection", conjugation and transduction, as used in the present context, are intended to comprise a multiplicity of prior-art processes for introducing foreign nucleic acid (for example DNA) into a host cell, including calcium phosphate, rubidium chloride or calcium chloride co-precipitation, DEAE-dextran-mediated transfection, lipofection, natural competence, carbon-based clusters, chemically mediated transfer, electroporation or particle bombardment. Suitable methods for the transformation or transfection of host cells, including plant cells, can be found in Sambrook et al. (Molecular Cloning: A Laboratory Manual, $2^{nd}$ ed., Cold Spring Harbor Laboratory, Cold Spring Harbor Laboratory Press, Cold Spring Harbor, N.Y., 1989) and other laboratory manuals, such as Methods in Molecular Biology, 1995, Vol. 44, *Agrobacterium* protocols, Ed.: Gartland and Davey, Humana Press, Totowa, N.J. Alternatively, a plasmid vector may be introduced by heat shock or electroporation techniques. Should the vector be a virus, it may be packaged in vitro using an appropriate packaging cell line prior to application to host cells.

Preferably, the vector referred to herein (VC-LJBXXX) is suitable as a cloning vector, i.e. replicable in microbial systems. Such vectors ensure efficient cloning in bacteria and, preferably, yeasts or fungi and make possible the stable transformation of plants. Those which must be mentioned are, in particular, various binary and co-integrated vector systems which are suitable for the T-DNA-mediated transformation. Such vector systems are, as a rule, characterized in that they contain at least the vir genes, which are required for the *Agrobacterium*-mediated transformation, and the sequences which delimit the T-DNA (T-DNA border). These vector systems, preferably, also comprise further cis-regulatory regions such as promoters and terminators and/or selection markers with which suitable transformed host cells or organisms can be identified. While co-integrated vector systems have vir genes and T-DNA sequences arranged on the same vector, binary systems are based on at least two vectors, one of which bears vir genes, but no T-DNA, while a second one bears T-DNA, but no vir gene. As a consequence, the last-mentioned vectors are relatively small, easy to manipulate and can be replicated both in *E. coli* and in *Agrobacterium*. These binary vectors include vectors from the pBIB-HYG, pPZP, pBecks, pGreen series. Preferably used in accordance with the invention are Bin19, pBI101, pBinAR, pGPTV and pCAMBIA. An overview of binary vectors and their use can be found in Hellens et al, Trends in Plant Science (2000) 5, 446-451. Furthermore, by using appropriate cloning vectors, the polynucleotides can be introduced into host cells or organisms such as plants or animals and, thus, be used in the transformation of plants, such as those which are published, and cited, in: Plant Molecular Biology and Biotechnology (CRC Press, Boca Raton, Fla.), chapter 6/7, pp. 71-119 (1993); F. F. White, Vectors for Gene Transfer in Higher Plants; in: Transgenic Plants, vol. 1, Engineering and Utilization, Ed.: Kung and R. Wu, Academic Press, 1993, 15-38; B. Jenes et al., Techniques for Gene Transfer, in: Transgenic Plants, vol. 1, Engineering and Utilization, Ed.: Kung and R. Wu, Academic Press (1993), 128-143; Potrykus 1991, Annu. Rev. Plant Physiol. Plant Molec. Biol. 42, 205-225.

More preferably, the vector of the present invention is an expression vector. In such an expression vector, i.e. a vector which comprises the polynucleotide of the invention having the nucleic acid sequence operatively linked to an expression control sequence (also called "expression cassette") allowing expression in prokaryotic or eukaryotic cells or isolated fractions thereof. Suitable expression vectors are known in the art such as Okayama-Berg cDNA expression vector pcDV1 (Pharmacia), pCDM8, pRc/CMV, pcDNA1, pcDNA3 (Invitrogene) or pSPORT1 (GIBCO BRL). Further examples of typical fusion expression vectors are pGEX (Pharmacia Biotech Inc; Smith 1988, Gene 67:31-40), pMAL (New England Biolabs, Beverly, Mass.) and pRIT5 (Pharmacia, Piscataway, N.J.), where glutathione S-transferase (GST), maltose E-binding protein and protein A, respectively, are fused with the recombinant target protein. Examples of suitable inducible nonfusion E. coli expression vectors are, inter alia, pTrc (Amann 1988, Gene 69:301-315) and pET 11d (Studier 1990, Methods in Enzymology 185, 60-89). The target gene expression of the pTrc vector is based on the transcription from a hybrid trp-lac fusion promoter by host RNA polymerase. The target gene expression from the pET 11d vector is based on the transcription of a T7-gn10-lac fusion promoter, which is mediated by a coexpressed viral RNA polymerase (T7 gn1). This viral polymerase is provided by the host strains BL21 (DE3) or HMS174 (DE3) from a resident λ-prophage which harbors a T7 gn1 gene under the transcriptional control of the lacUV 5 promoter. The skilled worker is familiar with other vectors which are suitable in prokaryotic organisms; these vectors are, for example, in E. coli, pLG338, pACYC184, the pBR series such as pBR322, the pUC series such as pUC18 or pUC19, the M113 mp series, pKC30, pRep4, pHS1, pHS2, pPLc236, pMBL24, pLG200, pUR290, pIN-III113-B1, λgt11 or pBdCI, in Streptomyces pIJ101, pIJ364, pIJ702 or pIJ361, in Bacillus pUB110, pC194 or pBD214, in Corynebacterium pSA77 or pAJ667. Examples of vectors for expression in the yeast S. cerevisiae comprise pYep Sec1 (Baldari 1987, Embo J. 6:229-234), pMFa (Kurjan 1982, Cell 30:933-943), pJRY88 (Schultz 1987, Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C.A.M.J.J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi (J. W. Bennett & L. L. Lasure, Ed., pp. 396-428: Academic Press: San Diego). Further suitable yeast vectors are, for example, pAG-1, YEp6, YEp13 or pEMBLYe23. As an alternative, the polynucleotides of the present invention can be also expressed in insect cells using baculovirus expression vectors. Baculovirus vectors which are available for the expression of proteins in cultured insect cells (for example Sf9 cells) comprise the pAc series (Smith 1983, Mol. Cell. Biol. 3:2156-2165) and the pVL series (Lucklow 1989, Virology 170:31-39).

The abovementioned vectors are only a small overview of vectors to be used in accordance with the present invention. Further vectors are known to the skilled worker and are described, for example, in: Cloning Vectors (Ed., Pouwels, P. H., et al., Elsevier, Amsterdam-New York-Oxford, 1985, ISBN 0 444 904018). For further suitable expression systems for prokaryotic and eukaryotic cells see the chapters 16 and 17 of Sambrook, loc cit.

It follows from the above that, preferably, said vector is an expression vector. More preferably, the said polynucleotide of the present invention is under the control of a seed-specific promoter in the vector of the present invention. A preferred seed-specific promoter as meant herein is selected from the group consisting of Conlinin 1, Conlinin 2, napin, LuFad3, USP, LeB4, Arc, Fae, ACP, LuPXR, and SBP. For details, see, e.g., US 2003-0159174.

The polynucleotide of the present invention can be expressed in single-cell plant cells (such as algae), see Falciatore 1999, Marine Biotechnology 1 (3):239-251 and the references cited therein, and plant cells from higher plants (for example Spermatophytes, such as arable crops) by using plant expression vectors. Examples of plant expression vectors comprise those which are described in detail in: Becker 1992, Plant Mol. Biol. 20:1195-1197; Bevan 1984, Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, p. 15-38. A plant expression cassette, preferably, comprises regulatory sequences which are capable of controlling the gene expression in plant cells and which are functionally linked so that each sequence can fulfill its function, such as transcriptional termination, for example polyadenylation signals. Preferred polyadenylation signals are those which are derived from Agrobacterium tumefaciens T-DNA, such as the gene 3 of the Ti plasmid pTiACH5, which is known as octopine synthase (Gielen 1984, EMBO J. 3, 835) or functional equivalents of these, but all other terminators which are functionally active in plants are also suitable. Since plant gene expression is very often not limited to transcriptional levels, a plant expression cassette preferably comprises other functionally linked sequences such as translation enhancers, for example the overdrive sequence, which comprises the 5'-untranslated tobacco mosaic virus leader sequence, which increases the protein/RNA ratio (Gallie 1987, Nucl. Acids Research 15:8693-8711). As described above, plant gene expression must be functionally linked to a suitable promoter which performs the expression of the gene in a timely, cell-specific or tissue-specific manner. Promoters which can be used are constitutive promoters (Benfey 1989, EMBO J. 8:2195-2202) such as those which are derived from plant viruses such as 35S CAMV (Franck 1980, Cell 21:285-294), 19S CaMV (see U.S. Pat. No. 5,352,605 and WO 84/02913) or plant promoters such as the promoter of the Rubisco small subunit, which is described in U.S. Pat. No. 4,962,028. Other preferred sequences for the use in functional linkage in plant gene expression cassettes are targeting sequences which are required for targeting the gene product into its relevant cell compartment (for a review, see Kermode 1996, Crit. Rev. Plant Sci. 15, 4: 285-423 and references cited therein), for example into the vacuole, the nucleus, all types of plastids, such as amyloplasts, chloroplasts, chromoplasts, the extracellular space, the mitochondria, the endoplasmic reticulum, oil bodies, peroxisomes and other compartments of plant cells. As described above, plant gene expression can also be facilitated via a chemically inducible promoter (for a review, see Gatz 1997, Annu. Rev. Plant Physiol. Plant Mol. Biol., 48:89-108). Chemically inducible promoters are particularly suitable if it is desired that genes are expressed in a time-specific manner. Examples of such promoters are a salicylic-acid-inducible promoter (WO 95/19443), a tetracyclin-inducible promoter (Gatz 1992, Plant J. 2, 397-404)

and an ethanol-inducible promoter. Promoters which respond to biotic or abiotic stress conditions are also suitable promoters, for example the pathogen-induced PRP1-gene promoter (Ward 1993, Plant Mol. Biol. 22:361-366), the heat-inducible hsp80 promoter from tomato (U.S. Pat. No. 5,187,267), the cold-inducible alpha-amylase promoter from potato (WO 96/12814) or the wound-inducible pinII promoter (EP 0 375 091 A). The promoters which are especially preferred are those which bring about the expression of genes in tissues and organs in which fatty acid, lipid and oil biosynthesis takes place, in seed cells such as the cells of endosperm and of the developing embryo. Suitable promoters are the napin gene promoter from oilseed rape (U.S. Pat. No. 5,608,152), the USP promoter from *Vicia faba* (Baeumlein 1991, Mol. Gen. Genet. 225 (3):459-67), the oleosin promoter from *Arabidopsis* (WO 98/45461), the phaseolin promoter from *Phaseolus vulgaris* (U.S. Pat. No. 5,504, 200), the Bce4 promoter from *Brassica* (WO 91/13980) or the legumin B4 promoter (LeB4; Baeumlein 1992, Plant Journal, 2 (2):233-9), and promoters which bring about the seed-specific expression in monocotyledonous plants such as maize, barley, wheat, rye, rice and the like. Suitable promoters to be taken into consideration are the lpt2 or lpt1 gene promoter from barley (WO 95/15389 and WO 95/23230) or those which are described in WO 99/16890 (promoters from the barley hordein gene, the rice glutelin gene, the rice oryzin gene, the rice prolamin gene, the wheat gliadin gene, wheat glutelin gene, the maize zein gene, the oat glutelin gene, the *sorghum* kasirin gene, the rye secalin gene). Likewise, especially suitable are promoters which bring about the plastid-specific expression since plastids are the compartment in which the precursors and some end products of lipid biosynthesis are synthesized. Suitable promoters such as the viral RNA-polymerase promoter, are described in WO 95/16783 and WO 97/06250, and the clpP promoter from *Arabidopsis*, described in WO 99/46394.

Moreover, the present invention relates to a host cell comprising the polynucleotide or the vector of the present invention. The term "host cell" is also meant as "host cell culture".

Preferably, said host cell is a plant cell or plant cell culture and, more preferably, a plant cell obtained from an oilseed crop. More preferably, said oilseed crop is selected from the group consisting of flax (*Linum* sp.), rapeseed (*Brassica* sp.), soybean (*Glycine* sp.), sunflower (*Helianthus* sp.), cotton (*Gossypium* sp.), corn (*Zea mays*), olive (*Olea* sp.), safflower (*Carthamus* sp.), cocoa (*Theobroma cacoa*), peanut (*Arachis* sp.), hemp, camelina, crambe, oil palm, coconuts, groundnuts, sesame seed, castor bean, *lesquerella*, tallow tree, sheanuts, tungnuts, kapok fruit, poppy seed, jojoba seeds and *perilla*.

Also preferably, said host cell is a microorganism. More preferably, said microorganism is a bacterium, a fungus or algae. More preferably, it is selected from the group consisting of *Candida, Cryptococcus, Lipomyces, Rhodosporidium, Yarrowia* and *Schizochytrium*.

Moreover, a host cell host cell culture according to the present invention may also be an animal cell. Preferably, said animal host cell is a host cell of a fish or a cell line obtained therefrom. More preferably, the fish host cell is from herring, salmon, sardine, redfish, eel, carp, trout, halibut, mackerel, zander or tuna.

Generally, the controlling steps in the production of LCPUFAs, i.e., the long chain unsaturated fatty acid biosynthetic pathway, are catalyzed by membrane-associated fatty acid desaturases and elongases. Plants and most other eukaryotic organisms have specialized desaturase and elongase systems for the introduction of double bonds and the extension of fatty acids beyond C18 atoms. The elongase reactions have several important features in common with the fatty acid synthase complex (FAS). However, the elongase complex is different from the FAS complex as the complex is localized in the cytosol and membrane bound, ACP is not involved and the elongase 3-keto-acyl-CoA-synthase catalyzes the condensation of malonyl-CoA with an acyl primer. The elongase complex consists of four components with different catalytic functions, the keto-acyl-synthase (condensation reaction of malonyl-CoA to acyl-CoA, creation of a 2 C atom longer keto-acyl-CoA fatty acid), the keto-acyl-reductase (reduction of the 3-keto group to a 3-hydroxy-group), the dehydratase (dehydration results in a 3-enoyl-acyl-CoA fatty acid) and the enoly-CoA-reductase (reduction of the double bond at position 3, release from the complex). For the production of LCPUFAs including ARA, EPA and/or DHA the elongation reactions, beside the desaturation reactions, are essential. Higher plants do not have the necessary enzyme set to produce LCPUFAs (4 or more double bonds, 20 or more C atoms). Therefore the catalytic activities have to be conferred to the plants or plant cells. The polynucleotides of the present invention catalyze the desaturation and elongation activities necessary for the formation of ARA, EPA and/or DHA. By delivering the novel desaturases and elongases increased levels of PUFAs and LCPUFAs are produced.

However, person skilled in the art knows that dependent on the host cell, further, enzymatic activities may be conferred to the host cells, e.g., by recombinant technologies. Accordingly, the present invention, preferably, envisages a host cell which in addition to the polynucleotide of the present invention comprises polynucleotides encoding such desaturases and/or elongases as required depending on the selected host cell. Preferred desaturases and/or elongases which shall be present in the host cell are at least one enzyme selected from the group consisting of: $\Delta$-4-desaturase, $\Delta$-5-desaturase, $\Delta$-5-elongase, $\Delta$-6-desaturase, $\Delta$12-desaturase, 415-desaturase, $\omega$3-desaturase and $\Delta$-6-elongase. Especially preferred are the bifunctional d12d15-Desaturases d12d15Des(Ac) from *Acanthamoeba castellanii* (WO2007042510), d12d15Des(Cp) from *Claviceps purpurea* (WO2008006202) and d12d15Des(Lg)1 from *Lottia gigantea* (WO2009016202), the d12-Desaturases d12Des (Co) from *Calendula officinalis* (WO200185968), d12Des (Lb) from *Laccaria bicolor* (WO2009016202), d12Des(Mb) from *Monosiga brevicollis* (WO2009016202), d12Des(Mg) from *Mycosphaerella graminicola* (WO2009016202), d12Des(Nh) from *Nectria haematococca* (WO2009016202), d12Des(Ol) from *Ostreococcus lucimarinus* (WO2008040787), d12Des(Pb) from *Phycomyces blakesleeanus* (WO2009016202), d12Des(Ps) from *Phytophthora sojae* (WO2006100241) and d12Des(Tp) from *Thalassiosira pseudonana* (WO2006069710), the d15-Desaturases d15Des(Hr) from *Helobdella robusta* (WO2009016202), d15Des(Mc) from *Microcoleus chthonoplastes* (WO2009016202), d15Des(Mf) from *Mycosphaerella fijiensis* (WO2009016202), d15Des(Mg) from *Mycosphaerella graminicola* (WO2009016202) and d15Des (Nh)2 from *Nectria haematococca* (WO2009016202), the d4-Desaturases d4Des(Eg) from *Euglena gracilis* (WO2004090123), d4Des(Tc) from *Thraustochytrium* sp. (WO2002026946) and d4Des(Tp) from *Thalassiosira pseudonana* (WO2006069710), the d5-Desaturases d5Des (Ol)2 from *Ostreococcus lucimarinus* (WO2008040787), d5Des(Pp) from *Physcomitrella patens* (WO2004057001), d5Des(Pt) from *Phaeodactylum tricornutum*

(WO2002057465), d5Des(Tc) from *Thraustochytrium* sp. (WO2002026946), d5Des(Tp) from *Thalassiosira pseudonana* (WO2006069710) and the d6-Desaturases d6Des(Cp) from *Ceratodon purpureus* (WO2000075341), d6Des(Ol) from *Ostreococcus lucimarinus* (WO2008040787), d6Des(Ot) from *Ostreococcus tauri* (WO2006069710), d6Des(Pf) from *Primula farinosa* (WO2003072784), d6Des(Pir)_BO from *Pythium irregulare* (WO2002026946), d6Des(Pir) from *Pythium irregulare* (WO2002026946), d6Des(Plu) from *Primula luteola* (WO2003072784), d6Des(Pp) from *Physcomitrella patens* (WO200102591), d6Des(Pt) from *Phaeodactylum tricornutum* (WO2002057465), d6Des(Pv) from *Primula vialii* (WO2003072784) and d6Des(Tp) from *Thalassiosira pseudonana* (WO2006069710), the d8-Desaturases d8Des(Ac) from *Acanthamoeba castellanii* (EP1790731), d8Des(Eg) from *Euglena gracilis* (WO200034439) and d8Des(Pm) from *Perkinsus marinus* (WO2007093776), the o3-Desaturases o3Des(Pi) from *Phytophthora infestans* (WO2005083053), o3Des(Pir) from *Pythium irregulare* (WO2008022963), o3Des(Pir)2 from *Pythium irregulare* (WO2008022963) and o3Des(Ps) from *Phytophthora sojae* (WO2006100241), the bifunctional d5d6-elongases d5d6Elo(Om)2 from *Oncorhynchus mykiss* (WO2005012316), d5d6Elo(Ta) from *Thraustochytrium aureum* (WO2005012316) and d5d6Elo(Tc) from *Thraustochytrium* sp. (WO2005012316), the d5-elongases d5Elo(At) from *Arabidopsis thaliana* (WO2005012316), d5Elo(At)2 from *Arabidopsis thaliana* (WO2005012316), d5Elo(Ci) from *Ciona intestinalis* (WO2005012316), d5Elo(Ol) from *Ostreococcus lucimarinus* (WO2008040787), d5Elo(Ot) from *Ostreococcus tauri* (WO2005012316), d5Elo(Tp) from *Thalassiosira pseudonana* (WO2005012316) and d5Elo(Xl) from *Xenopus laevis* (WO2005012316), the d6-elongases d6Elo(Ol) from *Ostreococcus lucimarinus* (WO2008040787), d6Elo(Ot) from *Ostreococcus tauri* (WO2005012316), d6Elo(Pi) from *Phytophthora infestans* (WO2003064638), d6Elo(Pir) from *Pythium irregulare* (WO2009016208), d6Elo(Pp) from *Physcomitrella patens* (WO2001059128), d6Elo(Ps) from *Phytophthora sojae* (WO2006100241), d6Elo(Ps)2 from *Phytophthora sojae* (WO2006100241), d6Elo(Ps)3 from *Phytophthora sojae* (WO2006100241), d6Elo(Pt) from *Phaeodactylum tricornutum* (WO2005012316), d6Elo(Tc) from *Thraustochytrium* sp. (WO2005012316) and d6Elo(Tp) from *Thalassiosira pseudonana* (WO2005012316), the d9-elongases d9Elo (Ig) from *Isochrysis galbana* (WO2002077213), d9Elo(Pm) from *Perkinsus marinus* (WO2007093776) and d9Elo(Ro) from *Rhizopus oryzae* (WO2009016208). Particularly, if the manufacture of ARA is envisaged in higher plants, the enzymes recited in Table 3, below (i.e. additionally a d6-desaturase, d6-elongase, d5-elongase, d5-desaturase, d12-desaturase, and d6-elongase) or enzymes having essentially the same activity may be combined in a host cell. If the manufacture of EPA is envisaged in higher plants, the enzymes having additionally a d6-desaturase, d6-elongase, d5-desaturase, d12-desaturase, d6-elongase, omega 3-desaturase and d15-desaturase, or enzymes having essentially the same activity may be combined in a host cell. If the manufacture of DHA is envisaged in higher plants, the enzymes having additionally a d6-desaturase, d6-elongase, d5-desaturase, d12-desaturase, d6-elongase, omega 3-desaturase, d15-desaturase, d5-elongase, and d4-desaturase activity, or enzymes having essentially the same activity may be combined in a host cell.

The present invention also relates to a cell, preferably a host cell as specified above or a cell of a non-human organism specified elsewhere herein, said cell comprising a polynucleotide which is obtained from the polynucleotide of the present invention by a point mutation, a truncation, an inversion, a deletion, an addition, a substitution and homologous recombination. How to carry out such modifications to a polynucleotide is well known to the skilled artisan and has been described elsewhere in this specification in detail.

The present invention furthermore pertains to a method for the manufacture of a polypeptide encoded by a polynucleotide of any the present invention comprising
a) cultivating the host cell of the invention under conditions which allow for the production of the said polypeptide; and
b) obtaining the polypeptide from the host cell of step a).

Suitable conditions which allow for expression of the polynucleotide of the invention comprised by the host cell depend on the host cell as well as the expression control sequence used for governing expression of the said polynucleotide. These conditions and how to select them are very well known to those skilled in the art. The expressed polypeptide may be obtained, for example, by all conventional purification techniques including affinity chromatography, size exclusion chromatography, high pressure liquid chromatography (HPLC) and precipitation techniques including antibody precipitation. It is to be understood that the method may—although preferred—not necessarily yield an essentially pure preparation of the polypeptide. It is to be understood that depending on the host cell which is used for the aforementioned method, the polypeptides produced thereby may become posttranslationally modified or processed otherwise.

The present invention also encompasses a polypeptide encoded by the polynucleotide of the present invention or which is obtainable by the aforementioned method.

The term "polypeptide" as used herein encompasses essentially purified polypeptides or polypeptide preparations comprising other proteins in addition. Further, the term also relates to the fusion proteins or polypeptide fragments being at least partially encoded by the polynucleotide of the present invention referred to above. Moreover, it includes chemically modified polypeptides. Such modifications may be artificial modifications or naturally occurring modifications such as phosphorylation, glycosylation, myristylation and the like (Review in Mann 2003, Nat. Biotechnol. 21, 255-261, review with focus on plants in Huber 2004, Curr. Opin. Plant Biol. 7, 318-322). Currently, more than 300 posttranslational modifications are known (see full ABFRC Delta mass list at abrforg/index.cfm/dm.home). The polypeptides of the present invention shall exhibit the desaturase or elongase activitiy referred to above.

Moreover, the present invention contemplates a non-human transgenic organism comprising the polynucleotide or the vector of the present invention.

Preferably, the non-human transgenic organism is a plant or a plant part. Preferred plants to be used for introducing the polynucleotide or the vector of the invention are plants which are capable of synthesizing fatty acids, such as all dicotyledonous or monocotyledonous plants, algae or mosses. It is to be understood that host cells derived from a plant may also be used for producing a plant according to the present invention. Preferred plant parts are seeds from the plants. Preferred plants are selected from the group of the plant families Adelotheciaceae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae, Prasinophyceae or vegetable plants or ornamentals such as *Tagetes*. Examples which may be mentioned are the following plants selected from the group consisting of: Adelotheciaceae such as the genera *Physcomitrella*, such as the genus and species *Physcomitrella patens*, Anacardiaceae such as the genera *Pistacia*, *Mangifera*, *Anacardium*, for example the genus and species *Pistacia vera* [pistachio], *Mangifer indica* [mango] or *Anacardium occidentale* [cashew], Asteraceae, such as the genera *Calendula*, *Carthamus*, *Centaurea*, *Cichorium*, *Cynara*, *Helianthus*, *Lactuca*, *Locusta*, *Tagetes*, *Valeriana*, for example the genus and species *Calendula officinalis* [common marigold], *Carthamus tinctorius* [safflower], *Centaurea cyanus* [cornflower], *Cichorium intybus* [chicory], *Cynara scolymus* [artichoke], *Helianthus annus* [sunflower], *Lactuca sativa*, *Lactuca crispa*, *Lactuca esculenta*, *Lactuca scariola* L. ssp. *sativa*, *Lactuca scariola* L. var. *integrate*, *Lactuca scariola* L. var. *integrifolia*, *Lactuca sativa* subsp. *romana*, *Locusta communis*, *Valeriana locusta* [salad vegetables], *Tagetes lucida*, *Tagetes erecta* or *Tagetes tenuifolia* [african or french marigold], Apiaceae, such as the genus *Daucus*, for example the genus and species *Daucus carota* [carrot], Betulaceae, such as the genus *Corylus*, for example the genera and species *Corylus avellana* or *Corylus colurna* [hazelnut], Boraginaceae, such as the genus *Borago*, for example the genus and species *Borago officinalis* [borage], Brassicaceae, such as the genera *Brassica*, *Melanosinapis*, *Sinapis*, *Arabadopsis*, for example the genera and species *Brassica napus*, *Brassica rapa* ssp. [oilseed rape], *Sinapis arvensis Brassica juncea*, *Brassica juncea* var. *juncea*, *Brassica juncea* var. *crispifolia*, *Brassica juncea* var. *foliosa*, *Brassica nigra*, *Brassica sinapioides*, *Melanosinapis communis* [mustard], *Brassica oleracea* [fodder beet] or *Arabidopsis thaliana*, Bromeliaceae, such as the genera *Anana*, *Bromelia* (pineapple), for example the genera and species *Anana comosus*, *Ananas ananas* or *Bromelia comosa* [pineapple], Caricaceae, such as the genus *Carica*, such as the genus and species *Carica papaya* [pawpaw], Cannabaceae, such as the genus *Cannabis*, such as the genus and species *Cannabis sativa* [hemp], Convolvulaceae, such as the genera *Ipomea*, *Convolvulus*, for example the genera and species *Ipomoea batatus*, *Ipomoea pandurata*, *Convolvulus batatas*, *Convolvulus tiliaceus*, *Ipomoea fastigiata*, *Ipomoea tiliacea*, *Ipomoea triloba* or *Convolvulus panduratus* [sweet potato, batate], Chenopodiaceae, such as the genus *Beta*, such as the genera and species *Beta vulgaris*, *Beta vulgaris* var. *altissima*, *Beta vulgaris* var. *Vulgaris*, *Beta maritima*, *Beta vulgaris* var. *perennis*, *Beta vulgaris* var. *conditiva* or *Beta vulgaris* var. *esculenta* [sugarbeet], Crypthecodiniaceae, such as the genus *Crypthecodinium*, for example the genus and species *Cryptecodinium cohnii*, Cucurbitaceae, such as the genus *Cucurbita*, for example the genera and species *Cucurbita maxima*, *Cucurbita mixta*, *Cucurbita pepo* or *Cucurbita moschata* [pumpkin/squash], Cymbellaceae such as the genera *Amphora*, *Cymbella*, *Okedenia*, *Phaeodactylum*, *Reimeria*, for example the genus and species *Phaeodactylum tricornutum*, Ditrichaceae such as the genera *Ditrichaceae*, *Astomiopsis*, *Ceratodon*, *Chrysoblastella*, *Ditrichum*, *Distichium*, *Eccremidium*, *Lophidion*, *Philibertiella*, *Pleuridium*, *Saelania*, *Trichodon*, *Skottsbergia*, for example the genera and species *Ceratodon antarcticus*, *Ceratodon columbiae*, *Ceratodon heterophyllus*, *Ceratodon purpureus*, *Ceratodon purpureus*, *Ceratodon purpureus* ssp. *convolutus*, *Ceratodon*, *purpureus* spp. *stenocarpus*, *Ceratodon purpureus* var. *rotundifolius*, *Ceratodon ratodon*, *Ceratodon stenocarpus*, *Chrysoblastella chilensis*, *Ditrichum ambiguum*, *Ditrichum brevisetum*, *Ditrichum crispatissimum*, *Ditrichum difficile*, *Ditrichum falcifolium*, *Ditrichum flexicaule*, *Ditrichum giganteum*, *Ditrichum heteromallum*, *Ditrichum lineare*, *Ditrichum lineare*, *Ditrichum montanum*, *Ditrichum montanum*, *Ditrichum pallidum*, *Ditrichum punctulatum*, *Ditrichum pusillum*, *Ditrichum pusillum* var. *tortile*, *Ditrichum rhynchostegium*, *Ditrichum schimperi*, *Ditrichum tortile*, *Distichium capillaceum*, *Distichium hagenii*, *Distichium inclinatum*, *Distichium macounii*, *Eccremidium floridanum*, *Eccremidium whiteleggei*, *Lophidion strictus*, *Pleuridium acuminatum*, *Pleuridium alternifolium*, *Pleuridium holdridgei*, *Pleuridium mexicanum*, *Pleuridium ravenelii*, *Pleuridium subulatum*, *Saelania glaucescens*, *Trichodon borealis*, *Trichodon cylindricus* or *Trichodon cylindricus* var. *oblongus*, Elaeagnaceae such as the genus *Elaeagnus*, for example the genus and species *Olea europaea* [olive], Ericaceae such as the genus *Kalmia*, for example the genera and species *Kalmia latifolia*, *Kalmia angustifolia*, *Kalmia microphylla*, *Kalmia polifolia*, *Kalmia occidentalis*, *Cistus chamaerhodendros* or *Kalmia lucida* [mountain laurel], Euphorbiaceae such as the genera *Manihot*, *Janipha*, *Jatropha*, *Ricinus*, for example the genera and species *Manihot utilissima*, *Janipha manihot*, *Jatropha manihot*, *Manihot aipil*, *Manihot dulcis*, *Manihot manihot*, *Manihot melanobasis*, *Manihot esculenta* [manihot] or *Ricinus communis* [castor-oil plant], Fabaceae such as the genera *Pisum*, *Albizia*, *Cathormion*, *Feuillea*, *Inga*, *Pithecolobium*, *Acacia*, *Mimosa*, *Medicajo*, *Glycine*, *Dolichos*, *Phaseolus*, *Soja*, for example the genera and species *Pisum sativum*, *Pisum arvense*, *Pisum humile* [pea], *Albizia berteriana*, *Albizia julibrissin*, *Albizia lebbeck*, *Acacia berteriana*, *Acacia littoralis*, *Albizia berteriana*, *Albizzia berteriana*, *Cathormion berteriana*, *Feuillea berteriana*, *Inga fragrans*, *Pithecellobium berterianum*, *Pithecellobium fragrans*, *Pithecolobium berterianum*, *Pseudalbizzia berteriana*, *Acacia julibrissin*, *Acacia nemu*, *Albizia nemu*, *Feuilleea julibrissin*, *Mimosa julibrissin*, *Mimosa speciosa*, *Sericanrda julibrissin*, *Acacia lebbeck*, *Acacia macrophylla*, *Albizia lebbk*, *Feuilleea lebbeck*, *Mimosa lebbeck*, *Mimosa speciosa* [silk tree], *Medicago sativa*, *Medicago falcata*, *Medicago varia* [alfalfa], *Glycine max Dolichos soja*, *Glycine gracilis*, *Glycine hispida*, *Phaseolus max*, *Soja hispida* or *Soja max* [soybean], Funariaceae such as the genera *Aphanorrhegma*, *Entosthodon*, *Funaria*, *Physcomitrella*, *Physcomitrium*, for example the genera and species *Aphanorrhegma serratum*, *Entosthodon attenuatus*, *Entosthodon bolanderi*, *Entosthodon bonplandii*, *Entosthodon californicus*, *Entosthodon drummondii*, *Entosthodon jamesonii*, *Entosthodon leibergii*, *Entosthodon neoscoticus*, *Entosthodon rubrisetus*, *Entosthodon spathulifolius*, *Entosthodon tucsoni*, *Funaria americana*, *Funaria bolanderi*, *Funaria calcarea*, *Funaria californica*, *Funaria calvescens*, *Funaria convoluta*, *Funaria flavicans*, *Funaria groutiana*, *Funaria hygrometrica*, *Funaria hygrometrica* var. *arctica*, *Funaria hygrometrica* var. *calvescens*, *Funaria hygrometrica* var. *convoluta*, *Funaria hygrometrica* var. *muralis*, *Funaria hygrometrica* var. *utahensis*, *Funaria microstoma*, *Funaria microstoma* var. *obtusifolia*, *Funaria muhlenbergii*, *Funaria orcuttii*, *Funaria plano-convexa*, *Funaria polaris*, *Funaria ravenelii*, *Funaria rubriseta*, *Funaria serrata*, *Funaria sonorae*, *Funaria sublimbatus*, *Funaria tucsoni*, *Physcomitrella californica*, *Physcomitrella patens*, *Physcomitrella readeri*, *Physcomitrium australe*, *Physcomitrium californicum*, *Physcomitrium collenchymatum*, *Physcomitrium coloradense*, *Physcomitrium cupuliferum*, *Physcomitrium drummondii*, *Physcomitrium eurystomum*, *Physcomitrium flexifolium*, *Physcomitrium hookeri*, *Physcomitrium hookeri* var. *serratum*, *Physcomitrium immersum*, *Physcomitrium*

*kellermanii, Physcomitrium megalocarpum, Physcomitrium pyriforme, Physcomitrium pyriforme* var. *serratum, Physcomitrium rufipes, Physcomitrium sandbergii, Physcomitrium subsphaericum, Physcomitrium washingtoniense,* Geraniaceae, such as the genera *Pelargonium, Cocos, Oleum,* for example the genera and species *Cocos nucifera, Pelargonium grossularioides* or *Oleum cocois* [coconut], Gramineae, such as the genus *Saccharum,* for example the genus and species *Saccharum officinarum,* Juglandaceae, such as the genera *Juglans, Wallia,* for example the genera and species *Juglans regia, Juglans ailanthifolia, Juglans sieboldiana, Juglans cinerea, Wallia cinerea, Juglans bixbyi, Juglans californica, Juglans hindsii, Juglans intermedia, Juglans jamaicensis, Juglans major, Juglans microcarpa, Juglans nigra* or *Wallia nigra* [walnut], Lauraceae, such as the genera *Persea, Laurus,* for example the genera and species *Laurus nobilis* [bay], *Persea americana, Persea gratissima* or *Persea persea* [avocado], Leguminosae, such as the genus *Arachis,* for example the genus and species *Arachis hypogaea* [peanut], Linaceae, such as the genera *Linum, Adenolinum,* for example the genera and species *Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense* or *Linum trigynum* [linseed], Lythrarieae, such as the genus *Punica,* for example the genus and species *Punica granatum* [pomegranate], Malvaceae, such as the genus *Gossypium,* for example the genera and species *Gossypium hirsutum, Gossypium arboreum, Gossypium barbadense, Gossypium herbaceum* or *Gossypium thurberi* [cotton], Marchantiaceae, such as the genus *Marchantia,* for example the genera and species *Marchantia berteroana, Marchantia foliacea, Marchantia macropora,* Musaceae, such as the genus *Musa,* for example the genera and species *Musa nana, Musa acuminata, Musa paradisiaca, Musa* spp. [banana], Onagraceae, such as the genera *Camissonia, Oenothera,* for example the genera and species *Oenothera biennis* or *Camissonia brevipes* [evening primrose], Palmae, such as the genus *Elacis,* for example the genus and species *Elaeis guineensis* [oil palm], Papaveraceae, such as the genus *Papaver,* for example the genera and species *Papaver orientale, Papaver rhoeas, Papaver dubium* [poppy], Pedaliaceae, such as the genus *Sesamum,* for example the genus and species *Sesamum indicum* [sesame], Piperaceae, such as the genera *Piper, Artanthe, Peperomia, Steffensia,* for example the genera and species *Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata* [cayenne pepper], Poaceae, such as the genera *Hordeum, Secale, Avena, Sorghum, Andropogon, Holcus, Panicum, Oryza, Zea* (maize), *Triticum,* for example the genera and species *Hordeum vulgare, Hordeum jubatum, Hordeum murinum, Hordeum secalinum, Hordeum distichon, Hordeum aegiceras, Hordeum hexastichon, Hordeum hexastichum, Hordeum irregulare, Hordeum sativum, Hordeum secalinum* [barley], *Secale cereale* [rye], *Avena sativa, Avena fatua, Avena byzantina, Avena fatua* var. *sativa, Avena hybrida* [oats], *Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum, Panicum militaceum* [millet], *Oryza sativa, Oryza latifolia* [rice], *Zea mays* [maize], *Triticum aestivum, Triticum durum, Triticum turgidum, Triticum hybernum, Triticum macha, Triticum sativum* or *Triticum vulgare* [wheat], Porphyridiaceae, such as the genera *Chroothece, Flintiella, Petrovanella, Porphyridium, Rhodella, Rhodosorus, Vanhoeffenia,* for example the genus and species *Porphyridium cruentum,* Proteaceae, such as the genus *Macadamia,* for example the genus and species *Macadamia intergrifolia* [macadamia], Prasinophyceae such as the genera *Nephroselmis, Prasinococcus, Scherffelia, Tetraselmis, Mantoniella, Ostreococcus,* for example the genera and species *Nephroselmis olivacea, Prasinococcus capsulatus, Scherffelia dubia, Tetraselmis chui, Tetraselmis suecica, Mantoniella squamata, Ostreococcus tauri,* Rubiaceae such as the genus *Cofea,* for example the genera and species *Cofea* spp., *Coffea arabica, Coffea canephora* or *Coffea liberica* [coffee], Scrophulariaceae such as the genus *Verbascum,* for example the genera and species *Verbascum blattaria, Verbascum chaixii, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentum* or *Verbascum thapsus* [mullein], Solanaceae such as the genera *Capsicum, Nicotiana, Solanum, Lycopersicon,* for example the genera and species *Capsicum annuum, Capsicum annuum* var. *glabriusculum, Capsicum frutescens* [pepper], *Capsicum annuum* [paprika], *Nicotiana tabacum, Nicotiana alata, Nicotiana attenuata, Nicotiana glauca, Nicotiana langsdorffii, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [eggplant], *Lycopersicon esculentum, Lycopersicon lycopersicum, Lycopersicon pyriforme, Solanum integrifolium* or *Solanum lycopersicum* [tomato], Sterculiaceae, such as the genus *Theobroma,* for example the genus and species *Theobroma cacao* [cacao] or Theaceae, such as the genus *Camellia,* for example the genus and species *Camellia sinensis* [tea]. In particular preferred plants to be used as transgenic plants in accordance with the present invention are oil fruit crops which comprise large amounts of lipid compounds, such as peanut, oilseed rape, canola, sunflower, safflower, poppy, mustard, hemp, castor-oil plant, olive, sesame, *Calendula, Punica,* evening primrose, mullein, thistle, wild roses, hazelnut, almond, *macadamia,* avocado, bay, pumpkin/squash, linseed, soybean, pistachios, borage, trees (oil palm, coconut, walnut) or crops such as maize, wheat, rye, oats, triticale, rice, barley, cotton, cassava, pepper, *Tagetes,* Solanaceae plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, *Calendula, Punica,* evening primrose, pumpkin/squash, linseed, soybean, borage, trees (oil palm, coconut). Especially preferred are sunflower, safflower, tobacco, mullein, sesame, cotton, pumpkin/squash, poppy, evening primrose, walnut, linseed, hemp, thistle or safflower. Very especially preferred plants are plants such as safflower, sunflower, poppy, evening primrose, walnut, linseed, or hemp.

Preferred mosses are *Physcomitrella* or *Ceratodon.* Preferred algae are *Isochrysis, Mantoniella, Ostreococcus* or *Crypthecodinium,* and algae/diatoms such as *Phaeodacty-*

*lum* or *Thraustochytrium*. More preferably, said algae or mosses are selected from the group consisting of: *Emiliana, Shewanella, Physcomitrella, Thraustochytrium, Fusarium, Phytophthora, Ceratodon, Isochrysis, Aleurita, Muscarioides, Mortierella, Phaeodactylum, Cryphthecodinium*, specifically from the genera and species *Thallasiosira pseudonona, Euglena gracilis, Physcomitrella patens, Phytophtora infestans, Fusarium graminaeum, Cryptocodinium cohnii, Ceratodon purpureus, Isochrysis galbana, Aleurita farinosa, Thraustochytrium sp., Muscarioides viallii, Mortierella alpina, Phaeodactylum tricornutum* or *Caenorhabditis elegans* or especially advantageously *Phytophtora infestans, Thallasiosira pseudonona* and *Cryptocodinium cohnii*.

Transgenic plants may be obtained by transformation techniques as elsewhere in this specification. Preferably, transgenic plants can be obtained by T-DNA-mediated transformation. Such vector systems are, as a rule, characterized in that they contain at least the vir genes, which are required for the *Agrobacterium*-mediated transformation, and the sequences which delimit the T-DNA (T-DNA border). Suitable vectors are described elsewhere in the specification in detail.

Also encompassed are transgenic non-human animals comprising the vector or polynucleotide of the present invention. Preferred non-human transgenic animals envisaged by the present invention are fish, such as herring, salmon, sardine, redfish, eel, carp, trout, halibut, mackerel, zander or tuna.

However, it will be understood that dependent on the non-human transgenic organism specified above, further, enzymatic activities may be conferred to the said organism, e.g., by recombinant technologies. Accordingly, the present invention, preferably, envisages a non-human transgenic organism specified above which in addition to the polynucleotide of the present invention comprises polynucleotides encoding such desaturases and/or elongases as required depending on the selected host cell. Preferred desaturases and/or elongases which shall be present in the organism are at least one enzyme selected from the group of desaturases and/or elongases or the combinations specifically recited elsewhere in this specification (see above and Tables 3, 4 and 5).

Furthermore, the present invention encompasses a method for the manufacture of polyunsaturated fatty acids comprising:
  a) cultivating the host cell of the invention under conditions which allow for the production of polyunsaturated fatty acids in said host cell;
  b) obtaining said polyunsaturated fatty acids from the said host cell.

The term "polyunsaturated fatty acids (PUFA)" as used herein refers to fatty acids comprising at least two, preferably, three, four, five or six, double bonds. Moreover, it is to be understood that such fatty acids comprise, preferably from 18 to 24 carbon atoms in the fatty acid chain. More preferably, the term relates to long chain PUFA (LCPUFA) having from 20 to 24 carbon atoms in the fatty acid chain. Preferred unsaturated fatty acids in the sense of the present invention are selected from the group consisting of DGLA 20:3 (8,11,14), ARA 20:4 (5,8,11,14), iARA 20:4(8,11,14,17), EPA 20:5 (5,8,11,14,17), DPA 22:5 (4,7,10,13,16), DHA 22:6 (4,7,10,13,16,19), 20:4 (8,11,14,17), more preferably, arachidonic acid (ARA) 20:4 (5,8,11,14), eicosapentaenoic acid (EPA) 20:5 (5,8,11,14,17), and docosahexaenoic acid (DHA) 22:6 (4,7,10,13,16,19). Thus, it will be understood that most preferably, the methods provided by the present invention pertaining to the manufacture of ARA, EPA or DHA. Moreover, also encompassed are the intermediates of LCPUFA which occur during synthesis. Such intermediates are, preferably, formed from substrates by the desaturase or elongase activity of the polypeptides of the present invention. Preferably, substrates encompass LA 18:2 (9,12), ALA 18:3(9,12,15), Eicosadienoic acid 20:2 (11,14), Eicosatrienoic acid 20:3 (11,14,17)), DGLA 20:3 (8,11,14), ARA 20:4 (5,8,11,14), eicosatetraenoic acid 20:4 (8,11,14, 17), Eicosapentaenoic acid 20:5 (5,8,11,14,17), Docosahexapentanoic acid 22:5 (7,10,13,16,19).

The term "cultivating" as used herein refers maintaining and growing the host cells under culture conditions which allow the cells to produce the said polyunsaturated fatty acid, i.e. the PUFA and/or LCPUFA referred to above. This implies that the polynucleotide of the present invention is expressed in the host cell so that the desaturase and/or elongase activity is present. Suitable culture conditions for cultivating the host cell are described in more detail below.

The term "obtaining" as used herein encompasses the provision of the cell culture including the host cells and the culture medium as well as the provision of purified or partially purified preparations thereof comprising the polyunsaturated fatty acids, preferably, ARA, EPA, DHA, in free or in -CoA bound form, as membrane phospholipids or as triacylglyceride estres. More preferably, the PUFA and LCPUFA are to be obtained as triglyceride esters, e.g., in form of an oil. More details on purification techniques can be found elsewhere herein below.

The host cells to be used in the method of the invention are grown or cultured in the manner with which the skilled worker is familiar, depending on the host organism. Usually, host cells are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C. under oxygen or anaerobic atmosphere dependent on the type of organism. The pH of the liquid medium can either be kept constant, that is to say regulated during the culturing period, or not. The cultures can be grown batchwise, semibatchwise or continuously. Nutrients can be provided at the beginning of the fermentation or administered semicontinuously or continuously: The produced PUFA or LCPUFA can be isolated from the host cells as described above by processes known to the skilled worker, e.g., by extraction, distillation, crystallization, if appropriate precipitation with salt, and/or chromatography. It might be required to disrupt the host cells prior to purification. To this end, the host cells can be disrupted beforehand. The culture medium to be used must suitably meet the requirements of the host cells in question. Descriptions of culture media for various microorganisms which can be used as host cells according to the present invention can be found in the textbook "Manual of Methods for General Bacteriology" of the American Society for Bacteriology (Washington D.C., USA, 1981). Culture media can also be obtained from various commercial suppliers. All media components are sterilized, either by heat or by filter sterilization. All media components may be present at the start of the cultivation or added continuously or batchwise, as desired. If the polynucleotide or vector of the invention which has been introduced in the host cell further comprises an expressible selection marker, such as an antibiotic resistance gene, it might be necessary to add a selection agent to the culture, such as a antibiotic in order to maintain the stability of the introduced polynucleotide. The culture is continued until formation of the desired product is at a maximum. This is normally achieved within 10 to 160 hours. The fermentation broths can be used directly or can be processed further. The biomass may, according to requirement, be removed completely or partially from the fermentation broth by separation methods such as, for example, centrifugation, filtration, decanting or a combination of these methods or be left completely in said broth. The fatty acid preparations obtained by the method of the invention, e.g., oils, comprising the desired PUFA or LCPUFA as triglyceride esters are also suitable as starting material for the chemical synthesis of further products of interest. For example, they can be used in combination with one another or alone for the preparation of pharmaceutical or cosmetic compositions, foodstuffs, or animal feeds. Chemically pure triglycerides comprising the desired PUFA or LCPUFA can also be manufactured by the methods described above. To this end, the fatty acid preparations are further purified by extraction, distillation, crystallization, chromatography or combinations of these methods. In order to release the fatty acid moieties from the triglycerides, hydrolysis may be also required. The said chemically pure triglycerides or free fatty acids are, in particular, suitable for applications in the food industry or for cosmetic and pharmacological compositions.

Moreover, the present invention relates to a method for the manufacture of poly-unsaturated fatty acids comprising:
a) cultivating the non-human transgenic organism of the invention under conditions which allow for the production of poly-unsaturated fatty acids in said non-human transgenic organism; and
b) obtaining said poly-unsaturated fatty acids from the said non-human transgenic organism.

Further, it follows from the above that a method for the manufacture of an oil, lipid or fatty acid composition is also envisaged by the present invention comprising the steps of any one of the aforementioned methods and the further step of formulating PUFA or LCPUFA as oil, lipid or fatty acid composition. Preferably, said oil, lipid or fatty acid composition is to be used for feed, foodstuffs, cosmetics or medicaments. Accordingly, the formulation of the PUFA or LCPUFA shall be carried out according to the GMP standards for the individual envisaged products. For example, an oil may be obtained from plant seeds by an oil mill. However, for product safety reasons, sterilization may be required under the applicable GMP standard. Similar standards will apply for lipid or fatty acid compositions to be applied in cosmetic or pharmaceutical compositions. All these measures for formulating oil, lipid or fatty acid compositions as products are comprised by the aforementioned manufacture.

The term "oil" refers to a fatty acid mixture comprising unsaturated and/or saturated fatty acids which are esterified to triglycerides. Preferably, the triglycerides in the oil of the invention comprise PUFA or LCPUFA as referred to above. The amount of esterified PUFA and/or LCPUFA is, preferably, approximately 30%, a content of 50% is more preferred, a content of 60%, 70%, 80% or more is even more preferred. The oil may further comprise free fatty acids, preferably, the PUFA and LCPUFA referred to above. For the analysis, the fatty acid content can be, e.g., determined by GC analysis after converting the fatty acids into the methyl esters by transesterification. The content of the various fatty acids in the oil or fat can vary, in particular depending on the source. The oil, however, shall have a non-naturally occurring composition with respect to the PUFA and/or LCPUFA composition and content. It will be understood that such a unique oil composition and the unique esterification pattern of PUFA and LCPUFA in the triglycerides of the oil shall only be obtainable by applying the methods of the present invention specified above. Moreover, the oil of the invention may comprise other molecular species as well. Specifically, it may comprise minor impurities of the polynucleotide or vector of the invention. Such impurities, however, can be detected only by highly sensitive techniques such as PCR.

Another embodiment is the use of the polynucleotide comprising NEENA or the recombinant vector comprising the polynucleotide with NEENA as defined above for enhancing expression of at least one enzyme of the polyunsaturated fatty acid biosynthetic pathway as defined in plants or parts thereof, in a more preferably embodiment the polynucleotide comprising NEENA or the recombinant vector comprising the polynucleotide with NEENA as defined above for enhancing expression of at least one enzyme of the polyunsaturated fatty acid biosynthetic pathway is used in plant seeds.

Another preferred embodiment is the use of a host cell or a host cell culture or of a non-human transgenic organism, transgenic plant, plant parts or plant seeds derived from the transgenic non-human organism or plant as described above for the production of foodstuffs, animal feeds, seeds, pharmaceuticals or fine chemicals.

DEFINITIONS

Abbreviations: NEENA—nucleic acid expression enhancing nucleic acid, GFP—green fluorescence protein, GUS—beta-Glucuronidase, BAP—6-benzylaminopurine; MS—Murashige and Skoog medium; Kan: Kanamycin sulfate; GA3—Gibberellic acid; microl: Microliter.

It is to be understood that this invention is not limited to the particular methodology or protocols. It is also to be understood that the terminology used herein is for the purpose of describing particular embodiments only, and is not intended to limit the scope of the present invention which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth. The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). As used herein, the word "or" means any one member of a particular list and also includes any combination of members of that list. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. For clarity, certain terms used in the specification are defined and used as follows:

Antiparallel: "Antiparallel" refers herein to two nucleotide sequences paired through hydrogen bonds between complementary base residues with phosphodiester bonds running in the 5'-3' direction in one nucleotide sequence and in the 3'-5' direction in the other nucleotide sequence.

Antisense: The term "antisense" refers to a nucleotide sequence that is inverted relative to its normal orientation for transcription or function and so expresses an RNA transcript that is complementary to a target gene mRNA molecule expressed within the host cell (e.g., it can hybridize to the target gene mRNA molecule or single stranded genomic DNA through Watson-Crick base pairing) or that is complementary to a target DNA molecule such as, for example genomic DNA present in the host cell.

Coding region: As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5'-side by the nucleotide triplet "ATG" which encodes the initiator methionine and on the 3'-side by one of the three triplets which specify stop codons (i.e., TAA, TAG, TGA). In addition to containing introns, genomic forms of a gene may also include sequences located on both the 5'- and 3'-end of the sequences which are present on the RNA transcript. These sequences are referred to as "flanking" sequences or regions (these flanking sequences are located 5' or 3' to the non-translated sequences present on the mRNA transcript). The 5'-flanking region may contain regulatory sequences such as promoters and enhancers which control or influence the transcription of the gene. The 3'-flanking region may contain sequences which direct the termination of transcription, post-transcriptional cleavage and polyadenylation.

Complementary: "Complementary" or "complementarity" refers to two nucleotide sequences which comprise antiparallel nucleotide sequences capable of pairing with one another (by the base-pairing rules) upon formation of hydrogen bonds between the complementary base residues in the antiparallel nucleotide sequences. For example, the sequence 5'-AGT-3' is complementary to the sequence 5'-ACT-3'. Complementarity can be "partial" or "total." "Partial" complementarity is where one or more nucleic acid bases are not matched according to the base pairing rules. "Total" or "complete" complementarity between nucleic acid molecules is where each and every nucleic acid base is matched with another base under the base pairing rules. The degree of complementarity between nucleic acid molecule strands has significant effects on the efficiency and strength of hybridization between nucleic acid molecule strands. A "complement" of a nucleic acid sequence as used herein refers to a nucleotide sequence whose nucleic acid molecules show total complementarity to the nucleic acid molecules of the nucleic acid sequence.

Double-stranded RNA: A "double-stranded RNA" molecule or "dsRNA" molecule comprises a sense RNA fragment of a nucleotide sequence and an antisense RNA fragment of the nucleotide sequence, which both comprise nucleotide sequences complementary to one another, thereby allowing the sense and antisense RNA fragments to pair and form a double-stranded RNA molecule.

Endogenous: An "endogenous" nucleotide sequence refers to a nucleotide sequence, which is present in the genome of the untransformed plant cell.

Enhanced expression: "enhance" or "increase" the expression of a nucleic acid molecule in a plant cell are used equivalently herein and mean that the level of expression of the nucleic acid molecule in a plant, part of a plant or plant cell after applying a method of the present invention is higher than its expression in the plant, part of the plant or plant cell before applying the method, or compared to a reference plant lacking a recombinant nucleic acid molecule of the invention. For example, the reference plant is comprising the same construct which is only lacking the respective NEENA. The term "enhanced" or "increased" as used herein are synonymous and means herein higher, preferably significantly higher expression of the nucleic acid molecule to be expressed. As used herein, an "enhancement" or "increase" of the level of an agent such as a protein, mRNA or RNA means that the level is increased relative to a substantially identical plant, part of a plant or plant cell grown under substantially identical conditions, lacking a recombinant nucleic acid molecule of the invention, for example lacking the NEENA molecule, the recombinant construct or recombinant vector of the invention. As used herein, "enhancement" or "increase" of the level of an agent, such as for example a preRNA, mRNA, rRNA, tRNA, snoRNA, snRNA expressed by the target gene and/or of the protein product encoded by it, means that the level is increased 50% or more, for example 100% or more, preferably 200% or more, more preferably 5 fold or more, even more preferably 10 fold or more, most preferably 20 fold or more for example 50 fold relative to a cell or organism lacking a recombinant nucleic acid molecule of the invention. The enhancement or increase can be determined by methods with which the skilled worker is familiar. Thus, the enhancement or increase of the nucleic acid or protein quantity can be determined for example by an immunological detection of the protein. Moreover, techniques such as protein assay, fluorescence, Northern hybridization, nuclease protection assay, reverse transcription (quantitative RT-PCR), ELISA (enzyme-linked immunosorbent assay), Western blotting, radioimmunoassay (RIA) or other immunoassays and fluorescence-activated cell analysis (FACS) can be employed to measure a specific protein or RNA in a plant or plant cell. Depending on the type of the induced protein product, its activity or the effect on the phenotype of the organism or the cell may also be determined. Methods for determining the protein quantity are known to the skilled worker. Examples, which may be mentioned, are: the micro-Biuret method (Goa J (1953) Scand J Clin Lab Invest 5:218-222), the Folin-Ciocalteau method (Lowry O H et al. (1951) J Biol Chem 193:265-275) or measuring the absorption of CBB G-250 (Bradford M M (1976) Analyt Biochem 72:248-254). As one example for quantifying the activity of a protein, the detection of luciferase activity is described in the Examples below.

Expression: "Expression" refers to the biosynthesis of a gene product, preferably to the transcription and/or translation of a nucleotide sequence, for example an endogenous gene or a heterologous gene, in a cell. For example, in the case of a structural gene, expression involves transcription of the structural gene into mRNA and—optionally—the subsequent translation of mRNA into one or more polypeptides. In other cases, expression may refer only to the transcription of the DNA harboring an RNA molecule.

Expression construct: "Expression construct" as used herein mean a DNA sequence capable of directing expression of a particular nucleotide sequence in an appropriate part of a plant or plant cell, comprising a promoter functional in said part of a plant or plant cell into which it will be introduced, operatively linked to the nucleotide sequence of interest which is—optionally—operatively linked to termination signals. If translation is required, it also typically comprises sequences required for proper translation of the nucleotide sequence. The coding region may code for a protein of interest but may also code for a functional RNA of interest, for example RNAa, siRNA, snoRNA, snRNA, microRNA, ta-siRNA or any other noncoding regulatory RNA, in the sense or antisense direction. The expression construct comprising the nucleotide sequence of interest may be chimeric, meaning that one or more of its components is heterologous with respect to one or more of its other components. The expression construct may also be one, which is naturally occurring but has been obtained in a recombinant form useful for heterologous expression. Typically, however, the expression construct is heterologous with respect to the host, i.e., the particular DNA sequence of the expression construct does not occur naturally in the host cell and must have been introduced into the host cell or an ancestor of the host cell by a transformation event. The expression of the nucleotide sequence in the expression construct may be under the control of a seed-specific promoter or of an inducible promoter, which initiates transcription only when the host cell is exposed to some particular external stimulus. In the case of a plant, the promoter can also be specific to a particular tissue or organ or stage of development.

Foreign: The term "foreign" refers to any nucleic acid molecule (e.g., gene sequence) which is introduced into the genome of a cell by experimental manipulations and may include sequences found in that cell so long as the introduced sequence contains some modification (e.g., a point mutation, the presence of a selectable marker gene, etc.) and is therefore distinct relative to the naturally-occurring sequence.

Functional linkage: The term "functional linkage" or "functionally linked" is to be understood as meaning, for example, the sequential arrangement of a regulatory element (e.g. a promoter) with a nucleic acid sequence to be expressed and, if appropriate, further regulatory elements (such as e.g., a terminator or a NEENA) in such a way that each of the regulatory elements can fulfill its intended function to allow, modify, facilitate or otherwise influence expression of said nucleic acid sequence. As a synonym the wording "operable linkage" or "operably linked" may be used. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as promoter, so that the two sequences are linked covalently to each other. The distance between the promoter sequence and the nucleic acid sequence to be expressed recombinantly is preferably less than 200 base pairs, especially preferably less than 100 base pairs, very especially preferably less than 50 base pairs. In a preferred embodiment, the nucleic acid sequence to be transcribed is located behind the promoter in such a way that the transcription start is identical with the desired beginning of the chimeric RNA of the invention. Functional linkage, and an expression construct, can be generated by means of customary recombination and cloning techniques as described (e.g., in Maniatis T, Fritsch E F and Sambrook J (1989) Molecular Cloning: A Laboratory Manual, 2nd Ed., Cold Spring Harbor Laboratory, Cold Spring Harbor (NY); Silhavy et al. (1984) Experiments with Gene Fusions, Cold Spring Harbor Laboratory, Cold Spring Harbor (NY); Ausubel et al. (1987) Current Protocols in Molecular Biology, Greene Publishing Assoc. and Wiley Interscience; Gelvin et al. (Eds) (1990) Plant Molecular Biology Manual; Kluwer Academic Publisher, Dordrecht, The Netherlands). However, further sequences, which, for example, act as a linker with specific cleavage sites for restriction enzymes, or as a signal peptide, may also be positioned between the two sequences. The insertion of sequences may also lead to the expression of fusion proteins. Preferably, the expression construct, consisting of a linkage of a regulatory region for example a promoter and nucleic acid sequence to be expressed, can exist in a vector-integrated form and be inserted into a plant genome, for example by transformation.

Gene: The term "gene" refers to a region operably joined to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (downstream) the coding region (open reading frame, ORF) as well as, where applicable, intervening sequences (i.e., introns) between individual coding regions (i.e., exons). The term "structural gene" as used herein is intended to mean a DNA sequence that is transcribed into mRNA which is then translated into a sequence of amino acids characteristic of a specific polypeptide.

Genome and genomic DNA: The terms "genome" or "genomic DNA" is referring to the heritable genetic information of a host organism. Said genomic DNA comprises the DNA of the nucleus (also referred to as chromosomal DNA) but also the DNA of the plastids (e.g., chloroplasts) and other cellular organelles (e.g., mitochondria). Preferably the terms genome or genomic DNA is referring to the chromosomal DNA of the nucleus.

Heterologous: The term "heterologous" with respect to a nucleic acid molecule or DNA refers to a nucleic acid molecule which is operably linked to, or is manipulated to become operably linked to, a second nucleic acid molecule to which it is not operably linked in nature, or to which it is operably linked at a different location in nature. A heterologous expression construct comprising a nucleic acid molecule and one or more regulatory nucleic acid molecule (such as a promoter or a transcription termination signal) linked thereto for example is a constructs originating by experimental manipulations in which either a) said nucleic acid molecule, or b) said regulatory nucleic acid molecule or c) both (i.e. (a) and (b)) is not located in its natural (native) genetic environment or has been modified by experimental manipulations, an example of a modification being a substitution, addition, deletion, inversion or insertion of one or more nucleotide residues. Natural genetic environment refers to the natural chromosomal locus in the organism of origin, or to the presence in a genomic library. In the case of a genomic library, the natural genetic environment of the sequence of the nucleic acid molecule is preferably retained, at least in part. The environment flanks the nucleic acid sequence at least at one side and has a sequence of at least 50 bp, preferably at least 500 bp, especially preferably at least 1,000 bp, very especially preferably at least 5,000 bp, in length. A naturally occurring expression construct—for example the naturally occurring combination of a promoter with the corresponding gene—becomes a transgenic expression construct when it is modified by non-natural, synthetic "artificial" methods such as, for example, mutagenization. Such methods have been described (U.S. Pat. No. 5,565,350; WO 00/15815). For example a protein encoding nucleic acid molecule operably linked to a promoter, which is not the native promoter of this molecule, is considered to be heterologous with respect to the promoter. Preferably, heterologous DNA is not endogenous to or not naturally associated with the cell into which it is introduced, but has been obtained from another cell or has been synthesized. Heterologous DNA also includes an endogenous DNA sequence, which contains some modification, non-naturally occurring, multiple copies of an endogenous DNA sequence, or a DNA sequence which is not naturally associated with another DNA sequence physically linked thereto. Generally, although not necessarily, heterologous DNA encodes RNA or proteins that are not normally produced by the cell into which it is expressed.

High expression seed-specific promoter: A "high expression seed-specific promoter" as used herein means a promoter causing seed-specific or seed-preferential expression in a plant or part thereof wherein the accumulation or rate of synthesis of RNA or stability of RNA derived from the nucleic acid molecule under the control of the respective promoter is higher, preferably significantly higher than the expression caused by the promoter lacking the NEENA of the invention. Preferably the amount of RNA and/or the rate of RNA synthesis and/or stability of RNA is increased 50% or more, for example 100% or more, preferably 200% or more, more preferably 5 fold or more, even more preferably 10 fold or more, most preferably 20 fold or more for example 50 fold relative to a seed-specific or a seed-preferential promoter lacking a NEENA of the invention.

Hybridization: The term "hybridization" as used herein includes "any process by which a strand of nucleic acid molecule joins with a complementary strand through base pairing." (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules. As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: Tm=81.5+0.41(% G+C), when a nucleic acid molecule is in aqueous solution at 1 M NaCl [see e.g., Anderson and Young, Quantitative Filter Hybridization, in Nucleic Acid Hybridization (1985)]. Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

"Identity": "Identity" when used in respect to the comparison of two or more nucleic acid or amino acid molecules means that the sequences of said molecules share a certain degree of sequence similarity, the sequences being partially identical.

To determine the percentage identity (homology is herein used interchangeably) of two amino acid sequences or of two nucleic acid molecules, the sequences are written one underneath the other for an optimal comparison (for example gaps may be inserted into the sequence of a protein or of a nucleic acid in order to generate an optimal alignment with the other protein or the other nucleic acid).

The amino acid residues or nucleic acid molecules at the corresponding amino acid positions or nucleotide positions are then compared. If a position in one sequence is occupied by the same amino acid residue or the same nucleic acid molecule as the corresponding position in the other sequence, the molecules are homologous at this position (i.e. amino acid or nucleic acid "homology" as used in the present context corresponds to amino acid or nucleic acid "identity". The percentage homology between the two sequences is a function of the number of identical positions shared by the sequences (i.e. % homology=number of identical positions/total number of positions×100). The terms "homology" and "identity" are thus to be considered as synonyms.

For the determination of the percentage identity of two or more amino acids or of two or more nucleotide sequences several computer software programs have been developed. The identity of two or more sequences can be calculated with for example the software fasta, which presently has been used in the version fasta 3 (W. R. Pearson and D. J. Lipman, PNAS 85, 2444 (1988); W. R. Pearson, Methods in Enzymology 183, 63 (1990); W. R. Pearson and D. J. Lipman, PNAS 85, 2444 (1988); W. R. Pearson, Enzymology 183, 63 (1990)). Another useful program for the calculation of identities of different sequences is the standard blast program, which is included in the Biomax pedant software (Biomax, Munich, Federal Republic of Germany). This leads unfortunately sometimes to suboptimal results since blast does not always include complete sequences of the subject and the query. Nevertheless as this program is very efficient it can be used for the comparison of a huge number of sequences. The following settings are typically used for such a comparisons of sequences:

Intron: refers to sections of DNA (intervening sequences) within a gene that do not encode part of the protein that the gene produces, and that is spliced out of the mRNA that is transcribed from the gene before it is exported from the cell nucleus. Intron sequence refers to the nucleic acid sequence of an intron. Thus, introns are those regions of DNA sequences that are transcribed along with the coding sequence (exons) but are removed during the formation of mature mRNA. Introns can be positioned within the actual coding region or in either the 5' or 3' untranslated leaders of the pre-mRNA (unspliced mRNA). Introns in the primary transcript are excised and the coding sequences are simultaneously and precisely ligated to form the mature mRNA. The junctions of introns and exons form the splice site. The sequence of an intron begins with GU and ends with AG. Furthermore, in plants, two examples of AU-AC introns have been described: the fourteenth intron of the RecA-like protein gene and the seventh intron of the G5 gene from *Arabidopsis thaliana* are AT-AC introns. Pre-mRNAs containing introns have three short sequences that are—beside other sequences—essential for the intron to be accurately spliced. These sequences are the 5' splice-site, the 3' splice-site, and the branchpoint. mRNA splicing is the removal of intervening sequences (introns) present in primary mRNA transcripts and joining or ligation of exon sequences. This is also known as cis-splicing which joins two exons on the same RNA with the removal of the intervening sequence (intron). The functional elements of an intron is comprising sequences that are recognized and bound by the specific protein components of the spliceosome (e.g. splicing consensus sequences at the ends of introns). The interaction of the functional elements with the spliceosome results in the removal of the intron sequence from the premature mRNA and the rejoining of the exon sequences. Introns have three short sequences that are essential—although not sufficient—for the intron to be accurately spliced. These sequences are the 5' splice site, the 3' splice site and the branch point. The branchpoint sequence is important in splicing and splice-site selection in plants. The branchpoint sequence is usually located 10-60 nucleotides upstream of the 3' splice site.

Isolated: The term "isolated" as used herein means that a material has been removed by the hand of man and exists apart from its original, native environment and is therefore not a product of nature. An isolated material or molecule (such as a DNA molecule or enzyme) may exist in a purified form or may exist in a non-native environment such as, for example, in a transgenic host cell. For example, a naturally occurring polynucleotide or polypeptide present in a living plant is not isolated, but the same polynucleotide or polypeptide, separated from some or all of the coexisting materials in the natural system, is isolated. Such polynucleotides can be part of a vector and/or such polynucleotides or polypeptides could be part of a composition, and would be isolated in that such a vector or composition is not part of its original environment. Preferably, the term "isolated" when used in relation to a nucleic acid molecule, as in "an isolated nucleic acid sequence" refers to a nucleic acid sequence that is identified and separated from at least one contaminant nucleic acid molecule with which it is ordinarily associated in its natural source. Isolated nucleic acid molecule is nucleic acid molecule present in a form or setting that is different from that in which it is found in nature. In contrast, non-isolated nucleic acid molecules are nucleic acid molecules such as DNA and RNA, which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs, which encode a multitude of proteins. However, an isolated nucleic acid sequence comprising for example SEQ ID NO: 1 includes, by way of example, such nucleic acid sequences in cells which ordinarily contain SEQ ID NO:1 where the nucleic acid sequence is in a chromosomal or extrachromosomal location different from that of natural cells, or is otherwise flanked by a different nucleic acid sequence than that found in nature. The isolated nucleic acid sequence may be present in single-stranded or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and anti-sense strands (i.e., the nucleic acid sequence may be double-stranded).

Minimal Promoter: promoter elements, particularly a TATA element, that are inactive or that have greatly reduced promoter activity in the absence of upstream activation. In the presence of a suitable transcription factor, the minimal promoter functions to permit transcription.

NEENA: see "Nucleic acid expression enhancing nucleic acid".

Nucleic acid expression enhancing nucleic acid (NEENA): The term "nucleic acid expression enhancing nucleic acid" refers to a sequence and/or a nucleic acid molecule of a specific sequence having the intrinsic property to enhance expression of a nucleic acid under the control of a promoter to which the NEENA is functionally linked. Unlike promoter sequences, the NEENA as such is not able to drive expression. In order to fulfill the function of enhancing expression of a nucleic acid molecule functionally linked to the NEENA, the NEENA itself has to be functionally linked to a promoter. In distinction to enhancer sequences known in the art, the NEENA is acting in cis but not in trans and has to be located close to the transcription start site of the nucleic acid to be expressed.

Nucleic acids and nucleotides: The terms "Nucleic Acids" and "Nucleotides" refer to naturally occurring or synthetic or artificial nucleic acid or nucleotides. The terms "nucleic acids" and "nucleotides" comprise deoxyribonucleotides or ribonucleotides or any nucleotide analogue and polymers or hybrids thereof in either single- or double-stranded, sense or antisense form. Unless otherwise indicated, a particular nucleic acid sequence also implicitly encompasses conservatively modified variants thereof (e.g., degenerate codon substitutions) and complementary sequences, as well as the sequence explicitly indicated. The term "nucleic acid" is used inter-changeably herein with "gene", "cDNA, "mRNA", "oligonucleotide," and "polynucleotide". Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, NH2, NHR, NR2, or CN. Short hairpin RNAs (shRNAs) also can comprise non-natural elements such as non-natural bases, e.g., ionosin and xanthine, non-natural sugars, e.g., 2'-methoxy ribose, or non-natural phosphodiester linkages, e.g., methylphosphonates, phosphorothioates and peptides.

Nucleic acid sequence: The phrase "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. In one embodiment, a nucleic acid can be a "probe" which is a relatively short nucleic acid, usually less than 100 nucleotides in length. Often a nucleic acid probe is from about 50 nucleotides in length to about 10 nucleotides in length. A "target region" of a nucleic acid is a portion of a nucleic acid that is identified to be of interest.

Oligonucleotide: The term "oligonucleotide" refers to an oligomer or polymer of ribonucleic acid (RNA) or deoxyribonucleic acid (DNA) or mimetics thereof, as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. An oligonucleotide preferably includes two or more nucleomonomers covalently coupled to each other by linkages (e.g., phosphodiesters) or substitute linkages.

Plant: is generally understood as meaning any eukaryotic single- or multi-celled organism or a cell, tissue, organ, part or propagation material (such as seeds or fruit) of same which is capable of photosynthesis. Included for the purpose of the invention are all genera and species of higher and lower plants of the Plant Kingdom. Annual, perennial, monocotyledonous and dicotyledonous plants are preferred. The term includes the mature plants, seed, shoots and seedlings and their derived parts, propagation material (such as seeds or microspores), plant organs, tissue, protoplasts, callus and other cultures, for example cell cultures, and any other type of plant cell grouping to give functional or structural units. Mature plants refer to plants at any desired developmental stage beyond that of the seedling. Seedling refers to a young immature plant at an early developmental stage. Annual, biennial, monocotyledonous and dicotyledonous plants are preferred host organisms for the generation of transgenic plants. The expression of genes is furthermore advantageous in all ornamental plants, useful or ornamental trees, flowers, cut flowers, shrubs or lawns. Plants which may be mentioned by way of example but not by limitation are angiosperms, bryophytes such as, for example, Hepaticae (liverworts) and Musci (mosses); Pteridophytes such as ferns, horsetail and club mosses; gymnosperms such as conifers, cycads, ginkgo and Gnetatae; algae such as Chlorophyceae, Phaeophpyceae, Rhodophyceae, Myxophyceae, Xanthophyceae, Bacillariophyceae (diatoms), and Euglenophyceae. Preferred are plants which are used for food or feed purpose such as the families of the Leguminosae such as pea, alfalfa and soya; Gramineae such as rice, maize, wheat, barley, *sorghum*, millet, rye, triticale, or oats; the family of the Umbelliferae, especially the genus *Daucus*, very especially the species carota (carrot) and Apium, very especially the species *Graveolens dulce* (celery) and many others; the family of the Solanaceae, especially the genus *Lycopersicon*, very especially the species esculentum (tomato) and the genus *Solanum*, very especially the species tuberosum (potato) and melongena (egg plant), and many others (such as tobacco); and the genus *Capsicum*, very especially the species annuum (peppers) and many others; the family of the Leguminosae, especially the genus *Glycine*, very especially the species max (soybean), alfalfa, pea, lucerne, beans or peanut and many others; and the family of the Cruciferae (Brassicacae), especially the genus *Brassica*, very especially the species *napus* (oil seed rape), campestris (beet), *oleracea* cv Tastie (cabbage), *oleracea* cv Snowball Y (cauliflower) and *oleracea* cv Emperor (broccoli); and of the genus *Arabidopsis*, very especially the species thaliana and many others; the family of the Compositae, especially the genus *Lactuca*, very especially the species *sativa* (lettuce) and many others; the family of the Asteraceae such as sunflower, *Tagetes*, lettuce or *Calendula* and many other; the family of the Cucurbitaceae such as melon, pumpkin/squash or zucchini, and linseed. Further preferred are cotton, sugar cane, hemp, flax, chilies, and the various tree, nut and wine species.

Polypeptide: The terms "polypeptide", "peptide", "oligopeptide", "polypeptide", "gene product", "expression product" and "protein" are used interchangeably herein to refer to a polymer or oligomer of consecutive amino acid residues.

Primary transcript: The term "primary transcript" as used herein refers to a premature RNA transcript of a gene. A "primary transcript" for example still comprises introns and/or is not yet comprising a polyA tail or a cap structure and/or is missing other modifications necessary for its correct function as transcript such as for example trimming or editing.

Promoter: The terms "promoter", or "promoter sequence" are equivalents and as used herein, refer to a DNA sequence which when ligated to a nucleotide sequence of interest is capable of controlling the transcription of the nucleotide sequence of interest into RNA. Such promoters can for example be found in the following public databases grassius.org/grasspromdb.html, mendel.cs.rhul.ac.uk/mendel.php?topic=plantprom, ppdb.gene.nagoya-u.ac.jp/cgi-bin/index.cgi. Promoters listed there may be addressed with the methods of the invention and are herewith included by reference. A promoter is located 5' (i.e., upstream), proximal to the transcriptional start site of a nucleotide sequence of interest whose transcription into mRNA it controls, and provides a site for specific binding by RNA polymerase and other transcription factors for initiation of transcription. Said promoter comprises for example the at least 10 kb, for example 5 kb or 2 kb proximal to the transcription start site. It may also comprise the at least 1500 bp proximal to the transcriptional start site, preferably the at least 1000 bp, more preferably the at least 500 bp, even more preferably the at least 400 bp, the at least 300 bp, the at least 200 bp or the at least 100 bp. In a further preferred embodiment, the promoter comprises the at least 50 bp proximal to the transcription start site, for example, at least 25 bp. The promoter does not comprise exon and/or intron regions or 5' untranslated regions. The promoter may for example be heterologous or homologous to the respective plant. A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur or from pathogens for this host cells (e.g., plants or plant pathogens like plant viruses). A plant specific promoter is a promoter suitable for regulating expression in a plant. It may be derived from a plant but also from plant pathogens or it might be a synthetic promoter designed by man. If a promoter is an inducible promoter, then the rate of transcription increases in response to an inducing agent. Also, the promoter may be regulated in a tissue-specific or tissue preferred manner such that it is only or predominantly active in transcribing the associated coding region in a specific tissue type(s) such as leaves, roots or meristem. The term "tissue specific" as it applies to a promoter refers to a promoter that is capable of directing selective expression of a nucleotide sequence of interest to a specific type of tissue (e.g., petals) in the relative absence of expression of the same nucleotide sequence of interest in a different type of tissue (e.g., roots). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter, which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., GUS activity staining, GFP protein or immunohistochemical staining. The term "constitutive" when made in reference to a promoter or the expression derived from a promoter means that the promoter is capable of directing transcription of an operably linked nucleic acid molecule in the absence of a stimulus (e.g., heat shock, chemicals, light, etc.) in the majority of plant tissues and cells throughout substantially the entire lifespan of a plant or part of a plant. Typically, constitutive promoters are capable of directing expression of a transgene in substantially any cell and any tissue.

Promoter specificity: The term "specificity" when referring to a promoter means the pattern of expression conferred by the respective promoter. The specificity describes the tissues and/or developmental status of a plant or part thereof, in which the promoter is conferring expression of the nucleic acid molecule under the control of the respective promoter. Specificity of a promoter may also comprise the environmental conditions, under which the promoter may be activated or down-regulated such as induction or repression by biological or environmental stresses such as cold, drought, wounding or infection.

Purified: As used herein, the term "purified" refers to molecules, either nucleic or amino acid sequences that are removed from their natural environment, isolated or separated. "Substantially purified" molecules are at least 60% free, preferably at least 75% free, and more preferably at least 90% free from other components with which they are naturally associated. A purified nucleic acid sequence may be an isolated nucleic acid sequence.

Recombinant: The term "recombinant" with respect to nucleic acid molecules refers to nucleic acid molecules produced by recombinant DNA techniques. Recombinant nucleic acid molecules may also comprise molecules, which as such does not exist in nature but are modified, changed, mutated or otherwise manipulated by man. Preferably, a "recombinant nucleic acid molecule" is a non-naturally occurring nucleic acid molecule that differs in sequence from a naturally occurring nucleic acid molecule by at least one nucleic acid. A "recombinant nucleic acid molecule" may also comprise a "recombinant construct" which comprises, preferably operably linked, a sequence of nucleic acid molecules not naturally occurring in that order. Preferred methods for producing said recombinant nucleic acid molecule may comprise cloning techniques, directed or non-directed mutagenesis, synthesis or recombination techniques.

"Seed-specific promoter" in the context of this invention means a promoter which is regulating transcription of a nucleic acid molecule under control of the respective promoter in seeds wherein the transcription in any tissue or cell of the seeds contribute to more than 90%, preferably more than 95%, more preferably more than 99% of the entire quantity of the RNA transcribed from said nucleic acid sequence in the entire plant during any of its developmental stage. The term "seed-specific expression" and "seed-specific NEENA" are to be understood accordingly. Hence a "seed-specific NEENA" enhances the transcription of a seed-specific or seed-preferential promoter in a way, that the transcription in seeds derived from said promoter functionally linked to a respective NEENA contribute to more than 90%, preferably more than 95%, more preferably more than 99% of the entire quantity of the RNA transcribed from the respective promoter functionally linked to a NEENA in the entire plant during any of its developmental stage.

"Seed-preferential promoter" in the context of this invention means a promoter which is regulating transcription of a nucleic acid molecule under control of the respective promoter in seeds wherein the transcription in any tissue or cell of the seeds contribute to more than 50%, preferably more than 70%, more preferably more than 80% of the entire quantity of the RNA transcribed from said nucleic acid sequence in the entire plant during any of its developmental stage. The term "seed-preferential expression" and "seed-preferential NEENA" are to be understood accordingly. Hence a "seed-preferential NEENA" enhances the transcription of a seed-specific or seed-preferential promoter in a way, that the transcription in seeds derived from said promoter functionally linked to a respective NEENA contribute to more than 50%, preferably more than 70%, more preferably more than 80% of the entire quantity of the RNA transcribed from the respective promoter functionally linked to a NEENA in the entire plant during any of its developmental stage.

Sense: The term "sense" is understood to mean a nucleic acid molecule having a sequence which is complementary or identical to a target sequence, for example a sequence which binds to a protein transcription factor and which is involved in the expression of a given gene. According to a preferred embodiment, the nucleic acid molecule comprises a gene of interest and elements allowing the expression of the said gene of interest.

Significant increase or decrease: An increase or decrease, for example in enzymatic activity or in gene expression, that is larger than the margin of error inherent in the measurement technique, preferably an increase or decrease by about 2-fold or greater of the activity of the control enzyme or expression in the control cell, more preferably an increase or decrease by about 5-fold or greater, and most preferably an increase or decrease by about 10-fold or greater.

Substantially complementary: In its broadest sense, the term "substantially complementary", when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, more desirably at least 70%, more desirably at least 80% or 85%, preferably at least 90%, more preferably at least 93%, still more preferably at least 95% or 96%, yet still more preferably at least 97% or 98%, yet still more preferably at least 99% or most preferably 100% (the later being equivalent to the term "identical" in this context). Preferably identity is assessed over a length of at least 19 nucleotides, preferably at least 50 nucleotides, more preferably the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J. Mol. Biol. 48: 443-453; as defined above). A nucleotide sequence "substantially complementary" to a reference nucleotide sequence hybridizes to the reference nucleotide sequence under low stringency conditions, preferably medium stringency conditions, most preferably high stringency conditions (as defined above).

Transgene: The term "transgene" as used herein refers to any nucleic acid sequence, which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence, which is naturally found in the cell into which it is introduced so long as it does not contain some modification (e.g., a point mutation, the presence of a selectable marker gene, etc.) relative to the naturally-occurring sequence.

Transgenic: The term transgenic when referring to an organism means transformed, preferably stably transformed, with a recombinant DNA molecule that preferably comprises a suitable promoter operatively linked to a DNA sequence of interest.

Vector: As used herein, the term "vector" refers to a nucleic acid molecule capable of transporting another nucleic acid molecule to which it has been linked. One type of vector is a genomic integrated vector, or "integrated vector", which can become integrated into the chromosomal DNA of the host cell. Another type of vector is an episomal vector, i.e., a nucleic acid molecule capable of extra-chromosomal replication. Vectors capable of directing the expression of genes to which they are operatively linked are referred to herein as "expression vectors". In the present specification, "plasmid" and "vector" are used interchangeably unless otherwise clear from the context. Expression vectors designed to produce RNAs as described herein in vitro or in vivo may contain sequences recognized by any RNA polymerase, including mitochondrial RNA polymerase, RNA pol I, RNA pol II, and RNA pol III. These vectors can be used to transcribe the desired RNA molecule in the cell according to this invention. A plant transformation vector is to be understood as a vector suitable in the process of plant transformation.

Wild-type: The term "wild-type", "natural" or "natural origin" means with respect to an organism, polypeptide, or nucleic acid sequence, that said organism is naturally occurring or available in at least one naturally occurring organism which is not changed, mutated, or otherwise manipulated by man.

The contents of all references cited throughout this application are herewith incorporated by reference in general and with respect to their specific disclosure content referred to above.

FIGURES

FIG. 1: Schematical figure of the different enzymatic activities leading to the production of ARA, EPA and DHA.

FIG. 2 Strategy employed for stepwise buildup of plant expression plasmids of the invention. A detailed description is given in example 4. Abbreviations: Nco I, Pac I, Kas I, Sfo I, Fse I, Sbf I, Xma I, Not I indicate restriction endonucleases used for cloning; attLx and attRx—where x are numbers from 1 to 4—designate attachment sites for site specific recombination of the Multisite Gateway™ System (Invitrogen); pENTR_A, pENTR_B, pENTR_C are Multisite Gateway™ System-Entry-vectors; Kan (Kanaycin) and Strep (Streptinomycin) designate antibiotic selection markers used for cloning; on-origin of replication.

FIG. 3 Orientation and combination of the functional elements (promoter, NEENA, gene, terminator) of the plant expression vecotrs VC-LJB913-1qcz (SEQ-ID 38), VC-LJB1327-1qcz (SEQ-ID 39), VC-LJB2003-1qcz (SEQ-ID 40) and VC-LJB2197-1qcz (SEQ-ID 146).

EXAMPLES

Example 1

General Cloning Methods

Cloning methods as e.g. use of restriction endonucleases to cut double stranded DNA at specific sites, agarose gel electrophoreses, purification of DNA fragments, transfer of nucleic acids onto nitrocellulose and nylon membranes, joining of DNA-fragments, transformation of *E. coli* cells and culture of bacteria where performed as described in Sambrook et al. (1989) (Cold Spring Harbor Laboratory Press: ISBN 0-87965-309-6). Polymerase chain reaction was performed using Phusion™ High-Fidelity DNA Polymerase (NEB, Frankfurt, Germany) according to the manufactures instructions. In general, primers used in PCR were designed such, that at least 20 nucleotides of the 3' end of the primer anneal perfectly with the template to amplify. Restriction site were added by attaching the corresponding nucleotides of the recognition sites to the 5' end of the primer. Fusion PCR, for example described by K. Heckman and L. R. Pease, Nature Protocols (2207) 2, 924-932 was used as an alternative method to join two fragments of interest, e.g. a promoter to a gene or a gene to a terminator.

Example 2

Sequence Analysis of Recombinant DNA

Sequencing of recombinant DNA-molecules was performed using a laser-fluorescence DNA sequencer (Applied Biosystems Inc, USA) employing the sanger method (Sanger et al. (1977) Proc. Natl. Acad. Sci. USA 74, 5463-5467). Expression constructs harboring fragments obtained by polymerase chain reactions (PCR) were subjected to sequencing to confirm the correctness of expression cassettes consisting of promoter, nucleic acid molecule to be expressed and terminator to avoid mutations that might result from handling of the DNA during cloning, e.g. due to incorrect primers, mutations from exposure to UV-light or errors of polymerases.

Example 3

Identification of Nucleic Acid Expression Enhancing Nucleic Acids (NEENA) from Genes with Seed Preferred Expression 3.1 Identification of NEENA Molecules from *A. thaliana* Genes Using publicly available genomic DNA sequences (e.g. ncbi.nlm.nih.gov/genomes/PLANTS/PlantList.html) and transcript expression data (e.g. weigelworld.org/resources/microarray/AtGenExpress/), a set of 19 NEENA candidates deriving from *Arabidopsis thaliana* transcripts with seed preferred expression was selected for detailed analyses. The candidates were named as follows:

TABLE 1 seed specific NEENA candidates (NEENAss).

| NEENA name | Locus | Annotation | SEQ ID No |
|---|---|---|---|
| NEENAss1 | At1g62290 | aspartyl protease family protein | 6 |
| NEENAss2 | At1g65090 | expressed protein | 7 |

TABLE 1-continued seed specific NEENA candidates (NEENAss).

| NEENA name | Locus | Annotation | SEQ ID No |
|---|---|---|---|
| NEENAss15 | At2g27040 | PAZ domain-containing protein | 9 |
| NEENAss18 | At1g01170 | ozone-responsive stress-related protein, putative | 10 |
| NEENAss14 | At5g63190 | MA3 domain-containing protein | 8 |
| NEENAss4 | At5g07830 | glycosyl hydrolase family 79 N-terminal domain-containing protein similar to beta-glucuronidase AtGUS2 | 11 |
| NEENAss13 | At2g04520 | eukaryotic translation initiation factor 1A, putative/eIF-1A | 12 |
| NEENAss3 | At5g60760 | 2-phosphoglycerate kinase-related | 13 |
| NEENAss5 | At1g11170 | expressed protein contains Pfam profile PF05212 | 14 |
| NEENAss11 | At4g37050 | PLA V/PLP4 (Patatin-like protein 4) | 15 |
| NEENAss8 | At1g56170 | HAP5B (Heme activator protein (yeast) homolog 5B) | 16 |
| NEENAss16 | At1g54100 | aldehyde dehydrogenase, putative/antiquitin | 17 |
| NEENAss9 | At3g12670 | CTP synthase, putative/UTP--ammonia ligase, putative | 18 |
| NEENAss20 | At4g04460 | aspartyl protease family protein | 19 |
| NEENAss10 | At1g04120 | ATMRP5 (*Arabidopsis thaliana* multidrug resistance-associated protein 5) | 20 |
| NEENAss6 | At2g41070 | basic leucine zipper transcription factor (BZIP12) | 21 |
| NEENAss12 | At1g05450 | protease inhibitor/seed storage/lipid transfer protein (LTP)-related | 22 |
| NEENAss7 | At4g03050 | 2-oxoglutarate-dependent dioxygenase, putative (AOP3) | 23 |
| NEENAss17 | At3g12490 | cysteine protease inhibitor, putative/cystatin | 24 |

3.2 Isolation of the NEENA Candidates

Genomic DNA was extracted from *A. thaliana* green tissue using the Qiagen DNeasy Plant Mini Kit (Qiagen, Hilden, Germany). Genomic DNA fragments containing NEENA molecules were isolated by conventional polymerase chain reaction (PCR). Primers were designed on the basis of the *A. thaliana* genome sequence with a multitude of NEENA candidates. The reaction comprised 19 sets of primers (Table 2) and followed the protocol outlined by Phusion High Fidelity DNA Polymerase (Cat No F-540L, New England Biolabs, Ipswich, Mass., USA). The isolated DNA was used as template DNA in a PCR amplification using the following primers:

TABLE 2

Primer sequences for isolation of NEENAs

| Primer name | Sequence | SEQ ID No | PCR yielding SEQ ID No |
|---|---|---|---|
| NEENAss1_for | tggtgcttaaacactctggtgagt | 42 | 6 |
| NEENAss1_rev | tttgacctacaaaatcaaagcagtca | 43 | |
| NEENAss2_for | agttctttgctttcgaagttgc | 44 | 7 |
| NEENAss2_rev | tactacgtactgttttcaattct | 45 | |
| NEENAss3_for | atttccacacgctttctatcatttc | 46 | 13 |
| NEENAss3_rev | ttatctctctctaaaaaataaaaacgaatc | 47 | |
| NEENAss4_for | gtccagaattttctccattga | 48 | 11 |
| NEENAss4_rev | tcttcactatccaaagctctca | 49 | |
| NEENAss5_for | gtctactttcattacagtgactctg | 50 | 14 |
| NEENAss5_rev | ttatattttacctgcaacacaattcaa | 51 | |
| NEENAss6_for | cactcgaatactgcatgcaa | 52 | 21 |
| NEENAss6_rev | ttatgtagcctttacacagaaaacaa | 53 | |
| NEENAss7_for | aacaactatggcctgagggt | 54 | 23 |
| NEENAss7_rev | ttatcttactgtttttaaccaaaaaataaaat | 55 | |
| NEENAss8_for | atcttagggtttcgcgagatctca | 56 | 16 |
| NEENAss8_rev | tgctaagctatctctgttaatataaaattg | 57 | |
| NEENAss9_for | attttttgttggtgaaaggtaga | 58 | 18 |
| NEENAss9_rev | ttacgttttttgtctctgcttcttct | 59 | |

TABLE 2-continued

Primer sequences for isolation of NEENAs

| Primer name | Sequence | SEQ ID No | PCR yielding SEQ ID No |
|---|---|---|---|
| NEENAss10_for | tctgggaaatatcgattttgatct | 60 | 20 |
| NEENAss10_rev | tctcaccacatcccaaagctc | 61 | |
| NEENAss11_for | gcacaatcttagcttaccttgaa | 62 | 15 |
| NEENAss11_rev | ttatttaatccacaagccttgcctc | 63 | |
| NEENAss12_for | tgtcggagaagtgggcg | 64 | 22 |
| NEENAss12-rev | agaagtgggcggacg | 65 | |
| NEENAss13_for | tagcttaatctcagattcgaatcgt | 66 | 12 |
| NEENAss13_rev | tagtatctacataccaatcatacaaatg | 67 | |
| NEENAss14_for | tttcacgatttggaatttga | 68 | 8 |
| NEENAss14_rev | tctacaacattaaaacgaccatta | 69 | |
| NEENAss15_for | agggtttcgtttttgtttca | 70 | 9 |
| NEENAss15_rev | ttatctcctgctcaaagaaacca | 71 | |
| NEENAss16_for | agaagctcatttcttcgatac | 72 | 17 |
| NEENAss16_rev | tctctgcgcaaaaattcacc | 73 | |
| NEENAss17_for | tctaaaaatacagggcacc | 74 | 24 |
| NEENAss17_rev | ttactcttcgttgcagaagccta | 75 | |
| NEENAss18_for | actgtttaagcttcactgtct | 76 | 10 |
| NEENAss18_rev | tttcttctaaagctgaaagt | 77 | |
| NEENAss20_for | ttaagcttttaagaatctctactcaca | 78 | 19 |
| NEENAss20_rev | ttaaattttacctgtcatcaaaaacaaca | 79 | |

Amplification during the PCR was carried out with the following composition (50 microl):
3.00 microl *A. thaliana* genomic DNA
10.00 microl 5× Phusion HF Buffer
4.00 microl dNTP (2.5 mM)
2.50 microl for Primer (10 microM)
2.50 microl rev Primer (10 microM)
0.50 microl Phusion HF DNA Polymerase (2 U/microl)

A touch-down approach was employed for the PCR with the following parameters: 98.0° C. for 30 sec (1 cycle), 98.0° C. for 30 sec, 56.0° C. for 30 sec and 72.0° C. for 60 sec (4 cycles), 4 additional cycles each for 54.0° C., 51.0° C. and 49.0° C. annealing temperature, followed by 20 cycles with 98.0° C. for 30 sec, 46.0° C. for 30 sec and 72.0° C. for 60 sec (4 cycles) and 72.0° C. for 5 min. The amplification products was loaded on a 2% (w/v) agarose gel and separated at 80V. The PCR products were excised from the gel and purified with the Qiagen Gel Extraction Kit (Qiagen, Hilden, Germany). The purified PCR products were cloned into the pCR2.1 TOPO (Invitrogen) vector according to the manufacturer's manual and subsequently sequenced. These plasmids served as source for further cloning steps or as template for further PCR, e.g. fusion PCR for fusion with promoters as described in example 4.

Example 4

Assembly of Genes Required for PUFA Synthesis within a T-Plasmid

For synthesis of LC-PUFA in *Brassica napus* seeds, the set of genes encoding the proteins of the metabolic LC-PUFA pathway (table 3) was combined with expression elements (promoter, terminators, NEENAs, table 5) and transferred into binary t-plasmids that were used for agrobacteria mediated transformation of plants as described in example 5. To this end, the general cloning strategy depicted in FIG. 2 was employed: Genes listed in table 3 were PCR-amplified using Phusion™ High-Fidelity DNA Polymerase (NEB, Frankfurt, Germany) according to the manufactures instructions from cDNA using primer introducing a Nco I and/or Asc I restriction site at the 5' terminus, and a Pac I restriction site at the 3' terminus (FIG. 2A). Promoter-terminator modules or promoter-NEENA-terminator modules were created by joining the corresponding expression elements listed in table 2 using fusion PCR as described in example 1 and cloning the PCR-product into the TOPO-vector pCR2.1 (Invitrogen) according to the manufactures instructions (FIG. 2B). As a non limiting example, primer combinations are listed in table 6 were used to create fusions of promoter-NEENAs harbored by the plasmid VC-LJB2003-1qcz (SEQ-ID 40) and VC-LJB2197-1qcz (SEQ-ID 146) containing the required set of pathway genes to synthesize arachidonic acid in seeds of rapeseed. While joining terminator sequences to promoter sequences or promoter-NEENA sequences using fusion PCR, primers were designed such, that recognition sequences for the restriction endonucleases depicted in FIG. 2 were added to either side of the modules, and the recognition sites for the restriction endonucleases Nco I, Asc I and Pac I were introduced between promoter and terminator or between NEENA and terminator (see FIG. 2B). To obtain the final expression modules, PCR-amplified genes were cloned between promoter and terminator or NEENA and terminator via Nco I and/or Pac I restriction sites (FIG. 2C). Employing the custom multiple cloning site (MCS) SEQ-ID 41, up to three of those expression modules were combined as desired to expression cassettes harbored by either one of pENTR/A, pENTR/B or pENTR/C (FIG. 2D). Deviating from the strategy depicted in FIG. 2, some elements or joined elements were synthesized by a service provider or cloned using blunt-end ligation. Finally, the Multisite Gateway™ System (Invitrogen) was used to combine three expression cassette harbored by pENTR/A, pENTR/B and pENTR/C (FIG. 2E) to obtain the final binary pSUN T-plasmids VC-LJB913-1qcz (SEQ-ID 38), VC-LJB1327-1qcz (SEQ-ID 39) and VC-LJB2003-1qcz (SEQ-ID 40) and VC-LJB2197-1qcz (SEQ-ID 146). The orientation and combination of the functional elements (promoter, NEENA, gene, terminator) is depicted in FIGS. 3A, 3B, 3C and 3D. An overview of binary vectors and their usage is given by Hellens et al, Trends in Plant Science (2000) 5: 446-451.

TABLE 3

Genes used for synthesis of 20:4n − 6 (ARA) in rapeseed.

| Gene | Source Organism | Activity | SEQ-ID |
|---|---|---|---|
| d12Des(Ps_GA) | *Phytophtora sojae* | Δ 12-Desaturase | 95 |
| d6Des(Ot_febit) | *Ostreococcus tauri* | Δ 6-Desaturase | 96 |
| d6Des(Ot_GA2) | *Ostreococcus tauri* | Δ 6-Desaturase | 97 |
| d6Des(Pir_GAI) | *Pythium irregulare* | Δ 6-Desaturase | 98 |
| d6Elo(Pp_GA2) | *Physcomitrella patens* | Δ 6-Elongase | 99 |
| d6Elo(Tp_GA2) | *Thalassiosira pseudonana* | Δ 6-Elongase | 100 |
| d5Des(Tc_GA2) | *Thraustochytrium* ssp. | Δ 5-Desaturase | 101 |

TABLE 4

Genes used in addition to genes listed in table 1 for synthesis of 22:6n − 3 (DHA) in rapeseed.

| Gene | Source Organism | Activity | SEQ-ID |
|---|---|---|---|
| d5Elo(Ot_GA3) | *Ostreococcus tauri* | Δ 5-Elongase | 102 |
| d4Des(Tc_GA3) | *Traustochytrium* ssp. | Δ 4-Desaturase | 103 |

TABLE 5

Expression elements used for synthesis of 20:4n − 6 (ARA) or 22:6n − 3 (DHA) in rapeseed

| Element | Source Organism | Function | SEQ-ID |
|---|---|---|---|
| p-VfSBP-NEENAss1 | *Vicia faba*; *Arabidopsis* | Promotor + NEENA | 1 |
| p-BnNapin-NEENAss2 | *Brassica napus*; *Arabidopsis* | Promotor + NEENA | 2 |
| p-LuCnl-NEENAss14 | *Linum usitatissimum*; *Arabidopsis* | Promotor + NEENA | 3 |
| p-LuPxr-NEENAss15 | *Linum usitatissimum*; *Arabidopsis* | Promotor + NEENA | 4 |
| p-VfUSP-NEENAss18 | *Vicia faba*; *Arabidopsis* | Promotor + NEENA | 5 |
| p-VfSBP-NEENAss2 | *Vicia faba*, *Arabidopsis* | Promotor + NEENA | 147 |
| p-LuPxr-NEENAss1 | *Linum usitatissimum*, *Arabidopsis* | Promotor + NEENA | 148 |
| p-BnNapin-NEENAss14 | *Brassica napus*, *Arabidopsis* | Promotor + NEENA | 149 |
| NEENAss1 | *Arabidopsis* | NEENA from locus At1g62290 (aspartyl protease family protein) | 6 |
| NEENAss2 | *Arabidopsis* | NEENA from locus At1g65090 (expressed protein) | 7 |
| NEENAss14 | *Arabidopsis* | NEENA from locus At5g63190 (MA3 domain-containing protein) | 8 |
| NEENAss15 | *Arabidopsis* | NEENA from locus At2g27040 (PAZ domain-containing protein) | 9 |
| NEENAss18 | *Arabidopsis* | NEENA from locus At1g01170 (ozone-responsive stress-related protein, putative) | 10 |
| NEENAss4 | *Arabidopsis* | NEENA from locus At5g07830 (glycosyl hydrolase family 79 N-terminal domain-containing protein similar to beta-glucuronidase AtGUS2) | 11 |
| NEENAss13 | *Arabidopsis* | NEENA from locus At2g04520 (eukaryotic translation initiation factor 1A, putative/eIF-1A) | 12 |
| NEENAss3 | *Arabidopsis* | NEENA from locus At5g60760 (2-phosphoglycerate kinase-related) | 13 |
| NEENAss5 | *Arabidopsis* | NEENA from locus At1g11170 (expressed protein contains Pfam profile PF05212) | 14 |
| NEENAss11 | *Arabidopsis* | NEENA from locus At4g37050 (PLA V/PLP4 (Patatin-like protein 4)) | 15 |

TABLE 5-continued

Expression elements used for synthesis of 20:4n − 6 (ARA) or 22:6n − 3 (DHA) in rapeseed

| Element | Source Organism | Function | SEQ-ID |
|---|---|---|---|
| NEENAss8 | Arabidopsis | NEENA from locus At1g56170 (HAP5B (Heme activator protein (yeast) homolog 5B)) | 16 |
| NEENAss16 | Arabidopsis | NEENA from locus At1g54100 (aldehyde dehydrogenase, putative/antiquitin) | 17 |
| NEENAss9 | Arabidopsis | NEENA from locus At3g12670 (CTP synthase, putative/UTP--ammonia ligase, putative) | 18 |
| NEENAss20 | Arabidopsis | NEENA from locus At4g04460 (aspartyl protease family protein) | 19 |
| NEENAss10 | Arabidopsis | NEENA from locus At1g04120 (ATMRP5 (Arabidopsis thaliana multidrug resistance-associated protein 5)) | 20 |
| NEENAss6 | Arabidopsis | NEENA from locus At2g41070 (basic leucine zipper transcription factor (BZIP12)) | 21 |
| NEENAss12 | Arabidopsis | NEENA from locus At1g05450 (protease inhibitor/seed storage/lipid transfer protein (LTP)-related) | 22 |
| NEENAss7 | Arabidopsis | NEENA from locus At4g03050 (2-oxoglutarate-dependent dioxygenase, putative (AOP3)) | 23 |
| NEENAss17 | Arabidopsis | NEENA from locus At3g12490 (cysteine protease inhibitor, putative/cystatin) | 24 |
| p-BnNapin | Brassica napus | Promotor | 25 |
| p-LuCnl | Linum usitatissimum | Promotor | 26 |
| p-LuPXR | Linum usitatissimum | Promotor | 27 |
| p-VfSBP | Vicia faba | Promotor | 28 |
| p-VfUSP | Vicia faba | Promotor | 29 |
| p-VfLeB4 | Vicia faba | Promotor | 30 |
| t-AtPXR | Arabidopsis | Terminator | 31 |
| t-CaMV35S | CaMV | Terminator | 32 |
| t-E9 | Pisum sativum | Terminator | 33 |
| t-AgrOCS | Agrobacterium tumefaciens | Terminator | 34 |
| t-PvArc | Phaseolus vulgaris | Terminator | 35 |
| t-StCat | Solanum tuberosum | Terminator | 36 |
| t-VfLeB3 | Vicia faba | Terminator | 37 |

TABLE 6

Primers used for creation of fusions between promotor and NEENA elements using fusion PCR as described in example 1.

| Promoter/NEENA cassette | Primer pair 1. PCR Promoter | Primer pair 1. PCR NEENA | Primer pair 2. PCR Promotor-NEENA |
|---|---|---|---|
| p-VfSBP-NEENAss1 | Forw: tcgacggcccggactgta tccaac (SEQ-ID No: 80) Rev: actcaccagagtgtttaag caccagttcagcttgatcg ctctattaat (SEQ-ID No: 81) | Forw: attaatagagcgatcaag ctgaactggtgcttaaaca ctctggtgagt (SEQ-ID No: 82) Rev: tttgacctacaaaatcaaa gcagtca (SEQ-ID No: 43) | Forw: tcgacggcccggactgta tccaac (SEQ-ID No: 80) Rev: tttgacctacaaaatcaaa gcagtca (SEQ-ID No: 43) |
| p-BnNapin-NEENAss2 | Forw: taaggatgacctacccatt cttga (SEQ-ID No: 83) Rev: gcaacttcgaaagcaaa gaacttgttttaatcttgtttg tattga (SEQ-ID No: 84) | Forw: tcaatacaaacaagatta aaaacaagttctttgctttc gaagttgc (SEQ-ID No: 85) Rev: tactacgtactgttttcaatt ct (SEQ-ID No: 45) | Forw: taaggatgacctacccatt cttga (SEQ-ID No: 83) Rev: tactacgtactgttttcaatt ct (SEQ-ID No: 45) |

TABLE 6-continued

Primers used for creation of fusions between promotor and NEENA elements using fusion PCR as described in example 1.

| Promoter/NEENA cassette | Primer pair 1. PCR Promoter | Primer pair 1. PCR NEENA | Primer pair 2. PCR Promotor-NEENA |
|---|---|---|---|
| p-LuCnl-NEENAss14 | Forw:<br>ttagcagatatttggtgtctaaat<br>(SEQ-ID No: 86)<br>Rev:<br>tcaaattccaaatcgtgaaatttttggtggtgattggttcttt<br>(SEQ-ID No: 87) | Forw:<br>aaagaaccaatcaccaccaaaaaatttcacgatttggaatttga<br>(SEQ-ID No: 88)<br>Rev:<br>tctacaacattaaaacgaccatta<br>(SEQ-ID No: 69) | Forw:<br>ttagcagatatttggtgtctaaat<br>(SEQ-ID No: 86)<br>Rev:<br>tctacaacattaaaacgaccatta<br>(SEQ-ID No: 69) |
| p-LuPxr-NEENAss15 | Forw:<br>cacgggcaggacataggggactact<br>(SEQ-ID No: 89)<br>Rev:<br>tgaaacaaaaacgaaacctgatttatgataaaaatgtcggttt<br>(SEQ-ID No: 90) | Forw:<br>aaaccgacattttatcataaatcagggtttcgttttgtttca<br>(SEQ-ID No: 91)<br>Rev:<br>ttatctcctgctcaaagaaacca<br>(SEQ-ID No: 71) | Forw:<br>cacgggcaggacataggggactact<br>(SEQ-ID No: 89)<br>Rev:<br>ttatctcctgctcaaagaaacca<br>(SEQ-ID No: 71) |
| p-VfUSP-NEENAss18 | Forw:<br>ctgcagcaaatttacacattgcca<br>(SEQ-ID No: 92)<br>Rev:<br>agacagtgaagcttaaacagtactggctatgaagaaattataatc<br>(SEQ-ID No: 93) | Forw:<br>gattataatttcttcatagccagtactgtttaagcttcactgtct<br>(SEQ-ID No: 94)<br>Rev:<br>tttcttctaaagctgaaagt<br>(SEQ-ID No: 77) | Forw:<br>ctgcagcaaatttacacattgcca<br>(SEQ-ID No: 92)<br>Rev:<br>tttcttctaaagctgaaagt<br>(SEQ-ID No: 77) |
| p-VfSBP-NEENAss2 | Forw:<br>Tcgacggcccggactgtatccaac<br>(SEQ-ID No: 80)<br>Rev:<br>Gcaacttcgaaagcaaagaactgttcagcttgatcgctctattaat<br>(SEQ_ID No: 150) | Forw:<br>Attaatagagcgatcaagctgaacagttctttgctttcgaagttgc<br>(SEQ-ID No: 151)<br>Rev:<br>Tactacgtactgttttcaattct<br>(SEQ-ID No: 45) | Forw:<br>Tcgacggcccggactgtatccaac<br>(SEQ-ID No: 80)<br>Rev:<br>Tactacgtactgttttcaattct<br>(SEQ-ID No: 45) |
| p-LuPxr-NEENAss1 | Forw:<br>Cacgggcaggacatagggactact<br>(SEQ-ID No: 89)<br>Rev:<br>Actcaccagagtgtttaagcaccagatttatgataaaaatgtcggttt<br>(SEQ_ID No: 152) | Forw:<br>aaaccgacattttatcataaatctggtgcttaaacactctggtgagt<br>(SEQ-ID No: 153)<br>Rev:<br>tggtgcttaaacactctggtgagt<br>(SEQ-ID No: 42) | Forw:<br>Cacgggcaggacatagggactact<br>(SEQ-ID No: 89)<br>Rev:<br>tggtgcttaaacactctggtgagt<br>(SEQ-ID No: 42) |
| p-BnNapin-NEENAss14 | Forw:<br>taaggatgacctacccattcttga<br>(SEQ-ID No: 83)<br>Rev:<br>tcaaattccaaatcgtgaaatgttttaatcttgtttgtattga<br>(SEQ_ID No: 154) | Forw:<br>tcaatacaaacaagattaaaacatttcacgatttggaatttga<br>(SEQ-ID No: 155)<br>Rev:<br>tctacaacattaaaacgaccatta<br>(SEQ_ID No: 69) | Forw:<br>taaggatgacctacccattcttga<br>(SEQ-ID No: 83)<br>Rev:<br>tctacaacattaaaacgaccatta<br>(SEQ-ID No: 69) |

Binary T-plasmids harboring functional expression modules for synthesis of docosahexaenoic acid (DHA) in rapeseed can be obtained in a similar manner. To this end, in addition to the functional modules (promoter-gene-terminator and/or promoter-NEENA-gene-terminator) described for synthesis ARA, constructs also contain functional modules required for the expression of the genes listed in table 4. Promoters used in those expression modules can be SEQ-ID No. 25, 26, 27, 28, 29 and/or 30, NEENAs can be any or none of SEQ-ID No. 6, 7, 8, 9, 10, 11, 12, 13, 14, 15, 16, 17, 18, 19, 20, 21, 22, 23, and (or 24, and terminators can be SEQ-ID No. 31, 32, 33, 34, 35, 36 and 37.

Example 5

Production of Transgenic Plants a) Generation of Transgenic Rape Seed Plants (Amended Protocol According to Moloney et al. 1992, Plant Cell Reports, 8:238-242)

For the generation of transgenic rapeseed plants, the binary vectors described in example 3 were transformed into *Agrobacterium tumefaciens* C58C1:pGV2260 (Deblaere et al. 1984, Nucl. Acids. Res. 13: 4777-4788). For the transformation of rapeseed plants (cv. Kumily,) a 1:50 dilution of an overnight culture of positive transformed acrobacteria colonies grown in Murashige-Skoog Medium (Murashige and Skoog 1962 Physiol. Plant. 15, 473) supplemented by 3% saccharose (3MS-Medium) was used. Petiols or Hypocotyledones of sterial rapeseed plants were incubated in a petri dish with a 1:50 acrobacterial dilusion for 5-10 minutes. This was followed by a tree day co-incubation in darkness at 25° C. on 3MS-Medium with 0.8% bacto-Agar. After three days the culture was put on to 16 hours light/8 hours darkness weekly on MS-medium containing 500 mg/l Claforan (Cefotaxime-Natrium), 100 nM Imazetapyr, 20 mikroM Benzylaminopurin (BAP) and 1.6 g/l Glucose. Growing sprouts were transferred to MS-Medium containing 2% saccharose, 250 mg/l Claforan and 0.8% Bacto-Agar. Even after three weeks no root formation was observed, a growth hormone 2-Indolbutyl acid was added to the medium for enhancing root formation.

Regenerated sprouts have been obtained on 2MS-Medium with Imazetapyr and Claforan and were transferred to the green house for sprouting. After flowering, the mature seeds were harvested and analysed for expression of the Desaturase gene via lipid analysis as described in Qui et al. 2001, J. Biol. Chem. 276, 31561-31566.

b) Production of Transgenic Flax Plants

The production of transgenic flax plants can be carried out according to the method of Bell et al., 1999, In Vitro Cell. Dev. Biol. Plant 35(6):456-465 using particle bombardment. Acrobacterial transformation could be carried out according to Mlynarova et al. (1994), Plant Cell Report 13: 282-285.

Example 6

Lipid Extraction and Lipid Analysis of Plant Oils

The results of genetic modifications in plants or on the production of a desired molecule, e.g. a certain fatty acid, can be determined by growing the plant under suitable conditions, e.g. as described below, and analysing the growth media and/or the cellular components for enhanced production of the desired molecule, e.g. lipids or a certain fatty acid. Lipids can be extracted as described in the standard literature including Ullman, Encyclopedia of Industrial Chemistry, Bd. A2, S. 89-90 und S. 443-613, VCH: Weinheim (1985); Fallon, A., et al., (1987) "Applications of HPLC in Biochemistry" in: Laboratory Techniques in Biochemistry and Molecular Biology, Bd. 17; Rehm et al. (1993) Biotechnology, Bd. 3, Kapitel III: "Product recovery and purification", S. 469-714, VCH: Weinheim; Belter, P. A., et al. (1988) Bioseparations: downstream processing for Biotechnology, John Wiley and Sons; Kennedy, J. F., und Cabral, J. M. S. (1992) Recovery processes for biological Materials, John Wiley and Sons; Shaeiwitz, J. A., und Henry, J. D. (1988) Biochemical Separations, in: Ullmann's Encyclopedia of Industrial Chemistry, Bd. B3; Kapitel 11, S. 1-27, VCH: Weinheim; und Dechow, F. J. (1989) Separation and purification techniques in biotechnology, Noyes Publications.

Alternatively, extraction will be carried out as described in Cahoon et al. (1999) Proc. Natl. Acad. Sci. USA 96 (22):12935-12940, und Browse et al. (1986) Analytic Biochemistry 152:141-145. Quantitative and qualitative analysis of lipids or fatty acids are described in Christie, William W., Advances in Lipid Methodology, Ayr/Scotland: Oily Press (Oily Press Lipid Library; 2); Christie, William W., Gas Chromatography and Lipids. A Practical Guide—Ayr, Scotland: Oily Press, 1989, Repr. 1992, IX, 307 S. (Oily Press Lipid Library; 1); "Progress in Lipid Research, Oxford: Pergamon Press, 1 (1952)-16 (1977) u.d.T.: Progress in the Chemistry of Fats and Other Lipids CODEN.

The binary T-plasmids described in example 4 were transformed into rapeseed (*Brassica napus*) as described in example 5. After selection of transgenic plants using PCR, plats were grown until development of mature seeds (Day/night cycle: 16 h at 200 mE and 21° C., 8 h at darkness and 19° C.). Fatty acids from harvested seeds were extracted and analysed using gas chromatography. Based on the analysed lipids, the effect of the NEENAs on expression of desaturases and elongases can be determined since the lipid pattern of successfully transformed plant seeds will differ from the pattern of control plant seeds, e.g. of plants expressing a set of desaturases and elongases without the enhancing effect of NEENAs. Table 7 shows results of single seed measurements of the five best performing transgenic lines obtained for each binary T-plasmid. Table 8 shows the nomenclature for the fatty acids listed in the header of table 3.

Surprisingly, transgenic plants obtained from transformations with construct VC-VC-LJB1327-1qcz (SEQ-ID 39) VC-LJB2003-1qcz (SEQ-ID 40) and VC-LJB2197-1qcz (SEQ-ID 146) showed a much higher ARA to GLA ratio compared to plants transformed with VC-LJB913-1qcz (SEQ-ID 38) and was highest for plants transformed with VC-LJB2003-1qcz (ARA:GLA ratio of up to 53.3). Such a ratio is beneficial if GLA is not desired. Even more surprising was that plants of constructs VC-LJB2003-1qcz and VC-LJB2197-1qcz (incorporating NEENAs) reached higher ARA levels than VC-LJB913-1qcz and VC-LJB1327-1qcz (maximal for VC-LJB913-1qcz: 25.6%; VC-LJB1327-1qcz: 22%, VC-LJB2003-1qcz: 28.7% and for VC-LJBV2197-1qcz: 33.1%), despite removal of the expression module expressing the enzyme d6Des(Pir_GAI) compared to VC-LJB913-1qcz transformed plants.

TABLE 7

Gaschromatographical anaylsis of the fatty acid composition of seedoil from transgenic rapeseed plants.

| Sample name | 16:0 | 16:1n-7 | 16:3n-3 | 18:0 | 18:1n-9 | 18:2n-9 | 18:2n-6 | 18:3n-6 | 18:3n-3 | 18:4n-3 | 20:0 | 20:1n-9 | 20:2n-6 |
|---|---|---|---|---|---|---|---|---|---|---|---|---|---|
| LJB2197_169_37 | 2.9 | 0.0 | 0.0 | 2.0 | 17.9 | 0.9 | 25.1 | 1.2 | 3.8 | 0.0 | 0.5 | 0.7 | 2.5 |
| LJB2197_169_5 | 3.2 | 0.0 | 0.0 | 2.0 | 16.3 | 1.2 | 25.8 | 2.1 | 4.5 | 0.2 | 0.6 | 0.6 | 1.5 |
| LJB2197_169_11 | 3.0 | 0.0 | 0.0 | 2.1 | 17.5 | 0.9 | 27.6 | 1.6 | 4.1 | 0.0 | 0.6 | 0.6 | 1.5 |
| LJB2197_169_51 | 3.1 | 0.0 | 0.0 | 2.2 | 17.5 | 0.9 | 27.6 | 1.6 | 4.1 | 0.0 | 0.6 | 0.6 | 1.5 |

TABLE 7-continued

Gaschromatographical anaylsis of the fatty acid composition of seedoil from transgenic rapeseed plants.

| | | | | | | | | | | | | | |
|---|---|---|---|---|---|---|---|---|---|---|---|---|---|
| LJB2197_169_9 | 3.4 | 0.0 | 0.0 | 2.2 | 18.3 | 1.9 | 25.9 | 3.1 | 4.0 | 0.2 | 0.6 | 0.6 | 1.1 |
| LJB2197_169_22 | 3.2 | 0.0 | 0.0 | 2.4 | 17.7 | 0.7 | 28.5 | 1.7 | 3.6 | 0.2 | 0.7 | 0.8 | 0.8 |
| LJB2197_169_36 | 3.5 | 0.0 | 0.0 | 2.3 | 17.1 | 0.6 | 29.5 | 1.5 | 3.8 | 0.2 | 0.7 | 0.8 | 1.0 |
| LJB2197_169_40 | 3.4 | 0.0 | 0.0 | 2.4 | 18.2 | 1.2 | 28.6 | 2.8 | 3.4 | 0.2 | 0.7 | 0.7 | 0.8 |
| LJB2197_169_42 | 3.5 | 0.0 | 0.0 | 2.1 | 18.4 | 0.7 | 27.2 | 1.5 | 4.3 | 0.2 | 0.6 | 0.8 | 1.0 |
| LJB2197_169_26 | 3.7 | 0.0 | 0.0 | 2.3 | 19.3 | 1.3 | 27.4 | 2.7 | 4.0 | 0.3 | 0.7 | 0.7 | 0.6 |
| LJB2197_169_61 | 3.7 | 0.0 | 0.0 | 2.7 | 20.1 | 1.1 | 28.5 | 2.2 | 3.2 | 0.2 | 0.8 | 0.9 | 1.1 |
| LJB2197_169_14 | 3.3 | 0.0 | 0.0 | 1.7 | 18.0 | 0.7 | 30.9 | 1.5 | 4.9 | 0.2 | 0.6 | 0.7 | 1.1 |
| LJB2197_169_16 | 3.3 | 0.0 | 0.0 | 2.2 | 20.3 | 0.7 | 28.3 | 1.2 | 4.5 | 0.1 | 0.7 | 0.8 | 0.8 |
| LJB2197_169_65 | 3.7 | 0.1 | 0.0 | 2.7 | 20.1 | 1.2 | 29.1 | 2.3 | 3.8 | 0.2 | 0.7 | 0.7 | 0.8 |
| LJB2197_169_7 | 3.1 | 0.0 | 0.0 | 2.3 | 18.6 | 0.5 | 30.1 | 1.1 | 4.1 | 0.1 | 0.7 | 0.9 | 1.8 |
| LJB2197_169_34 | 3.3 | 0.0 | 0.0 | 2.5 | 20.9 | 0.8 | 28.8 | 1.3 | 4.2 | 0.2 | 0.8 | 0.8 | 0.8 |
| LJB2197_169_47 | 3.2 | 0.0 | 0.0 | 2.1 | 18.0 | 0.9 | 33.4 | 1.7 | 3.9 | 0.1 | 0.7 | 0.7 | 0.7 |
| LJB2197_169_24 | 3.2 | 0.0 | 0.0 | 2.2 | 18.6 | 0.5 | 30.0 | 1.2 | 4.4 | 0.1 | 0.7 | 0.8 | 1.5 |
| LJB2197_169_31 | 3.2 | 0.0 | 0.0 | 1.8 | 19.4 | 0.6 | 31.1 | 1.4 | 4.2 | 0.1 | 0.6 | 0.8 | 1.3 |
| LJB2197_169_73 | 3.7 | 0.0 | 0.0 | 2.9 | 18.7 | 0.8 | 31.2 | 1.7 | 4.5 | 0.0 | 0.8 | 0.7 | 0.7 |
| LJB2197_169_21 | 3.3 | 0.0 | 0.0 | 2.4 | 19.5 | 0.7 | 30.5 | 1.3 | 4.2 | 0.1 | 0.7 | 0.8 | 0.9 |
| LJB2197_169_29 | 3.2 | 0.0 | 0.0 | 2.2 | 19.6 | 0.6 | 29.7 | 1.3 | 4.0 | 0.1 | 0.7 | 0.9 | 1.5 |
| LJB2003_110_11 | 3.0 | 0.0 | 0.0 | 2.6 | 15.7 | 0.2 | 32.1 | 0.6 | 2.8 | 0.0 | 0.7 | 1.0 | 4.8 |
| LJB2003_110_17 | 3.3 | 0.0 | 0.0 | 2.7 | 16.5 | 0.1 | 31.4 | 0.5 | 2.7 | 0.0 | 0.7 | 1.1 | 5.6 |
| LJB2003_110_16 | 3.3 | 0.1 | 0.0 | 3.2 | 17.4 | 0.2 | 32.6 | 0.5 | 2.6 | 0.0 | 0.8 | 1.1 | 5.1 |
| LJB2003_8_54 | 3.5 | 0.1 | 0.0 | 2.5 | 19.4 | 0.8 | 36.2 | 2.3 | 3.3 | 0.2 | 0.8 | 0.7 | 0.4 |
| LJB2003_8_7 | 3.3 | 0.1 | 0.0 | 2.8 | 19.4 | 0.8 | 35.1 | 2.3 | 3.7 | 0.2 | 0.8 | 0.8 | 0.5 |
| LJB2003_53_11 | 2.7 | 0.0 | 0.0 | 2.1 | 14.0 | 0.3 | 38.0 | 0.7 | 5.3 | 0.0 | 0.7 | 0.7 | 1.6 |
| LJB2003_110_49 | 3.9 | 0.0 | 0.0 | 3.4 | 18.6 | 0.3 | 34.9 | 0.5 | 2.5 | 0.0 | 0.8 | 1.1 | 4.4 |
| LJB2003_53_37 | 3.2 | 0.0 | 0.0 | 3.4 | 16.0 | 0.4 | 36.4 | 1.0 | 3.5 | 0.0 | 0.8 | 0.7 | 1.3 |
| LJB2003_8_49 | 3.4 | 0.1 | 0.0 | 2.7 | 20.0 | 0.9 | 37.1 | 2.1 | 3.4 | 0.1 | 0.8 | 0.7 | 0.5 |
| LJB2003_8_23 | 3.6 | 0.1 | 0.0 | 3.0 | 20.7 | 1.0 | 33.6 | 2.9 | 4.0 | 0.3 | 0.8 | 0.8 | 0.5 |
| LJB2003_8_42 | 3.6 | 0.1 | 0.0 | 2.6 | 20.7 | 0.8 | 35.3 | 2.4 | 3.8 | 0.2 | 0.7 | 0.7 | 0.5 |
| LJB2003_8_57 | 3.7 | 0.1 | 0.0 | 3.0 | 20.8 | 1.0 | 36.0 | 2.3 | 3.1 | 0.2 | 0.9 | 0.7 | 0.4 |
| LJB2003_53_34 | 2.8 | 0.0 | 0.0 | 2.6 | 16.4 | 0.3 | 39.3 | 0.8 | 4.2 | 0.0 | 0.7 | 0.7 | 1.7 |
| LJB2003_54_13 | 3.7 | 0.1 | 0.0 | 2.3 | 17.9 | 0.5 | 39.5 | 1.3 | 4.0 | 0.1 | 0.8 | 0.7 | 0.8 |
| LJB2003_8_58 | 3.7 | 0.1 | 0.0 | 2.5 | 23.6 | 0.9 | 34.1 | 2.1 | 3.5 | 0.2 | 0.7 | 0.8 | 0.3 |
| LJB2003_8_62 | 3.7 | 0.1 | 0.0 | 2.5 | 21.3 | 0.8 | 35.6 | 2.2 | 3.9 | 0.2 | 0.7 | 0.7 | 0.4 |
| LJB2003_110_25 | 3.2 | 0.0 | 0.0 | 3.2 | 20.1 | 0.2 | 34.7 | 0.4 | 2.9 | 0.0 | 0.9 | 1.1 | 3.9 |
| LJB2003_54_17 | 3.4 | 0.2 | 0.0 | 2.4 | 18.2 | 0.4 | 39.5 | 1.1 | 4.2 | 0.1 | 0.8 | 0.7 | 1.0 |
| LJB2003_8_19 | 3.6 | 0.1 | 0.0 | 3.1 | 20.6 | 0.9 | 36.9 | 2.5 | 3.1 | 0.2 | 0.8 | 0.8 | 0.4 |
| LJB2003_53_23 | 3.4 | 0.2 | 0.0 | 2.3 | 18.0 | 0.2 | 37.0 | 0.7 | 4.3 | 0.1 | 0.6 | 0.8 | 2.0 |
| LJB2003_8_68 | 3.5 | 0.1 | 0.0 | 2.8 | 20.8 | 0.8 | 36.4 | 2.2 | 3.7 | 0.2 | 0.8 | 0.7 | 0.4 |
| LJB1327_305_31 | 3.7 | 0.1 | 0.0 | 2.8 | 21.0 | 1.3 | 35.3 | 3.4 | 3.1 | 0.2 | 0.9 | 0.7 | 0.2 |
| LJB1327_305_48 | 4.3 | 0.1 | 0.0 | 2.2 | 19.5 | 0.9 | 37.5 | 1.9 | 4.2 | 0.1 | 0.7 | 0.6 | 0.2 |
| LJB1327_305_32 | 4.0 | 0.0 | 0.0 | 2.1 | 18.8 | 0.7 | 39.2 | 1.8 | 4.2 | 0.1 | 0.8 | 0.6 | 0.2 |
| LJB1327_458_92 | 3.3 | 0.0 | 0.0 | 2.0 | 17.8 | 0.9 | 39.1 | 2.1 | 4.6 | 0.2 | 0.8 | 0.7 | 0.2 |
| LJB1327_305_38 | 4.0 | 0.1 | 0.0 | 2.7 | 19.7 | 1.0 | 36.9 | 2.9 | 4.1 | 0.3 | 0.9 | 0.6 | 0.2 |
| LJB1327_305_43 | 4.0 | 0.1 | 0.0 | 2.6 | 19.2 | 1.0 | 37.2 | 2.2 | 4.0 | 0.1 | 0.9 | 0.6 | 0.2 |
| LJB1327_305_45 | 3.9 | 0.1 | 0.0 | 2.7 | 19.9 | 0.9 | 37.3 | 2.4 | 4.3 | 0.2 | 0.9 | 0.6 | 0.2 |
| LJB1327_305_30 | 3.9 | 0.1 | 0.0 | 2.7 | 22.0 | 1.0 | 36.4 | 2.5 | 3.5 | 0.2 | 0.9 | 0.7 | 0.2 |
| LJB1327_305_35 | 4.2 | 0.1 | 0.0 | 2.7 | 20.3 | 1.0 | 38.0 | 2.2 | 3.7 | 0.2 | 0.9 | 0.6 | 0.2 |
| LJB1327_305_37 | 4.3 | 0.0 | 0.0 | 3.0 | 19.7 | 1.1 | 38.8 | 2.6 | 3.2 | 0.2 | 1.1 | 0.6 | 0.2 |
| LJB1327_305_47 | 4.1 | 0.1 | 0.0 | 2.4 | 20.4 | 1.1 | 38.3 | 2.4 | 3.8 | 0.2 | 0.8 | 0.6 | 0.2 |
| LJB1327_305_34 | 3.9 | 0.0 | 0.0 | 2.8 | 18.9 | 1.0 | 39.0 | 2.6 | 3.6 | 0.2 | 1.1 | 0.6 | 0.1 |
| LJB1327_305_44 | 4.1 | 0.1 | 0.0 | 2.9 | 20.3 | 1.0 | 38.0 | 2.3 | 4.3 | 0.2 | 0.9 | 0.6 | 0.2 |
| LJB1327_458_94 | 4.0 | 0.0 | 0.0 | 2.1 | 18.8 | 0.8 | 37.1 | 2.2 | 5.9 | 0.3 | 0.8 | 0.6 | 0.2 |
| LJB1327_305_50 | 4.0 | 0.0 | 0.0 | 2.4 | 19.6 | 0.8 | 40.3 | 2.2 | 4.2 | 0.2 | 0.9 | 0.6 | 0.2 |
| LJB1327_305_42 | 3.7 | 0.1 | 0.0 | 2.5 | 23.6 | 1.1 | 37.0 | 2.4 | 3.8 | 0.2 | 0.8 | 0.7 | 0.2 |
| LJB1327_305_54 | 4.4 | 0.1 | 0.0 | 3.4 | 21.5 | 1.4 | 37.4 | 2.8 | 2.7 | 0.1 | 1.3 | 0.8 | 0.6 |
| LJB1327_305_41 | 4.2 | 0.1 | 0.0 | 2.5 | 22.4 | 1.0 | 38.6 | 2.0 | 3.6 | 0.1 | 0.8 | 0.6 | 0.2 |
| LJB1327_305_40 | 3.9 | 0.0 | 0.0 | 2.5 | 21.1 | 0.9 | 39.4 | 2.0 | 4.3 | 0.2 | 0.8 | 0.6 | 0.2 |
| LJB1327_305_55 | 4.5 | 0.1 | 0.0 | 3.3 | 21.9 | 1.3 | 37.7 | 2.0 | 3.3 | 0.2 | 1.2 | 0.7 | 0.7 |
| LJB1327_305_33 | 4.2 | 0.1 | 0.0 | 2.7 | 23.8 | 1.1 | 37.0 | 2.1 | 3.7 | 0.2 | 0.9 | 0.7 | 0.2 |
| LJB913_64-13a | 4.4 | 0.0 | 0.0 | 3.9 | 11.3 | 0.0 | 21.7 | 11.7 | 3.7 | 0.7 | 1.1 | 0.9 | 3.7 |
| LJB913_64_9 | 3.8 | 0.0 | 0.2 | 2.7 | 9.8 | 0.0 | 21.8 | 12.7 | 4.3 | 0.8 | 0.9 | 1.0 | 4.5 |
| LJB913_64_3 | 4.2 | 0.1 | 0.2 | 3.6 | 12.0 | 0.0 | 22.4 | 11.7 | 3.5 | 0.7 | 1.0 | 1.2 | 5.7 |
| LJB913_64_20 | 3.5 | 0.2 | 0.1 | 3.3 | 14.1 | 0.1 | 25.9 | 8.7 | 3.0 | 0.5 | 0.9 | 1.2 | 5.0 |
| LJB913_64_8 | 3.7 | 0.1 | 0.2 | 3.0 | 13.9 | 0.2 | 24.1 | 16.4 | 3.7 | 1.1 | 0.9 | 0.8 | 2.0 |
| LJB913_91_5 | 3.5 | 0.1 | 0.1 | 2.8 | 15.7 | 0.1 | 27.1 | 9.0 | 4.9 | 0.5 | 0.8 | 0.9 | 3.1 |
| LJB913_64_22 | 4.8 | 0.2 | 0.1 | 4.0 | 13.4 | 0.0 | 25.9 | 9.3 | 3.9 | 0.7 | 1.2 | 1.0 | 4.3 |
| LJB913_64_23 | 4.5 | 0.1 | 0.1 | 3.9 | 13.4 | 0.0 | 25.0 | 9.9 | 3.9 | 0.7 | 1.1 | 1.1 | 5.2 |
| LJB913_64-07a | 4.2 | 0.0 | 0.0 | 4.5 | 13.7 | 0.0 | 25.9 | 7.3 | 4.4 | 0.0 | 1.3 | 1.4 | 7.6 |
| LJB913_91_4 | 4.1 | 0.2 | 0.2 | 3.7 | 16.2 | 0.2 | 32.4 | 5.2 | 6.1 | 0.4 | 1.0 | 0.7 | 1.7 |
| LJB913_64-05a | 4.2 | 0.0 | 0.0 | 4.8 | 14.0 | 0.0 | 25.3 | 8.0 | 4.8 | 0.5 | 1.3 | 1.3 | 5.8 |
| LJB913_64_10 | 3.9 | 0.0 | 0.1 | 4.6 | 15.0 | 0.0 | 27.3 | 6.0 | 4.5 | 0.3 | 1.2 | 1.3 | 6.2 |
| LJB913_64_13 | 3.9 | 0.0 | 0.1 | 3.5 | 15.0 | 0.1 | 29.4 | 4.5 | 4.5 | 0.5 | 0.9 | 1.1 | 4.5 |
| LJB913_91_14 | 3.6 | 0.0 | 0.2 | 3.5 | 17.0 | 0.1 | 26.6 | 9.3 | 5.1 | 0.5 | 0.9 | 0.9 | 2.8 |
| LJB913_64-12a | 4.8 | 0.0 | 0.0 | 4.8 | 13.9 | 0.0 | 24.1 | 7.1 | 5.0 | 0.0 | 1.4 | 1.3 | 7.7 |
| LJB913_91_28 | 4.2 | 0.0 | 0.2 | 4.0 | 17.1 | 0.0 | 27.4 | 7.5 | 5.9 | 0.4 | 1.1 | 0.9 | 2.9 |
| LJB913_91_20 | 3.2 | 0.1 | 0.1 | 3.0 | 18.7 | 0.1 | 28.9 | 7.2 | 4.7 | 0.3 | 0.7 | 0.9 | 2.5 |
| LJB913_64_17 | 4.7 | 0.1 | 0.1 | 4.3 | 14.3 | 0.0 | 27.0 | 9.6 | 3.8 | 0.5 | 1.1 | 1.0 | 4.0 |

TABLE 7-continued

Gaschromatographical anaylsis of the fatty acid composition of seedoil from transgenic rapeseed plants.

| | | | | | | | | | | | | |
|---|---|---|---|---|---|---|---|---|---|---|---|---|
| LJB913_91_18 | 3.6 | 0.0 | 0.1 | 4.0 | 17.8 | 0.1 | 31.0 | 6.1 | 4.6 | 0.3 | 1.0 | 0.9 | 2.5 |
| LJB913_64_14 | 4.0 | 0.0 | 0.3 | 4.2 | 14.9 | 0.0 | 26.2 | 8.9 | 5.5 | 0.7 | 1.1 | 1.0 | 3.9 |
| LJB913_91_3 | 3.8 | 0.1 | 0.2 | 3.1 | 18.1 | 0.0 | 29.7 | 6.5 | 6.8 | 0.5 | 0.9 | 0.8 | 1.9 |

| Sample name | 20:3n-6 | 20:3n-3 | 20:4n-6 (ARA) | 20:4n-3 | 20:5n-3 | 22:0 | Ratio ARA:GLA | Ratio ARA:DGLA | Ratio LA:ALA | Ratio ARA:EPA |
|---|---|---|---|---|---|---|---|---|---|---|
| LJB2197_169_37 | 3.0 | 0.0 | 33.1 | 0.5 | 5.9 | 0.0 | 27.0 | 11.2 | 6.7 | 5.6 |
| LJB2197_169_5 | 2.8 | 0.0 | 32.1 | 0.5 | 6.7 | 0.0 | 15.2 | 11.5 | 5.8 | 4.8 |
| LJB2197_169_11 | 3.3 | 0.0 | 31.2 | 0.5 | 5.5 | 0.0 | 19.9 | 9.4 | 6.7 | 5.7 |
| LJB2197_169_51 | 3.3 | 0.0 | 31.1 | 0.5 | 5.5 | 0.0 | 19.8 | 9.3 | 6.7 | 5.7 |
| LJB2197_169_9 | 2.0 | 0.0 | 30.2 | 0.4 | 5.7 | 0.3 | 9.9 | 14.9 | 6.5 | 5.3 |
| LJB2197_169_22 | 3.8 | 0.0 | 29.8 | 0.6 | 5.3 | 0.4 | 18.0 | 7.9 | 8.0 | 5.7 |
| LJB2197_169_36 | 3.2 | 0.0 | 29.5 | 0.5 | 5.5 | 0.4 | 19.8 | 9.3 | 7.8 | 5.4 |
| LJB2197_169_40 | 2.6 | 0.0 | 29.2 | 0.4 | 5.0 | 0.3 | 10.2 | 11.4 | 8.4 | 5.8 |
| LJB2197_169_42 | 3.3 | 0.0 | 29.1 | 0.6 | 6.6 | 0.3 | 19.1 | 8.9 | 6.4 | 4.4 |
| LJB2197_169_26 | 2.1 | 0.0 | 29.0 | 0.4 | 5.5 | 0.0 | 10.6 | 13.5 | 6.9 | 5.3 |
| LJB2197_169_61 | 3.0 | 0.0 | 27.4 | 0.4 | 4.6 | 0.3 | 12.5 | 9.3 | 9.0 | 6.0 |
| LJB2197_169_14 | 3.1 | 0.0 | 26.8 | 0.6 | 5.7 | 0.4 | 18.4 | 8.7 | 6.4 | 4.7 |
| LJB2197_169_16 | 3.0 | 0.0 | 26.6 | 0.6 | 6.3 | 0.4 | 21.5 | 8.8 | 6.2 | 4.2 |
| LJB2197_169_65 | 1.8 | 0.0 | 26.6 | 0.3 | 5.5 | 0.3 | 11.5 | 14.4 | 7.7 | 4.8 |
| LJB2197_169_7 | 4.1 | 0.0 | 26.5 | 0.7 | 5.1 | 0.4 | 24.6 | 6.5 | 7.4 | 5.2 |
| LJB2197_169_34 | 2.9 | 0.0 | 26.5 | 0.5 | 5.4 | 0.4 | 19.8 | 9.2 | 6.9 | 4.9 |
| LJB2197_169_47 | 2.7 | 0.0 | 26.3 | 0.4 | 4.6 | 0.4 | 15.2 | 9.8 | 8.7 | 5.7 |
| LJB2197_169_24 | 3.9 | 0.0 | 26.2 | 0.7 | 5.6 | 0.3 | 22.7 | 6.8 | 6.7 | 4.7 |
| LJB2197_169_31 | 3.5 | 0.0 | 26.0 | 0.6 | 5.0 | 0.4 | 18.6 | 7.5 | 7.4 | 5.2 |
| LJB2197_169_73 | 2.4 | 0.0 | 26.0 | 0.4 | 5.4 | 0.0 | 15.1 | 10.8 | 6.9 | 4.8 |
| LJB2197_169_21 | 3.6 | 0.0 | 25.9 | 0.6 | 5.0 | 0.4 | 19.3 | 7.2 | 7.2 | 5.2 |
| LJB2197_169_29 | 4.0 | 0.0 | 25.8 | 0.7 | 5.1 | 0.4 | 19.4 | 6.5 | 7.4 | 5.0 |
| LJB2003_110_11 | 3.0 | 0.3 | 28.7 | 0.3 | 3.7 | 0.3 | 48.9 | 9.7 | 11.4 | 7.8 |
| LJB2003_110_17 | 2.5 | 0.4 | 28.1 | 0.3 | 3.6 | 0.3 | 53.3 | 11.2 | 11.5 | 7.7 |
| LJB2003_110_16 | 2.7 | 0.4 | 26.1 | 0.3 | 3.2 | 0.3 | 50.1 | 9.6 | 12.6 | 8.1 |
| LJB2003_8_54 | 2.0 | 0.0 | 24.2 | 0.2 | 3.0 | 0.4 | 10.5 | 12.2 | 11.0 | 8.1 |
| LJB2003_8_7 | 1.8 | 0.0 | 24.0 | 0.3 | 3.7 | 0.4 | 10.2 | 13.6 | 9.5 | 6.5 |
| LJB2003_53_11 | 4.3 | 0.0 | 23.9 | 0.7 | 4.7 | 0.4 | 33.1 | 5.6 | 7.2 | 5.1 |
| LJB2003_110_49 | 2.4 | 0.5 | 23.6 | 0.2 | 2.7 | 0.3 | 45.1 | 9.9 | 13.9 | 8.7 |
| LJB2003_53_37 | 5.2 | 0.0 | 23.5 | 0.7 | 3.4 | 0.4 | 23.6 | 4.5 | 10.3 | 6.8 |
| LJB2003_8_49 | 1.7 | 0.0 | 22.8 | 0.2 | 2.9 | 0.4 | 11.1 | 13.1 | 11.0 | 7.9 |
| LJB2003_8_23 | 1.4 | 0.0 | 22.8 | 0.2 | 3.8 | 0.4 | 7.8 | 16.5 | 8.4 | 6.1 |
| LJB2003_8_42 | 1.6 | 0.0 | 22.6 | 0.2 | 3.7 | 0.4 | 9.6 | 14.1 | 9.3 | 6.0 |
| LJB2003_8_57 | 1.8 | 0.0 | 22.6 | 0.2 | 2.8 | 0.5 | 9.8 | 12.6 | 11.8 | 8.0 |
| LJB2003_53_34 | 4.1 | 0.0 | 22.5 | 0.5 | 3.1 | 0.4 | 28.5 | 5.5 | 9.4 | 7.2 |
| LJB2003_54_13 | 1.9 | 0.0 | 22.4 | 0.2 | 3.2 | 0.5 | 17.4 | 11.9 | 9.8 | 6.9 |
| LJB2003_8_58 | 1.4 | 0.0 | 22.3 | 0.2 | 3.4 | 0.3 | 10.7 | 16.3 | 9.9 | 6.5 |
| LJB2003_8_62 | 1.4 | 0.0 | 22.2 | 0.2 | 3.6 | 0.4 | 10.2 | 15.4 | 9.1 | 6.3 |
| LJB2003_110_25 | 3.2 | 0.4 | 22.2 | 0.4 | 3.0 | 0.3 | 49.8 | 7.0 | 12.1 | 7.5 |
| LJB2003_54_17 | 2.1 | 0.0 | 21.9 | 0.3 | 3.4 | 0.4 | 20.5 | 10.7 | 9.5 | 6.5 |
| LJB2003_8_19 | 1.5 | 0.0 | 21.9 | 0.2 | 2.9 | 0.4 | 8.7 | 14.6 | 11.7 | 7.6 |
| LJB2003_53_23 | 3.6 | 0.2 | 21.9 | 0.6 | 3.8 | 0.4 | 31.0 | 6.1 | 8.5 | 5.7 |
| LJB2003_8_68 | 1.7 | 0.0 | 21.8 | 0.2 | 3.4 | 0.4 | 9.9 | 13.1 | 9.9 | 6.4 |
| LJB1327_305_31 | 1.5 | 0.9 | 22.0 | 0.1 | 2.2 | 0.5 | 6.4 | 15.1 | 11.4 | 9.8 |
| LJB1327_305_48 | 2.1 | 0.7 | 21.6 | 0.2 | 2.8 | 0.5 | 11.5 | 10.4 | 8.9 | 7.8 |
| LJB1327_305_32 | 1.7 | 1.2 | 21.4 | 0.2 | 2.5 | 0.6 | 11.7 | 12.9 | 9.3 | 8.7 |
| LJB1327_458_92 | 2.0 | 1.4 | 21.2 | 0.2 | 3.1 | 0.6 | 10.2 | 10.4 | 8.6 | 6.9 |
| LJB1327_305_38 | 1.7 | 0.6 | 20.9 | 0.2 | 2.8 | 0.6 | 7.2 | 12.6 | 9.0 | 7.5 |
| LJB1327_305_43 | 3.1 | 0.8 | 20.8 | 0.3 | 2.4 | 0.6 | 9.5 | 6.8 | 9.3 | 8.7 |
| LJB1327_305_45 | 1.7 | 0.9 | 20.7 | 0.2 | 2.7 | 0.6 | 8.6 | 12.0 | 8.7 | 7.7 |
| LJB1327_305_30 | 1.6 | 0.6 | 20.6 | 0.2 | 2.5 | 0.5 | 8.3 | 13.1 | 10.3 | 8.3 |
| LJB1327_305_35 | 1.5 | 0.8 | 20.6 | 0.2 | 2.3 | 0.5 | 9.3 | 14.1 | 10.4 | 9.0 |
| LJB1327_305_37 | 1.4 | 0.7 | 20.5 | 0.1 | 1.9 | 0.6 | 7.9 | 14.9 | 12.2 | 10.9 |
| LJB1327_305_47 | 1.4 | 0.7 | 20.4 | 0.1 | 2.2 | 0.5 | 8.5 | 14.4 | 10.0 | 9.3 |
| LJB1327_305_34 | 1.7 | 1.2 | 20.4 | 0.2 | 2.1 | 0.7 | 8.0 | 11.7 | 10.7 | 9.9 |
| LJB1327_305_44 | 1.4 | 0.7 | 19.9 | 0.1 | 2.5 | 0.6 | 8.5 | 14.2 | 8.9 | 8.0 |
| LJB1327_458_94 | 2.2 | 1.5 | 19.3 | 0.3 | 3.5 | 0.5 | 8.7 | 8.9 | 6.3 | 5.5 |
| LJB1327_305_50 | 1.5 | 0.7 | 19.2 | 0.2 | 2.4 | 0.6 | 8.8 | 12.6 | 9.7 | 8.0 |
| LJB1327_305_42 | 1.1 | 0.7 | 19.2 | 0.2 | 2.4 | 0.5 | 8.1 | 16.8 | 9.7 | 8.0 |
| LJB1327_305_54 | 1.5 | 0.7 | 19.1 | 0.0 | 1.6 | 0.6 | 6.8 | 12.9 | 13.9 | 11.8 |
| LJB1327_305_41 | 1.3 | 0.7 | 19.1 | 0.2 | 2.3 | 0.5 | 9.6 | 14.6 | 10.7 | 8.3 |
| LJB1327_305_40 | 1.3 | 0.7 | 18.8 | 0.2 | 2.6 | 0.5 | 9.2 | 14.5 | 9.1 | 7.1 |
| LJB1327_305_55 | 1.4 | 0.9 | 18.6 | 0.0 | 1.7 | 0.5 | 9.3 | 13.7 | 11.3 | 11.1 |
| LJB1327_305_33 | 1.3 | 0.8 | 18.6 | 0.1 | 2.1 | 0.6 | 8.9 | 14.6 | 10.1 | 8.8 |
| LJB913_64-13a | 6.7 | 0.0 | 25.6 | 0.7 | 3.8 | 0.0 | 2.2 | 3.8 | 5.9 | 6.7 |
| LJB913_64_9 | 8.7 | 0.0 | 23.6 | 1.0 | 3.8 | 0.0 | 1.8 | 2.7 | 5.1 | 6.1 |
| LJB913_64_3 | 6.5 | 0.7 | 22.0 | 0.7 | 3.5 | 0.5 | 1.9 | 3.4 | 6.5 | 6.4 |
| LJB913_64_20 | 7.4 | 0.5 | 21.2 | 0.8 | 3.2 | 0.4 | 2.4 | 2.9 | 8.5 | 6.6 |
| LJB913_64_8 | 5.8 | 0.0 | 20.4 | 0.7 | 3.1 | 0.0 | 1.2 | 3.5 | 6.6 | 6.6 |
| LJB913_91_5 | 6.0 | 0.4 | 20.3 | 0.7 | 3.5 | 0.4 | 2.2 | 3.4 | 5.5 | 5.8 |
| LJB913_64_22 | 6.0 | 0.6 | 19.8 | 0.8 | 3.3 | 0.7 | 2.1 | 3.3 | 6.6 | 6.0 |

TABLE 7-continued

Gaschromatographical anaylsis of the fatty acid composition of seedoil from transgenic rapeseed plants.

| | | | | | | | | | |
|---|---|---|---|---|---|---|---|---|---|
| LJB913_64_23 | 6.1 | 0.7 | 19.5 | 0.8 | 3.4 | 0.5 | 2.0 | 3.2 | 6.4 | 5.8 |
| LJB913_64-07a | 6.2 | 1.0 | 19.4 | 0.0 | 3.1 | 0.0 | 2.7 | 3.1 | 5.9 | 6.3 |
| LJB913_91_4 | 4.7 | 0.0 | 19.4 | 0.6 | 3.4 | 0.0 | 3.7 | 4.1 | 5.3 | 5.7 |
| LJB913_64-05a | 7.0 | 0.0 | 19.1 | 0.8 | 3.2 | 0.0 | 2.4 | 2.7 | 5.2 | 6.0 |
| LJB913_64_10 | 6.4 | 0.7 | 18.9 | 0.6 | 2.5 | 0.5 | 3.2 | 3.0 | 6.0 | 7.6 |
| LJB913_64_13 | 7.8 | 0.6 | 18.7 | 1.0 | 3.1 | 0.0 | 2.0 | 2.4 | 5.6 | 6.0 |
| LJB913_91_14 | 6.5 | 0.4 | 18.7 | 0.7 | 3.1 | 0.0 | 2.0 | 2.9 | 5.2 | 6.0 |
| LJB913_64-12a | 6.5 | 1.2 | 18.5 | 0.0 | 3.5 | 0.0 | 2.6 | 2.8 | 4.8 | 5.2 |
| LJB913_91_28 | 6.5 | 0.0 | 18.4 | 0.7 | 2.9 | 0.0 | 2.4 | 2.8 | 4.7 | 6.3 |
| LJB913_91_20 | 7.1 | 0.3 | 18.3 | 0.8 | 2.9 | 0.0 | 2.5 | 2.6 | 6.1 | 6.3 |
| LJB913_64_17 | 6.5 | 0.5 | 18.2 | 0.7 | 2.9 | 0.6 | 1.9 | 2.8 | 7.1 | 6.2 |
| LJB913_91_18 | 5.6 | 0.3 | 18.2 | 0.6 | 2.8 | 0.5 | 3.0 | 3.2 | 6.8 | 6.6 |
| LJB913_64_14 | 6.5 | 0.6 | 17.8 | 0.9 | 3.5 | 0.0 | 2.0 | 2.7 | 4.7 | 5.1 |
| LJB913_91_3 | 5.3 | 0.0 | 17.7 | 0.8 | 3.7 | 0.0 | 2.7 | 3.3 | 4.4 | 4.8 |

TABLE 8

Used Nomenclature

| Fatty acid | Nomenclature | |
|---|---|---|
| Oleic acid | 18:1Δ9 | 18:1n − 9 |
| Linoleic acid | 18:2Δ6, 12 | 18:2n − 6 |
| α-Linolenic acid | 18:3Δ9, 12, 15 | α18:3n − 3 |
| γ-Linolenic acid | 18:3Δ6, 9, 12 | γ18:3n − 6 |
| Stearidonic acid | 18:4Δ6, 9, 12, 15 | 18:4n − 3 |
| Dihomo-γ-linolenic acid | 20:3Δ8, 11, 14 | 20:3n − 6 |
| Eicosatrienoic acid | 20:3Δ11, 14, 17 | 20:3n − 3 |
| iso-Arachidonic acid | 20:4Δ8, 11, 14, 17 | 20:4n − 3 |
| Arachidonic acid | 20:4Δ5, 8, 11, 14 | 20:4n − 6 |
| Eicosapentaenoic acid | 20:5Δ5, 8, 11, 14, 17 | 20:5n − 3 |

The invention claimed is:

1. A polynucleotide comprising:
   a) at least one nucleic acid sequence encoding a polypeptide having desaturase or elongase activity;
   b) at least one seed-specific plant promoter operatively linked to the nucleic acid sequence of a);
   c) at least one terminator sequence operatively linked to the nucleic acid sequence of a); and
   d) at least one nucleic acid expression enhancing nucleic acid (NEENA) molecule functionally linked to the promoter of b),
   wherein said at least one NEENA molecule is heterologous to the promoter of b) and to the polypeptide of a),
   wherein said at least one NEENA molecule comprises a nucleotide sequence having at least 95% sequence identity to the nucleotide sequence of SEQ ID NO: 6, 7, 8, 9, 10, 11, 12, 13, 14, 15, 16, 17, 18, 19, 20, 21, 22, 23 or 24,
   wherein said at least one NEENA molecule is not able to drive expression of the nucleic acid sequence of a) but is able to enhance expression of said nucleic acid sequence when functionally linked to the promoter of b),
   and wherein said at least one NEENA molecule enhances seed-specific expression of said nucleic acid sequence of a) in the plant or part thereof as compared to a corresponding control plant or part thereof.

2. The polynucleotide of claim 1, comprising:
   e) at least one nucleic acid sequence encoding a polypeptide having beta-ketoacyl reductase activity;
   f) at least one nucleic acid sequence encoding a polypeptide having dehydratase activity; and/or
   g) at least one nucleic acid sequence encoding a polypeptide having enoyl-CoA reductase activity,
   wherein the nucleic acid sequences of e) to g) are heterologous to said polypeptide having desaturase or elongase activity.

3. The polynucleotide of claim 2, comprising at least one nucleic acid sequence encoding a polypeptide having acyltransferase activity, wherein the nucleic acid sequence is heterologous to said polypeptide having desaturase, elongase, beta-ketoacyl reductase, dehydratase, or enoyl-CoA reductase activity.

4. A vector comprising the polynucleotide of claim 1.

5. A host cell comprising:
   a) the polynucleotide of claim 1; or
   b) a vector comprising said polynucleotide.

6. A method for the manufacture of a polypeptide encoded by the polynucleotide of claim 1, comprising:
   a) cultivating a host cell comprising the polynucleotide of claim 1 or a vector comprising said polynucleotide under conditions which allow for the production of the polypeptide; and
   b) obtaining the polypeptide from the host cell.

7. A non-human transgenic organism comprising the polynucleotide of claim 1 or a vector comprising said polynucleotide.

8. The non-human transgenic organism of claim 7, which is a plant or a plant part.

9. A method for the manufacture of polyunsaturated fatty acids comprising:
   a) cultivating the host cell of claim 5 under conditions which allow for the production of polyunsaturated fatty acids in said host cell; and
   b) obtaining said polyunsaturated fatty acids from the host cell.

10. A method for the manufacture of polyunsaturated fatty acids comprising:

a) cultivating the non-human transgenic organism of claim 7 under conditions which allow for the production of a polyunsaturated fatty acid in said non-human transgenic organism; and b) obtaining said polyunsaturated fatty acid from the non-human transgenic organism.

11. The method of claim 9, wherein said polyunsaturated fatty acid is arachidonic acid (ARA), eicosapentaenoic acid (EPA), or docosahexaenoic acid (DHA).

12. A method for the manufacture of an oil, lipid, or fatty acid composition comprising:

a) cultivating the host cell of claim 5 under conditions which allow for the production of a polyunsaturated fatty acid in said host cell;

b) obtaining said polyunsaturated fatty acid from said host cell; and c) formulating said polyunsaturated fatty acid as an oil, lipid, or fatty acid composition.

13. A method for the production of foodstuffs, animal feed, a seed, a pharmaceutical, or a fine chemical, comprising:

a) providing the host cell of claim 5, or a host cell culture, non-human transgenic organism, transgenic plant, plant part, or plant seed derived from a transgenic non-human organism or plant comprising said host cell; and b) preparing foodstuffs, animal feed, a seed, a pharmaceutical, or a fine chemical.

14. A method for enhancing expression of at least one enzyme of the polyunsaturated fatty acid biosynthetic pathway in a plant or part thereof, comprising transforming a plant or part thereof with a polynucleotide comprising:

i) at least one nucleic acid sequence encoding a polypeptide selected from the group consisting of:
   a) a polypeptide having desaturase or elongase activity;
   b) a polypeptide having beta-ketoacyl reductase activity;
   c) a polypeptide having dehydratase activity; and
   d) a polypeptide having enoyl-CoA reductase activity;

ii) at least one seed-specific plant promoter operatively linked to the nucleic acid sequence of i);

iii) at least one terminator sequence operatively linked to the nucleic acid sequence of i); and iv) at least one nucleic acid expression enhancing nucleic acid (NEENA) molecule functionally linked to the promoter of ii), wherein said at least one NEENA molecule is heterologous to the promoter of ii) and to the nucleic acid sequence of i), wherein said at least one NEENA molecule comprises a nucleotide sequence having at least 95% sequence identity to the nucleotide sequence of SEQ ID NO: 6, 7, 8, 9, 10, 11, 12, 13, 14, 15, 16, 17, 18, 19, 20, 21, 22, 23 or 24, wherein said at least one NEENA molecule is not able to drive expression of the nucleic acid sequence of i) but is able to enhance expression of said nucleic acid sequence when functionally linked to the promoter of ii), and wherein said at least one NEENA molecule enhances seed-specific expression of said nucleic acid sequence of i) in the plant or part thereof as compared to a corresponding control plant or part thereof.

15. The method of claim 14, wherein said at least one NEENA molecule comprises the nucleotide sequence of SEQ ID NO: 6, 7, 8, 9, 10, 11, 12, 13, 14, 15, 16, 17, 18, 19, 20, 21, 22, 23 or 24.

16. The polynucleotide of claim 1, wherein said at least one NEENA molecule comprises the nucleotide sequence of SEQ ID NO: 6, 7, 8, 9, 10, 11, 12, 13, 14, 15, 16, 17, 18, 19, 20, 21, 22, 23 or 24.

\* \* \* \* \*